US012582334B2

(12) United States Patent
Pace et al.

(10) Patent No.: US 12,582,334 B2
(45) Date of Patent: *Mar. 24, 2026

(54) ANALYTE SENSOR DEVICES, CONNECTIONS, AND METHODS

(71) Applicant: ABBOTT DIABETES CARE INC., Alameda, CA (US)

(72) Inventors: Louis Pace, San Carlos, CA (US); Peter G. Robinson, Alamo, CA (US); Udo Hoss, Castro Valley, CA (US); Samuel Mason Curry, San Francisco, CA (US); Phillip William Carter, Oakland, CA (US); Vincent Michael DiPalma, Oakland, CA (US); Amit Mhatre, Sunnyvale, CA (US); Jennifer Olson, San Francisco, CA (US); Manuel Luis Miguel Donnay, San Francisco, CA (US); Marc Barry Taub, Mountain View, CA (US)

(73) Assignee: ABBOTT DIABETES CARE INC., Alameda, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/979,330

(22) Filed: Nov. 2, 2022

(65) Prior Publication Data

US 2023/0046619 A1 Feb. 16, 2023

Related U.S. Application Data

(63) Continuation of application No. 17/531,265, filed on Nov. 19, 2021, which is a continuation of application
(Continued)

(51) Int. Cl.
*A61B 5/145* (2006.01)
*A61B 5/00* (2006.01)
(Continued)

(52) U.S. Cl.
CPC ........ *A61B 5/14503* (2013.01); *A61B 5/0002* (2013.01); *A61B 5/0004* (2013.01);
(Continued)

(58) Field of Classification Search
CPC .............. A61B 5/14503; A61B 5/0002; A61B 5/14532
See application file for complete search history.

(56) References Cited

U.S. PATENT DOCUMENTS 2,402,306 A 6/1946 Turkel
2,752,918 A 7/1956 Uytenbogaart
(Continued)

FOREIGN PATENT DOCUMENTS

AU 2003259741 2/2004
CA 2291105 12/1998
(Continued)

OTHER PUBLICATIONS

CA, 2,872,576 Examiner's Report, dated Feb. 17, 2015.
(Continued)

*Primary Examiner* — Christian Jang
(74) *Attorney, Agent, or Firm* — ONE LLP

(57) ABSTRACT

Devices associated with on-body analyte sensor units are disclosed. These devices include any of packaging and/or loading systems, applicators and elements of the on-body sensor units themselves. Also, various approaches to connecting electrochemical analyte sensors to and/or within associated on-body analyte sensor units are disclosed. The connector approaches variously involve the use of unique sensor and ancillary element arrangements to facilitate assembly of separate electronics assemblies and sensor elements that are kept apart until the end user brings them together.

26 Claims, 64 Drawing Sheets

Related U.S. Application Data

No. 15/908,616, filed on Feb. 28, 2018, now Pat. No. 11,179,068, which is a continuation of application No. 15/610,334, filed on May 31, 2017, now Pat. No. 9,931,066, which is a continuation of application No. 15/193,499, filed on Jun. 27, 2016, now Pat. No. 9,693,713, which is a continuation of application No. 13/710,460, filed on Dec. 11, 2012, now Pat. No. 9,402,570.

(60)  Provisional application No. 61/569,287, filed on Dec. 11, 2011.

(51)  Int. Cl.

| | |
|---|---|
| *A61B 5/15* | (2006.01) |
| *A61B 5/151* | (2006.01) |
| *A61B 5/157* | (2006.01) |
| *A61B 50/30* | (2016.01) |
| *H04L 67/12* | (2022.01) |

(52)  U.S. Cl.

CPC ............ *A61B 5/1411* (2013.01); *A61B 5/145* (2013.01); *A61B 5/1451* (2013.01); *A61B 5/14532* (2013.01); *A61B 5/150022* (2013.01); *A61B 5/150305* (2013.01); *A61B 5/150335* (2013.01); *A61B 5/150358* (2013.01); *A61B 5/150389* (2013.01); *A61B 5/150503* (2013.01); *A61B 5/150748* (2013.01); *A61B 5/15087* (2013.01); *A61B 5/150877* (2013.01); *A61B 5/15105* (2013.01); *A61B 5/15144* (2013.01); *A61B 5/157* (2013.01); *A61B 5/6849* (2013.01); *A61B 50/3001* (2016.02); *H04L 67/12* (2013.01); *A61B 2560/0406* (2013.01); *A61B 2560/0443* (2013.01); *A61B 2560/063* (2013.01); *A61B 2562/16* (2013.01); *A61B 2562/242* (2013.01)

(56)  References Cited

U.S. PATENT DOCUMENTS

| | | |
|---|---|---|
| 3,123,790 A | 3/1964 | Tyler |
| 3,132,123 A | 5/1964 | Harris, Jr. et al. |
| 3,173,200 A | 3/1965 | Dunmire et al. |
| 3,180,221 A | 4/1965 | Porter |
| 3,211,001 A | 10/1965 | Petit |
| 3,260,656 A | 7/1966 | Ross, Jr. |
| 3,517,670 A | 6/1970 | Speelman |
| 3,522,807 A | 8/1970 | Millenbach |
| 3,581,062 A | 5/1971 | Aston |
| 3,653,841 A | 4/1972 | Klein |
| 3,670,727 A | 6/1972 | Reiterman |
| 3,719,564 A | 3/1973 | Lilly, Jr. et al. |
| 3,776,832 A | 12/1973 | Oswin et al. |
| 3,837,339 A | 9/1974 | Aisenberg et al. |
| 3,926,760 A | 12/1975 | Allen et al. |
| 3,949,388 A | 4/1976 | Fuller |
| 3,960,497 A | 6/1976 | Acord et al. |
| 3,972,320 A | 8/1976 | Kalman |
| 3,979,274 A | 9/1976 | Newman |
| 4,008,717 A | 2/1977 | Kowarski |
| 4,016,866 A | 4/1977 | Lawton |
| 4,033,330 A | 7/1977 | Willis et al. |
| 4,036,749 A | 7/1977 | Anderson |
| 4,055,175 A | 10/1977 | Clemens et al. |
| 4,059,406 A | 11/1977 | Fleet |
| 4,076,596 A | 2/1978 | Connery et al. |
| 4,098,574 A | 7/1978 | Dappen |
| 4,100,048 A | 7/1978 | Pompei et al. |
| 4,120,292 A | 10/1978 | LeBlanc, Jr. et al. |
| 4,129,128 A | 12/1978 | McFarlane |
| 4,151,845 A | 5/1979 | Clemens |

| | | |
|---|---|---|
| 4,168,205 A | 9/1979 | Danninger et al. |
| 4,172,770 A | 10/1979 | Semersky et al. |
| 4,178,916 A | 12/1979 | McNamara |
| 4,203,446 A | 5/1980 | Hofert et al. |
| 4,206,755 A | 6/1980 | Klein |
| 4,224,125 A | 9/1980 | Nakamura et al. |
| 4,240,438 A | 12/1980 | Updike et al. |
| 4,240,889 A | 12/1980 | Yoda et al. |
| 4,245,634 A | 1/1981 | Albisser et al. |
| 4,247,297 A | 1/1981 | Berti et al. |
| 4,286,039 A | 8/1981 | Landa et al. |
| 4,294,258 A | 10/1981 | Bernard |
| 4,305,401 A | 12/1981 | Reissmueller et al. |
| 4,308,981 A | 1/1982 | Miura |
| 4,327,725 A | 5/1982 | Cortese et al. |
| 4,340,458 A | 7/1982 | Lerner et al. |
| 4,344,438 A | 8/1982 | Schultz |
| 4,349,728 A | 9/1982 | Phillips et al. |
| 4,352,960 A | 10/1982 | Dormer et al. |
| 4,353,888 A | 10/1982 | Sefton |
| 4,356,074 A | 10/1982 | Johnson |
| 4,365,637 A | 12/1982 | Johnson |
| 4,366,033 A | 12/1982 | Richter et al. |
| 4,373,527 A | 2/1983 | Fischell |
| 4,375,399 A | 3/1983 | Havas et al. |
| 4,384,586 A | 5/1983 | Christiansen |
| 4,390,621 A | 6/1983 | Bauer |
| 4,392,849 A | 7/1983 | Petre et al. |
| 4,401,122 A | 8/1983 | Clark, Jr. |
| 4,404,066 A | 9/1983 | Johnson |
| 4,418,148 A | 11/1983 | Oberhardt |
| 4,425,920 A | 1/1984 | Bourland et al. |
| 4,427,004 A | 1/1984 | Miller et al. |
| 4,427,770 A | 1/1984 | Chen et al. |
| 4,431,004 A | 2/1984 | Bessman et al. |
| 4,436,094 A | 3/1984 | Cerami |
| 4,440,175 A | 4/1984 | Wilkins |
| 4,441,968 A | 4/1984 | Emmer et al. |
| 4,450,842 A | 5/1984 | Zick et al. |
| 4,458,686 A | 7/1984 | Clark, Jr. |
| 4,461,691 A | 7/1984 | Frank |
| 4,464,170 A | 8/1984 | Clemens et al. |
| 4,469,110 A | 9/1984 | Slama |
| 4,477,314 A | 10/1984 | Richter et al. |
| 4,478,976 A | 10/1984 | Goertz et al. |
| 4,484,987 A | 11/1984 | Gough |
| 4,494,950 A | 1/1985 | Fischell |
| 4,509,531 A | 4/1985 | Ward |
| 4,522,690 A | 6/1985 | Venkatasetty |
| 4,524,114 A | 6/1985 | Samuels et al. |
| 4,526,661 A | 7/1985 | Steckhan et al. |
| 4,527,240 A | 7/1985 | Kvitash |
| 4,534,356 A | 8/1985 | Papadakis |
| 4,538,616 A | 9/1985 | Rogoff |
| 4,543,955 A | 10/1985 | Schroeppel |
| 4,545,382 A | 10/1985 | Higgins et al. |
| 4,552,840 A | 11/1985 | Riffe |
| 4,553,541 A | 11/1985 | Burns |
| 4,560,534 A | 12/1985 | Kung et al. |
| 4,561,443 A | 12/1985 | Hogrefe et al. |
| 4,561,963 A | 12/1985 | Owen et al. |
| 4,571,292 A | 2/1986 | Liu et al. |
| 4,573,994 A | 3/1986 | Fischell et al. |
| 4,581,336 A | 4/1986 | Malloy et al. |
| 4,592,745 A | 6/1986 | Rex et al. |
| 4,595,011 A | 6/1986 | Phillips |
| 4,619,754 A | 10/1986 | Niki et al. |
| 4,619,793 A | 10/1986 | Lee |
| 4,622,966 A | 11/1986 | Beard |
| 4,627,445 A | 12/1986 | Garcia et al. |
| 4,627,842 A | 12/1986 | Katz |
| 4,627,908 A | 12/1986 | Miller |
| 4,633,878 A | 1/1987 | Bombardieri |
| 4,637,403 A | 1/1987 | Garcia et al. |
| 4,639,062 A | 1/1987 | Taniguchi et al. |
| 4,650,547 A | 3/1987 | Gough |
| 4,654,197 A | 3/1987 | Lilja et al. |
| 4,655,880 A | 4/1987 | Liu |
| 4,655,885 A | 4/1987 | Hill et al. |

(56)                    References Cited

U.S. PATENT DOCUMENTS

| | | | |
|---|---|---|---|
| 4,663,824 A | 5/1987 | Kenmochi |
| 4,665,906 A | 5/1987 | Jervis |
| 4,671,288 A | 6/1987 | Gough |
| 4,675,346 A | 6/1987 | Lin et al. |
| 4,679,562 A | 7/1987 | Luksha |
| 4,680,268 A | 7/1987 | Clark, Jr. |
| 4,682,602 A | 7/1987 | Prohaska |
| 4,684,245 A | 8/1987 | Goldring |
| 4,684,537 A | 8/1987 | Graetzel et al. |
| 4,685,463 A | 8/1987 | Williams |
| 4,685,466 A | 8/1987 | Rau |
| 4,690,675 A | 9/1987 | Katz |
| 4,698,057 A | 10/1987 | Joishy |
| 4,703,324 A | 10/1987 | White |
| 4,703,756 A | 11/1987 | Gough et al. |
| 4,711,245 A | 12/1987 | Higgins et al. |
| 4,711,247 A | 12/1987 | Fishman |
| 4,717,673 A | 1/1988 | Wrighton et al. |
| 4,721,601 A | 1/1988 | Wrighton et al. |
| 4,721,677 A | 1/1988 | Clark, Jr. |
| 4,726,378 A | 2/1988 | Kaplan |
| 4,726,716 A | 2/1988 | McGuire |
| 4,729,672 A | 3/1988 | Takagi |
| 4,731,726 A | 3/1988 | Allen, III |
| 4,749,985 A | 6/1988 | Corsberg |
| 4,752,935 A | 6/1988 | Beck |
| 4,755,173 A | 7/1988 | Konopka |
| 4,757,022 A | 7/1988 | Shults et al. |
| 4,758,323 A | 7/1988 | Davis et al. |
| 4,759,371 A | 7/1988 | Franetzki |
| 4,759,828 A | 7/1988 | Young et al. |
| 4,764,416 A | 8/1988 | Ueyama et al. |
| 4,776,944 A | 10/1988 | Janata et al. |
| 4,777,953 A | 10/1988 | Ash et al. |
| 4,779,618 A | 10/1988 | Mund et al. |
| 4,781,683 A | 11/1988 | Wozniak et al. |
| 4,781,798 A | 11/1988 | Gough |
| 4,784,736 A | 11/1988 | Lonsdale et al. |
| 4,785,868 A | 11/1988 | Koenig, Jr. |
| 4,795,707 A | 1/1989 | Niiyama et al. |
| 4,796,634 A | 1/1989 | Huntsman et al. |
| 4,805,624 A | 2/1989 | Yao et al. |
| 4,813,424 A | 3/1989 | Wilkins |
| 4,815,469 A | 3/1989 | Cohen et al. |
| 4,817,603 A | 4/1989 | Turner et al. |
| 4,818,994 A | 4/1989 | Orth et al. |
| 4,820,399 A | 4/1989 | Senda et al. |
| 4,822,337 A | 4/1989 | Newhouse et al. |
| 4,830,959 A | 5/1989 | McNeil et al. |
| 4,832,797 A | 5/1989 | Vadgama et al. |
| RE32,947 E | 6/1989 | Dormer et al. |
| 4,840,893 A | 6/1989 | Hill et al. |
| 4,847,785 A | 7/1989 | Stephens |
| 4,848,351 A | 7/1989 | Finch |
| 4,852,025 A | 7/1989 | Herpichbdhm |
| 4,854,322 A | 8/1989 | Ash et al. |
| 4,856,648 A | 8/1989 | Krueger |
| 4,861,454 A | 8/1989 | Ushizawa et al. |
| 4,865,038 A | 9/1989 | Rich et al. |
| 4,871,351 A | 10/1989 | Feingold |
| 4,871,440 A | 10/1989 | Nagata et al. |
| 4,874,500 A | 10/1989 | Madou et al. |
| 4,890,620 A | 1/1990 | Gough |
| 4,894,137 A | 1/1990 | Takizawa et al. |
| 4,895,147 A | 1/1990 | Bodicky et al. |
| 4,897,162 A | 1/1990 | Lewandowski et al. |
| 4,897,173 A | 1/1990 | Nankai et al. |
| 4,909,908 A | 3/1990 | Ross et al. |
| 4,911,794 A | 3/1990 | Parce et al. |
| 4,917,800 A | 4/1990 | Lonsdale et al. |
| 4,919,141 A | 4/1990 | Zier et al. |
| 4,919,767 A | 4/1990 | Vadgama et al. |
| 4,921,199 A | 5/1990 | Villaveces |
| 4,923,586 A | 5/1990 | Katayama et al. |
| 4,924,879 A | 5/1990 | O'Brien |
| 4,925,268 A | 5/1990 | Iyer et al. |
| 4,927,516 A | 5/1990 | Yamaguchi et al. |
| 4,934,369 A | 6/1990 | Maxwell |
| 4,935,105 A | 6/1990 | Churchouse |
| 4,935,345 A | 6/1990 | Guibeau et al. |
| 4,938,860 A | 7/1990 | Wogoman |
| 4,944,299 A | 7/1990 | Silvian |
| 4,950,378 A | 8/1990 | Nagara |
| 4,953,552 A | 9/1990 | DeMarzo |
| 4,954,129 A | 9/1990 | Giuliani et al. |
| 4,969,468 A | 11/1990 | Byers et al. |
| 4,970,145 A | 11/1990 | Bennetto et al. |
| 4,974,929 A | 12/1990 | Curry |
| 4,985,142 A | 1/1991 | Laycock et al. |
| 4,986,271 A | 1/1991 | Wilkins |
| 4,988,341 A | 1/1991 | Columbus et al. |
| 4,994,167 A | 2/1991 | Shults et al. |
| 4,995,402 A | 2/1991 | Smith et al. |
| 5,000,180 A | 3/1991 | Kuypers et al. |
| 5,001,054 A | 3/1991 | Wagner |
| 5,002,054 A | 3/1991 | Ash et al. |
| 5,006,110 A | 4/1991 | Garrison et al. |
| 5,013,161 A | 5/1991 | Zaragoza et al. |
| 5,019,974 A | 5/1991 | Beckers |
| 5,035,860 A | 7/1991 | Kleingeld et al. |
| 5,036,860 A | 8/1991 | Leigh et al. |
| 5,047,044 A | 9/1991 | Smith et al. |
| 5,050,612 A | 9/1991 | Matsumura |
| 5,051,688 A | 9/1991 | Murase et al. |
| 5,055,171 A | 10/1991 | Peck |
| 5,058,592 A | 10/1991 | Whisler |
| 5,067,957 A | 11/1991 | Jervis |
| 5,068,536 A | 11/1991 | Rosenthal |
| 5,070,535 A | 12/1991 | Hochmair et al. |
| 5,082,550 A | 1/1992 | Rishpon et al. |
| 5,082,786 A | 1/1992 | Nakamoto |
| 5,086,246 A | 2/1992 | Dymond et al. |
| 5,089,112 A | 2/1992 | Skotheim et al. |
| 5,095,904 A | 3/1992 | Seligman et al. |
| 5,101,814 A | 4/1992 | Palti |
| 5,106,365 A | 4/1992 | Hernandez |
| 5,108,564 A | 4/1992 | Szuminsky et al. |
| 5,108,889 A | 4/1992 | Smith et al. |
| 5,109,850 A | 5/1992 | Blanco et al. |
| 5,120,420 A | 6/1992 | Nankai et al. |
| 5,122,925 A | 6/1992 | Inpyn |
| 5,124,661 A | 6/1992 | Zelin et al. |
| 5,126,034 A | 6/1992 | Carter et al. |
| 5,133,856 A | 7/1992 | Yamaguchi et al. |
| 5,135,003 A | 8/1992 | Souma |
| 5,135,004 A | 8/1992 | Adams et al. |
| 5,140,985 A | 8/1992 | Schroeder et al. |
| 5,141,868 A | 8/1992 | Shanks et al. |
| 5,161,532 A | 11/1992 | Joseph |
| 5,162,407 A | 11/1992 | Turner |
| 5,165,407 A | 11/1992 | Wilson et al. |
| 5,173,165 A | 12/1992 | Schmid et al. |
| 5,174,291 A | 12/1992 | Schoonen et al. |
| 5,188,534 A | 2/1993 | Bertho et al. |
| 5,190,041 A | 3/1993 | Palti |
| 5,190,546 A | 3/1993 | Jervis |
| 5,192,416 A | 3/1993 | Wang et al. |
| 5,193,545 A | 3/1993 | Marsoner et al. |
| 5,198,367 A | 3/1993 | Aizawa et al. |
| 5,202,261 A | 4/1993 | Musho et al. |
| 5,204,264 A | 4/1993 | Kaminer et al. |
| 5,205,297 A | 4/1993 | Montecalvo et al. |
| 5,205,920 A | 4/1993 | Oyama et al. |
| 5,208,154 A | 5/1993 | Weaver et al. |
| 5,209,229 A | 5/1993 | Gilli |
| 5,217,595 A | 6/1993 | Smith et al. |
| 5,228,449 A | 7/1993 | Christ et al. |
| 5,229,282 A | 7/1993 | Yoshioka et al. |
| 5,231,988 A | 8/1993 | Wernicke et al. |
| 5,234,835 A | 8/1993 | Nestor et al. |
| 5,238,729 A | 8/1993 | Debe |
| 5,243,696 A | 9/1993 | Carr et al. |
| 5,245,314 A | 9/1993 | Kah et al. |
| 5,246,867 A | 9/1993 | Lakowicz et al. |

(56) References Cited

U.S. PATENT DOCUMENTS

| | | | |
|---|---|---|---|
| 5,250,439 A | 10/1993 | Musho et al. |
| 5,251,126 A | 10/1993 | Kahn et al. |
| 5,259,793 A | 11/1993 | Yamada et al. |
| 5,262,035 A | 11/1993 | Gregg et al. |
| 5,262,305 A | 11/1993 | Heller et al. |
| 5,264,103 A | 11/1993 | Yoshioka et al. |
| 5,264,104 A | 11/1993 | Gregg et al. |
| 5,264,105 A | 11/1993 | Gregg et al. |
| 5,264,106 A | 11/1993 | McAleer et al. |
| 5,267,963 A | 12/1993 | Bachynsky |
| 5,271,815 A | 12/1993 | Wong |
| 5,279,294 A | 1/1994 | Anderson |
| 5,284,156 A | 2/1994 | Schramm et al. |
| 5,285,792 A | 2/1994 | Sjoquist et al. |
| 5,286,362 A | 2/1994 | Hoenes et al. |
| 5,286,364 A | 2/1994 | Yacynych et al. |
| 5,288,636 A | 2/1994 | Pollmann et al. |
| 5,289,497 A | 2/1994 | Jackobson et al. |
| 5,293,546 A | 3/1994 | Tadros et al. |
| 5,293,877 A | 3/1994 | O'Hara et al. |
| 5,299,571 A | 4/1994 | Mastrototaro |
| 5,305,008 A | 4/1994 | Turner et al. |
| 5,318,583 A | 6/1994 | Rabenau et al. |
| 5,320,098 A | 6/1994 | Davidson |
| 5,320,715 A | 6/1994 | Berg |
| 5,320,725 A | 6/1994 | Gregg et al. |
| 5,322,063 A | 6/1994 | Allen et al. |
| 5,333,615 A | 8/1994 | Craelius et al. |
| 5,337,747 A | 8/1994 | Neftel |
| 5,340,722 A | 8/1994 | Wolfbeis et al. |
| 5,342,789 A | 8/1994 | Chick et al. |
| 5,352,348 A | 10/1994 | Young et al. |
| 5,356,420 A | 10/1994 | Czernecki et al. |
| 5,356,786 A | 10/1994 | Heller et al. |
| 5,360,404 A | 11/1994 | Novacek et al. |
| 5,368,028 A | 11/1994 | Palti |
| 5,372,133 A | 12/1994 | Hogen Esch |
| 5,372,427 A | 12/1994 | Padovani et al. |
| 5,376,251 A | 12/1994 | Kaneko et al. |
| 5,378,628 A | 1/1995 | Gratzel et al. |
| 5,379,238 A | 1/1995 | Stark |
| 5,384,547 A | 1/1995 | Lynk et al. |
| 5,387,327 A | 2/1995 | Khan |
| 5,390,670 A | 2/1995 | Centa et al. |
| 5,390,671 A | 2/1995 | Lord et al. |
| 5,391,250 A | 2/1995 | Cheney, II et al. |
| 5,394,877 A | 3/1995 | Orr et al. |
| 5,395,504 A | 3/1995 | Saurer et al. |
| 5,400,782 A | 3/1995 | Beaubiah |
| 5,400,794 A | 3/1995 | Gorman |
| 5,402,780 A | 4/1995 | Faasse, Jr. |
| 5,407,431 A | 4/1995 | Botich et al. |
| 5,408,999 A | 4/1995 | Singh et al. |
| 5,410,326 A | 4/1995 | Goldstein |
| 5,411,647 A | 5/1995 | Johnson et al. |
| 5,425,361 A | 6/1995 | Fenzlein et al. |
| 5,425,868 A | 6/1995 | Pedersen |
| 5,431,160 A | 7/1995 | Wilkins |
| 5,431,921 A | 7/1995 | Thombre |
| 5,437,999 A | 8/1995 | Diebold et al. |
| 5,438,983 A | 8/1995 | Falcone |
| 5,462,051 A | 10/1995 | Oka et al. |
| 5,462,645 A | 10/1995 | Albery et al. |
| 5,469,846 A | 11/1995 | Khan |
| 5,472,317 A | 12/1995 | Field et al. |
| 5,482,473 A | 1/1996 | Lord et al. |
| 5,484,403 A | 1/1996 | Yoakum et al. |
| 5,489,414 A | 2/1996 | Schreiber et al. |
| 5,491,474 A | 2/1996 | Suni et al. |
| 5,494,562 A | 2/1996 | Maley et al. |
| 5,496,453 A | 3/1996 | Uenoyama et al. |
| 5,497,772 A | 3/1996 | Schulman et al. |
| 5,499,243 A | 3/1996 | Hall |
| 5,507,288 A | 4/1996 | Bocker et al. |
| 5,509,410 A | 4/1996 | Hill et al. |
| 5,514,718 A | 5/1996 | Lewis et al. |
| 5,516,821 A | 5/1996 | Bae et al. |
| 5,516,832 A | 5/1996 | Kennan et al. |
| 5,527,288 A | 6/1996 | Gross et al. |
| 5,529,676 A | 6/1996 | Maley et al. |
| 5,531,878 A | 7/1996 | Vadgama et al. |
| 5,532,686 A | 7/1996 | Urbas et al. |
| 5,533,977 A | 7/1996 | Metcalf et al. |
| 5,536,259 A | 7/1996 | Utterberg |
| 5,543,326 A | 8/1996 | Heller et al. |
| 5,544,196 A | 8/1996 | Tiedmann, Jr. et al. |
| 5,545,191 A | 8/1996 | Mann et al. |
| 5,549,568 A | 8/1996 | Sheilds |
| 5,551,427 A | 9/1996 | Altman |
| 5,555,190 A | 9/1996 | Derby et al. |
| 5,558,638 A | 9/1996 | Evers et al. |
| 5,560,357 A | 10/1996 | Faupei et al. |
| 5,562,713 A | 10/1996 | Silvian |
| 5,564,434 A | 10/1996 | Halperin et al. |
| 5,565,085 A | 10/1996 | Ikeda et al. |
| 5,567,302 A | 10/1996 | Song et al. |
| 5,568,806 A | 10/1996 | Cheney, II et al. |
| 5,569,186 A | 10/1996 | Lord et al. |
| 5,571,022 A | 11/1996 | Schaarschmidt |
| 5,575,563 A | 11/1996 | Chiu et al. |
| 5,581,206 A | 12/1996 | Chevallier et al. |
| 5,582,184 A | 12/1996 | Erickson et al. |
| 5,582,697 A | 12/1996 | Ikeda et al. |
| 5,582,698 A | 12/1996 | Flaherty et al. |
| 5,584,813 A | 12/1996 | Livingston et al. |
| 5,586,553 A | 12/1996 | Halli et al. |
| 5,589,326 A | 12/1996 | Deng et al. |
| 5,591,137 A | 1/1997 | Stevens |
| 5,593,852 A | 1/1997 | Heller et al. |
| 5,596,150 A | 1/1997 | Arndt et al. |
| 5,597,378 A | 1/1997 | Jervis |
| 5,600,301 A | 2/1997 | Robinson, III |
| 5,601,435 A | 2/1997 | Quy |
| 5,609,575 A | 3/1997 | Larson et al. |
| 5,613,978 A | 3/1997 | Harding |
| 5,617,851 A | 4/1997 | Lipkovker |
| 5,623,933 A | 4/1997 | Amano et al. |
| 5,626,566 A | 5/1997 | Petersen et al. |
| 5,628,310 A | 5/1997 | Rao et al. |
| 5,628,324 A | 5/1997 | Sarbach |
| 5,628,890 A | 5/1997 | Carter et al. |
| 5,632,557 A | 5/1997 | Simons |
| 5,634,468 A | 6/1997 | Platt et al. |
| 5,636,640 A | 6/1997 | Staehlin |
| 5,638,832 A | 6/1997 | Singer et al. |
| 5,640,954 A | 6/1997 | Pfeiffer et al. |
| 5,651,869 A | 7/1997 | Yoshioka et al. |
| 5,653,239 A | 8/1997 | Pompei et al. |
| 5,659,454 A | 8/1997 | Vermesse |
| 5,660,163 A | 8/1997 | Schulman et al. |
| 5,665,071 A | 9/1997 | Wyrick |
| 5,665,222 A | 9/1997 | Heller et al. |
| 5,669,543 A | 9/1997 | Ueno |
| 5,669,890 A | 9/1997 | Grimm |
| 5,670,031 A | 9/1997 | Hintsche et al. |
| 5,673,322 A | 9/1997 | Pepe et al. |
| 5,673,694 A | 10/1997 | Rivers |
| 5,680,858 A | 10/1997 | Hansen et al. |
| 5,682,233 A | 10/1997 | Brinda |
| 5,690,119 A | 11/1997 | Rytky et al. |
| 5,695,623 A | 12/1997 | Michel et al. |
| 5,707,502 A | 1/1998 | McCaffrey et al. |
| 5,708,247 A | 1/1998 | McAleer et al. |
| 5,711,001 A | 1/1998 | Bussan et al. |
| 5,711,297 A | 1/1998 | Iliff et al. |
| 5,711,685 A | 1/1998 | Wood |
| 5,711,861 A | 1/1998 | Ward et al. |
| 5,711,862 A | 1/1998 | Sakoda et al. |
| 5,724,030 A | 3/1998 | Urbas et al. |
| 5,726,646 A | 3/1998 | Bane et al. |
| 5,733,044 A | 3/1998 | Rose et al. |
| 5,733,259 A | 3/1998 | Valcke et al. |
| 5,733,262 A | 3/1998 | Paul |
| 5,733,313 A | 3/1998 | Barreras, Sr. et al. |

(56)                References Cited

U.S. PATENT DOCUMENTS

| | | | |
|---|---|---|---|
| 5,735,285 A | 4/1998 | Albert et al. |
| 5,738,220 A | 4/1998 | Geszler |
| 5,741,211 A | 4/1998 | Renirie et al. |
| 5,743,262 A | 4/1998 | Lepper, Jr. et al. |
| 5,746,217 A | 5/1998 | Erickson et al. |
| 5,746,697 A | 5/1998 | Swedlow et al. |
| 5,748,103 A | 5/1998 | Flach et al. |
| 5,749,656 A | 5/1998 | Boehm et al. |
| 5,749,907 A | 5/1998 | Mann |
| 5,758,290 A | 5/1998 | Nealon et al. |
| 5,763,787 A | 6/1998 | Gravel et al. |
| 5,766,131 A | 6/1998 | Kondo et al. |
| 5,770,028 A | 6/1998 | Maley et al. |
| 5,770,208 A | 6/1998 | Fattom et al. |
| 5,771,001 A | 6/1998 | Cobb |
| 5,771,891 A | 6/1998 | Gozani |
| 5,772,586 A | 6/1998 | Heinonen et al. |
| 5,778,879 A | 7/1998 | Ota et al. |
| 5,779,665 A | 7/1998 | Mastrototaro et al. |
| 5,786,439 A | 7/1998 | Van Antwerp et al. |
| 5,791,344 A | 8/1998 | Schulman et al. |
| 5,798,961 A | 8/1998 | Heyden et al. |
| 5,800,420 A | 9/1998 | Gross et al. |
| 5,804,047 A | 9/1998 | Karube et al. |
| 5,807,375 A | 9/1998 | Gross et al. |
| 5,814,020 A | 9/1998 | Gross |
| 5,820,551 A | 10/1998 | Hill et al. |
| 5,820,570 A | 10/1998 | Erickson et al. |
| 5,820,622 A | 10/1998 | Gross et al. |
| 5,822,715 A | 10/1998 | Worthington et al. |
| 5,823,802 A | 10/1998 | Bartley |
| 5,827,184 A | 10/1998 | Netherly et al. |
| 5,830,064 A | 11/1998 | Bradish et al. |
| 5,833,603 A | 11/1998 | Kovacs et al. |
| 5,840,020 A | 11/1998 | Heinonen et al. |
| 5,842,473 A | 12/1998 | Fenster et al. |
| 5,842,983 A | 12/1998 | Abel et al. |
| 5,851,197 A | 12/1998 | Marano et al. |
| 5,856,758 A | 1/1999 | Joffe et al. |
| 5,858,001 A | 1/1999 | Tsais et al. |
| 5,865,804 A | 2/1999 | Bachynsky |
| 5,871,494 A | 2/1999 | Simons et al. |
| 5,875,186 A | 2/1999 | Belanger et al. |
| 5,879,311 A | 3/1999 | Duchon et al. |
| 5,885,211 A | 3/1999 | Eppstein et al. |
| 5,891,049 A | 4/1999 | Cyrus et al. |
| 5,899,855 A | 5/1999 | Brown |
| 5,899,856 A | 5/1999 | Schoendorfer et al. |
| 5,914,026 A | 6/1999 | Blubaugh, Jr. et al. |
| 5,918,603 A | 7/1999 | Brown |
| 5,919,141 A | 7/1999 | Money et al. |
| 5,921,963 A | 7/1999 | Erez et al. |
| 5,924,979 A | 7/1999 | Swedlow et al. |
| 5,925,021 A | 7/1999 | Castellano et al. |
| 5,931,814 A | 8/1999 | Alex et al. |
| 5,931,868 A | 8/1999 | Gross |
| 5,935,224 A | 8/1999 | Svancarek et al. |
| 5,938,679 A | 8/1999 | Freeman et al. |
| 5,942,979 A | 8/1999 | Luppino |
| 5,948,006 A | 9/1999 | Mann |
| 5,951,485 A | 9/1999 | Cyrus et al. |
| 5,951,492 A | 9/1999 | Douglas et al. |
| 5,951,521 A | 9/1999 | Mastrototaro et al. |
| 5,951,582 A | 9/1999 | Thorne et al. |
| 5,954,643 A | 9/1999 | Antwerp |
| 5,954,685 A | 9/1999 | Tierny |
| 5,957,854 A | 9/1999 | Besson et al. |
| 5,961,451 A | 10/1999 | Reber et al. |
| 5,964,718 A | 10/1999 | Duchon et al. |
| 5,964,993 A | 10/1999 | Blubaugh, Jr. et al. |
| 5,965,380 A | 10/1999 | Heller et al. |
| 5,971,922 A | 10/1999 | Arita et al. |
| 5,971,941 A | 10/1999 | Simons et al. |
| 5,972,199 A | 10/1999 | Heller et al. |
| 5,987,353 A | 11/1999 | Khatchatrian et al. |
| 5,993,411 A | 11/1999 | Choi |
| 5,995,860 A | 11/1999 | Sun et al. |
| 5,997,501 A | 12/1999 | Gross et al. |
| 6,001,067 A | 12/1999 | Shults et al. |
| 6,004,278 A | 12/1999 | Botich et al. |
| 6,017,335 A | 1/2000 | Burnham |
| 6,022,315 A | 2/2000 | Iliff |
| 6,022,368 A | 2/2000 | Gavronsky et al. |
| 6,024,699 A | 2/2000 | Surwit et al. |
| 6,026,321 A | 2/2000 | Miyata et al. |
| 6,027,459 A | 2/2000 | Shain et al. |
| 6,028,413 A | 2/2000 | Brockmann |
| 6,032,064 A | 2/2000 | Devlin et al. |
| 6,036,924 A | 3/2000 | Simons et al. |
| 6,045,671 A | 4/2000 | Wu et al. |
| 6,048,352 A | 4/2000 | Douglas et al. |
| 6,049,727 A | 4/2000 | Crothall |
| 6,052,565 A | 4/2000 | Ishikura et al. |
| 6,054,194 A | 4/2000 | Kane |
| 6,056,718 A | 5/2000 | Funderburk et al. |
| 6,059,946 A | 5/2000 | Yukawa et al. |
| 6,066,243 A | 5/2000 | Anderson et al. |
| 6,068,399 A | 5/2000 | Tseng |
| 6,071,294 A | 6/2000 | Simons et al. |
| 6,071,391 A | 6/2000 | Gotoh et al. |
| 6,081,736 A | 6/2000 | Colvin et al. |
| 6,083,710 A | 7/2000 | Heller et al. |
| 6,085,342 A | 7/2000 | Marholev et al. |
| 6,088,605 A | 7/2000 | Griffith et al. |
| 6,088,608 A | 7/2000 | Schulman et al. |
| 6,091,975 A | 7/2000 | Daddona et al. |
| 6,091,976 A | 7/2000 | Pfeiffer et al. |
| 6,091,987 A | 7/2000 | Thompson |
| 6,093,172 A | 7/2000 | Funderburk et al. |
| 6,096,268 A | 8/2000 | Inbar |
| 6,096,364 A | 8/2000 | Bok et al. |
| 6,097,480 A | 8/2000 | Kaplan |
| 6,099,484 A | 8/2000 | Douglas et al. |
| 6,102,896 A | 8/2000 | Roser |
| 6,103,033 A | 8/2000 | Say et al. |
| 6,106,484 A | 8/2000 | Terwilliger |
| 6,117,290 A | 9/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,121,611 A | 9/2000 | Lindsay et al. |
| 6,122,351 A | 9/2000 | Schlueter, Jr. et al. |
| 6,129,666 A | 10/2000 | DeLuca et al. |
| 6,130,623 A | 10/2000 | MacLellan et al. |
| 6,132,449 A | 10/2000 | Lum et al. |
| 6,134,461 A | 10/2000 | Say et al. |
| 6,141,573 A | 10/2000 | Kurnik et al. |
| 6,143,164 A | 11/2000 | Heller et al. |
| 6,144,837 A | 11/2000 | Quy |
| 6,144,871 A | 11/2000 | Saito et al. |
| 6,144,922 A | 11/2000 | Douglas et al. |
| 6,149,626 A | 11/2000 | Bachynsky et al. |
| 6,157,850 A | 12/2000 | Diab et al. |
| 6,159,147 A | 12/2000 | Lichter et al. |
| 6,159,181 A | 12/2000 | Crossman et al. |
| 6,161,095 A | 12/2000 | Brown |
| 6,162,611 A | 12/2000 | Heller et al. |
| 6,168,606 B1 | 1/2001 | Levin et al. |
| 6,175,752 B1 | 1/2001 | Say et al. |
| 6,180,221 B1 | 1/2001 | Crotzer et al. |
| 6,186,982 B1 | 2/2001 | Gross et al. |
| 6,192,891 B1 | 2/2001 | Gravel et al. |
| 6,197,040 B1 | 3/2001 | LeVaughn et al. |
| 6,198,946 B1 | 3/2001 | Shin et al. |
| 6,198,969 B1 | 3/2001 | Kuzma |
| 6,200,265 B1 | 3/2001 | Walsh et al. |
| 6,203,495 B1 | 3/2001 | Bardy et al. |
| 6,212,416 B1 | 4/2001 | Ward et al. |
| 6,212,417 B1 | 4/2001 | Ikeda et al. |
| 6,213,972 B1 | 4/2001 | Butterfield et al. |
| 6,219,574 B1 | 4/2001 | Cormier et al. |
| 6,223,283 B1 | 4/2001 | Chaiken et al. |
| 6,231,531 B1 | 5/2001 | Lum et al. |
| 6,233,471 B1 | 5/2001 | Berner et al. |

(56)　　　　　　References Cited

U.S. PATENT DOCUMENTS

| | | | |
|---|---|---|---|
| 6,237,394 B1 | 5/2001 | Harris et al. |
| 6,248,067 B1 | 6/2001 | Causey, III et al. |
| 6,254,536 B1 | 7/2001 | DeVito |
| 6,254,586 B1 | 7/2001 | Mann et al. |
| 6,264,810 B1 | 7/2001 | Stol et al. |
| 6,270,455 B1 | 8/2001 | Brown |
| 6,275,717 B1 | 8/2001 | Gross et al. |
| 6,283,761 B1 | 9/2001 | Joao |
| 6,283,982 B1 | 9/2001 | Levaughn et al. |
| 6,284,478 B1 | 9/2001 | Heller et al. |
| 6,291,200 B1 | 9/2001 | LeJeune et al. |
| 6,293,925 B1 | 9/2001 | Safabash et al. |
| 6,294,997 B1 | 9/2001 | Paratore et al. |
| 6,295,506 B1 | 9/2001 | Heinonen et al. |
| 6,298,255 B1 | 10/2001 | Cordero et al. |
| 6,299,347 B1 | 10/2001 | Pompei |
| 6,299,757 B1 | 10/2001 | Feldman et al. |
| 6,302,866 B1 | 10/2001 | Marggi |
| 6,304,766 B1 | 10/2001 | Colvin, Jr. |
| 6,306,104 B1 | 10/2001 | Cunningham et al. |
| 6,306,141 B1 | 10/2001 | Jervis |
| 6,309,884 B1 | 10/2001 | Cooper et al. |
| 6,314,317 B1 | 11/2001 | Willis |
| 6,329,161 B1 | 12/2001 | Heller et al. |
| 6,331,244 B1 | 12/2001 | Lewis et al. |
| 6,336,269 B1 | 1/2002 | Eldridge et al. |
| 6,338,790 B1 | 1/2002 | Feldman et al. |
| 6,340,588 B1 | 1/2002 | Nova et al. |
| 6,341,232 B1 | 1/2002 | Conn et al. |
| 6,348,640 B1 | 2/2002 | Navot et al. |
| 6,359,270 B1 | 3/2002 | Bridson |
| 6,359,444 B1 | 3/2002 | Grimes |
| 6,360,888 B1 | 3/2002 | McIvor et al. |
| 6,364,890 B1 | 4/2002 | Lum et al. |
| 6,366,794 B1 | 4/2002 | Moussy et al. |
| 6,368,141 B1 | 4/2002 | Van Antwerp et al. |
| 6,368,274 B1 | 4/2002 | Van Antwerp et al. |
| 6,368,339 B1 | 4/2002 | Amplatz |
| 6,377,828 B1 | 4/2002 | Chaiken et al. |
| 6,377,829 B1 | 4/2002 | Al-Ali |
| 6,377,894 B1 | 4/2002 | Deweese et al. |
| 6,379,301 B1 | 4/2002 | Worthington et al. |
| 6,387,048 B1 | 5/2002 | Schulman et al. |
| 6,400,974 B1 | 6/2002 | Lesho |
| 6,405,066 B1 | 6/2002 | Essenpreis et al. |
| 6,409,740 B1 | 6/2002 | Kuhr et al. |
| 6,413,393 B1 | 7/2002 | Van Antwerp et al. |
| 6,416,471 B1 | 7/2002 | Kumar et al. |
| 6,418,332 B1 | 7/2002 | Mastrototaro et al. |
| 6,418,346 B1 | 7/2002 | Nelson et al. |
| 6,424,847 B1 | 7/2002 | Mastrototaro et al. |
| 6,427,088 B1 | 7/2002 | Bowman, IV et al. |
| 6,433,743 B1 | 8/2002 | Massy et al. |
| 6,435,017 B1 | 8/2002 | Nowicki, Jr. et al. |
| 6,437,679 B1 | 8/2002 | Roques |
| 6,438,414 B1 | 8/2002 | Conn et al. |
| 6,440,068 B1 | 8/2002 | Brown et al. |
| 6,442,413 B1 | 8/2002 | Silver |
| 6,445,374 B2 | 9/2002 | Albert et al. |
| 6,451,025 B1 | 9/2002 | Jervis |
| 6,458,109 B1 | 10/2002 | Henley et al. |
| 6,461,496 B1 | 10/2002 | Feldman et al. |
| 6,471,689 B1 | 10/2002 | Joseph et al. |
| 6,472,220 B1 | 10/2002 | Simons et al. |
| 6,478,736 B1 | 11/2002 | Mault |
| 6,482,176 B1 | 11/2002 | Wich |
| 6,484,045 B1 | 11/2002 | Holker et al. |
| 6,484,046 B1 | 11/2002 | Say et al. |
| 6,493,069 B1 | 12/2002 | Nagashimada et al. |
| 6,494,830 B1 | 12/2002 | Wessel |
| 6,496,729 B2 | 12/2002 | Thompson |
| 6,497,655 B1 | 12/2002 | Linberg et al. |
| 6,498,941 B1 | 12/2002 | Jackson |
| 6,503,381 B1 | 1/2003 | Gotoh et al. |
| 6,510,344 B1 | 1/2003 | Halpern |
| 6,514,460 B1 | 2/2003 | Fendrock |
| 6,514,689 B2 | 2/2003 | Han et al. |
| 6,514,718 B2 | 2/2003 | Heller et al. |
| 6,520,326 B2 | 2/2003 | McIvor et al. |
| 6,522,927 B1 | 2/2003 | Bishay et al. |
| 6,533,805 B1 | 3/2003 | Jervis |
| 6,537,242 B1 | 3/2003 | Palmer |
| 6,540,891 B1 | 4/2003 | Stewart et al. |
| 6,544,212 B2 | 4/2003 | Galley et al. |
| 6,546,268 B1 | 4/2003 | Ishikawa et al. |
| 6,549,796 B2 | 4/2003 | Sohrab |
| 6,551,494 B1 | 4/2003 | Heller et al. |
| 6,551,496 B1 | 4/2003 | Moles et al. |
| 6,554,795 B2 | 4/2003 | Bagaoisan et al. |
| 6,554,798 B1 | 4/2003 | Mann et al. |
| 6,558,320 B1 | 5/2003 | Causey, III et al. |
| 6,558,321 B1 | 5/2003 | Burd et al. |
| 6,558,351 B1 | 5/2003 | Steil et al. |
| 6,560,471 B1 | 5/2003 | Heller et al. |
| 6,561,975 B1 | 5/2003 | Pool et al. |
| 6,561,978 B1 | 5/2003 | Conn et al. |
| 6,562,001 B2 | 5/2003 | Lebel et al. |
| 6,564,105 B2 | 5/2003 | Starkweather et al. |
| 6,565,509 B1 | 5/2003 | Say et al. |
| 6,571,128 B2 | 5/2003 | Lebel et al. |
| 6,572,542 B1 | 6/2003 | Houben et al. |
| 6,572,566 B2 | 6/2003 | Effenhauser |
| 6,574,490 B2 | 6/2003 | Abbink et al. |
| 6,574,510 B2 | 6/2003 | Von Arx et al. |
| 6,575,895 B1 | 6/2003 | Blair |
| 6,576,101 B1 | 6/2003 | Heller et al. |
| 6,577,899 B2 | 6/2003 | Lebel et al. |
| 6,579,231 B1 | 6/2003 | Phipps |
| 6,579,690 B1 | 6/2003 | Bonnecaze et al. |
| 6,584,335 B1 | 6/2003 | Haar et al. |
| 6,585,644 B2 | 7/2003 | Lebel et al. |
| 6,589,229 B1 | 7/2003 | Connelly et al. |
| 6,591,125 B1 | 7/2003 | Buse et al. |
| 6,592,745 B1 | 7/2003 | Feldman et al. |
| 6,595,919 B2 | 7/2003 | Berner et al. |
| 6,600,997 B2 | 7/2003 | Deweese et al. |
| 6,602,268 B2 | 8/2003 | Kuhr et al. |
| 6,603,995 B1 | 8/2003 | Carter |
| 6,604,050 B2 | 8/2003 | Trippel et al. |
| 6,605,200 B1 | 8/2003 | Mao et al. |
| 6,605,201 B1 | 8/2003 | Mao et al. |
| 6,607,509 B2 | 8/2003 | Bobroff et al. |
| 6,607,543 B2 | 8/2003 | Purcell et al. |
| 6,608,562 B1 | 8/2003 | Kimura et al. |
| 6,610,012 B2 | 8/2003 | Mault |
| 6,611,206 B2 | 8/2003 | Eshelman et al. |
| 6,613,015 B2 | 9/2003 | Sandstrom et al. |
| 6,616,819 B1 | 9/2003 | Liamos et al. |
| 6,618,934 B1 | 9/2003 | Feldman et al. |
| 6,627,154 B1 | 9/2003 | Goodman et al. |
| 6,631,281 B1 | 10/2003 | Kastle |
| 6,633,772 B2 | 10/2003 | Ford et al. |
| 6,635,014 B2 | 10/2003 | Starkweather et al. |
| 6,635,167 B1 | 10/2003 | Batman et al. |
| 6,637,611 B2 | 10/2003 | Luch |
| 6,641,533 B2 | 11/2003 | Causey, III et al. |
| 6,645,359 B1 | 11/2003 | Bhullar et al. |
| 6,648,821 B2 | 11/2003 | Lebel et al. |
| 6,650,471 B2 | 11/2003 | Doi |
| 6,654,625 B1 | 11/2003 | Say et al. |
| 6,656,114 B1 | 12/2003 | Poulson et al. |
| 6,658,396 B1 | 12/2003 | Tang et al. |
| 6,659,948 B2 | 12/2003 | Lebel et al. |
| 6,662,439 B1 | 12/2003 | Bhullar |
| 6,666,849 B1 | 12/2003 | Marshall et al. |
| 6,668,196 B1 | 12/2003 | Villegas et al. |
| 6,671,534 B2 | 12/2003 | Putz |
| 6,675,030 B2 | 1/2004 | Ciurczak et al. |
| 6,676,290 B1 | 1/2004 | Lu |
| 6,676,816 B2 | 1/2004 | Mao et al. |
| 6,682,546 B2 | 1/2004 | Amplatz |
| 6,687,546 B2 | 2/2004 | Lebel et al. |
| 6,689,056 B1 | 2/2004 | Kilcoyne et al. |
| 6,694,191 B2 | 2/2004 | Starkweather et al. |

(56) References Cited

U.S. PATENT DOCUMENTS

| | | | |
|---|---|---|---|
| 6,695,860 B1 | 2/2004 | Ward et al. |
| 6,698,269 B2 | 3/2004 | Baber et al. |
| 6,699,188 B2 | 3/2004 | Wessel |
| 6,702,857 B2 | 3/2004 | Brauker et al. |
| 6,706,159 B2 | 3/2004 | Moerman et al. |
| 6,721,582 B2 | 4/2004 | Trepagnier et al. |
| 6,730,025 B1 | 5/2004 | Platt |
| 6,730,072 B2 | 5/2004 | Shawgo et al. |
| 6,730,200 B1 | 5/2004 | Stewart et al. |
| 6,731,976 B2 | 5/2004 | Penn et al. |
| 6,733,446 B2 | 5/2004 | Lebel et al. |
| 6,735,183 B2 | 5/2004 | O'Toole et al. |
| 6,735,479 B2 | 5/2004 | Fabian et al. |
| 6,736,957 B1 | 5/2004 | Forrow et al. |
| 6,740,075 B2 | 5/2004 | Lebel et al. |
| 6,741,877 B1 | 5/2004 | Shults et al. |
| 6,743,635 B2 | 6/2004 | Neel et al. |
| 6,746,582 B2 | 6/2004 | Heller et al. |
| 6,748,445 B1 | 6/2004 | Darcey et al. |
| 6,749,740 B2 | 6/2004 | Liamos et al. |
| 6,758,810 B2 | 7/2004 | Lebel et al. |
| 6,758,835 B2 | 7/2004 | Close et al. |
| 6,764,581 B1 | 7/2004 | Forrow et al. |
| 6,767,440 B1 | 7/2004 | Bhullar et al. |
| 6,770,030 B1 | 8/2004 | Schaupp et al. |
| 6,773,671 B1 | 8/2004 | Lewis et al. |
| 6,781,522 B2 | 8/2004 | Sleva et al. |
| 6,790,178 B1 | 9/2004 | Mault et al. |
| 6,804,558 B2 | 10/2004 | Haller et al. |
| 6,804,561 B2 | 10/2004 | Stover |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,814,844 B2 | 11/2004 | Bhullar et al. |
| 6,830,551 B1 | 12/2004 | Uchigaki et al. |
| 6,837,858 B2 | 1/2005 | Cunningham et al. |
| 6,837,885 B2 | 1/2005 | Koblish et al. |
| 6,837,988 B2 | 1/2005 | Leong et al. |
| 6,849,052 B2 | 2/2005 | Uchigaki et al. |
| 6,850,790 B2 | 2/2005 | Berner et al. |
| 6,850,859 B1 | 2/2005 | Schuh |
| 6,854,882 B2 | 2/2005 | Chen |
| 6,862,465 B2 | 3/2005 | Shults et al. |
| 6,873,268 B2 | 3/2005 | Lebel et al. |
| 6,878,112 B2 | 4/2005 | Linberg et al. |
| 6,881,551 B2 | 4/2005 | Heller et al. |
| 6,892,085 B2 | 5/2005 | McIvor et al. |
| 6,893,545 B2 | 5/2005 | Gotoh et al. |
| 6,895,263 B2 | 5/2005 | Shin et al. |
| 6,895,265 B2 | 5/2005 | Silver |
| 6,923,763 B1 | 8/2005 | Kovatchev et al. |
| 6,923,764 B2 | 8/2005 | Aceti et al. |
| 6,925,393 B1 | 8/2005 | Kalatz et al. |
| 6,931,327 B2 | 8/2005 | Goode, Jr. et al. |
| 6,932,892 B2 | 8/2005 | Chen |
| 6,932,894 B2 | 8/2005 | Mao et al. |
| 6,936,006 B2 | 8/2005 | Sabra |
| 6,937,222 B2 | 8/2005 | Numao |
| 6,940,403 B2 | 9/2005 | Kail, IV |
| 6,941,163 B2 | 9/2005 | Ford et al. |
| 6,942,518 B2 | 9/2005 | Liamos et al. |
| 6,950,708 B2 | 9/2005 | Bowman IV et al. |
| 6,954,662 B2 | 10/2005 | Freger et al. |
| 6,958,705 B2 | 10/2005 | Lebel et al. |
| 6,959,211 B2 | 10/2005 | Rule et al. |
| 6,960,192 B2 | 11/2005 | Flaherty et al. |
| 6,965,791 B1 | 11/2005 | Hitchcock et al. |
| 6,968,294 B2 | 11/2005 | Gutta et al. |
| 6,971,274 B2 | 12/2005 | Olin |
| 6,971,999 B2 | 12/2005 | Py et al. |
| 6,973,706 B2 | 12/2005 | Say et al. |
| 6,974,437 B2 | 12/2005 | Lebel et al. |
| 6,975,893 B2 | 12/2005 | Say et al. |
| 6,983,867 B1 | 1/2006 | Fugere |
| 6,990,366 B2 | 1/2006 | Say et al. |
| 6,997,907 B2 | 2/2006 | Safabash et al. |
| 6,998,247 B2 | 2/2006 | Monfre et al. |
| 6,999,854 B2 | 2/2006 | Roth |
| 7,003,336 B2 | 2/2006 | Holker et al. |
| 7,003,340 B2 | 2/2006 | Say et al. |
| 7,003,341 B2 | 2/2006 | Say et al. |
| 7,005,857 B2 | 2/2006 | Stiene et al. |
| 7,009,511 B2 | 3/2006 | Mazar et al. |
| 7,010,356 B2 | 3/2006 | Jog et al. |
| 7,015,817 B2 | 3/2006 | Copley et al. |
| 7,016,713 B2 | 3/2006 | Gardner et al. |
| 7,020,508 B2 | 3/2006 | Stivoric et al. |
| 7,022,072 B2 | 4/2006 | Fox et al. |
| 7,022,219 B2 | 4/2006 | Mansouri et al. |
| 7,024,236 B2 | 4/2006 | Ford et al. |
| 7,024,245 B2 | 4/2006 | Lebel et al. |
| 7,025,743 B2 | 4/2006 | Mann et al. |
| 7,025,774 B2 | 4/2006 | Freeman et al. |
| 7,027,848 B2 | 4/2006 | Robinson et al. |
| 7,027,859 B1 | 4/2006 | McNichols et al. |
| 7,027,931 B1 | 4/2006 | Jones et al. |
| 7,029,444 B2 | 4/2006 | Shin et al. |
| 7,041,057 B1 | 5/2006 | Faupel et al. |
| 7,041,068 B2 | 5/2006 | Freeman et al. |
| 7,041,468 B2 | 5/2006 | Drucker et al. |
| 7,043,305 B2 | 5/2006 | Kenknight et al. |
| 7,046,153 B2 | 5/2006 | Oja et al. |
| 7,052,483 B2 | 5/2006 | Wojcik |
| 7,056,302 B2 | 6/2006 | Douglas |
| 7,058,453 B2 | 6/2006 | Nelson et al. |
| 7,060,031 B2 | 6/2006 | Webb et al. |
| 7,073,246 B2 | 7/2006 | Bhullar et al. |
| 7,074,307 B2 | 7/2006 | Simpson et al. |
| 7,081,195 B2 | 7/2006 | Simpson et al. |
| 7,082,334 B2 | 7/2006 | Boute et al. |
| 7,097,637 B2 | 8/2006 | Triplett et al. |
| 7,098,803 B2 | 8/2006 | Mann et al. |
| 7,108,778 B2 | 9/2006 | Simpson et al. |
| 7,110,803 B2 | 9/2006 | Shults et al. |
| 7,113,821 B1 | 9/2006 | Sun et al. |
| 7,118,667 B2 | 10/2006 | Lee |
| 7,120,483 B2 | 10/2006 | Russel et al. |
| 7,123,950 B2 | 10/2006 | Mannheimer |
| 7,124,027 B1 | 10/2006 | Ernst et al. |
| 7,125,382 B2 | 10/2006 | Zhou et al. |
| 7,131,984 B2 | 11/2006 | Sato et al. |
| 7,134,999 B2 | 11/2006 | Brauker et al. |
| 7,136,689 B2 | 11/2006 | Shults et al. |
| 7,144,384 B2 | 12/2006 | Gorman et al. |
| 7,146,202 B2 | 12/2006 | Ward et al. |
| 7,154,398 B2 | 12/2006 | Chen et al. |
| 7,155,290 B2 | 12/2006 | Von Arx et al. |
| 7,167,818 B2 | 1/2007 | Brown |
| 7,169,600 B2 | 1/2007 | Hoss et al. |
| 7,171,274 B2 | 1/2007 | Starkweather et al. |
| 7,174,199 B2 | 2/2007 | Berner et al. |
| 7,179,226 B2 | 2/2007 | Crothall et al. |
| 7,183,102 B2 | 2/2007 | Monfre et al. |
| 7,190,988 B2 | 3/2007 | Say et al. |
| 7,192,450 B2 | 3/2007 | Brauker et al. |
| 7,198,606 B2 | 4/2007 | Boecker et al. |
| 7,203,549 B2 | 4/2007 | Schommer et al. |
| 7,207,974 B2 | 4/2007 | Safabash et al. |
| 7,220,387 B2 | 5/2007 | Flaherty et al. |
| 7,223,276 B2 | 5/2007 | List et al. |
| 7,225,535 B2 | 6/2007 | Feldman et al. |
| 7,226,442 B2 | 6/2007 | Sheppard et al. |
| 7,226,978 B2 | 6/2007 | Tapsak et al. |
| 7,228,162 B2 | 6/2007 | Ward et al. |
| 7,228,182 B2 | 6/2007 | Healy et al. |
| 7,237,712 B2 | 7/2007 | DeRocco et al. |
| 7,267,665 B2 | 9/2007 | Steil et al. |
| 7,276,029 B2 | 10/2007 | Goode, Jr. et al. |
| 7,276,146 B2 | 10/2007 | Wilsey |
| 7,276,147 B2 | 10/2007 | Wilsey |
| 7,278,983 B2 | 10/2007 | Ireland et al. |
| 7,286,894 B1 | 10/2007 | Grant et al. |

(56) References Cited

U.S. PATENT DOCUMENTS

| 7,287,318 | B2 | 10/2007 | Bhullar et al. |
| 7,291,497 | B2 | 11/2007 | Holmes et al. |
| 7,295,867 | B2 | 11/2007 | Berner et al. |
| 7,297,151 | B2 | 11/2007 | Boecker et al. |
| 7,299,082 | B2 | 11/2007 | Feldman et al. |
| 7,310,544 | B2 | 12/2007 | Brister et al. |
| 7,318,816 | B2 | 1/2008 | Bobroff et al. |
| 7,324,012 | B2 | 1/2008 | Mann et al. |
| 7,324,850 | B2 | 1/2008 | Persen et al. |
| 7,329,239 | B2 | 2/2008 | Safabash et al. |
| 7,335,294 | B2 | 2/2008 | Heller et al. |
| 7,340,287 | B2 | 3/2008 | Mason et al. |
| 7,340,309 | B2 | 3/2008 | Miazga et al. |
| 7,344,500 | B2 | 3/2008 | Talbot et al. |
| 7,347,819 | B2 | 3/2008 | Lebel et al. |
| 7,354,420 | B2 | 4/2008 | Steil et al. |
| 7,364,592 | B2 | 4/2008 | Carr-Brendel et al. |
| 7,366,556 | B2 | 4/2008 | Brister et al. |
| 7,379,765 | B2 | 5/2008 | Petisce et al. |
| 7,381,184 | B2 | 6/2008 | Funderburk et al. |
| 7,384,397 | B2 | 6/2008 | Zhang et al. |
| 7,386,937 | B2 | 6/2008 | Bhullar et al. |
| 7,387,010 | B2 | 6/2008 | Sunshine et al. |
| 7,399,277 | B2 | 7/2008 | Saidara et al. |
| 7,400,111 | B2 | 7/2008 | Batman et al. |
| 7,401,111 | B1 | 7/2008 | Batman et al. |
| 7,402,153 | B2 | 7/2008 | Steil et al. |
| 7,404,796 | B2 | 7/2008 | Ginsberg |
| 7,407,493 | B2 | 8/2008 | Cane |
| 7,408,132 | B2 | 8/2008 | Wambsganss et al. |
| 7,416,541 | B2 | 8/2008 | Yuzhakov et al. |
| 7,419,573 | B2 | 9/2008 | Gundel |
| 7,424,318 | B2 | 9/2008 | Brister et al. |
| 7,429,255 | B2 | 9/2008 | Thompson |
| 7,433,727 | B2 | 10/2008 | Ward |
| 7,448,996 | B2 | 11/2008 | Khanuja et al. |
| 7,455,663 | B2 | 11/2008 | Bikovsky |
| 7,460,898 | B2 | 12/2008 | Brister et al. |
| 7,462,264 | B2 | 12/2008 | Heller et al. |
| 7,467,003 | B2 | 12/2008 | Brister et al. |
| 7,468,125 | B2 | 12/2008 | Kraft et al. |
| 7,471,972 | B2 | 12/2008 | Rhodes et al. |
| 7,476,827 | B1 | 1/2009 | Bhullar et al. |
| 7,481,819 | B2 | 1/2009 | Koeppel et al. |
| 7,492,254 | B2 | 2/2009 | Bandy et al. |
| 7,494,465 | B2 | 2/2009 | Brister et al. |
| 7,497,827 | B2 | 3/2009 | Brister et al. |
| 7,499,002 | B2 | 3/2009 | Blasko et al. |
| 7,519,408 | B2 | 4/2009 | Rasdal et al. |
| 7,545,272 | B2 | 6/2009 | Goodnow et al. |
| 7,547,281 | B2 | 6/2009 | Hayes et al. |
| 7,565,197 | B2 | 7/2009 | Haubrich et al. |
| 7,568,619 | B2 | 8/2009 | Todd et al. |
| 7,569,030 | B2 | 8/2009 | Lebel et al. |
| 7,574,266 | B2 | 8/2009 | Dudding et al. |
| 7,582,059 | B2 | 9/2009 | Funderburk et al. |
| 7,583,990 | B2 | 9/2009 | Goode, Jr. et al. |
| 7,585,287 | B2 | 9/2009 | Bresina et al. |
| 7,591,801 | B2 | 9/2009 | Brauker et al. |
| 7,599,726 | B2 | 10/2009 | Goode, Jr. et al. |
| 7,602,310 | B2 | 10/2009 | Mann et al. |
| 7,604,178 | B2 | 10/2009 | Stewart |
| 7,604,592 | B2 | 10/2009 | Freeman et al. |
| 7,613,491 | B2 | 11/2009 | Boock et al. |
| 7,615,007 | B2 | 11/2009 | Shults et al. |
| 7,618,369 | B2 | 11/2009 | Hayter et al. |
| 7,632,228 | B2 | 12/2009 | Brauker et al. |
| 7,635,594 | B2 | 12/2009 | Holmes et al. |
| 7,637,868 | B2 | 12/2009 | Saint et al. |
| 7,640,048 | B2 | 12/2009 | Dobbies et al. |
| 7,643,798 | B2 | 1/2010 | Ljung |
| 7,651,596 | B2 | 1/2010 | Petisce et al. |
| 7,651,845 | B2 | 1/2010 | Doyle, III et al. |
| 7,653,425 | B2 | 1/2010 | Hayter et al. |
| 7,654,956 | B2 | 2/2010 | Brister et al. |
| 7,657,297 | B2 | 2/2010 | Simpson et al. |
| 7,659,823 | B1 | 2/2010 | Killian et al. |
| 7,660,615 | B2 | 2/2010 | VanAntwerp et al. |
| 7,666,149 | B2 | 2/2010 | Simons et al. |
| 7,668,596 | B2 | 2/2010 | Von Arx et al. |
| 7,682,338 | B2 | 3/2010 | Griffin |
| 7,697,967 | B2 | 4/2010 | Stafford |
| 7,699,775 | B2 | 4/2010 | Desai et al. |
| 7,699,807 | B2 | 4/2010 | Faust et al. |
| 7,701,052 | B2 | 4/2010 | Borland et al. |
| 7,711,402 | B2 | 5/2010 | Shults et al. |
| 7,713,574 | B2 | 5/2010 | Brister et al. |
| 7,715,893 | B2 | 5/2010 | Kamath et al. |
| 7,727,147 | B1 | 6/2010 | Osorio et al. |
| 7,729,737 | B2 | 6/2010 | Ward |
| 7,731,657 | B2 | 6/2010 | Stafford |
| 7,731,691 | B2 | 6/2010 | Cote et al. |
| 7,736,310 | B2 | 6/2010 | Taub et al. |
| 7,736,344 | B2 | 6/2010 | Moberg et al. |
| 7,741,734 | B2 | 6/2010 | Joannopoulos et al. |
| 7,763,042 | B2 | 7/2010 | Iio et al. |
| 7,766,829 | B2 | 8/2010 | Sloan et al. |
| 7,768,387 | B2 | 8/2010 | Fennell et al. |
| 7,771,352 | B2 | 8/2010 | Shults et al. |
| 7,774,145 | B2 | 8/2010 | Brauker et al. |
| 7,775,444 | B2 | 8/2010 | DeRocco et al. |
| 7,778,680 | B2 | 8/2010 | Goode, Jr. et al. |
| 7,779,332 | B2 | 8/2010 | Karr et al. |
| 7,780,827 | B1 | 8/2010 | Bhullar et al. |
| 7,782,192 | B2 | 8/2010 | Jeckelmann et al. |
| 7,783,333 | B2 | 8/2010 | Brister et al. |
| 7,791,467 | B2 | 9/2010 | Mazar et al. |
| 7,792,562 | B2 | 9/2010 | Shults et al. |
| 7,811,231 | B2 | 10/2010 | Jin et al. |
| 7,813,809 | B2 | 10/2010 | Strother et al. |
| 7,822,454 | B1 | 10/2010 | Alden et al. |
| 7,826,981 | B2 | 11/2010 | Goode, Jr. et al. |
| 7,831,310 | B2 | 11/2010 | Lebel et al. |
| 7,833,151 | B2 | 11/2010 | Khait et al. |
| 7,833,170 | B2 | 11/2010 | Matsumoto et al. |
| 7,837,633 | B2 | 11/2010 | Conway et al. |
| 7,842,046 | B1 | 11/2010 | Nakao |
| 7,846,132 | B2 | 12/2010 | Gravesen et al. |
| 7,850,652 | B2 | 12/2010 | Liniger et al. |
| 7,860,574 | B2 | 12/2010 | Von Arx et al. |
| 7,866,026 | B1 | 1/2011 | Wang et al. |
| 7,867,244 | B2 | 1/2011 | Lathrop et al. |
| 7,873,299 | B2 | 1/2011 | Berner et al. |
| 7,882,611 | B2 | 2/2011 | Shah et al. |
| 7,883,464 | B2 | 2/2011 | Stafford |
| 7,883,473 | B2 | 2/2011 | LeVaughn et al. |
| 7,885,697 | B2 | 2/2011 | Brister et al. |
| 7,889,069 | B2 | 2/2011 | Fifolt et al. |
| 7,896,844 | B2 | 3/2011 | Thalmann et al. |
| 7,899,511 | B2 | 3/2011 | Shults et al. |
| 7,899,545 | B2 | 3/2011 | John |
| 7,905,833 | B2 | 3/2011 | Brister et al. |
| 7,912,655 | B2 | 3/2011 | Power et al. |
| 7,912,674 | B2 | 3/2011 | Killoren Clark et al. |
| 7,914,450 | B2 | 3/2011 | Goode, Jr. et al. |
| 7,914,460 | B2 | 3/2011 | Melker et al. |
| 7,916,013 | B2 | 3/2011 | Stevenson |
| 7,920,906 | B2 | 4/2011 | Goode, Jr. et al. |
| 7,920,907 | B2 | 4/2011 | McGarraugh et al. |
| 7,938,797 | B2 | 5/2011 | Estes |
| 7,941,200 | B2 | 5/2011 | Weinart et al. |
| 7,946,984 | B2 | 5/2011 | Brister et al. |
| 7,946,985 | B2 | 5/2011 | Mastrototaro et al. |
| 7,955,258 | B2 | 6/2011 | Goscha et al. |
| 7,955,297 | B2 | 6/2011 | Radmer et al. |
| 7,970,448 | B2 | 6/2011 | Shults et al. |
| 7,970,449 | B2 | 6/2011 | Ward |
| 7,972,296 | B2 | 7/2011 | Braig et al. |
| 7,974,672 | B2 | 7/2011 | Shults et al. |
| 7,976,467 | B2 | 7/2011 | Young et al. |
| 7,978,063 | B2 | 7/2011 | Baldus et al. |
| 7,985,203 | B2 | 7/2011 | Haueter et al. |
| 7,985,222 | B2 | 7/2011 | Gall et al. |
| 7,996,158 | B2 | 8/2011 | Hayter et al. |

(56) References Cited

U.S. PATENT DOCUMENTS

| | | | |
|---|---|---|---|
| 7,999,674 B2 | 8/2011 | Kamen |
| 8,000,918 B2 | 8/2011 | Fjield et al. |
| 8,005,524 B2 | 8/2011 | Brauker et al. |
| 8,010,174 B2 | 8/2011 | Goode, Jr. et al. |
| 8,010,256 B2 | 8/2011 | Oowada |
| 8,016,774 B2 | 9/2011 | Freeman et al. |
| 8,028,837 B2 | 10/2011 | Gerstle et al. |
| 8,029,441 B2 | 10/2011 | Mazza et al. |
| 8,029,442 B2 | 10/2011 | Funderburk et al. |
| 8,072,310 B1 | 12/2011 | Everhart |
| 8,090,445 B2 | 1/2012 | Ginggen |
| 8,093,991 B2 | 1/2012 | Stevenson et al. |
| 8,094,009 B2 | 1/2012 | Allen et al. |
| 8,098,159 B2 | 1/2012 | Batra et al. |
| 8,098,160 B2 | 1/2012 | Howarth et al. |
| 8,098,161 B2 | 1/2012 | Lavedas |
| 8,098,201 B2 | 1/2012 | Choi et al. |
| 8,098,208 B2 | 1/2012 | Ficker et al. |
| 8,102,021 B2 | 1/2012 | Degani |
| 8,102,154 B2 | 1/2012 | Bishop et al. |
| 8,102,263 B2 | 1/2012 | Yeo et al. |
| 8,102,789 B2 | 1/2012 | Rosar et al. |
| 8,103,241 B2 | 1/2012 | Young et al. |
| 8,103,325 B2 | 1/2012 | Swedlow et al. |
| 8,103,471 B2 | 1/2012 | Hayter |
| 8,111,042 B2 | 2/2012 | Bennett |
| 8,112,240 B2 | 2/2012 | Fennell |
| 8,115,488 B2 | 2/2012 | McDowell |
| 8,116,681 B2 | 2/2012 | Baarman |
| 8,116,683 B2 | 2/2012 | Baarman |
| 8,117,481 B2 | 2/2012 | Anselmi et al. |
| 8,120,493 B2 | 2/2012 | Burr |
| 8,124,452 B2 | 2/2012 | Sheats |
| 8,130,093 B2 | 3/2012 | Mazar et al. |
| 8,131,351 B2 | 3/2012 | Kalgren et al. |
| 8,131,365 B2 | 3/2012 | Zhang et al. |
| 8,131,565 B2 | 3/2012 | Docks et al. |
| 8,132,037 B2 | 3/2012 | Fehr et al. |
| 8,135,352 B2 | 3/2012 | Langsweirdt et al. |
| 8,136,735 B2 | 3/2012 | Arai et al. |
| 8,138,925 B2 | 3/2012 | Downie et al. |
| 8,140,160 B2 | 3/2012 | Pless et al. |
| 8,140,168 B2 | 3/2012 | Olson et al. |
| 8,140,299 B2 | 3/2012 | Siess |
| 8,140,312 B2 | 3/2012 | Hayter et al. |
| 8,150,321 B2 | 4/2012 | Winter et al. |
| 8,150,516 B2 | 4/2012 | Levine et al. |
| 8,160,670 B2 | 4/2012 | Quyang et al. |
| 8,160,900 B2 | 4/2012 | Taub et al. |
| 8,172,805 B2 | 5/2012 | Mogensen et al. |
| 8,175,673 B2 | 5/2012 | Say et al. |
| 8,179,266 B2 | 5/2012 | Hermle |
| 8,180,423 B2 | 5/2012 | Mang et al. |
| 8,192,394 B2 | 6/2012 | Estes et al. |
| 8,216,138 B1 | 7/2012 | McGaraugh et al. |
| 8,221,332 B2 | 7/2012 | Robbins et al. |
| 8,224,410 B2 | 7/2012 | Hadvary et al. |
| 8,239,166 B2 | 8/2012 | Hayter et al. |
| 8,255,026 B1 | 8/2012 | Al-Ali |
| 8,260,558 B2 | 9/2012 | Hayter et al. |
| 8,262,618 B2 | 9/2012 | Scheurer |
| 8,282,549 B2 | 10/2012 | Brauker et al. |
| 8,333,714 B2 | 12/2012 | Stafford |
| 8,346,335 B2 | 1/2013 | Harper et al. |
| 8,346,337 B2 | 1/2013 | Heller et al. |
| 8,373,544 B2 | 2/2013 | Pitt-Plady |
| 8,374,668 B1 | 2/2013 | Hayter et al. |
| 8,376,945 B2 | 2/2013 | Hayter et al. |
| 8,377,271 B2 | 2/2013 | Mao et al. |
| 8,382,671 B2 | 2/2013 | Anthony et al. |
| 8,398,664 B2 | 3/2013 | Lamps et al. |
| 8,409,093 B2 | 4/2013 | Bugler |
| 8,409,145 B2 | 4/2013 | Raymond et al. |
| 8,439,838 B2 | 5/2013 | Mogensen et al. |
| 8,444,560 B2 | 5/2013 | Hayter et al. |
| 8,461,985 B2 | 6/2013 | Fennell et al. |
| 8,469,986 B2 | 6/2013 | Schraga |
| 8,512,243 B2 | 8/2013 | Stafford |
| 8,515,518 B2 | 8/2013 | Ouyang et al. |
| 8,515,519 B2 | 8/2013 | Brister et al. |
| 8,538,512 B1 | 9/2013 | Bibian et al. |
| 8,545,403 B2 | 10/2013 | Peyser et al. |
| 8,560,038 B2 | 10/2013 | Hayter et al. |
| 8,562,567 B2 | 10/2013 | Gundberg |
| 8,571,808 B2 | 10/2013 | Hayter |
| 8,583,205 B2 | 11/2013 | Budiman et al. |
| 8,585,591 B2 | 11/2013 | Sloan et al. |
| 8,597,570 B2 | 12/2013 | Terashima et al. |
| 8,600,681 B2 | 12/2013 | Hayter et al. |
| 8,602,991 B2 | 12/2013 | Stafford |
| 8,612,163 B2 | 12/2013 | Hayter et al. |
| 8,615,282 B2 | 12/2013 | Brister et al. |
| 8,617,069 B2 | 12/2013 | Bernstein et al. |
| 8,617,071 B2 | 12/2013 | Say et al. |
| 8,622,903 B2 | 1/2014 | Jin et al. |
| 8,628,498 B2 | 1/2014 | Safabach et al. |
| 8,641,674 B2 | 2/2014 | Bobroff et al. |
| 8,652,043 B2 | 2/2014 | Drucker et al. |
| 8,671,237 B2 | 3/2014 | Ma et al. |
| 8,682,408 B2 | 3/2014 | Boock et al. |
| 8,682,615 B2 | 3/2014 | Hayter et al. |
| 8,684,930 B2 | 4/2014 | Feldman et al. |
| 8,692,655 B2 | 4/2014 | Zimman et al. |
| 8,710,993 B2 | 4/2014 | Hayter et al. |
| 8,747,363 B2 | 6/2014 | Nielsen et al. |
| 8,750,955 B2 | 6/2014 | Brister et al. |
| 8,771,183 B2 | 7/2014 | Sloan |
| 8,797,163 B2 | 8/2014 | Finkenzeller |
| 8,808,515 B2 | 8/2014 | Feldman et al. |
| 8,834,366 B2 | 9/2014 | Hayter et al. |
| 8,845,536 B2 | 9/2014 | Brauker et al. |
| 8,870,822 B2 | 10/2014 | Thalmann et al. |
| 8,880,138 B2 | 11/2014 | Cho |
| 8,945,056 B2 | 2/2015 | Iio et al. |
| 8,961,413 B2 | 2/2015 | Teller et al. |
| 9,007,781 B2 | 4/2015 | Moein et al. |
| 9,014,774 B2 | 4/2015 | Mao et al. |
| 9,031,630 B2 | 5/2015 | Hoss et al. |
| 9,060,719 B2 | 6/2015 | Hayter et al. |
| 9,060,805 B2 | 6/2015 | Goodnow et al. |
| 9,066,697 B2 | 6/2015 | Peyser et al. |
| 9,101,302 B2 | 8/2015 | Mace et al. |
| 9,186,098 B2 | 11/2015 | Lee et al. |
| 9,215,992 B2 | 12/2015 | Donnay et al. |
| 9,241,631 B2 | 1/2016 | Valdes et al. |
| 9,259,175 B2 | 2/2016 | Stafford |
| 9,265,453 B2 | 2/2016 | Curry et al. |
| 9,289,179 B2 | 3/2016 | Hayter et al. |
| 9,295,786 B2 | 3/2016 | Gottlieb et al. |
| 9,357,951 B2 | 6/2016 | Simpson et al. |
| 9,398,872 B2 | 7/2016 | Hayter et al. |
| 9,402,544 B2 | 8/2016 | Yee et al. |
| 9,402,570 B2 | 8/2016 | Pace et al. |
| 9,439,586 B2 | 9/2016 | Bugler |
| 9,451,910 B2 | 9/2016 | Brister et al. |
| 9,474,479 B2 | 10/2016 | Pusey et al. |
| 9,480,421 B2 | 11/2016 | Stafford |
| 9,483,608 B2 | 11/2016 | Hayter et al. |
| 9,504,471 B2 | 11/2016 | Vaitekunas et al. |
| 9,558,325 B2 | 1/2017 | Hayter et al. |
| 9,566,384 B2 | 2/2017 | Gyrn et al. |
| 9,636,068 B2 | 5/2017 | Yee et al. |
| 9,668,682 B2 | 6/2017 | Brister et al. |
| 9,743,876 B2 | 8/2017 | Gelfand et al. |
| 9,808,574 B2 | 11/2017 | Yodfat et al. |
| 9,814,414 B2 | 11/2017 | Brister et al. |
| 10,213,139 B2 | 2/2019 | Rao et al. |
| 10,292,632 B2 | 5/2019 | Lee et al. |
| 10,342,489 B2 | 7/2019 | Stafford |
| 10,705,719 B2 | 7/2020 | Jakowitz |
| 10,772,547 B1 | 9/2020 | Lee et al. |
| 10,820,842 B2 | 11/2020 | Harper |
| 10,827,954 B2 | 11/2020 | Hoss et al. |
| 10,874,338 B2 | 12/2020 | Stafford |

(56)                References Cited

U.S. PATENT DOCUMENTS

| | | | |
|---|---|---|---|
| 10,881,340 B2 | 1/2021 | Curry et al. | |
| 10,881,341 B1 | 1/2021 | Curry et al. | |
| 10,945,647 B2 | 3/2021 | Mazza et al. | |
| 10,945,649 B2 | 3/2021 | Lee et al. | |
| 10,952,653 B2 | 3/2021 | Harper | |
| 10,959,654 B2 | 3/2021 | Curry et al. | |
| 10,966,644 B2 | 4/2021 | Stafford | |
| 10,973,443 B2 | 4/2021 | Funderburk et al. | |
| 10,980,461 B2 | 4/2021 | Bohm et al. | |
| 11,000,213 B2 | 5/2021 | Kamath et al. | |
| 11,000,216 B2 | 5/2021 | Curry et al. | |
| 11,006,870 B2 | 5/2021 | Yee et al. | |
| 11,006,871 B2 | 5/2021 | Yee et al. | |
| 11,013,440 B2 | 5/2021 | Lee et al. | |
| 11,051,724 B2 | 7/2021 | Pace et al. | |
| 11,064,917 B2 | 7/2021 | Simpson et al. | |
| 11,116,430 B2 | 9/2021 | Funderburk et al. | |
| 11,141,084 B2 | 10/2021 | Funderburk et al. | |
| 11,166,656 B2 | 11/2021 | Yee et al. | |
| 11,179,068 B2 * | 11/2021 | Pace ................ A61B 5/150748 |
| 11,197,625 B1 | 12/2021 | Schleicher et al. | |
| 11,202,591 B2 | 12/2021 | Yee et al. | |
| 11,213,229 B2 | 1/2022 | Yee et al. | |
| 11,246,519 B2 | 2/2022 | Donnay et al. | |
| 11,266,335 B2 | 3/2022 | Donnay et al. | |
| 11,298,056 B2 | 4/2022 | Harper | |
| 11,298,058 B2 | 4/2022 | Stafford | |
| 11,510,625 B2 | 11/2022 | Gray et al. | |
| 2001/0016682 A1 | 8/2001 | Berner et al. | |
| 2001/0020546 A1 | 9/2001 | Eldridge et al. | |
| 2001/0034479 A1 | 10/2001 | Ring et al. | |
| 2001/0037060 A1 | 11/2001 | Thompson et al. | |
| 2001/0037366 A1 | 11/2001 | Webb et al. | |
| 2001/0039387 A1 | 11/2001 | Rutynowski et al. | |
| 2001/0044608 A1 | 11/2001 | Odell et al. | |
| 2001/0047127 A1 | 11/2001 | New et al. | |
| 2001/0056262 A1 | 12/2001 | Cabiri et al. | |
| 2002/0002344 A1 | 1/2002 | Douglas et al. | |
| 2002/0010390 A1 | 1/2002 | Guice et al. | |
| 2002/0013522 A1 | 1/2002 | Lav et al. | |
| 2002/0013538 A1 | 1/2002 | Teller | |
| 2002/0016534 A1 | 2/2002 | Trepagnier et al. | |
| 2002/0016568 A1 | 2/2002 | Lebel et al. | |
| 2002/0019022 A1 | 2/2002 | Dunn et al. | |
| 2002/0019584 A1 | 2/2002 | Schulze et al. | |
| 2002/0019586 A1 | 2/2002 | Teller et al. | |
| 2002/0019606 A1 | 2/2002 | Lebel et al. | |
| 2002/0022855 A1 | 2/2002 | Bobroff et al. | |
| 2002/0023852 A1 | 2/2002 | McIvor et al. | |
| 2002/0029058 A1 | 3/2002 | LeVaughn et al. | |
| 2002/0032386 A1 | 3/2002 | Sackner et al. | |
| 2002/0032531 A1 | 3/2002 | Mansky et al. | |
| 2002/0039026 A1 | 4/2002 | Stroth et al. | |
| 2002/0042090 A1 | 4/2002 | Heller et al. | |
| 2002/0045808 A1 | 4/2002 | Ford et al. | |
| 2002/0049482 A1 | 4/2002 | Fabian et al. | |
| 2002/0050250 A1 | 5/2002 | Peterson et al. | |
| 2002/0055711 A1 | 5/2002 | Lavi et al. | |
| 2002/0057993 A1 | 5/2002 | Maisey et al. | |
| 2002/0065454 A1 | 5/2002 | Lebel et al. | |
| 2002/0066764 A1 | 6/2002 | Perry et al. | |
| 2002/0072720 A1 | 6/2002 | Hague et al. | |
| 2002/0072784 A1 | 6/2002 | Sheppard et al. | |
| 2002/0074162 A1 | 6/2002 | Su et al. | |
| 2002/0076966 A1 | 6/2002 | Carron et al. | |
| 2002/0077599 A1 | 6/2002 | Wojcik | |
| 2002/0082487 A1 | 6/2002 | Kollias et al. | |
| 2002/0084196 A1 | 7/2002 | Liamos et al. | |
| 2002/0091796 A1 | 7/2002 | Higginson et al. | |
| 2002/0093969 A1 | 7/2002 | Lin et al. | |
| 2002/0095076 A1 | 7/2002 | Krausman et al. | |
| 2002/0103499 A1 | 8/2002 | Perez et al. | |
| 2002/0106709 A1 | 8/2002 | Potts et al. | |
| 2002/0111832 A1 | 8/2002 | Judge | |
| 2002/0117639 A1 | 8/2002 | Paolini et al. | |
| 2002/0118528 A1 | 8/2002 | Su et al. | |
| 2002/0119711 A1 | 8/2002 | VanAntwerp et al. | |
| 2002/0120186 A1 | 8/2002 | Keimel | |
| 2002/0124017 A1 | 9/2002 | Mault | |
| 2002/0128594 A1 | 9/2002 | Das et al. | |
| 2002/0130042 A1 | 9/2002 | Moerman et al. | |
| 2002/0133066 A1 | 9/2002 | Miller et al. | |
| 2002/0147135 A1 | 10/2002 | Schnell | |
| 2002/0150959 A1 | 10/2002 | Lejeune et al. | |
| 2002/0151770 A1 | 10/2002 | Noll et al. | |
| 2002/0151796 A1 | 10/2002 | Koulik | |
| 2002/0151816 A1 | 10/2002 | Rich et al. | |
| 2002/0154050 A1 | 10/2002 | Krupp et al. | |
| 2002/0161288 A1 | 10/2002 | Shin et al. | |
| 2002/0161290 A1 | 10/2002 | Chance | |
| 2002/0161338 A1 | 10/2002 | Peterson | |
| 2002/0164836 A1 | 11/2002 | Ho | |
| 2002/0165462 A1 | 11/2002 | Westbrook et al. | |
| 2002/0169369 A1 | 11/2002 | Ward et al. | |
| 2002/0169439 A1 | 11/2002 | Flaherty et al. | |
| 2002/0169635 A1 | 11/2002 | Shillingburg | |
| 2002/0183604 A1 | 12/2002 | Gowda et al. | |
| 2002/0185128 A1 | 12/2002 | Theobald | |
| 2002/0185130 A1 | 12/2002 | Wright et al. | |
| 2002/0188748 A1 | 12/2002 | Blackwell et al. | |
| 2002/0197522 A1 | 12/2002 | Lawrence et al. | |
| 2002/0198444 A1 | 12/2002 | Ughigaki et al. | |
| 2002/0198543 A1 | 12/2002 | Burdulis et al. | |
| 2003/0004403 A1 | 1/2003 | Drinan et al. | |
| 2003/0020477 A1 | 1/2003 | Goldstein | |
| 2003/0023189 A1 | 1/2003 | Kuo | |
| 2003/0023317 A1 | 1/2003 | Brauker et al. | |
| 2003/0023461 A1 | 1/2003 | Quintanilla et al. | |
| 2003/0028089 A1 | 2/2003 | Galley et al. | |
| 2003/0028184 A1 | 2/2003 | Lebel et al. | |
| 2003/0032077 A1 | 2/2003 | Itoh et al. | |
| 2003/0032867 A1 | 2/2003 | Crothall et al. | |
| 2003/0032874 A1 | 2/2003 | Rhodes et al. | |
| 2003/0042137 A1 | 3/2003 | Mao et al. | |
| 2003/0050546 A1 | 3/2003 | Desai et al. | |
| 2003/0054428 A1 | 3/2003 | Monfre et al. | |
| 2003/0055380 A1 | 3/2003 | Flaherty | |
| 2003/0060692 A1 | 3/2003 | Ruchti et al. | |
| 2003/0060753 A1 | 3/2003 | Starkweather et al. | |
| 2003/0065308 A1 | 4/2003 | Lebel et al. | |
| 2003/0065536 A1 | 4/2003 | Hansen et al. | |
| 2003/0069509 A1 | 4/2003 | Matzinger et al. | |
| 2003/0069510 A1 | 4/2003 | Semler | |
| 2003/0076792 A1 | 4/2003 | Theimer | |
| 2003/0077642 A1 | 4/2003 | Fritsch et al. | |
| 2003/0078481 A1 | 4/2003 | McIvor et al. | |
| 2003/0078560 A1 | 4/2003 | Miller et al. | |
| 2003/0083686 A1 | 5/2003 | Freeman et al. | |
| 2003/0088166 A1 | 5/2003 | Say et al. | |
| 2003/0097092 A1 | 5/2003 | Flaherty | |
| 2003/0100040 A1 | 5/2003 | Bonnecaze et al. | |
| 2003/0100821 A1 | 5/2003 | Heller et al. | |
| 2003/0109775 A1 | 6/2003 | O'Neil et al. | |
| 2003/0114897 A1 | 6/2003 | Von Arx et al. | |
| 2003/0114898 A1 | 6/2003 | Von Arx et al. | |
| 2003/0119457 A1 | 6/2003 | Standke | |
| 2003/0125612 A1 | 7/2003 | Fox et al. | |
| 2003/0130616 A1 | 7/2003 | Steil et al. | |
| 2003/0134347 A1 | 7/2003 | Heller et al. | |
| 2003/0135127 A1 | 7/2003 | Sackner et al. | |
| 2003/0135333 A1 | 7/2003 | Aceti et al. | |
| 2003/0144579 A1 | 7/2003 | Buss | |
| 2003/0144581 A1 | 7/2003 | Conn et al. | |
| 2003/0144608 A1 | 7/2003 | Kojima et al. | |
| 2003/0153900 A1 | 8/2003 | Aceti et al. | |
| 2003/0155656 A1 | 8/2003 | Chiu et al. | |
| 2003/0168338 A1 | 9/2003 | Gao et al. | |
| 2003/0176933 A1 | 9/2003 | Lebel et al. | |
| 2003/0187338 A1 | 10/2003 | Say et al. | |
| 2003/0188427 A1 | 10/2003 | Say et al. | |
| 2003/0199744 A1 | 10/2003 | Buse et al. | |
| 2003/0199790 A1 | 10/2003 | Boecker et al. | |
| 2003/0199910 A1 | 10/2003 | Boecker et al. | |
| 2003/0204290 A1 | 10/2003 | Sadler et al. | |

(56) References Cited

U.S. PATENT DOCUMENTS

| | | |
|---|---|---|
| 2003/0208113 A1 | 11/2003 | Mault et al. |
| 2003/0208114 A1 | 11/2003 | Ackerman |
| 2003/0212317 A1 | 11/2003 | Kovatchev et al. |
| 2003/0212379 A1 | 11/2003 | Bylund et al. |
| 2003/0212579 A1 | 11/2003 | Brown et al. |
| 2003/0216621 A1 | 11/2003 | Alpert et al. |
| 2003/0216630 A1 | 11/2003 | Jersey-Willuhn et al. |
| 2003/0217966 A1 | 11/2003 | Tapsak |
| 2003/0225361 A1 | 12/2003 | Sabra |
| 2003/0225373 A1 | 12/2003 | Bobroff et al. |
| 2003/0236489 A1 | 12/2003 | Jacobson et al. |
| 2004/0002682 A1 | 1/2004 | Kovelman et al. |
| 2004/0010207 A1 | 1/2004 | Flaherty et al. |
| 2004/0011671 A1 | 1/2004 | Shults et al. |
| 2004/0015131 A1 | 1/2004 | Flaherty et al. |
| 2004/0017300 A1 | 1/2004 | Kotzin et al. |
| 2004/0030226 A1 | 2/2004 | Quy |
| 2004/0030531 A1 | 2/2004 | Miller et al. |
| 2004/0030581 A1 | 2/2004 | Levin et al. |
| 2004/0034289 A1 | 2/2004 | Teller et al. |
| 2004/0039255 A1 | 2/2004 | Simonsen et al. |
| 2004/0039298 A1 | 2/2004 | Abreu |
| 2004/0040840 A1 | 3/2004 | Mao et al. |
| 2004/0045879 A1 | 3/2004 | Shults et al. |
| 2004/0054263 A1 | 3/2004 | Moerman et al. |
| 2004/0060818 A1 | 4/2004 | Feldman et al. |
| 2004/0061232 A1 | 4/2004 | Shah et al. |
| 2004/0063435 A1 | 4/2004 | Sakamoto et al. |
| 2004/0064068 A1 | 4/2004 | DeNuzzio et al. |
| 2004/0064133 A1 | 4/2004 | Miller et al. |
| 2004/0072357 A1 | 4/2004 | Steine et al. |
| 2004/0073266 A1 | 4/2004 | Haefner et al. |
| 2004/0078215 A1 | 4/2004 | Dahlin et al. |
| 2004/0096959 A1 | 5/2004 | Steine et al. |
| 2004/0100376 A1 | 5/2004 | Lye et al. |
| 2004/0105411 A1 | 6/2004 | Boatwright et al. |
| 2004/0106858 A1 | 6/2004 | Say et al. |
| 2004/0106859 A1 | 6/2004 | Say et al. |
| 2004/0106860 A1 | 6/2004 | Say et al. |
| 2004/0111017 A1 | 6/2004 | Say et al. |
| 2004/0116847 A1 | 6/2004 | Wall |
| 2004/0116865 A1 | 6/2004 | Bengtsson |
| 2004/0116866 A1 | 6/2004 | Gorman et al. |
| 2004/0117204 A1 | 6/2004 | Mazar et al. |
| 2004/0119169 A1 | 6/2004 | Hanawa |
| 2004/0122353 A1 | 6/2004 | Shahmirian et al. |
| 2004/0122489 A1 | 6/2004 | Mazar et al. |
| 2004/0133089 A1 | 7/2004 | Kilcoyne et al. |
| 2004/0133164 A1 | 7/2004 | Funderburk et al. |
| 2004/0133390 A1 | 7/2004 | Osorio et al. |
| 2004/0135571 A1 | 7/2004 | Uutela et al. |
| 2004/0135684 A1 | 7/2004 | Steinthal et al. |
| 2004/0138544 A1 | 7/2004 | Ward et al. |
| 2004/0138588 A1 | 7/2004 | Saikley et al. |
| 2004/0138688 A1 | 7/2004 | Giraud |
| 2004/0140211 A1 | 7/2004 | Broy et al. |
| 2004/0142403 A1 | 7/2004 | Hetzel et al. |
| 2004/0146909 A1 | 7/2004 | Duong et al. |
| 2004/0147872 A1 | 7/2004 | Thompson |
| 2004/0147996 A1 | 7/2004 | Miazga et al. |
| 2004/0152366 A1 | 8/2004 | Schultz et al. |
| 2004/0152622 A1 | 8/2004 | Keith et al. |
| 2004/0158207 A1 | 8/2004 | Hunn et al. |
| 2004/0162521 A1 | 8/2004 | Bengtsson et al. |
| 2004/0162678 A1 | 8/2004 | Hetzel et al. |
| 2004/0167801 A1 | 8/2004 | Say et al. |
| 2004/0171910 A1 | 9/2004 | Moore-Steele |
| 2004/0171921 A1 | 9/2004 | Say et al. |
| 2004/0176672 A1 | 9/2004 | Silver et al. |
| 2004/0186362 A1 | 9/2004 | Brauker et al. |
| 2004/0186365 A1 | 9/2004 | Jin et al. |
| 2004/0193020 A1 | 9/2004 | Chiba et al. |
| 2004/0193025 A1 | 9/2004 | Steil et al. |
| 2004/0193090 A1 | 9/2004 | Lebel et al. |
| 2004/0197846 A1 | 10/2004 | Hockersmith et al. |
| 2004/0199056 A1 | 10/2004 | Husemann et al. |
| 2004/0199059 A1 | 10/2004 | Brauker et al. |
| 2004/0204673 A1 | 10/2004 | Flaherty |
| 2004/0204687 A1 | 10/2004 | Mogensen et al. |
| 2004/0204744 A1 | 10/2004 | Penner et al. |
| 2004/0204868 A1 | 10/2004 | Maynard et al. |
| 2004/0206625 A1 | 10/2004 | Bhullar et al. |
| 2004/0206916 A1 | 10/2004 | Colvin, Jr. et al. |
| 2004/0210122 A1 | 10/2004 | Sieburg |
| 2004/0221057 A1 | 11/2004 | Darcey et al. |
| 2004/0223876 A1 | 11/2004 | Kirollos et al. |
| 2004/0223985 A1 | 11/2004 | Dunfield et al. |
| 2004/0225199 A1 | 11/2004 | Evanyk et al. |
| 2004/0225262 A1 | 11/2004 | Fathallah et al. |
| 2004/0225338 A1 | 11/2004 | Lebel et al. |
| 2004/0236200 A1 | 11/2004 | Say et al. |
| 2004/0236251 A1 | 11/2004 | Roe et al. |
| 2004/0240426 A1 | 12/2004 | Wu et al. |
| 2004/0249253 A1 | 12/2004 | Racchini et al. |
| 2004/0249999 A1 | 12/2004 | Connolly et al. |
| 2004/0254433 A1 | 12/2004 | Bandis et al. |
| 2004/0254434 A1 | 12/2004 | Goodnow et al. |
| 2004/0258564 A1 | 12/2004 | Charlton |
| 2004/0260224 A1 | 12/2004 | Binder et al. |
| 2004/0267300 A1 | 12/2004 | Mace |
| 2005/0001024 A1 | 1/2005 | Kusaka et al. |
| 2005/0003470 A1 | 1/2005 | Nelson et al. |
| 2005/0004439 A1 | 1/2005 | Shin et al. |
| 2005/0004494 A1 | 1/2005 | Perez et al. |
| 2005/0006122 A1 | 1/2005 | Burnette |
| 2005/0010269 A1 | 1/2005 | Lebel et al. |
| 2005/0017864 A1 | 1/2005 | Tsoukalis |
| 2005/0027177 A1 | 2/2005 | Shin et al. |
| 2005/0027180 A1 | 2/2005 | Goode, Jr. et al. |
| 2005/0027181 A1 | 2/2005 | Goode, Jr. et al. |
| 2005/0027462 A1 | 2/2005 | Goode, Jr. et al. |
| 2005/0027463 A1 | 2/2005 | Goode et al. |
| 2005/0031689 A1 | 2/2005 | Shults et al. |
| 2005/0033132 A1 | 2/2005 | Shults et al. |
| 2005/0038332 A1 | 2/2005 | Saidara et al. |
| 2005/0038465 A1 | 2/2005 | Shraga |
| 2005/0038680 A1 | 2/2005 | McMahon |
| 2005/0043598 A1 | 2/2005 | Goode, Jr. et al. |
| 2005/0049179 A1 | 3/2005 | Davidson et al. |
| 2005/0051427 A1 | 3/2005 | Brauker et al. |
| 2005/0051440 A1 | 3/2005 | Simpson et al. |
| 2005/0056552 A1 | 3/2005 | Simpson et al. |
| 2005/0065464 A1 | 3/2005 | Talbot et al. |
| 2005/0070774 A1 | 3/2005 | Addison et al. |
| 2005/0070819 A1 | 3/2005 | Poux et al. |
| 2005/0085872 A1 | 4/2005 | Yanagihara et al. |
| 2005/0090607 A1 | 4/2005 | Tapsak |
| 2005/0090850 A1 | 4/2005 | Thoes et al. |
| 2005/0096511 A1 | 5/2005 | Fox et al. |
| 2005/0096512 A1 | 5/2005 | Fox et al. |
| 2005/0096516 A1 | 5/2005 | Soykan et al. |
| 2005/0096520 A1 | 5/2005 | Maekawa et al. |
| 2005/0096587 A1 | 5/2005 | Santini, Jr. et al. |
| 2005/0101912 A1 | 5/2005 | Faust et al. |
| 2005/0101932 A1 | 5/2005 | Cote et al. |
| 2005/0103624 A1 | 5/2005 | Bhullar et al. |
| 2005/0104457 A1 | 5/2005 | Jordan et al. |
| 2005/0106713 A1 | 5/2005 | Phan et al. |
| 2005/0112169 A1 | 5/2005 | Brauker et al. |
| 2005/0112544 A1 | 5/2005 | Xu et al. |
| 2005/0113648 A1 | 5/2005 | Yang et al. |
| 2005/0113653 A1 | 5/2005 | Fox et al. |
| 2005/0113886 A1 | 5/2005 | Fischell et al. |
| 2005/0114068 A1 | 5/2005 | Chey et al. |
| 2005/0115832 A1 | 6/2005 | Simpson et al. |
| 2005/0116683 A1 | 6/2005 | Cheng et al. |
| 2005/0121322 A1 | 6/2005 | Say et al. |
| 2005/0131346 A1 | 6/2005 | Douglas |
| 2005/0131347 A1 | 6/2005 | Marano-Ford et al. |
| 2005/0134731 A1 | 6/2005 | Lee et al. |
| 2005/0137488 A1 | 6/2005 | Henry et al. |
| 2005/0137530 A1 | 6/2005 | Campbell et al. |
| 2005/0143635 A1 | 6/2005 | Kamath et al. |
| 2005/0149066 A1 | 7/2005 | Stafford |

(56) References Cited

U.S. PATENT DOCUMENTS

| | | |
|---|---|---|
| 2005/0151976 A1 | 7/2005 | Toma |
| 2005/0154271 A1 | 7/2005 | Rasdal et al. |
| 2005/0154410 A1 | 7/2005 | Conway et al. |
| 2005/0159678 A1 | 7/2005 | Taniike et al. |
| 2005/0161346 A1 | 7/2005 | Simpson et al. |
| 2005/0165404 A1 | 7/2005 | Miller |
| 2005/0171442 A1 | 8/2005 | Shirasaki et al. |
| 2005/0173245 A1 | 8/2005 | Feldman et al. |
| 2005/0176136 A1 | 8/2005 | Burd et al. |
| 2005/0177398 A1 | 8/2005 | Watanabe et al. |
| 2005/0181010 A1 | 8/2005 | Hunter et al. |
| 2005/0182306 A1 | 8/2005 | Sloan |
| 2005/0182358 A1 | 8/2005 | Heit et al. |
| 2005/0187442 A1 | 8/2005 | Cho et al. |
| 2005/0187720 A1 | 8/2005 | Goode, Jr. et al. |
| 2005/0192494 A1 | 9/2005 | Ginsberg |
| 2005/0192557 A1 | 9/2005 | Brauker et al. |
| 2005/0195930 A1 | 9/2005 | Spital et al. |
| 2005/0197554 A1 | 9/2005 | Polcha |
| 2005/0197793 A1 | 9/2005 | Baker |
| 2005/0199494 A1 | 9/2005 | Say et al. |
| 2005/0203360 A1 | 9/2005 | Brauker et al. |
| 2005/0204134 A1 | 9/2005 | Von Arx et al. |
| 2005/0214892 A1 | 9/2005 | Kovatchev et al. |
| 2005/0215871 A1 | 9/2005 | Feldman et al. |
| 2005/0221504 A1 | 10/2005 | Petruno et al. |
| 2005/0222518 A1 | 10/2005 | Dib |
| 2005/0222599 A1 | 10/2005 | Czernecki et al. |
| 2005/0236277 A9 | 10/2005 | Imran et al. |
| 2005/0236361 A1 | 10/2005 | Ufer et al. |
| 2005/0239154 A1 | 10/2005 | Feldman et al. |
| 2005/0239156 A1 | 10/2005 | Drucker et al. |
| 2005/0240245 A1 | 10/2005 | Bange et al. |
| 2005/0241957 A1 | 11/2005 | Mao et al. |
| 2005/0242479 A1 | 11/2005 | Petisce et al. |
| 2005/0245795 A1 | 11/2005 | Goode et al. |
| 2005/0245799 A1 | 11/2005 | Brauker et al. |
| 2005/0245839 A1 | 11/2005 | Stivoric et al. |
| 2005/0245844 A1 | 11/2005 | Mace et al. |
| 2005/0245904 A1 | 11/2005 | Estes et al. |
| 2005/0247319 A1 | 11/2005 | Berger |
| 2005/0251033 A1 | 11/2005 | Scarantino et al. |
| 2005/0261563 A1 | 11/2005 | Zhou et al. |
| 2005/0267325 A1 | 12/2005 | Bouchier et al. |
| 2005/0267327 A1 | 12/2005 | Iizuka et al. |
| 2005/0269214 A1 | 12/2005 | Lee |
| 2005/0277164 A1 | 12/2005 | Drucker et al. |
| 2005/0277912 A1 | 12/2005 | John |
| 2005/0281234 A1 | 12/2005 | Kawamura et al. |
| 2005/0283114 A1 | 12/2005 | Bresina et al. |
| 2005/0283208 A1 | 12/2005 | Von Arx et al. |
| 2005/0283209 A1 | 12/2005 | Katoozi et al. |
| 2005/0284758 A1 | 12/2005 | Funke et al. |
| 2005/0287620 A1 | 12/2005 | Heller et al. |
| 2006/0001538 A1 | 1/2006 | Kraft et al. |
| 2006/0001550 A1 | 1/2006 | Mann et al. |
| 2006/0001551 A1 | 1/2006 | Kraft et al. |
| 2006/0004270 A1 | 1/2006 | Bedard et al. |
| 2006/0004272 A1 | 1/2006 | Shah et al. |
| 2006/0004303 A1 | 1/2006 | Weidenhaupt et al. |
| 2006/0006141 A1 | 1/2006 | Ufer et al. |
| 2006/0009727 A1 | 1/2006 | O'Mahony et al. |
| 2006/0010098 A1 | 1/2006 | Goodnow et al. |
| 2006/0011474 A1 | 1/2006 | Schulein et al. |
| 2006/0012464 A1 | 1/2006 | Nitzan et al. |
| 2006/0015020 A1 | 1/2006 | Neale et al. |
| 2006/0015024 A1 | 1/2006 | Brister et al. |
| 2006/0016700 A1 | 1/2006 | Brister et al. |
| 2006/0019327 A1 | 1/2006 | Brister et al. |
| 2006/0020186 A1 | 1/2006 | Brister et al. |
| 2006/0020187 A1 | 1/2006 | Brister et al. |
| 2006/0020188 A1 | 1/2006 | Kamath et al. |
| 2006/0020189 A1 | 1/2006 | Brister et al. |
| 2006/0020190 A1 | 1/2006 | Kamath et al. |
| 2006/0020191 A1 | 1/2006 | Brister et al. |
| 2006/0020192 A1 | 1/2006 | Brister et al. |
| 2006/0020300 A1 | 1/2006 | Nghiem et al. |
| 2006/0025662 A1 | 2/2006 | Buse et al. |
| 2006/0025663 A1 | 2/2006 | Talbot et al. |
| 2006/0029177 A1 | 2/2006 | Cranford et al. |
| 2006/0030789 A1 | 2/2006 | Allen |
| 2006/0031094 A1 | 2/2006 | Cohen et al. |
| 2006/0036139 A1 | 2/2006 | Brister et al. |
| 2006/0036140 A1 | 2/2006 | Brister et al. |
| 2006/0036141 A1 | 2/2006 | Kamath et al. |
| 2006/0036142 A1 | 2/2006 | Brister et al. |
| 2006/0036143 A1 | 2/2006 | Brister et al. |
| 2006/0036144 A1 | 2/2006 | Brister et al. |
| 2006/0036145 A1 | 2/2006 | Brister et al. |
| 2006/0040402 A1 | 2/2006 | Brauker et al. |
| 2006/0040793 A1 | 2/2006 | Martens et al. |
| 2006/0041276 A1 | 2/2006 | Chan |
| 2006/0042080 A1 | 3/2006 | Say et al. |
| 2006/0047220 A1 | 3/2006 | Sakata et al. |
| 2006/0049359 A1 | 3/2006 | Busta et al. |
| 2006/0058588 A1 | 3/2006 | Zdeblick |
| 2006/0064035 A1 | 3/2006 | Wang et al. |
| 2006/0068208 A1 | 3/2006 | Tapsak |
| 2006/0079740 A1 | 4/2006 | Silver et al. |
| 2006/0081469 A1 | 4/2006 | Lee |
| 2006/0086624 A1 | 4/2006 | Tapsak |
| 2006/0091006 A1 | 5/2006 | Wang et al. |
| 2006/0094944 A1 | 5/2006 | Chuang |
| 2006/0095014 A1 | 5/2006 | Ethelfeld |
| 2006/0116607 A1 | 6/2006 | Nakamura et al. |
| 2006/0129173 A1 | 6/2006 | Wilkinson |
| 2006/0129733 A1 | 6/2006 | Solbelman |
| 2006/0135908 A1 | 6/2006 | Liniger et al. |
| 2006/0142651 A1 | 6/2006 | Brister et al. |
| 2006/0154642 A1 | 7/2006 | Scannell |
| 2006/0155180 A1 | 7/2006 | Brister et al. |
| 2006/0155210 A1 | 7/2006 | Beckman et al. |
| 2006/0155317 A1 | 7/2006 | List |
| 2006/0161194 A1 | 7/2006 | Freeman et al. |
| 2006/0161664 A1 | 7/2006 | Motoyama |
| 2006/0166629 A1 | 7/2006 | Reggiardo |
| 2006/0173260 A1 | 8/2006 | Gaoni et al. |
| 2006/0173406 A1 | 8/2006 | Hayes et al. |
| 2006/0173444 A1 | 8/2006 | Choy et al. |
| 2006/0181695 A1 | 8/2006 | Sage, Jr. |
| 2006/0183984 A1 | 8/2006 | Dobbies et al. |
| 2006/0183985 A1 | 8/2006 | Brister et al. |
| 2006/0189851 A1 | 8/2006 | Tvig et al. |
| 2006/0189863 A1 | 8/2006 | Peyser et al. |
| 2006/0189939 A1 | 8/2006 | Gonnelli et al. |
| 2006/0193375 A1 | 8/2006 | Lee et al. |
| 2006/0195029 A1 | 8/2006 | Shults et al. |
| 2006/0195133 A1 | 8/2006 | Freeman et al. |
| 2006/0200020 A1 | 9/2006 | Brister et al. |
| 2006/0200022 A1 | 9/2006 | Brauker et al. |
| 2006/0200181 A1 | 9/2006 | Fukuzawa et al. |
| 2006/0200970 A1 | 9/2006 | Brister et al. |
| 2006/0200981 A1 | 9/2006 | Bhullar et al. |
| 2006/0200982 A1 | 9/2006 | Bhullar et al. |
| 2006/0202805 A1 | 9/2006 | Schulman et al. |
| 2006/0202859 A1 | 9/2006 | Mastrototaro et al. |
| 2006/0211921 A1 | 9/2006 | Brauker et al. |
| 2006/0220839 A1 | 10/2006 | Fifolt et al. |
| 2006/0222566 A1 | 10/2006 | Brauker et al. |
| 2006/0222866 A1 | 10/2006 | Nakamura et al. |
| 2006/0224108 A1 | 10/2006 | Brauker et al. |
| 2006/0224109 A1 | 10/2006 | Steil et al. |
| 2006/0224141 A1 | 10/2006 | Rush et al. |
| 2006/0224171 A1 | 10/2006 | Sakata et al. |
| 2006/0226985 A1 | 10/2006 | Goodnow et al. |
| 2006/0229512 A1 | 10/2006 | Petisce et al. |
| 2006/0233839 A1 | 10/2006 | Jacquet |
| 2006/0247508 A1 | 11/2006 | Fennell |
| 2006/0247710 A1 | 11/2006 | Goetz et al. |
| 2006/0247895 A1 | 11/2006 | Liamos et al. |
| 2006/0248398 A1 | 11/2006 | Neel et al. |
| 2006/0253085 A1 | 11/2006 | Geismar et al. |
| 2006/0253086 A1 | 11/2006 | Moberg et al. |
| 2006/0258929 A1 | 11/2006 | Goode et al. |

(56)             References Cited

U.S. PATENT DOCUMENTS

| | | |
|---|---|---|
| 2006/0258939 A1 | 11/2006 | Pesach et al. |
| 2006/0258959 A1 | 11/2006 | Sode |
| 2006/0264785 A1 | 11/2006 | Dring et al. |
| 2006/0264888 A1 | 11/2006 | Moberg et al. |
| 2006/0270922 A1 | 11/2006 | Brauker et al. |
| 2006/0270923 A1 | 11/2006 | Brauker et al. |
| 2006/0271013 A1 | 11/2006 | Triplett et al. |
| 2006/0272652 A1 | 12/2006 | Stocker et al. |
| 2006/0273759 A1 | 12/2006 | Reggiardo |
| 2006/0276714 A1 | 12/2006 | Holt et al. |
| 2006/0276724 A1 | 12/2006 | Freeman et al. |
| 2006/0276771 A1 | 12/2006 | Galley et al. |
| 2006/0281985 A1 | 12/2006 | Ward et al. |
| 2006/0282042 A1 | 12/2006 | Walters et al. |
| 2006/0287591 A1 | 12/2006 | Ocvirk et al. |
| 2006/0287691 A1 | 12/2006 | Drew |
| 2006/0290496 A1 | 12/2006 | Peeters et al. |
| 2006/0293607 A1 | 12/2006 | Alt et al. |
| 2007/0007133 A1 | 1/2007 | Mang et al. |
| 2007/0010950 A1 | 1/2007 | Abensour et al. |
| 2007/0016129 A1 | 1/2007 | Liniger et al. |
| 2007/0016381 A1 | 1/2007 | Kamath et al. |
| 2007/0017983 A1 | 1/2007 | Frank et al. |
| 2007/0027381 A1 | 2/2007 | Stafford |
| 2007/0027384 A1 | 2/2007 | Brister et al. |
| 2007/0027385 A1 | 2/2007 | Brister et al. |
| 2007/0027507 A1 | 2/2007 | Burdett et al. |
| 2007/0030154 A1 | 2/2007 | Aiki et al. |
| 2007/0032706 A1 | 2/2007 | Kamath et al. |
| 2007/0032717 A1 | 2/2007 | Brister et al. |
| 2007/0032718 A1 | 2/2007 | Shults et al. |
| 2007/0033074 A1 | 2/2007 | Nitzan et al. |
| 2007/0038044 A1 | 2/2007 | Dobbies et al. |
| 2007/0045902 A1 | 3/2007 | Brauker et al. |
| 2007/0049865 A1 | 3/2007 | Radmer et al. |
| 2007/0055799 A1 | 3/2007 | Koehler et al. |
| 2007/0056858 A1 | 3/2007 | Chen et al. |
| 2007/0059196 A1 | 3/2007 | Brister et al. |
| 2007/0060801 A1 | 3/2007 | Neinast |
| 2007/0060814 A1 | 3/2007 | Stafford |
| 2007/0060869 A1 | 3/2007 | Tolle et al. |
| 2007/0066873 A1 | 3/2007 | Kamath et al. |
| 2007/0068807 A1 | 3/2007 | Feldman et al. |
| 2007/0071681 A1 | 3/2007 | Gadkar et al. |
| 2007/0073129 A1 | 3/2007 | Shah et al. |
| 2007/0078320 A1 | 4/2007 | Stafford |
| 2007/0078321 A1 | 4/2007 | Mazza et al. |
| 2007/0078322 A1 | 4/2007 | Stafford |
| 2007/0078323 A1 | 4/2007 | Reggiardo et al. |
| 2007/0088300 A1 | 4/2007 | Cline et al. |
| 2007/0088377 A1 | 4/2007 | Levaughn et al. |
| 2007/0090511 A1 | 4/2007 | Borland et al. |
| 2007/0093704 A1 | 4/2007 | Brister et al. |
| 2007/0093754 A1 | 4/2007 | Mogensen et al. |
| 2007/0093786 A1 | 4/2007 | Goldsmith et al. |
| 2007/0095661 A1 | 5/2007 | Wang et al. |
| 2007/0100218 A1 | 5/2007 | Sweitzer et al. |
| 2007/0100222 A1 | 5/2007 | Mastrototaro et al. |
| 2007/0106133 A1 | 5/2007 | Satchwell et al. |
| 2007/0106135 A1 | 5/2007 | Sloan et al. |
| 2007/0108048 A1 | 5/2007 | Wang et al. |
| 2007/0110124 A1 | 5/2007 | Tolle et al. |
| 2007/0111196 A1 | 5/2007 | Alarcon et al. |
| 2007/0123819 A1 | 5/2007 | Mernoe et al. |
| 2007/0124002 A1 | 5/2007 | Estes et al. |
| 2007/0129621 A1 | 6/2007 | Kellogg et al. |
| 2007/0135696 A1 | 6/2007 | Ward |
| 2007/0135774 A1 | 6/2007 | Turner et al. |
| 2007/0149873 A1 | 6/2007 | Say et al. |
| 2007/0149875 A1 | 6/2007 | Ouyang et al. |
| 2007/0153705 A1 | 7/2007 | Rosar et al. |
| 2007/0156033 A1 | 7/2007 | Causey, III et al. |
| 2007/0156094 A1 | 7/2007 | Safabash et al. |
| 2007/0163880 A1 | 7/2007 | Woo et al. |
| 2007/0168224 A1 | 7/2007 | Letzt et al. |
| 2007/0173706 A1 | 7/2007 | Neinast et al. |
| 2007/0173709 A1 | 7/2007 | Petisce et al. |
| 2007/0173710 A1 | 7/2007 | Petisce et al. |
| 2007/0173711 A1 | 7/2007 | Shah et al. |
| 2007/0173741 A1 | 7/2007 | Deshmukh et al. |
| 2007/0173761 A1 | 7/2007 | Kanderian et al. |
| 2007/0179349 A1 | 8/2007 | Hoyme et al. |
| 2007/0179352 A1 | 8/2007 | Randlov et al. |
| 2007/0179406 A1 | 8/2007 | DeNuzzio et al. |
| 2007/0191701 A1 | 8/2007 | Feldman et al. |
| 2007/0191702 A1 | 8/2007 | Yodfat et al. |
| 2007/0197889 A1 | 8/2007 | Brister et al. |
| 2007/0199818 A1 | 8/2007 | Petyt et al. |
| 2007/0202562 A1 | 8/2007 | Curry et al. |
| 2007/0203407 A1 | 8/2007 | Hoss et al. |
| 2007/0203539 A1 | 8/2007 | Stone et al. |
| 2007/0203966 A1 | 8/2007 | Brauker et al. |
| 2007/0208244 A1 | 9/2007 | Brauker et al. |
| 2007/0208245 A1 | 9/2007 | Brauker et al. |
| 2007/0208246 A1 | 9/2007 | Brauker et al. |
| 2007/0213611 A1 | 9/2007 | Simpson et al. |
| 2007/0219480 A1 | 9/2007 | Kamen et al. |
| 2007/0219496 A1 | 9/2007 | Kamen et al. |
| 2007/0222609 A1 | 9/2007 | Duron et al. |
| 2007/0227911 A1 | 10/2007 | Wang et al. |
| 2007/0228071 A1 | 10/2007 | Kamen et al. |
| 2007/0231846 A1 | 10/2007 | Cosentino et al. |
| 2007/0232877 A1 | 10/2007 | He |
| 2007/0232878 A1 | 10/2007 | Kovatchev et al. |
| 2007/0232879 A1 | 10/2007 | Brister et al. |
| 2007/0232880 A1 | 10/2007 | Siddiqui et al. |
| 2007/0233013 A1 | 10/2007 | Schoenberg et al. |
| 2007/0235331 A1 | 10/2007 | Simpson et al. |
| 2007/0244368 A1 | 10/2007 | Bayloff et al. |
| 2007/0244379 A1 | 10/2007 | Boock et al. |
| 2007/0244383 A1 | 10/2007 | Talbot et al. |
| 2007/0244398 A1 | 10/2007 | Lo et al. |
| 2007/0249922 A1 | 10/2007 | Peyser et al. |
| 2007/0253021 A1 | 11/2007 | Mehta et al. |
| 2007/0255116 A1 | 11/2007 | Mehta et al. |
| 2007/0255125 A1 | 11/2007 | Moberg et al. |
| 2007/0255302 A1 | 11/2007 | Koeppel et al. |
| 2007/0255321 A1 | 11/2007 | Gerber et al. |
| 2007/0255348 A1 | 11/2007 | Holtzclaw |
| 2007/0255531 A1 | 11/2007 | Drew |
| 2007/0258395 A1 | 11/2007 | Jollota et al. |
| 2007/0270672 A1 | 11/2007 | Hayter |
| 2007/0282299 A1 | 12/2007 | Hellwig |
| 2007/0285238 A1 | 12/2007 | Batra |
| 2008/0004512 A1 | 1/2008 | Funderburk et al. |
| 2008/0004515 A1 | 1/2008 | Jennewine et al. |
| 2008/0004573 A1 | 1/2008 | Kaufmann et al. |
| 2008/0004601 A1 | 1/2008 | Jennewine et al. |
| 2008/0004904 A1 | 1/2008 | Tran |
| 2008/0009304 A1 | 1/2008 | Fry |
| 2008/0009692 A1 | 1/2008 | Stafford |
| 2008/0009805 A1 | 1/2008 | Ethelfeld |
| 2008/0017522 A1 | 1/2008 | Heller et al. |
| 2008/0018433 A1 | 1/2008 | Pitt-Pladdy |
| 2008/0021543 A1 | 1/2008 | Shrivastava |
| 2008/0021666 A1 | 1/2008 | Goode, Jr. et al. |
| 2008/0027296 A1 | 1/2008 | Hadvary et al. |
| 2008/0027474 A1 | 1/2008 | Curry et al. |
| 2008/0029390 A1 | 2/2008 | Roche et al. |
| 2008/0029391 A1 | 2/2008 | Mao et al. |
| 2008/0030369 A1 | 2/2008 | Mann et al. |
| 2008/0031941 A1 | 2/2008 | Pettersson |
| 2008/0033254 A1 | 2/2008 | Kamath et al. |
| 2008/0033268 A1 | 2/2008 | Stafford |
| 2008/0033273 A1 | 2/2008 | Zhou et al. |
| 2008/0033318 A1 | 2/2008 | Mace et al. |
| 2008/0039702 A1 | 2/2008 | Hayter et al. |
| 2008/0045824 A1 | 2/2008 | Tapsak |
| 2008/0046038 A1 | 2/2008 | Hill et al. |
| 2008/0055070 A1 | 3/2008 | Bange et al. |
| 2008/0057484 A1 | 3/2008 | Miyata et al. |
| 2008/0058625 A1 | 3/2008 | McGarraugh et al. |
| 2008/0058626 A1 | 3/2008 | Miyata et al. |
| 2008/0058678 A1 | 3/2008 | Miyata et al. |

(56) References Cited

U.S. PATENT DOCUMENTS

| | | |
|---|---|---|
| 2008/0058773 A1 | 3/2008 | John |
| 2008/0058830 A1 | 3/2008 | Cole et al. |
| 2008/0059227 A1 | 3/2008 | Clapp |
| 2008/0060955 A1 | 3/2008 | Goodnow |
| 2008/0061961 A1 | 3/2008 | John |
| 2008/0062055 A1 | 3/2008 | Cunningham et al. |
| 2008/0064437 A1 | 3/2008 | Chambers et al. |
| 2008/0064937 A1 | 3/2008 | McGarraugh et al. |
| 2008/0064941 A1 | 3/2008 | Funderburk et al. |
| 2008/0064943 A1 | 3/2008 | Talbot et al. |
| 2008/0064944 A1 | 3/2008 | VanAntwerp et al. |
| 2008/0065646 A1 | 3/2008 | Zhang et al. |
| 2008/0066305 A1 | 3/2008 | Wang et al. |
| 2008/0067627 A1 | 3/2008 | Boeck et al. |
| 2008/0071156 A1 | 3/2008 | Brister et al. |
| 2008/0071157 A1 | 3/2008 | McGarraugh et al. |
| 2008/0071158 A1 | 3/2008 | McGarraugh et al. |
| 2008/0071328 A1 | 3/2008 | Haubrich et al. |
| 2008/0071580 A1 | 3/2008 | Marcus |
| 2008/0081977 A1 | 4/2008 | Hayter et al. |
| 2008/0083617 A1 | 4/2008 | Simpson et al. |
| 2008/0086042 A1 | 4/2008 | Brister et al. |
| 2008/0086044 A1 | 4/2008 | Brister et al. |
| 2008/0086273 A1 | 4/2008 | Shults et al. |
| 2008/0092638 A1 | 4/2008 | Brenneman et al. |
| 2008/0092911 A1 | 4/2008 | Schulman et al. |
| 2008/0097246 A1 | 4/2008 | Stafford |
| 2008/0097289 A1 | 4/2008 | Steil et al. |
| 2008/0097908 A1 | 4/2008 | Dicks et al. |
| 2008/0099332 A1 | 5/2008 | Scott et al. |
| 2008/0102441 A1 | 5/2008 | Chen et al. |
| 2008/0108942 A1 | 5/2008 | Brister et al. |
| 2008/0112848 A1 | 5/2008 | Huffstodt et al. |
| 2008/0114228 A1 | 5/2008 | McCluskey et al. |
| 2008/0114280 A1 | 5/2008 | Stafford |
| 2008/0119705 A1 | 5/2008 | Patel et al. |
| 2008/0119707 A1 | 5/2008 | Stafford |
| 2008/0119710 A1 | 5/2008 | Reggiardo et al. |
| 2008/0125636 A1 | 5/2008 | Ward et al. |
| 2008/0127052 A1 | 5/2008 | Rostoker |
| 2008/0129486 A1 | 6/2008 | Jeckelmann et al. |
| 2008/0133059 A1 | 6/2008 | Trippel et al. |
| 2008/0133702 A1 | 6/2008 | Sharma et al. |
| 2008/0139910 A1 | 6/2008 | Mastrototaro et al. |
| 2008/0146904 A1 | 6/2008 | Hunn |
| 2008/0148873 A1 | 6/2008 | Wang |
| 2008/0154205 A1 | 6/2008 | Wojcik |
| 2008/0154286 A1 | 6/2008 | Abbott et al. |
| 2008/0154513 A1 | 6/2008 | Kovatchev et al. |
| 2008/0161664 A1 | 7/2008 | Mastrototaro et al. |
| 2008/0161666 A1 | 7/2008 | Feldman et al. |
| 2008/0167543 A1 | 7/2008 | Say et al. |
| 2008/0167572 A1 | 7/2008 | Stivoric et al. |
| 2008/0167578 A1 | 7/2008 | Bryer et al. |
| 2008/0172205 A1 | 7/2008 | Breton et al. |
| 2008/0177149 A1 | 7/2008 | Weinart et al. |
| 2008/0177165 A1 | 7/2008 | Blomquist et al. |
| 2008/0179187 A1 | 7/2008 | Ouyang |
| 2008/0182537 A1 | 7/2008 | Manku et al. |
| 2008/0183060 A1 | 7/2008 | Steil et al. |
| 2008/0183061 A1 | 7/2008 | Goode et al. |
| 2008/0183399 A1 | 7/2008 | Goode et al. |
| 2008/0188731 A1 | 8/2008 | Brister et al. |
| 2008/0188796 A1 | 8/2008 | Steil et al. |
| 2008/0189051 A1 | 8/2008 | Goode et al. |
| 2008/0194926 A1 | 8/2008 | Goh et al. |
| 2008/0194934 A1 | 8/2008 | Ray et al. |
| 2008/0194935 A1 | 8/2008 | Brister et al. |
| 2008/0194936 A1 | 8/2008 | Goode et al. |
| 2008/0194937 A1 | 8/2008 | Goode et al. |
| 2008/0194938 A1 | 8/2008 | Brister et al. |
| 2008/0195049 A1 | 8/2008 | Thalmann et al. |
| 2008/0195232 A1 | 8/2008 | Carr-Brendel et al. |
| 2008/0195967 A1 | 8/2008 | Goode et al. |
| 2008/0197024 A1 | 8/2008 | Simpson et al. |
| 2008/0200788 A1 | 8/2008 | Brister et al. |
| 2008/0200789 A1 | 8/2008 | Brister et al. |
| 2008/0200791 A1 | 8/2008 | Simpson et al. |
| 2008/0200897 A1 | 8/2008 | Hoss et al. |
| 2008/0201325 A1 | 8/2008 | Doniger et al. |
| 2008/0208025 A1 | 8/2008 | Shults et al. |
| 2008/0208026 A1 | 8/2008 | Noujaim et al. |
| 2008/0208113 A1 | 8/2008 | Damiano et al. |
| 2008/0214481 A1 | 9/2008 | Challoner et al. |
| 2008/0214900 A1 | 9/2008 | Fennell et al. |
| 2008/0214910 A1 | 9/2008 | Buck |
| 2008/0214915 A1 | 9/2008 | Brister et al. |
| 2008/0214918 A1 | 9/2008 | Brister et al. |
| 2008/0215035 A1 | 9/2008 | Yodfat et al. |
| 2008/0228051 A1 | 9/2008 | Shults et al. |
| 2008/0228054 A1 | 9/2008 | Shults et al. |
| 2008/0234561 A1 | 9/2008 | Roesicke et al. |
| 2008/0234992 A1 | 9/2008 | Ray et al. |
| 2008/0235469 A1 | 9/2008 | Drew |
| 2008/0242961 A1 | 10/2008 | Brister et al. |
| 2008/0242962 A1 | 10/2008 | Roesicke et al. |
| 2008/0242963 A1 | 10/2008 | Essenpreis et al. |
| 2008/0243051 A1 | 10/2008 | DeStefano |
| 2008/0252459 A1 | 10/2008 | Butler et al. |
| 2008/0254544 A1 | 10/2008 | Modzelewski et al. |
| 2008/0255434 A1 | 10/2008 | Hayter et al. |
| 2008/0255437 A1 | 10/2008 | Hayter |
| 2008/0255438 A1 | 10/2008 | Saidara et al. |
| 2008/0255440 A1 | 10/2008 | Eilerson et al. |
| 2008/0255808 A1 | 10/2008 | Hayter |
| 2008/0256048 A1 | 10/2008 | Hayter |
| 2008/0262300 A1 | 10/2008 | Reynolds et al. |
| 2008/0262469 A1 | 10/2008 | Brister et al. |
| 2008/0267823 A1 | 10/2008 | Wang et al. |
| 2008/0269584 A1 | 10/2008 | Shekalim |
| 2008/0269673 A1 | 10/2008 | Butoi et al. |
| 2008/0269683 A1 | 10/2008 | Bikovsky |
| 2008/0269687 A1 | 10/2008 | Chong et al. |
| 2008/0269714 A1 | 10/2008 | Mastrototaro et al. |
| 2008/0269719 A1 | 10/2008 | Balgobin et al. |
| 2008/0275313 A1 | 11/2008 | Brister et al. |
| 2008/0275327 A1 | 11/2008 | Faarbaek et al. |
| 2008/0278333 A1 | 11/2008 | Fennell et al. |
| 2008/0281178 A1 | 11/2008 | Chuang et al. |
| 2008/0281179 A1 | 11/2008 | Fennell et al. |
| 2008/0283396 A1 | 11/2008 | Wang et al. |
| 2008/0287755 A1 | 11/2008 | Sass et al. |
| 2008/0287761 A1 | 11/2008 | Hayter |
| 2008/0287762 A1 | 11/2008 | Hayter |
| 2008/0287763 A1 | 11/2008 | Hayter |
| 2008/0287764 A1 | 11/2008 | Rasdal et al. |
| 2008/0287765 A1 | 11/2008 | Rasdal et al. |
| 2008/0287766 A1 | 11/2008 | Rasdal et al. |
| 2008/0288180 A1 | 11/2008 | Hayter |
| 2008/0288204 A1 | 11/2008 | Hayter et al. |
| 2008/0294024 A1 | 11/2008 | Cosentino et al. |
| 2008/0294096 A1 | 11/2008 | Uber et al. |
| 2008/0296155 A1 | 12/2008 | Shults et al. |
| 2008/0300476 A1 | 12/2008 | Stafford |
| 2008/0300572 A1 | 12/2008 | Rankers et al. |
| 2008/0306368 A1 | 12/2008 | Goode, Jr. et al. |
| 2008/0306434 A1 | 12/2008 | Dobbies et al. |
| 2008/0306435 A1 | 12/2008 | Kamath et al. |
| 2008/0306444 A1 | 12/2008 | Brister et al. |
| 2008/0308523 A1 | 12/2008 | Krulevitch et al. |
| 2008/0312518 A1 | 12/2008 | Jina et al. |
| 2008/0312601 A1 | 12/2008 | Cane |
| 2008/0312841 A1 | 12/2008 | Hayter |
| 2008/0312842 A1 | 12/2008 | Hayter |
| 2008/0312844 A1 | 12/2008 | Hayter et al. |
| 2008/0312845 A1 | 12/2008 | Hayter et al. |
| 2008/0312859 A1 | 12/2008 | Skyggebjerg et al. |
| 2008/0319085 A1 | 12/2008 | Wright et al. |
| 2008/0319295 A1 | 12/2008 | Bernstein et al. |
| 2008/0319296 A1 | 12/2008 | Bernstein et al. |
| 2008/0319414 A1 | 12/2008 | Yodfat et al. |
| 2008/0319416 A1 | 12/2008 | Yodfat et al. |
| 2009/0005659 A1 | 1/2009 | Kollias et al. |
| 2009/0005665 A1 | 1/2009 | Hayter et al. |

(56)  References Cited

U.S. PATENT DOCUMENTS

| | | |
|---|---|---|
| 2009/0005666 A1 | 1/2009 | Shin et al. |
| 2009/0005729 A1 | 1/2009 | Hendrixson et al. |
| 2009/0006034 A1 | 1/2009 | Hayter et al. |
| 2009/0006061 A1 | 1/2009 | Thukral et al. |
| 2009/0006133 A1 | 1/2009 | Weinart et al. |
| 2009/0012376 A1 | 1/2009 | Agus |
| 2009/0012377 A1 | 1/2009 | Jennewine et al. |
| 2009/0012379 A1 | 1/2009 | Goode, Jr. et al. |
| 2009/0018424 A1 | 1/2009 | Kamath et al. |
| 2009/0018425 A1 | 1/2009 | Ouyang et al. |
| 2009/0020502 A1 | 1/2009 | Bhullar et al. |
| 2009/0028824 A1 | 1/2009 | Chiang et al. |
| 2009/0030293 A1 | 1/2009 | Cooper et al. |
| 2009/0030294 A1 | 1/2009 | Petisce et al. |
| 2009/0033482 A1 | 2/2009 | Hayter et al. |
| 2009/0036747 A1 | 2/2009 | Hayter et al. |
| 2009/0036758 A1 | 2/2009 | Brauker et al. |
| 2009/0036760 A1 | 2/2009 | Hayter |
| 2009/0036763 A1 | 2/2009 | Brauker et al. |
| 2009/0036915 A1 | 2/2009 | Karbowniczek et al. |
| 2009/0040022 A1 | 2/2009 | Finkenzeller |
| 2009/0043181 A1 | 2/2009 | Brauker et al. |
| 2009/0043182 A1 | 2/2009 | Brauker et al. |
| 2009/0043525 A1 | 2/2009 | Brauker et al. |
| 2009/0043541 A1 | 2/2009 | Brauker et al. |
| 2009/0043542 A1 | 2/2009 | Brauker et al. |
| 2009/0045055 A1 | 2/2009 | Rhodes et al. |
| 2009/0048499 A1 | 2/2009 | Glejbol |
| 2009/0048503 A1 | 2/2009 | Dalal et al. |
| 2009/0048563 A1 | 2/2009 | Ethelfeld et al. |
| 2009/0054737 A1 | 2/2009 | Magar et al. |
| 2009/0054745 A1 | 2/2009 | Jennewine et al. |
| 2009/0054747 A1 | 2/2009 | Fennell |
| 2009/0054748 A1 | 2/2009 | Feldman et al. |
| 2009/0054753 A1 | 2/2009 | Robinson et al. |
| 2009/0054866 A1 | 2/2009 | Teisen-Simony et al. |
| 2009/0055149 A1 | 2/2009 | Hayter et al. |
| 2009/0058635 A1 | 3/2009 | LaLonde et al. |
| 2009/0062633 A1 | 3/2009 | Brauker et al. |
| 2009/0062635 A1 | 3/2009 | Brauker et al. |
| 2009/0062767 A1 | 3/2009 | Van Antwerp et al. |
| 2009/0063187 A1 | 3/2009 | Johnson et al. |
| 2009/0063402 A1 | 3/2009 | Hayter |
| 2009/0069658 A1 | 3/2009 | Say et al. |
| 2009/0069750 A1 | 3/2009 | Schraga |
| 2009/0076356 A1 | 3/2009 | Simpson et al. |
| 2009/0076359 A1 | 3/2009 | Peyser |
| 2009/0076360 A1 | 3/2009 | Brister et al. |
| 2009/0076361 A1 | 3/2009 | Kamath et al. |
| 2009/0082693 A1 | 3/2009 | Stafford |
| 2009/0085768 A1 | 4/2009 | Patel et al. |
| 2009/0085873 A1 | 4/2009 | Betts et al. |
| 2009/0088614 A1 | 4/2009 | Taub |
| 2009/0088787 A1 | 4/2009 | Koike et al. |
| 2009/0093687 A1 | 4/2009 | Telfort et al. |
| 2009/0099436 A1 | 4/2009 | Brister et al. |
| 2009/0099521 A1 | 4/2009 | Gravesen et al. |
| 2009/0102678 A1 | 4/2009 | Mazza et al. |
| 2009/0105554 A1 | 4/2009 | Stahmann et al. |
| 2009/0105560 A1 | 4/2009 | Solomon |
| 2009/0105568 A1 | 4/2009 | Bugler |
| 2009/0105569 A1 | 4/2009 | Stafford |
| 2009/0105570 A1 | 4/2009 | Sloan et al. |
| 2009/0105571 A1 | 4/2009 | Fennell et al. |
| 2009/0105636 A1 | 4/2009 | Hayter et al. |
| 2009/0108992 A1 | 4/2009 | Shafer |
| 2009/0112123 A1 | 4/2009 | Freeman et al. |
| 2009/0112478 A1 | 4/2009 | Mueller, Jr. et al. |
| 2009/0118592 A1 | 5/2009 | Klitgaard |
| 2009/0124877 A1 | 5/2009 | Goode, Jr. et al. |
| 2009/0124878 A1 | 5/2009 | Goode, Jr. et al. |
| 2009/0124879 A1 | 5/2009 | Brister et al. |
| 2009/0124964 A1 | 5/2009 | Leach et al. |
| 2009/0124979 A1 | 5/2009 | Raymond et al. |
| 2009/0131768 A1 | 5/2009 | Simpson et al. |
| 2009/0131769 A1 | 5/2009 | Leach et al. |
| 2009/0131776 A1 | 5/2009 | Simpson et al. |
| 2009/0131777 A1 | 5/2009 | Simpson et al. |
| 2009/0131860 A1 | 5/2009 | Nielsen |
| 2009/0137886 A1 | 5/2009 | Shariati et al. |
| 2009/0137887 A1 | 5/2009 | Shariati et al. |
| 2009/0143659 A1 | 6/2009 | Li et al. |
| 2009/0143660 A1 | 6/2009 | Brister et al. |
| 2009/0149728 A1 | 6/2009 | Van Antwerp et al. |
| 2009/0150186 A1 | 6/2009 | Cohen et al. |
| 2009/0150454 A1 | 6/2009 | Gejdos et al. |
| 2009/0156919 A1 | 6/2009 | Brister et al. |
| 2009/0156924 A1 | 6/2009 | Shariati et al. |
| 2009/0163790 A1 | 6/2009 | Brister et al. |
| 2009/0163791 A1 | 6/2009 | Brister et al. |
| 2009/0163855 A1 | 6/2009 | Shin et al. |
| 2009/0164190 A1 | 6/2009 | Hayter |
| 2009/0164239 A1 | 6/2009 | Hayter et al. |
| 2009/0164251 A1 | 6/2009 | Hayter |
| 2009/0171182 A1 | 7/2009 | Stafford |
| 2009/0177068 A1 | 7/2009 | Stivoric et al. |
| 2009/0178459 A1 | 7/2009 | Li et al. |
| 2009/0182217 A1 | 7/2009 | Li et al. |
| 2009/0189738 A1 | 7/2009 | Hermle |
| 2009/0192366 A1 | 7/2009 | Mensinger et al. |
| 2009/0192380 A1 | 7/2009 | Shariati et al. |
| 2009/0192722 A1 | 7/2009 | Shariati et al. |
| 2009/0192724 A1 | 7/2009 | Brauker et al. |
| 2009/0192745 A1 | 7/2009 | Kamath et al. |
| 2009/0192751 A1 | 7/2009 | Kamath et al. |
| 2009/0198118 A1 | 8/2009 | Hayter et al. |
| 2009/0198186 A1 | 8/2009 | Mernoe et al. |
| 2009/0198215 A1 | 8/2009 | Chong et al. |
| 2009/0203981 A1 | 8/2009 | Brauker et al. |
| 2009/0204340 A1 | 8/2009 | Feldman et al. |
| 2009/0204341 A1 | 8/2009 | Brauker et al. |
| 2009/0210249 A1 | 8/2009 | Rasch-Menges et al. |
| 2009/0212766 A1 | 8/2009 | Olson et al. |
| 2009/0216100 A1 | 8/2009 | Ebner et al. |
| 2009/0216103 A1 | 8/2009 | Brister et al. |
| 2009/0216215 A1 | 8/2009 | Thalmann et al. |
| 2009/0234200 A1 | 9/2009 | Husheer |
| 2009/0240120 A1 | 9/2009 | Mensinger et al. |
| 2009/0240121 A1 | 9/2009 | Bickoff |
| 2009/0240128 A1 | 9/2009 | Mensinger et al. |
| 2009/0240193 A1 | 9/2009 | Mensinger et al. |
| 2009/0242399 A1 | 10/2009 | Kamath et al. |
| 2009/0242425 A1 | 10/2009 | Kamath et al. |
| 2009/0247855 A1 | 10/2009 | Boock et al. |
| 2009/0247856 A1 | 10/2009 | Boock et al. |
| 2009/0247857 A1 | 10/2009 | Harper et al. |
| 2009/0247931 A1 | 10/2009 | Damgaard-Sorenson |
| 2009/0253973 A1 | 10/2009 | Bashan et al. |
| 2009/0259118 A1 | 10/2009 | Feldman et al. |
| 2009/0259201 A1 | 10/2009 | Hwang et al. |
| 2009/0259202 A1 | 10/2009 | Leeflang et al. |
| 2009/0266573 A1 | 10/2009 | Engmark et al. |
| 2009/0267765 A1 | 10/2009 | Greene et al. |
| 2009/0270765 A1 | 10/2009 | Ghesquire et al. |
| 2009/0277242 A1 | 11/2009 | Crane et al. |
| 2009/0281406 A1 | 11/2009 | McGarraugh et al. |
| 2009/0287073 A1 | 11/2009 | Boock et al. |
| 2009/0287074 A1 | 11/2009 | Shults et al. |
| 2009/0289796 A1 | 11/2009 | Blumberg |
| 2009/0292184 A1 | 11/2009 | Funderburk et al. |
| 2009/0292185 A1 | 11/2009 | Funderburk et al. |
| 2009/0294277 A1 | 12/2009 | Thomas et al. |
| 2009/0298182 A1 | 12/2009 | Schulat et al. |
| 2009/0299152 A1 | 12/2009 | Taub et al. |
| 2009/0299155 A1 | 12/2009 | Yang et al. |
| 2009/0299156 A1 | 12/2009 | Simpson et al. |
| 2009/0299162 A1 | 12/2009 | Brauker et al. |
| 2009/0299167 A1 | 12/2009 | Seymour |
| 2009/0299276 A1 | 12/2009 | Brauker et al. |
| 2009/0299301 A1 | 12/2009 | Gottlieb et al. |
| 2010/0004597 A1 | 1/2010 | Gryn et al. |
| 2010/0010324 A1 | 1/2010 | Brauker et al. |
| 2010/0010329 A1 | 1/2010 | Taub et al. |
| 2010/0010331 A1 | 1/2010 | Brauker et al. |

(56) References Cited

U.S. PATENT DOCUMENTS

| | | |
|---|---|---|
| 2010/0010332 A1 | 1/2010 | Brauker et al. |
| 2010/0014626 A1 | 1/2010 | Fennell et al. |
| 2010/0016687 A1 | 1/2010 | Brauker et al. |
| 2010/0016698 A1 | 1/2010 | Rasdal et al. |
| 2010/0022855 A1 | 1/2010 | Brauker et al. |
| 2010/0022863 A1 | 1/2010 | Mogensen et al. |
| 2010/0022988 A1 | 1/2010 | Wochner et al. |
| 2010/0025238 A1 | 2/2010 | Gottlieb et al. |
| 2010/0030038 A1 | 2/2010 | Brauker et al. |
| 2010/0030053 A1 | 2/2010 | Goode, Jr. et al. |
| 2010/0030111 A1 | 2/2010 | Perriere |
| 2010/0030484 A1 | 2/2010 | Brauker et al. |
| 2010/0030485 A1 | 2/2010 | Brauker et al. |
| 2010/0036215 A1 | 2/2010 | Goode, Jr. et al. |
| 2010/0036216 A1 | 2/2010 | Goode, Jr. et al. |
| 2010/0036222 A1 | 2/2010 | Goode, Jr. et al. |
| 2010/0036223 A1 | 2/2010 | Goode, Jr. et al. |
| 2010/0036225 A1 | 2/2010 | Goode, Jr. et al. |
| 2010/0036281 A1 | 2/2010 | Doi |
| 2010/0041971 A1 | 2/2010 | Goode, Jr. et al. |
| 2010/0045465 A1 | 2/2010 | Brauker et al. |
| 2010/0049014 A1 | 2/2010 | Funderburk et al. |
| 2010/0049024 A1 | 2/2010 | Saint et al. |
| 2010/0049129 A1 | 2/2010 | Yokoi et al. |
| 2010/0057040 A1 | 3/2010 | Hayter |
| 2010/0057041 A1 | 3/2010 | Hayter |
| 2010/0057042 A1 | 3/2010 | Hayter |
| 2010/0057044 A1 | 3/2010 | Hayter |
| 2010/0057057 A1 | 3/2010 | Hayter et al. |
| 2010/0063373 A1 | 3/2010 | Kamath et al. |
| 2010/0069728 A1 | 3/2010 | Funderburk et al. |
| 2010/0076283 A1 | 3/2010 | Simpson et al. |
| 2010/0076379 A1 | 3/2010 | Matusch |
| 2010/0081905 A1 | 4/2010 | Bommakanti et al. |
| 2010/0081906 A1 | 4/2010 | Hayter et al. |
| 2010/0081908 A1 | 4/2010 | Dobbies et al. |
| 2010/0081910 A1 | 4/2010 | Brister et al. |
| 2010/0081953 A1 | 4/2010 | Syeda-Mahmood et al. |
| 2010/0087724 A1 | 4/2010 | Brauker et al. |
| 2010/0094251 A1 | 4/2010 | Estes et al. |
| 2010/0096259 A1 | 4/2010 | Zhang et al. |
| 2010/0099970 A1 | 4/2010 | Shults et al. |
| 2010/0099971 A1 | 4/2010 | Shults et al. |
| 2010/0100113 A1 | 4/2010 | Iio et al. |
| 2010/0105999 A1 | 4/2010 | Dixon et al. |
| 2010/0106088 A1 | 4/2010 | Yodfat et al. |
| 2010/0113897 A1 | 5/2010 | Brenneman et al. |
| 2010/0119693 A1 | 5/2010 | Tapsak |
| 2010/0119881 A1 | 5/2010 | Patel et al. |
| 2010/0121167 A1 | 5/2010 | McGarraugh et al. |
| 2010/0121169 A1 | 5/2010 | Petisce et al. |
| 2010/0137695 A1 | 6/2010 | Yodfat et al. |
| 2010/0141656 A1 | 6/2010 | Krieftewirth |
| 2010/0145229 A1 | 6/2010 | Perez et al. |
| 2010/0145377 A1 | 6/2010 | Lai et al. |
| 2010/0146300 A1 | 6/2010 | Brown |
| 2010/0152548 A1 | 6/2010 | Koski |
| 2010/0152554 A1 | 6/2010 | Steine et al. |
| 2010/0152674 A1 | 6/2010 | Kavazov et al. |
| 2010/0160757 A1 | 6/2010 | Weinart et al. |
| 2010/0160759 A1 | 6/2010 | Celentano et al. |
| 2010/0160760 A1 | 6/2010 | Shults et al. |
| 2010/0161269 A1 | 6/2010 | Kamath et al. |
| 2010/0168538 A1 | 7/2010 | Keenan et al. |
| 2010/0168540 A1 | 7/2010 | Kamath et al. |
| 2010/0168541 A1 | 7/2010 | Kamath et al. |
| 2010/0168542 A1 | 7/2010 | Kamath et al. |
| 2010/0168543 A1 | 7/2010 | Kamath et al. |
| 2010/0168544 A1 | 7/2010 | Kamath et al. |
| 2010/0168545 A1 | 7/2010 | Kamath et al. |
| 2010/0168546 A1 | 7/2010 | Kamath et al. |
| 2010/0168547 A1 | 7/2010 | Kamath et al. |
| 2010/0168660 A1 | 7/2010 | Galley et al. |
| 2010/0168677 A1 | 7/2010 | Gabriel et al. |
| 2010/0174157 A1 | 7/2010 | Brister et al. |
| 2010/0174158 A1 | 7/2010 | Kamath et al. |
| 2010/0174163 A1 | 7/2010 | Brister et al. |
| 2010/0174164 A1 | 7/2010 | Brister et al. |
| 2010/0174165 A1 | 7/2010 | Brister et al. |
| 2010/0174166 A1 | 7/2010 | Brister et al. |
| 2010/0174167 A1 | 7/2010 | Kamath et al. |
| 2010/0174168 A1 | 7/2010 | Goode, Jr. et al. |
| 2010/0174266 A1 | 7/2010 | Estes |
| 2010/0179399 A1 | 7/2010 | Goode, Jr. et al. |
| 2010/0179400 A1 | 7/2010 | Brauker et al. |
| 2010/0179401 A1 | 7/2010 | Rasdal et al. |
| 2010/0179402 A1 | 7/2010 | Goode, Jr. et al. |
| 2010/0179404 A1 | 7/2010 | Kamath et al. |
| 2010/0179405 A1 | 7/2010 | Goode, Jr. et al. |
| 2010/0179407 A1 | 7/2010 | Goode, Jr. et al. |
| 2010/0179408 A1 | 7/2010 | Kamath et al. |
| 2010/0179409 A1 | 7/2010 | Kamath et al. |
| 2010/0185065 A1 | 7/2010 | Goode, Jr. et al. |
| 2010/0185069 A1 | 7/2010 | Brister et al. |
| 2010/0185070 A1 | 7/2010 | Brister et al. |
| 2010/0185071 A1 | 7/2010 | Simpson et al. |
| 2010/0185072 A1 | 7/2010 | Goode, Jr. et al. |
| 2010/0185073 A1 | 7/2010 | Goode, Jr. et al. |
| 2010/0185074 A1 | 7/2010 | Goode, Jr. et al. |
| 2010/0185075 A1 | 7/2010 | Brister et al. |
| 2010/0185175 A1 | 7/2010 | Kamen et al. |
| 2010/0190435 A1 | 7/2010 | Cook et al. |
| 2010/0191082 A1 | 7/2010 | Brister et al. |
| 2010/0191087 A1 | 7/2010 | Talbot et al. |
| 2010/0191472 A1 | 7/2010 | Doniger et al. |
| 2010/0198033 A1 | 8/2010 | Krulevitch et al. |
| 2010/0198034 A1 | 8/2010 | Thomas et al. |
| 2010/0198035 A1 | 8/2010 | Kamath et al. |
| 2010/0198036 A1 | 8/2010 | Kamath et al. |
| 2010/0198042 A1 | 8/2010 | Sloan et al. |
| 2010/0198142 A1 | 8/2010 | Sloan et al. |
| 2010/0198314 A1 | 8/2010 | Wei |
| 2010/0204557 A1 | 8/2010 | Kiaie et al. |
| 2010/0204653 A1 | 8/2010 | Gryn et al. |
| 2010/0212583 A1 | 8/2010 | Brister et al. |
| 2010/0213057 A1 | 8/2010 | Feldman et al. |
| 2010/0213080 A1 | 8/2010 | Celentano et al. |
| 2010/0214104 A1 | 8/2010 | Goode, Jr. et al. |
| 2010/0217105 A1 | 8/2010 | Yodfat et al. |
| 2010/0217557 A1 | 8/2010 | Kamath et al. |
| 2010/0223013 A1 | 9/2010 | Kamath et al. |
| 2010/0223022 A1 | 9/2010 | Kamath et al. |
| 2010/0223023 A1 | 9/2010 | Kamath et al. |
| 2010/0228109 A1 | 9/2010 | Kamath et al. |
| 2010/0228111 A1 | 9/2010 | Friman et al. |
| 2010/0228497 A1 | 9/2010 | Kamath et al. |
| 2010/0230285 A1 | 9/2010 | Hoss et al. |
| 2010/0235439 A1 | 9/2010 | Goodnow et al. |
| 2010/0240975 A1 | 9/2010 | Goode, Jr. et al. |
| 2010/0240976 A1 | 9/2010 | Goode, Jr. et al. |
| 2010/0256471 A1 | 10/2010 | Say et al. |
| 2010/0259543 A1 | 10/2010 | Tarassenko et al. |
| 2010/0261987 A1 | 10/2010 | Kamath et al. |
| 2010/0262183 A1 | 10/2010 | Abbott et al. |
| 2010/0262201 A1 | 10/2010 | He et al. |
| 2010/0267161 A1 | 10/2010 | Wu et al. |
| 2010/0274107 A1 | 10/2010 | Boock et al. |
| 2010/0274111 A1 | 10/2010 | Say et al. |
| 2010/0274515 A1 | 10/2010 | Hoss et al. |
| 2010/0275108 A1 | 10/2010 | Sloan et al. |
| 2010/0280341 A1 | 11/2010 | Boock et al. |
| 2010/0286496 A1 | 11/2010 | Simpson et al. |
| 2010/0298684 A1 | 11/2010 | Leach et al. |
| 2010/0312176 A1 | 12/2010 | Lauer et al. |
| 2010/0313105 A1 | 12/2010 | Nekoomaram et al. |
| 2010/0317952 A1 | 12/2010 | Budiman et al. |
| 2010/0324392 A1 | 12/2010 | Yee et al. |
| 2010/0324403 A1 | 12/2010 | Brister et al. |
| 2010/0325868 A1 | 12/2010 | Wang et al. |
| 2010/0326842 A1 | 12/2010 | Mazza et al. |
| 2010/0331642 A1 | 12/2010 | Bruce et al. |
| 2010/0331644 A1 | 12/2010 | Neale et al. |
| 2010/0331647 A1 | 12/2010 | Shah et al. |
| 2010/0331648 A1 | 12/2010 | Kamath et al. |

(56) References Cited

U.S. PATENT DOCUMENTS

| | | |
|---|---|---|
| 2010/0331651 A1 | 12/2010 | Groll |
| 2010/0331653 A1 | 12/2010 | Stafford |
| 2010/0331656 A1 | 12/2010 | Mensinger et al. |
| 2010/0331657 A1 | 12/2010 | Mensinger et al. |
| 2011/0004085 A1 | 1/2011 | Mensinger et al. |
| 2011/0004276 A1 | 1/2011 | Blair et al. |
| 2011/0009727 A1 | 1/2011 | Mensinger et al. |
| 2011/0015509 A1 | 1/2011 | Peyser |
| 2011/0016691 A1 | 1/2011 | Alden et al. |
| 2011/0021889 A1 | 1/2011 | Hoss et al. |
| 2011/0022411 A1 | 1/2011 | Hjelm et al. |
| 2011/0024043 A1 | 2/2011 | Boock et al. |
| 2011/0024307 A1 | 2/2011 | Simpson et al. |
| 2011/0027127 A1 | 2/2011 | Simpson et al. |
| 2011/0027453 A1 | 2/2011 | Boock et al. |
| 2011/0027458 A1 | 2/2011 | Boock et al. |
| 2011/0028815 A1 | 2/2011 | Simpson et al. |
| 2011/0028816 A1 | 2/2011 | Simpson et al. |
| 2011/0031986 A1 | 2/2011 | Bhat et al. |
| 2011/0040163 A1 | 2/2011 | Telson et al. |
| 2011/0040256 A1 | 2/2011 | Bobroff et al. |
| 2011/0040263 A1 | 2/2011 | Hordum et al. |
| 2011/0046456 A1 | 2/2011 | Hordum et al. |
| 2011/0046467 A1 | 2/2011 | Simpson et al. |
| 2011/0046977 A1 | 2/2011 | Goodnow et al. |
| 2011/0054275 A1 | 3/2011 | Stafford |
| 2011/0054282 A1 | 3/2011 | Nekoomaram et al. |
| 2011/0060196 A1 | 3/2011 | Stafford |
| 2011/0060530 A1 | 3/2011 | Fennell |
| 2011/0070633 A1 | 3/2011 | Matsumoto et al. |
| 2011/0073475 A1 | 3/2011 | Kastanos et al. |
| 2011/0077469 A1 | 3/2011 | Blocker et al. |
| 2011/0077490 A1 | 3/2011 | Simpson et al. |
| 2011/0077494 A1 | 3/2011 | Doniger et al. |
| 2011/0077659 A1 | 3/2011 | Mandecki et al. |
| 2011/0081726 A1 | 4/2011 | Berman et al. |
| 2011/0082484 A1 | 4/2011 | Saravia et al. |
| 2011/0087196 A1 | 4/2011 | Hunn et al. |
| 2011/0097090 A1 | 4/2011 | Cao |
| 2011/0106126 A1 | 5/2011 | Love et al. |
| 2011/0112696 A1 | 5/2011 | Yodfat et al. |
| 2011/0118579 A1 | 5/2011 | Goode, Jr. et al. |
| 2011/0118580 A1 | 5/2011 | Goode, Jr. et al. |
| 2011/0123971 A1 | 5/2011 | Berkowitz et al. |
| 2011/0124992 A1 | 5/2011 | Brauker et al. |
| 2011/0124997 A1 | 5/2011 | Goode, Jr. et al. |
| 2011/0125040 A1 | 5/2011 | Crawford et al. |
| 2011/0125410 A1 | 5/2011 | Goode, Jr. et al. |
| 2011/0130970 A1 | 6/2011 | Goode, Jr. et al. |
| 2011/0130971 A1 | 6/2011 | Goode, Jr. et al. |
| 2011/0130998 A1 | 6/2011 | Goode, Jr. et al. |
| 2011/0137257 A1 | 6/2011 | Gyrn et al. |
| 2011/0137571 A1 | 6/2011 | Power et al. |
| 2011/0144465 A1 | 6/2011 | Shults et al. |
| 2011/0148905 A1 | 6/2011 | Simmons et al. |
| 2011/0152637 A1 | 6/2011 | Kateraas et al. |
| 2011/0172510 A1 | 7/2011 | Chickering, III et al. |
| 2011/0178378 A1 | 7/2011 | Brister et al. |
| 2011/0178461 A1 | 7/2011 | Chong et al. |
| 2011/0184258 A1 | 7/2011 | Stafford |
| 2011/0184482 A1 | 7/2011 | Eberman et al. |
| 2011/0184752 A1 | 7/2011 | Ray et al. |
| 2011/0190603 A1 | 8/2011 | Stafford |
| 2011/0190614 A1 | 8/2011 | Brister et al. |
| 2011/0191044 A1 | 8/2011 | Stafford |
| 2011/0193704 A1 | 8/2011 | Harper et al. |
| 2011/0201910 A1 | 8/2011 | Rasdal et al. |
| 2011/0201911 A1 | 8/2011 | Johnson et al. |
| 2011/0208027 A1 | 8/2011 | Wagner et al. |
| 2011/0213225 A1 | 9/2011 | Bernstein et al. |
| 2011/0218414 A1 | 9/2011 | Kamath et al. |
| 2011/0218490 A1 | 9/2011 | Ocvirk et al. |
| 2011/0230741 A1 | 9/2011 | Liang et al. |
| 2011/0231107 A1 | 9/2011 | Brauker et al. |
| 2011/0231140 A1 | 9/2011 | Goode, Jr. et al. |
| 2011/0231141 A1 | 9/2011 | Goode, Jr. et al. |
| 2011/0231142 A1 | 9/2011 | Goode, Jr. et al. |
| 2011/0253533 A1 | 10/2011 | Shults et al. |
| 2011/0257495 A1 | 10/2011 | Hoss et al. |
| 2011/0257521 A1 | 10/2011 | Fraden |
| 2011/0257895 A1 | 10/2011 | Brauker et al. |
| 2011/0263958 A1 | 10/2011 | Brauker et al. |
| 2011/0263959 A1 | 10/2011 | Young et al. |
| 2011/0264378 A1 | 10/2011 | Breton et al. |
| 2011/0270062 A1 | 11/2011 | Goode, Jr. et al. |
| 2011/0270158 A1 | 11/2011 | Brauker et al. |
| 2011/0275919 A1 | 11/2011 | Petisce et al. |
| 2011/0282327 A1 | 11/2011 | Kellogg et al. |
| 2011/0287528 A1 | 11/2011 | Fern et al. |
| 2011/0288574 A1* | 11/2011 | Curry .................. A61B 5/1519 |
| | | 606/185 |
| 2011/0289497 A1 | 11/2011 | Kiaie et al. |
| 2011/0290645 A1 | 12/2011 | Brister et al. |
| 2011/0313543 A1 | 12/2011 | Brauker et al. |
| 2011/0319729 A1 | 12/2011 | Donnay et al. |
| 2011/0319733 A1 | 12/2011 | Stafford |
| 2011/0319738 A1 | 12/2011 | Woodruff et al. |
| 2011/0319739 A1 | 12/2011 | Kamath et al. |
| 2011/0320130 A1 | 12/2011 | Valdes et al. |
| 2012/0010642 A1 | 1/2012 | Lee et al. |
| 2012/0035445 A1 | 2/2012 | Boock et al. |
| 2012/0040101 A1 | 2/2012 | Tapsak et al. |
| 2012/0046534 A1 | 2/2012 | Simpson et al. |
| 2012/0078071 A1 | 3/2012 | Bohm et al. |
| 2012/0088995 A1 | 4/2012 | Fennell et al. |
| 2012/0095406 A1 | 4/2012 | Gyrn et al. |
| 2012/0108934 A1 | 5/2012 | Valdes et al. |
| 2012/0108983 A1 | 5/2012 | Banet et al. |
| 2012/0116322 A1 | 5/2012 | Brink et al. |
| 2012/0123385 A1 | 5/2012 | Edwards et al. |
| 2012/0143135 A1 | 6/2012 | Cole et al. |
| 2012/0165626 A1 | 6/2012 | Irina et al. |
| 2012/0165640 A1 | 6/2012 | Galley et al. |
| 2012/0173200 A1 | 7/2012 | Breton et al. |
| 2012/0179113 A1 | 7/2012 | Yokota et al. |
| 2012/0184909 A1 | 7/2012 | Gyrn et al. |
| 2012/0190943 A1 | 7/2012 | Donnay et al. |
| 2012/0190989 A1 | 7/2012 | Kaiser et al. |
| 2012/0197098 A1 | 8/2012 | Donnay et al. |
| 2012/0197222 A1 | 8/2012 | Donnay et al. |
| 2012/0245447 A1 | 9/2012 | Karan et al. |
| 2012/0265042 A1 | 10/2012 | Neinast et al. |
| 2012/0296327 A1 | 11/2012 | Hutchins et al. |
| 2012/0303043 A1 | 11/2012 | Donnay et al. |
| 2013/0035575 A1 | 2/2013 | Mayou et al. |
| 2013/0047981 A1 | 2/2013 | Bacon |
| 2013/0109940 A1 | 5/2013 | Yang et al. |
| 2013/0111248 A1 | 5/2013 | Ghesquiere et al. |
| 2013/0150691 A1 | 6/2013 | Pace et al. |
| 2013/0184547 A1 | 7/2013 | Taub et al. |
| 2013/0199312 A1 | 8/2013 | Wilmer et al. |
| 2013/0225959 A1 | 8/2013 | Bugler |
| 2013/0235166 A1 | 9/2013 | Jones et al. |
| 2013/0253289 A1 | 9/2013 | Hadvary et al. |
| 2013/0267811 A1 | 10/2013 | Pryor et al. |
| 2013/0267812 A1 | 10/2013 | Pryor et al. |
| 2013/0317323 A1 | 11/2013 | Fujiwara et al. |
| 2014/0031655 A1 | 1/2014 | Stafford |
| 2014/0121480 A1 | 5/2014 | Budiman et al. |
| 2014/0148667 A1 | 5/2014 | Boock et al. |
| 2014/0171771 A1 | 6/2014 | Feldman et al. |
| 2014/0188053 A1 | 7/2014 | Lundquist |
| 2014/0228760 A1 | 8/2014 | Ethelfeld |
| 2014/0275907 A1 | 9/2014 | Feldman et al. |
| 2015/0005601 A1 | 1/2015 | Hoss et al. |
| 2015/0018643 A1 | 1/2015 | Cole et al. |
| 2015/0025338 A1 | 1/2015 | Lee et al. |
| 2015/0073238 A1 | 3/2015 | Matsumoto et al. |
| 2015/0105644 A1 | 4/2015 | Yang et al. |
| 2015/0141776 A1 | 5/2015 | Hadvary et al. |
| 2015/0164545 A1 | 6/2015 | Gyrn |
| 2015/0173661 A1 | 6/2015 | Myles |
| 2015/0241407 A1 | 8/2015 | Ou et al. |
| 2015/0326072 A1 | 11/2015 | Petras et al. |

(56) References Cited

U.S. PATENT DOCUMENTS

| 2016/0058342 A1 | 3/2016 | Maiz-Aguinaga et al. |
| 2016/0058470 A1 | 3/2016 | Peterson et al. |
| 2016/0058474 A1 | 3/2016 | Peterson et al. |
| 2016/0128615 A1 | 5/2016 | Curry et al. |
| 2016/0157759 A1 | 6/2016 | Yang |
| 2016/0256106 A1 | 9/2016 | Krasnow et al. |
| 2016/0331283 A1 | 11/2016 | Rao et al. |
| 2016/0331284 A1 | 11/2016 | Pace |
| 2016/0338733 A1 | 11/2016 | Shah et al. |
| 2016/0338734 A1 | 11/2016 | Shah et al. |
| 2016/0354555 A1 | 12/2016 | Gibson et al. |
| 2017/0112531 A1 | 4/2017 | Schoonmaker et al. |
| 2017/0112533 A1 | 4/2017 | Schoonmaker et al. |
| 2017/0112534 A1 | 4/2017 | Schoonmaker et al. |
| 2017/0127985 A1 | 5/2017 | Thompson et al. |
| 2017/0128011 A1 | 5/2017 | Frey et al. |
| 2017/0165451 A1 | 6/2017 | Frey et al. |
| 2017/0188908 A1 | 7/2017 | Hoss et al. |
| 2017/0188910 A1 | 7/2017 | Halac et al. |
| 2017/0188912 A1 | 7/2017 | Halac et al. |
| 2017/0216536 A1 | 8/2017 | Scott |
| 2017/0265791 A1 | 9/2017 | Pace et al. |
| 2017/0290533 A1 | 10/2017 | Antonio et al. |
| 2017/0290534 A1 | 10/2017 | Antonio et al. |
| 2017/0290535 A1 | 10/2017 | Rao et al. |
| 2017/0290546 A1 | 10/2017 | Antonio et al. |
| 2017/0319137 A1 | 11/2017 | Tsubouchi et al. |
| 2017/0367630 A1 | 12/2017 | Arita et al. |
| 2017/0368268 A1 | 12/2017 | Chopra |
| 2018/0116572 A1 | 5/2018 | Simpson et al. |
| 2018/0125464 A1 | 5/2018 | Kolb et al. |
| 2018/0235520 A1 | 8/2018 | Rao et al. |
| 2018/0360493 A1 | 12/2018 | Baker et al. |
| 2018/0368771 A1 | 12/2018 | Gray et al. |
| 2019/0076073 A1 | 3/2019 | Donnay et al. |
| 2019/0133501 A1 | 5/2019 | Rao et al. |
| 2019/0133638 A1 | 5/2019 | Ii et al. |
| 2019/0298240 A1 | 10/2019 | Lee et al. |
| 2020/0077928 A1 | 3/2020 | Brister et al. |
| 2020/0100712 A1 | 4/2020 | Stafford |
| 2020/0113494 A1 | 4/2020 | Akiyama |
| 2020/0178899 A1 | 6/2020 | Chae et al. |
| 2020/0196919 A1 | 6/2020 | Rao et al. |
| 2020/0397356 A1 | 12/2020 | Yee et al. |
| 2021/0030969 A1 | 2/2021 | Huang et al. |
| 2021/0113124 A1 | 4/2021 | Yee et al. |
| 2021/0161437 A1 | 6/2021 | Thomas et al. |
| 2021/0177315 A1 | 6/2021 | Thomas et al. |
| 2021/0204841 A1 | 7/2021 | Thomas et al. |
| 2021/0204843 A1 | 7/2021 | Mazza et al. |
| 2021/0378592 A1 | 12/2021 | Rodriguez et al. |
| 2022/0007973 A1 | 1/2022 | Rao et al. |
| 2022/0079475 A1 | 3/2022 | Cole et al. |
| 2022/0125480 A1 | 4/2022 | Rao et al. |
| 2022/0273240 A1 | 9/2022 | Hopcroft |
| 2023/0108476 A1 | 4/2023 | Rao |
| 2024/0293615 A1 | 9/2024 | Lanigan |

FOREIGN PATENT DOCUMENTS

| CA | 2468577 | 6/2003 |
| CA | 2495648 | 2/2004 |
| CA | 2143172 | 7/2005 |
| CA | 2498682 | 9/2005 |
| CA | 2555749 | 9/2005 |
| CA | 2632709 | 6/2007 |
| CA | 2396613 | 3/2008 |
| CA | 2678336 | 5/2008 |
| CA | 2615575 | 6/2008 |
| CA | 2626349 | 9/2008 |
| CA | 2701374 | 4/2009 |
| CA | 2413148 | 8/2010 |
| CA | 2728831 | 7/2011 |
| CA | 2766693 A1 | 9/2011 |
| CA | 2617965 | 10/2011 |
| CA | 2766685 A1 | 12/2011 |
| CA | 3050721 | 7/2018 |
| CN | 1202872 | 5/2005 |
| CN | 101163440 | 4/2008 |
| CN | 101268932 | 9/2008 |
| CN | 101296650 | 10/2008 |
| CN | 201370857 | 12/2009 |
| DE | 44 01 400 | 7/1995 |
| DE | 201 10 059 | 8/2002 |
| DE | 101 17 285 | 11/2002 |
| DE | 10 2008 053 216 | 5/2010 |
| EP | 0 010 375 | 4/1980 |
| EP | 0 026 995 | 4/1981 |
| EP | 0 048 090 | 3/1982 |
| EP | 0 078 636 | 5/1983 |
| EP | 0 096 288 | 12/1983 |
| EP | 0 098 592 | 1/1984 |
| EP | 0 125 139 | 11/1984 |
| EP | 0 127 958 | 12/1984 |
| EP | 0 136 362 | 4/1985 |
| EP | 0 170 375 | 2/1986 |
| EP | 0 177 743 | 4/1986 |
| EP | 0 080 304 | 5/1986 |
| EP | 0 184 909 | 6/1986 |
| EP | 0 206 218 | 12/1986 |
| EP | 0 230 472 | 8/1987 |
| EP | 0 241 309 | 10/1987 |
| EP | 0 245 073 | 11/1987 |
| EP | 0 255 291 | 2/1988 |
| EP | 0 278 647 | 8/1988 |
| EP | 0 319 277 A1 | 6/1989 |
| EP | 0 320 109 | 6/1989 |
| EP | 0 353 328 | 2/1990 |
| EP | 0 359 831 | 3/1990 |
| EP | 0 368 209 | 5/1990 |
| EP | 0 390 390 | 10/1990 |
| EP | 0 396 788 | 11/1990 |
| EP | O 400 918 | 12/1990 |
| EP | 0 453 283 | 10/1991 |
| EP | 0 470 290 | 2/1992 |
| EP | 0 567 725 | 11/1993 |
| EP | 0 286 118 | 1/1995 |
| EP | 0 680 727 | 11/1995 |
| EP | 0 724 859 | 8/1996 |
| EP | 0 805 574 | 11/1997 |
| EP | 1 897 488 | 12/1999 |
| EP | 0 973 289 | 1/2000 |
| EP | 0 678 308 | 5/2000 |
| EP | 1 048 264 | 11/2000 |
| EP | 1 177 802 | 2/2002 |
| EP | 0 729 366 | 7/2002 |
| EP | 1 292 218 | 3/2003 |
| EP | 1 077 634 | 7/2003 |
| EP | 1 092 390 | 7/2004 |
| EP | 1 568 309 | 8/2005 |
| EP | 1 630 898 | 3/2006 |
| EP | 1 666 091 | 6/2006 |
| EP | 1 669 020 | 6/2006 |
| EP | 1 703 697 | 9/2006 |
| EP | 1 704 889 | 9/2006 |
| EP | 1 704 893 | 9/2006 |
| EP | 1 729 128 | 12/2006 |
| EP | 0 987 982 | 1/2007 |
| EP | 1 956 371 | 8/2008 |
| EP | 1 972 270 A1 | 9/2008 |
| EP | 2 031 534 | 3/2009 |
| EP | 2 060 284 | 5/2009 |
| EP | 1 897 487 | 11/2009 |
| EP | 1 897 492 | 11/2009 |
| EP | 2 113 864 | 11/2009 |
| EP | 1 681 992 | 4/2010 |
| EP | 2 201 969 | 6/2010 |
| EP | 1 448 489 | 8/2010 |
| EP | 1 971 396 | 8/2010 |
| EP | 2 236 077 A1 | 10/2010 |
| EP | 1 725 163 | 12/2010 |
| EP | 2 260 757 | 12/2010 |
| EP | 1 413 245 | 6/2011 |
| EP | 2 327 362 | 6/2011 |

(56)　　　　　References Cited

FOREIGN PATENT DOCUMENTS

| EP | 2 327 984 | 6/2011 |
| EP | 2 335 587 | 6/2011 |
| EP | 2 407 094 A1 | 1/2012 |
| EP | 2 153 382 | 2/2012 |
| EP | 2 284 773 | 2/2012 |
| EP | 1 789 116 B1 | 5/2013 |
| EP | 1 075 209 B1 | 10/2014 |
| EP | 2 713 879 B1 | 7/2017 |
| EP | 2 393 417 B1 | 1/2019 |
| EP | 3 251 597 B1 | 11/2019 |
| EP | 3 632 314 A1 | 4/2020 |
| EP | 3 632 315 A1 | 4/2020 |
| EP | 3 851 045 A1 | 7/2021 |
| EP | 3 730 044 B1 | 12/2021 |
| EP | 3 730 045 B1 | 3/2022 |
| EP | 3 766 408 B1 | 4/2022 |
| EP | 3 928 688 B1 | 6/2022 |
| EP | 3 831 283 B1 | 4/2023 |
| EP | 4 111 949 B1 | 7/2023 |
| EP | 3 300 658 B1 | 1/2024 |
| EP | 4 238 496 B1 | 2/2024 |
| EP | 4 344 633 A2 | 4/2024 |
| EP | 4 203 819 B1 | 7/2024 |
| GB | 1 394 171 | 5/1975 |
| GB | 1 599 241 | 9/1981 |
| GB | 2 073 891 | 10/1981 |
| GB | 2 067 764 | 1/1984 |
| GB | 2 154 003 | 8/1985 |
| GB | 2 204 408 | 11/1988 |
| GB | 2 254 436 | 10/1992 |
| GB | 2 409 951 | 7/2005 |
| JP | 54-041191 | 4/1979 |
| JP | 55-010581 | 1/1980 |
| JP | 55-010583 | 1/1980 |
| JP | 55-010584 | 1/1980 |
| JP | 55-012406 | 1/1980 |
| JP | 56-163447 | 12/1981 |
| JP | 57-070448 | 4/1982 |
| JP | 60-173457 | 9/1985 |
| JP | 60-173458 | 9/1985 |
| JP | 60-173459 | 9/1985 |
| JP | 62-085855 | 4/1987 |
| JP | 62-114747 | 5/1987 |
| JP | 63-058149 | 3/1988 |
| JP | 63-128252 | 5/1988 |
| JP | 63-139246 | 6/1988 |
| JP | 63-294799 | 12/1988 |
| JP | 63-317757 | 12/1988 |
| JP | 63-317758 | 12/1988 |
| JP | 01-114746 | 5/1989 |
| JP | 01-114747 | 5/1989 |
| JP | 01-124060 | 5/1989 |
| JP | 01-134244 | 5/1989 |
| JP | 01-156658 | 6/1989 |
| JP | 02-062958 | 3/1990 |
| JP | 02-120655 | 5/1990 |
| JP | 02-287145 | 11/1990 |
| JP | 02-310457 | 12/1990 |
| JP | 03-020752 | 1/1991 |
| JP | 03-026956 | 2/1991 |
| JP | 03-028752 | 2/1991 |
| JP | 03-500940 | 2/1991 |
| JP | 03-194458 | 8/1991 |
| JP | 03-202764 | 9/1991 |
| JP | 05-072171 | 3/1993 |
| JP | 05-196595 | 8/1993 |
| JP | 06-190050 | 7/1994 |
| JP | 07-055757 | 3/1995 |
| JP | 07-072585 | 3/1995 |
| JP | 07-182462 | 7/1995 |
| JP | 07-311196 | 11/1995 |
| JP | 08-285814 | 11/1996 |
| JP | 08-285815 | 11/1996 |
| JP | 09-021778 | 1/1997 |
| JP | 09-101280 | 4/1997 |
| JP | 09-285459 | 4/1997 |
| JP | 10-170471 | 6/1998 |
| JP | 10-305016 | 11/1998 |
| JP | 11-506629 | 6/1999 |
| JP | 11-225359 | 8/1999 |
| JP | 2003-144417 | 5/2003 |
| JP | 2004-033438 | 2/2004 |
| JP | 2004-214014 | 7/2004 |
| JP | 2004-520103 | 7/2004 |
| JP | 2004-520898 | 7/2004 |
| JP | 2004-358016 | 12/2004 |
| JP | 2006-021031 | 1/2006 |
| JP | 2006-280464 | 10/2006 |
| JP | 2006-527036 | 11/2006 |
| JP | 2007-510499 | 4/2007 |
| JP | 2007-152037 | 6/2007 |
| JP | 2008-506468 | 3/2008 |
| JP | 2012-221588 A | 11/2012 |
| JP | 2014-056762 A | 3/2014 |
| KR | 10-2017-0068694 | 6/2017 |
| SU | 1281988 | 1/1987 |
| WO | WO 89/05119 | 6/1989 |
| WO | WO 89/08713 | 9/1989 |
| WO | WO 90/05300 | 5/1990 |
| WO | WO 90/05910 | 5/1990 |
| WO | WO 91/01680 | 2/1991 |
| WO | WO 91/04704 | 4/1991 |
| WO | WO 91/15993 | 10/1991 |
| WO | WO 92/13271 | 8/1992 |
| WO | WO 94/02062 | 9/1994 |
| WO | WO 95/28878 | 2/1995 |
| WO | WO 96/25089 | 8/1996 |
| WO | WO 96/35370 | 11/1996 |
| WO | WO 96/39977 | 12/1996 |
| WO | WO 97/02847 | 1/1997 |
| WO | WO 97/19344 | 5/1997 |
| WO | WO 97/21457 | 6/1997 |
| WO | WO 97/33513 | 9/1997 |
| WO | WO 97/42882 | 11/1997 |
| WO | WO 97/42883 | 11/1997 |
| WO | WO 97/42886 | 11/1997 |
| WO | WO 97/42888 | 11/1997 |
| WO | WO 97/43962 | 11/1997 |
| WO | WO 98/04902 | 2/1998 |
| WO | WO 98/35053 | 8/1998 |
| WO | WO 98/56293 | 12/1998 |
| WO | WO 99/27849 | 6/1999 |
| WO | WO 99/28736 | 6/1999 |
| WO | WO 99/33504 | 7/1999 |
| WO | WO 99/56613 | 11/1999 |
| WO | WO 99/58190 A1 | 11/1999 |
| WO | WO 00/40159 | 7/2000 |
| WO | WO 00/49940 | 8/2000 |
| WO | WO 00/49942 A2 | 8/2000 |
| WO | WO 00/59370 | 10/2000 |
| WO | WO 00/60350 | 10/2000 |
| WO | WO 00/74753 | 12/2000 |
| WO | WO 00/78992 | 12/2000 |
| WO | WO 01/17875 A1 | 3/2001 |
| WO | WO 01/52727 A1 | 7/2001 |
| WO | WO 01/52935 | 7/2001 |
| WO | WO 01/54753 | 8/2001 |
| WO | WO 01/58348 | 8/2001 |
| WO | WO 01/64105 A1 | 9/2001 |
| WO | WO 02/15778 | 2/2002 |
| WO | WO 02/16905 | 2/2002 |
| WO | WO 02/50534 | 6/2002 |
| WO | WO 02/058537 | 8/2002 |
| WO | WO 02/100457 | 12/2002 |
| WO | WO 03/026728 | 4/2003 |
| WO | WO 03/028784 | 4/2003 |
| WO | WO 03/032411 A2 | 4/2003 |
| WO | WO 03/056319 | 7/2003 |
| WO | WO 03/057027 | 7/2003 |
| WO | WO 03/072164 | 9/2003 |
| WO | WO 03/073936 | 9/2003 |
| WO | WO 03/076893 | 9/2003 |
| WO | WO 03/082091 | 10/2003 |
| WO | WO 03/085372 | 10/2003 |

(56)          References Cited

FOREIGN PATENT DOCUMENTS

| | | |
|---|---|---|
| WO | WO 2004/006982 | 1/2004 |
| WO | WO 2004/015539 | 2/2004 |
| WO | WO 2004/028337 | 4/2004 |
| WO | WO 2004/030726 | 4/2004 |
| WO | WO 2004/034024 | 4/2004 |
| WO | WO 2004/047445 | 6/2004 |
| WO | WO 2004/049237 | 6/2004 |
| WO | WO 2004/054445 | 7/2004 |
| WO | WO 2004/060436 | 7/2004 |
| WO | WO 2004/061420 | 7/2004 |
| WO | WO 2004/090503 | 10/2004 |
| WO | WO 2004/095648 A1 | 11/2004 |
| WO | WO 2004/098405 | 11/2004 |
| WO | WO 2004/098682 A2 | 11/2004 |
| WO | WO 2004/098683 | 11/2004 |
| WO | WO 2004/098684 | 11/2004 |
| WO | WO 2004/098685 | 11/2004 |
| WO | WO 2004/107971 | 12/2004 |
| WO | WO 2004/112602 | 12/2004 |
| WO | WO 2005/011779 A1 | 2/2005 |
| WO | WO 2005/018450 | 3/2005 |
| WO | WO 2005/026689 A2 | 3/2005 |
| WO | WO 2005/037184 | 4/2005 |
| WO | WO 2005/041766 | 5/2005 |
| WO | WO 2005/044116 | 5/2005 |
| WO | WO 2005/045744 | 5/2005 |
| WO | WO 2005/046780 | 5/2005 |
| WO | WO 2005/051170 | 6/2005 |
| WO | WO 2005/057175 | 6/2005 |
| WO | WO 2005/065538 | 7/2005 |
| WO | WO 2005/065542 A2 | 7/2005 |
| WO | WO 2005/084534 | 9/2005 |
| WO | WO 2005/089103 | 9/2005 |
| WO | WO 2005/092177 | 10/2005 |
| WO | WO 2005/121785 | 12/2005 |
| WO | WO 2005/123186 | 12/2005 |
| WO | WO 2006/001024 | 1/2006 |
| WO | WO 2006/015922 | 2/2006 |
| WO | WO 2006/017358 | 2/2006 |
| WO | WO 2006/020212 | 2/2006 |
| WO | WO 2006/024671 | 3/2006 |
| WO | WO 2006/026741 | 3/2006 |
| WO | WO 2006/032653 | 3/2006 |
| WO | WO 2006/036145 | 4/2006 |
| WO | WO 2006/040083 | 4/2006 |
| WO | WO 2006/042811 | 4/2006 |
| WO | WO 2006/061354 | 6/2006 |
| WO | WO 2006/064397 | 6/2006 |
| WO | WO 2006/072035 | 7/2006 |
| WO | WO 2006/079114 | 7/2006 |
| WO | WO 2006/086423 | 8/2006 |
| WO | WO 2006/094513 | 9/2006 |
| WO | WO 2006/108809 | 10/2006 |
| WO | WO 2006/110742 | 10/2006 |
| WO | WO 2006/114297 | 11/2006 |
| WO | WO 2006/118947 | 11/2006 |
| WO | WO 2006/121921 | 11/2006 |
| WO | WO 2006/124099 | 11/2006 |
| WO | WO 2007/002189 | 1/2007 |
| WO | WO 2007/007459 | 1/2007 |
| WO | WO 2007/016399 | 2/2007 |
| WO | WO 2007/019289 | 2/2007 |
| WO | WO 2007/027788 | 3/2007 |
| WO | WO 2007/041069 | 4/2007 |
| WO | WO 2007/041070 | 4/2007 |
| WO | WO 2007/041248 | 4/2007 |
| WO | WO 2007/053832 | 5/2007 |
| WO | WO 2007/056638 | 5/2007 |
| WO | WO 2007/065285 | 6/2007 |
| WO | WO 2007/089738 | 8/2007 |
| WO | WO 2007/092618 | 8/2007 |
| WO | WO 2007/097754 | 8/2007 |
| WO | WO 2007/101223 | 9/2007 |
| WO | WO 2007/120363 | 10/2007 |
| WO | WO 2007/126444 | 11/2007 |
| WO | WO 2007/140783 | 12/2007 |
| WO | WO 2007/143225 | 12/2007 |
| WO | WO 2007/149319 | 12/2007 |
| WO | WO 2008/001366 | 1/2008 |
| WO | WO 2008/014792 | 2/2008 |
| WO | WO 2008/021913 | 2/2008 |
| WO | WO 2008/031106 | 3/2008 |
| WO | WO 2008/031110 | 3/2008 |
| WO | WO 2008/039944 | 4/2008 |
| WO | WO 2008/042760 | 4/2008 |
| WO | WO 2008/048452 | 4/2008 |
| WO | WO 2008/051920 | 5/2008 |
| WO | WO 2008/051924 | 5/2008 |
| WO | WO 2008/052374 | 5/2008 |
| WO | WO 2008/061552 A1 | 5/2008 |
| WO | WO 2008/062099 | 5/2008 |
| WO | WO 2008/065646 | 6/2008 |
| WO | WO 2008/073813 | 6/2008 |
| WO | WO 2008/086541 | 7/2008 |
| WO | WO 2008/103620 | 8/2008 |
| WO | WO 2008/114223 | 9/2008 |
| WO | WO 2008/115409 | 9/2008 |
| WO | WO 2008/128210 | 10/2008 |
| WO | WO 2008/129532 | 10/2008 |
| WO | WO 2008/130896 | 10/2008 |
| WO | WO 2008/130897 | 10/2008 |
| WO | WO 2008/130898 | 10/2008 |
| WO | WO 2008/133702 | 11/2008 |
| WO | WO 2008/138006 | 11/2008 |
| WO | WO 2008/143943 | 11/2008 |
| WO | WO 2008/144445 | 11/2008 |
| WO | WO 2008/147921 | 12/2008 |
| WO | WO 2008/150917 | 12/2008 |
| WO | WO 2008/153693 | 12/2008 |
| WO | WO 2008/155377 | 12/2008 |
| WO | WO 2008/157821 | 12/2008 |
| WO | WO 2009/007287 | 1/2009 |
| WO | WO 2009/010396 | 1/2009 |
| WO | WO 2009/016635 | 2/2009 |
| WO | WO 2009/016638 | 2/2009 |
| WO | WO 2009/018058 | 2/2009 |
| WO | WO 2009/035773 | 3/2009 |
| WO | WO 2009/039013 | 3/2009 |
| WO | WO 2009/062674 | 5/2009 |
| WO | WO 2009/062675 | 5/2009 |
| WO | WO 2009/066288 A1 | 5/2009 |
| WO | WO 2009/068661 | 6/2009 |
| WO | WO 2009/086216 | 7/2009 |
| WO | WO 2009/096992 | 8/2009 |
| WO | WO 2009/097594 | 8/2009 |
| WO | WO 2010/062898 | 6/2010 |
| WO | WO 2010/077329 | 7/2010 |
| WO | WO 2010/091005 | 8/2010 |
| WO | WO 2010/099507 | 9/2010 |
| WO | WO 2010/112521 | 10/2010 |
| WO | WO 2010/141922 | 12/2010 |
| WO | WO 2011/000528 | 1/2011 |
| WO | WO 2011/002815 | 1/2011 |
| WO | WO 2011/015659 | 2/2011 |
| WO | WO 2011/022418 | 2/2011 |
| WO | WO 2011/025549 | 3/2011 |
| WO | WO 2011/025549 A1 | 3/2011 |
| WO | WO 2011/041531 A1 | 4/2011 |
| WO | WO 2011/077893 A1 | 6/2011 |
| WO | WO 2011/104616 | 9/2011 |
| WO | WO 2011/119896 | 9/2011 |
| WO | WO 2011/119898 A1 | 9/2011 |
| WO | WO 2012/103429 | 8/2012 |
| WO | WO 2013/090215 | 6/2013 |
| WO | WO 2016/183493 A1 | 11/2016 |
| WO | WO 2017/027749 | 2/2017 |
| WO | WO 2017/116915 A1 | 7/2017 |
| WO | WO 2017/134227 | 8/2017 |
| WO | WO 2018/136898 | 7/2018 |
| WO | WO 2018/166963 | 9/2018 |
| WO | WO 2019/005627 A1 | 1/2019 |
| WO | WO 2019/236850 | 12/2019 |
| WO | WO 2019/236859 | 12/2019 |

(56) References Cited

FOREIGN PATENT DOCUMENTS

| WO | WO 2019/236876 | 12/2019 |
| WO | WO 2022/046416 A1 | 3/2022 |
| WO | WO 2022/060677 A1 | 3/2022 |

OTHER PUBLICATIONS

CA, 2,872,576 Examiner's Report, dated Feb. 19, 2016.
EP, 06851063.5 Extended Search Report, dated Sep. 21, 2009.
EP, 07843396.8 Extended Search Report, dated Dec. 22, 2010.
EP, 10739031.2 Response to Response to Response to Grounds of Appeal, Jan. 18, 2023.
EP, 13000104.3 Extended Search Report, dated Mar. 12, 2013.
EP, 14179905.6 Summons to Attend Oral Proceedings, Apr. 10, 2017.
EP, 14179905.6 Notice of Opposition, May 19, 2016.
EP, 14179905.6 Extended Search Report, dated Dec. 23, 2014.
EP, 15002441.2 Extended Search Report, dated Dec. 18, 2015.
EP, 20177703.4 Examination Report, dated Jun. 25, 2021.
EP, 20177712.5 Grounds of Opposition Guide & Partner Patent, Dec. 22, 2022.
EP, 20177712.5 Grounds of Opposition Dexcom, Dec. 22, 2022.
EP, 20177712.5 Notice of Opposition Guide & Partner Patent, Dec. 22, 2022.
EP, 20177712.5 Notice of Opposition Dexcom, Dec. 22, 2022.
EP, 20195922.8 Grounds of Opposition Dexcom, Jan. 26, 2023.
EP, 20195922.8 Notice of Opposition Dexcom, Jan. 26, 2023.
WO, PCT/US2006/062690 ISR and Written Opinion, dated, Jan. 2, 2008.
WO, PCT/US2007/079774 ISR and Written Opinion, dated Jan. 2, 2008.
WO, PCT/US2022/037291 ISR and Written Opinion, dated Nov. 22, 2022.
Affidavit of Richard Paragas signed on May 18, 2016, pp. 1-4.
Affidavit of Paul Neale signed on May 18, 2016, pp. 1-2.
Choleau, C., et al., "Calibration of a Subcutaneous Amperometric Glucose Sensor Implanted for 7 Days in Diabetic Patients Part 2. Superiority of the One-Point Calibration Method", Biosensor & Bioelectronics, 2002, vol. 17, No. 8, pp. 647-654.
Choleau, C., et al., "Calibration of a Subcutaneous Amperometric Glucose Sensor Part 1. Effect of Measurement Uncertainties on the Determination of Sensor Sensitivity and Background Current", Biosensor & Bioelectronics, 2002, vol. 17, No. 8, pp. 641-646.
De Block, C., et al., "Minimally-Invasive and Non-Invasive Continuous Glucose Monitoring Systems: Indications, Advantages, Limitations and Clinical Aspects", Current Diabetes Reviews, 2008, vol. 4, No. 3, pp. 159-168.
U.S. Appl. No. 10/633,367.
Guerci, B., et al., "Clinical Performance of CGMS in Type 1 Diabetic Patients Treated by Continuous Subcutaneous Insulin Infusion Using Insulin Analogs", Diabetes Care, 2003, vol. 26, No. 3, pp. 582-589.
Mauras, N., et al., "Lack of Accuracy of Continuous Sensors in Healthy, Nondiabetic Children: Results of the Diabetes Research in Children Network (DirecNet) Accuracy Study", Journal of Pediatrics, 2004, pp. 770-775.
Schmidtke, D. W., et al., "Accuracy of the One-Point In Vivo Calibration of "Wired" Glucose Oxidase Electrodes Implanted in Jugular Veins of Rats in Periods of Rapid Rise and Decline of the Glucose Concentration", Analytical Chemistry, 1998, vol. 70, No. 10, pp. 2149-2155.
Tierney, M. J., et al., "Effect of Acetaminophen on the Accuracy of Glucose Measurements Obtained with the GlucoWatch Biographer", Diabetes Technology & Therapeutics, 2000, vol. 2, No. 2, pp. 199-207.
Tsalikian, e., et al., "Accuracy of the GlucoWatch G2® Biographer and the Continuous Glucose Moninitoring System During Hypoglycemia: Experience of the Diabetes Research in Children Network", Diabetes Care, 2004, vol. 27, No. 3, pp. 722-726.

Ward, W. K., et al., "Rise in Background Current Over Time in a Subcutaneous Glucose Sensor in the Rabbit: Relevance to Calibration and Accuracy", Biosensors & Bioelectronics, 2000, vol. 15, pp. 53-61.
AU, 2007309066 Examiner's Report, dated Jul. 12, 2012.
AU, 2007309066 Examiner's Report, dated Aug. 16, 2013.
AU, 2008265541 Examiner's Report, dated Oct. 15, 2012.
AU, 2008265541 Examiner's Report, dated Nov. 29, 2013.
AU, 2010286917 Examiner's Report, dated Sep. 8, 2014.
AU, 2011230596 Examiner's Report, dated Feb. 28, 2014.
AU, 2011269796 Examiner's Report, dated Apr. 3, 2014.
AU, 2016201703 Examiner's Report, dated Mar. 22, 2017.
AU, 2017254903 Examiner's Report, dated Dec. 11, 2018.
AU, 2018200899 Examiner's Report, dated Dec. 6, 2018.
CA, 2,765,712 Examiner's Report, dated Apr. 10, 2017.
CA, 2,765,712 Examiner's Report, dated Mar. 27, 2018.
CN, 200780045373.9 Notice of Allowance, dated May 18, 2011.
CN, 200780045373.9 Office Action, dated Apr. 14, 2010.
CN, 201080027344.1 Office Action, dated Jun. 5, 2014.
CN, 201080027344.1 Office Action, dated Feb. 6, 2015.
CN, 201080006480.2 Office Action, dated May 6, 2013.
CN, 201080006480.2 Office Action, dated Dec. 11, 2013.
CN, 201080006481.7 Office Action. dated Dec. 2, 2014.
CN, 201180002616.7 Office Action, dated Apr. 24, 2014.
CN, 201180002617.1 Office Action, dated Jul. 3, 2014.
CN, 20160144860.1 Office Action, dated Mar. 23, 2018.
CN, 20160144860.1 Office Action, dated Dec. 10, 2018.
CN, 20160144860.1 Office Action, dated May 23, 2019.
EP, 06804122.7 Decision to Refuse the Application, dated Feb. 25, 2013.
EP, 06804122.7 Examination Report, dated Nov. 30, 2013.
EP, 06804122.7 Examination Report, dated Jan. 25, 2011.
EP, 06815715.5 Extended Search Report, dated Oct. 30, 2009.
EP, 07842173.2 Examination Report, dated Mar. 21, 2013.
EP, 07842173.2 Extended Search Report, dated Dec. 29, 2010.
EP, 07842180.7 Examination Report, dated Oct. 23, 2012.
EP, 07842180.7 Examination Report, dated Dec. 14, 2011.
EP, 07842180.7 Examination Report, dated Feb. 23, 2011.
EP, 07842180.7 Extended Search Report, dated Sep. 28, 2009.
EP, 10739015.5 Extended Search Report, dated May 10, 2013.
EP, 10739031.2 Extended Search Report, dated May 7, 2013.
EP, 10739031.2 Examination Report, dated Oct. 28, 2016.
EP, 10739031.2 Notice of Opposition, Dec. 20, 2018.
EP, 10739031.2 Reply to Notice of Opposition, May 21, 2019.
EP, 10739031.2 Reply to Notice of Opposition Reply, Aug. 8, 2019.
EP, 10739031.2 Summons to Attend Oral Proceedings, Sep. 17, 2019.
EP, 10739031.2 Written Submissions, Dec. 3, 2019.
EP, 10739031.2 Response to Written Submissions, Jan. 24, 2020.
EP, 10739031.2 Summons to Attend Oral Proceedings, May 20, 2020.
EP, 10739031.2 Written Submissions, Nov. 20, 2020.
EP, 10739031.2 Response to Written Submissions, Jan. 7, 2021.
EP, 10739031.2 Decision and Grounds for Revoking Patent, dated Jun. 9, 2021.
EP, 10739031.2 Grounds of Appeal, Oct. 19, 2021.
EP, 10739031.2 Response to Grounds of Appeal, Mar. 1, 2022.
EP, 10739031.2 Response to Response to Grounds of Appeal, Jul. 29, 2022.
EP, 10812438.9 Extended Search Report, dated Dec. 10, 2013.
EP, 11760268.0 Decision of the Oral Proceedings, Sep. 27, 2022.
EP, 11760268.0 Minutes of Oral Proceedings, Aug. 11, 2022.
EP, 11760268.0 Communication from Board of Appeals, dated Mar. 31, 2022.
EP, 11760268.0 Response to Written Submissions, Jan. 14, 2020.
EP, 11760268.0 Response to Notice of Appeal, Sep. 5, 2019.
EP, 11760268.0 Statement of Grounds of Appeal, Apr. 23, 2019.
EP, 11760268.0 Grounds of Appeal, Apr. 18, 2019.
EP, 11760268.0 Notice of Appeal Abbott Diabetes Care Inc., Feb. 25, 2019.
EP, 11760268.0 Notice of Appeal Dexcom, Feb. 22, 2019.
EP, 11760268.0 Interlocutory Decision, Dec. 13, 2018.
EP, 11760268.0 Response to Summons to Attend Oral Proceedings, Sep. 13, 2018.

(56)                    References Cited

OTHER PUBLICATIONS

EP, 11760268.0 Letter Regarding the Opposition Procedure, Sep. 12, 2018.
EP, 11760268.0 Summons to Attend Oral Proceedings, Mar. 22, 2018.
EP, 11760268.0 Comments on Reply to Notice of Opposition, Dec. 27, 2017.
EP, 11760268.0 Reply to Notice of Opposition, Sep. 4, 2017.
EP, 11760268.0 Notice of Opposition, Mar. 29, 2017.
EP, 11760268.0 Extended Search Report, dated Apr. 14, 2014.
EP, 13000105.0 Examination Report, dated Oct. 18, 2016.
EP, 13000105.0 Minutes of the Oral Proceedings, Oct. 18, 2016.
EP, 13000105.0 Notice of Opposition, Jan. 4, 2019.
EP, 15184320.8 Examination Report, dated Apr. 18, 2017.
EP, 16176370.1 Extended Search Report, dated Dec. 7, 2016.
EP, 16793637.6 Extended Search Report, dated Oct. 9, 2016.
EP, 17182379.2 Extended Search Report, dated Feb. 21, 2016.
EP, 17201183.5 Extended Search Report, dated May 7, 2018.
EP, 17201183.5 Examination Report, dated May 7, 2019.
EP, 18192278.2 Extended Search Report, dated Mar. 13, 2019.
EP, 18208224.8 Extended Search Report, dated Oct. 11, 2019.
EP, 18741791.0 Extended Search Report, dated Sep. 23, 2020.
EP, 19151577.4 Extended Search Report, dated Aug. 16, 2019.
EP, 19151577.4 Examination Report, dated May 27, 2022.
EP, 19184881.1 Extended Search Report, dated Nov. 21, 2019.
EP, 19900891.3 Extended Search Report, dated Sep. 26, 2022.
EP, 20177703.4 Grounds of Opposition, Sep. 28, 2022.
EP, 20177703.4 Notice of Opposition, Sep. 28, 2022.
EP, 20177703.4 Extended Search Report, dated Sep. 25, 2020.
EP, 20177712.5 Extended Search Report, dated Sep. 30, 2020.
EP, 20195922.8 Extended Search Report, dated Dec. 16, 2020.
EP, 21192910.4 Extended Search Report, dated Jan. 31, 2022.
EP, 21211041.5 Extended Search Report, dated Mar. 3, 2022.
EP, 22168031.7 Extended Search Report, dated Aug. 17, 2022.
EP, 22169853.3 Extended Search Report, dated Sep. 2, 2022.
IL, 198329 Office Action, dated Mar. 5, 2012.
JP, 2009-534798 Office Action, dated Sep. 25, 2012.
JP, 2012-526736 Office Action, dated Apr. 15, 2014.
JP, 2012-526736 Office Action, dated Dec. 16, 2014.
JP, 2013-501503 Office Action, dated Mar. 3, 2015.
JP, 2015-159805 Office Action, dated Aug. 9, 2016.
JP, 2016-44196 Office Action, dated Apr. 11, 2017.
MX, MX/a/2009/004398 Office Action, dated Sep. 24, 2012.
MY, PI2021004760 Examination Report, dated Mar. 30, 2022.
MY, PI2021005830 Examination Report, dated Sep. 30, 2022.
MY, PI2021005830 Examination Report, dated Aug. 29, 2022.
NL, 2009963 Search Report, dated Aug. 12, 2013.
U.S., Institution Decision, IPR No. 2022-00605, dated Jul. 27, 2022.
U.S., Patent Owner's Preliminary Sur-Reply, IPR No. 2022-00605, dated Jun. 28, 2022.
U.S., Petitioner's Preliminary Reply to Patent Owner's Preliminary Response, IPR No. 2022-00605, dated Jun. 21, 2022.
U.S., Patent Owner's Preliminary Response, IPR No. 2022-00605, dated May 24, 2022.
U.S., Petition for Inter Partes Review of U.S. Pat. No. 10,945,649, IPR No. 2022-00605, dated Feb. 15, 2022.
U.S., Institution Decision, IPR No. 2022-00637, dated Jun. 28, 2022.
U.S., Patent Owner's Preliminary Sur-Reply, IPR No. 2022-00637, dated Jan. 28, 2022.
U.S., Petitioner's Preliminary Reply to Patent Owner's Preliminary Response, IPR No. 2022-00637, dated Jun. 21, 2022.
U.S., Patent Owner's Preliminary Response, IPR No. 2022-00637, dated Jun. 9, 2022.
U.S., Petition for Inter Partes Review of U.S. Pat. No. 11,013,440, IPR No. 2022-00637, dated Feb. 8, 2022.
U.S., Reexamination U.S. Appl. No. 95/002,162 Request to Review Order Denying Request for Reexamination, Dec. 13, 2012.
U.S., Reexamination U.S. Appl. No. 95/002,162 Order Denying Request for Reexamination, Nov. 13, 2012.
U.S., Request for Reexamination U.S. Appl. No. 95/002,162 of U.S. Pat. No. 8,175,673, Sep. 7, 2012.
U.S., Reexamination U.S. Appl. No. 95/002,113 Request to Review Order Denying Request for Reexamination, Dec. 13, 2012.
U.S., Reexamination U.S. Appl. No. 95/002,113 Order Denying Request for Reexamination, dated Nov. 13, 2012.
U.S., Request for Reexamination U.S. Appl. No. 95/002,113 of U.S. Pat. No. 6,990,366, dated Aug. 30, 2012.
U.S., Reexamination U.S. Appl. No. 90/011,730 Notice of Intent to Issue Ex Parte Reexamination Certificate, dated Apr. 5, 2012.
U.S., Reexamination U.S. Appl. No. 90/011,730 Office Action, dated Jan. 11, 2012.
U.S., Reexamination U.S. Appl. No. 90/011,730 Order Granting Request for Reexamination, dated Aug. 24, 2011.
U.S., Request for Reexamination U.S. Appl. No. 90/011,730 of U.S. Pat. No. 6,990,366, Jun. 3, 2011.
U.S., Reexamination U.S. Appl. No. 90/010,791 Ex Parte Reexamination Certificate, May 17, 2011.
U.S., Reexamination U.S. Appl. No. 90/010,791 Office Action, dated Dec. 17, 2010.
U.S., Reexamination U.S. Appl. No. 90/010,791 Office Action, dated May 28, 2010.
U.S., Reexamination U.S. Appl. No. 90/010,791 Order Granting Request for Reexamination, Feb. 22, 2010.
U.S., Request for Reexamination U.S. Appl. No. 90/010,791 of U.S. Pat. No. 6,990,366, Dec. 22, 2009.
U.S., Reexamination U.S. Appl. No. 90/009,328 Notice of Intent to Issue Ex Parte Reexamination Certificate, Nov. 20, 2009.
U.S., Reexamination U.S. Appl. No. 90/009,328 Office Action, dated Sep. 30, 2009.
U.S., Reexamination U.S. Appl. No. 90/009,328 Office Action, dated Aug. 4, 2009.
U.S., Reexamination U.S. Appl. No. 90/009,328 Order Granting Request for Reexamination, Dec. 9, 2008.
U.S., Request for Reexamination U.S. Appl. No. 90/009,328 of U.S. Pat. No. 6,990,366, Nov. 10, 2008.
U.S., Reexamination U.S. Appl. No. 90/009,104 Notice of Intent to Issue Ex Parte Reexamination Certificate, Nov. 20, 2009.
U.S., Reexamination U.S. Appl. No. 90/009,104 Office Action, dated Sep. 30, 2009.
U.S., Reexamination U.S. Appl. No. 90/009,104 Office Action, dated Aug. 4, 2009.
U.S., Reexamination U.S. Appl. No. 90/009,104 Office Action, dated Oct. 16, 2008.
U.S., Reexamination U.S. Appl. No. 90/009,104 Order Granting Request for Reexamination, Jun. 5, 2008.
U.S., Request for Reexamination U.S. Appl. No. 90/009,104 of U.S. Pat. No. 6,990,366, Apr. 8, 2008.
U.S., Reexamination U.S. Appl. No. 90/008,457 Notice of Intent to Issue Ex Parte Reexamination Certificate, dated Mar. 13, 2008.
U.S., Reexamination U.S. Appl. No. 90/008,457 Order Granting Request for Reexamination, dated Feb. 23, 2007.
U.S., Request for Reexamination U.S. Appl. No. 90/008,457 of U.S. Pat. No. 6,990,366, Jan. 23, 2007.
U.S., Request for Reexamination U.S. Appl. No. 90/008,172 of U.S. Pat. No. 6,990,366, Aug. 16, 2006.
U.S., Reexamination U.S. Appl. No. 90/007,910 Patent Board Decision, May 17, 2023.
U.S., Reexamination U.S. Appl. No. 90/007,910 Decision on Appeal, Jan. 18, 2011.
U.S., Reexamination U.S. Appl. No. 90/007,910 Advisory Action, dated Jul. 30, 2009.
U.S., Reexamination U.S. Appl. No. 90/007,910 Advisory Action, dated Feb. 6, 2009.
U.S., Reexamination U.S. Appl. No. 90/007,910 Examiner's Answer to Appeal Brief, Nov. 19, 2009.
U.S., Reexamination U.S. Appl. No. 90/007,910 Office Action, dated Oct. 2, 2008.
U.S., Reexamination U.S. Appl. No. 90/007,910 Office Action, dated Feb. 13, 2008.
U.S., Reexamination U.S. Appl. No. 90/007,910 Order Granting Request for Reexamination, Mar. 27, 2006.

(56) References Cited

OTHER PUBLICATIONS

U.S., Request for Reexamination U.S. Appl. No. 90/007,910 of U.S. Pat. No. 6,175,752, Feb. 1, 2006.
U.S., Reexamination U.S. Appl. No. 90/009,270 Order Denying Request for Reexamination, Dec. 1, 2008.
U.S., Request for Reexamination U.S. Appl. No. 90/009,270 of U.S. Pat. No. 6,175,752, Sep. 8, 2008.
U.S., Reexamination U.S. Appl. No. 90/009,497 Notice of Intent to Issue Reexamination Certificate, dated Aug. 23, 2010.
U.S., Reexamination U.S. Appl. No. 90/009,497 Order Granting Request, dated Jul. 30, 2009.
U.S., Request for Reexamination U.S. Appl. No. 90/009,497 of U.S. Pat. No. 6,175,752, Jun. 17, 2009.
WO, PCT/US2006/037312 ISR and Written Opinion, dated Apr. 17, 2007.
WO, PCT/US2006/037928 ISR and Written Opinion, dated Jul. 11, 2008.
WO, PCT/US2007/078065 ISR and Written Opinion, dated Apr. 11, 2008.
WO, PCT/US2007/078073 ISR and Written Opinion, dated Apr. 11, 2008.
WO, PCT/US2007/082114 ISR and Written Opinion, dated May 9, 2008.
WO, PCT/US2010/002401 ISR and Written Opinion, dated Nov. 12, 2010.
WO, PCT/US2010/022860 ISR and Written Opinion, dated Mar. 23, 2010.
WO, PCT/US2010/022928 ISR and Written Opinion, dated Mar. 21, 2010.
WO, PCT/US2010/047381 ISR and Written Opinion, dated Oct. 15, 2010.
WO, PCT/US2010/050772 ISR and Written Opinion, dated Dec. 3, 2010.
WO, PCT/US2010/050888 ISR and Written Opinion, dated Nov. 2, 2010.
WO, PCT/US2010/051861 ISR and Written Opinion, dated Nov. 30, 2010.
WO, PCT/US2011/029881 ISR and Written Opinion, dated May 20, 2011.
WO, PCT/US2011/029883 ISR and Written Opinion, dated Jun. 2, 2011.
WO, PCT/US2011/029884 ISR and Written Opinion, dated Jun. 1, 2011.
WO, PCT/US2012/068839 ISR and Written Opinion, dated Feb. 22, 2013.
WO, PCT/US2013/052397 ISR and Written Opinion, dated Dec. 2, 2013.
WO, PCT/US2016/032485 ISR and Written Opinion, dated Sep. 12, 2016.
WO, PCT/US2018/014745 ISR and Written Opinion, dated Jun. 4, 2018.
WO, PCT/US2019/035843 ISR and Written Opinion, dated Sep. 18, 2019.
WO, PCT/US2021/040541 ISR and Written Opinion, dated Dec. 20, 2021.
WO, PCT/US2021/045576 ISR and Written Opinion, dated Jan. 27, 2022.
WO, PCT/US2021/048086 ISR and Written Opinion, dated Feb. 28, 2022.
WO, PCT/US2021/050672 ISR and Written Opinion, dated Jan. 5, 2022.
WO, PCT/US22/37291 Invitation to Pay Additional Fees, Sep. 29, 2022.
Abruna, H. D., et al., "Rectifying Interfaces Using Two-Layer Films of Electrochemically Polymerized Vinylpyridine and Vinylbipyridine Complexes of Ruthenium and Iron on Electrodes", Journal of the American Chemical Society, 1981, vol. 103, No. 1, pp. 1-5.
ACCU-CHEK Compact Plus Owner's Booklet, 2008, pp. 1-100.

ACCU-CHEK Softclix Plus Lancet Device retrieved from https://web.archive.org/web/20061018055737/http://www.accu-check.com/us/rewrite/content/en_US/2.1.7.1:10/article/ACCM_general_article_3303.htm, 2006, pp. 1-2.
Ahson, S., et al., "RFID Handbook: Applications, Technology, Security, and Privacy", 2008, Chapter 4, Far-Field Tag Antenna Design Methodology, and Chapter 13, RFID Tags for Metallic Object Identification, pp. 71 and 253-254.
Albery, W.J., et al., "Amperometric Enzyme Electrodes Part II: Conducting Salts as Electrode Materials for the Oxidation of Glucose Oxidase", Journal of ElectroAnalytical Chemistry, 1985, vol. 194, pp. 223-235.
Albery, W.J., et al., "Amperometric Enzyme Electrodes", Philosophical Transactions of the Royal Society of London, 1987, vol. 316, pp. 107-119.
Alcock, S J, et al., "Continuous analyte monitoring to aid clinical practice," IEEE Engineering in Medicine & BioloXY Magazine, 1994, vol. 13. pp. 319-325.
Ambade, V. N., et al., "Methods for Estimation of Blood Glucose: A Comparative Evaluation", Medical Journal Armed Forces India, 1998, vol. 54, No. 2, pp. 131-133.
Anderson, L. B., et al., "Thin-Layer Electrochemistry: Steady-State Methods of Studying Rate Processes", Journal of ElectroAnalytical Chemistry, 1965, vol. 10, pp. 295-305.
Application Note AN048, Antenna Part No. FR05-S1-N-0-102, Compact Reach Xtend™, Bluetooth®, 802.11b/g WLAN Chip Antenna, 2008, pp. 1-13.
Application Note AVR2023-AT86RF231 PCB reference design for antenna diversity, Atmel Corporation, 2008, pp. 1-15.
Application Note nRF9E5 RF and antenna layout, Nordic Semiconductor, 2006, pp. 1-13.
Armour et al., "Application of Chronic Intravascular Blood Glucose Sensor in Dogs," Diabetes, 1990, vol. 39, pp. 1519-1526.
ASTM International, Designation D2240-05, 2010, pp. 1-13.
Aussedat, B., et al., "A User-Friendly Method for Calibrating a Subcutaneous Glucose Sensor-Based Hypoglycemic Alarm", Biosensors & Bioelectronics, 1997, vol. 12, No. 11, pp. 1061-1071.
Bartlett, P. N., et al., "Covalent Binding of Electron Relays to Glucose Oxidase", Journal of the Chemical Society, Chemical Communications, 1987, pp. 1603-1604.
Bartlett, P. N., et al., "Modification of Glucose Oxidase by Tetrathiafulvalene", Journal of the Chemical Society, Chemical Communications, 1990, pp. 1135-1136.
Benkiç, K., et al., "Using RSSI value for distance estimation in Wireless sensor networks based on ZigBee", 15th International Conference on Systems, Signals and Image Processing, Bratislava, Slovakia, 2008, pp. 1-4.
Bennion, N., et al., "Alternate Site Glucose Testing: A Crossover Design", Diabetes Technology & Therapeutics, 2002, vol. 4, No. 1, pp. 25-33.
Bindra, D.S., et al., "Pulsed Amperometric Detection of Glucose in Biological Fluids at a Surface-Modified Gold Electrode", American Chemical Society, 1989, vol. 61, No. 22, pp. 2566-2570.
Bindra, D.S., et al., "Design and in Vitro Studies of a Needle-Type Glucose Sensor for Subcutaneous Monitoring," Anal. Chem., 1991, vol. 63, No. 17, pp. 1692-1696.
Biosensors: Fundamentals and Applications, Turner et al., Eds., 1987, pp. 1-786.
Blank, T. B., et al., "Clinical Results From a Non-Invasive Blood Glucose Monitor", Optical Diagnostics and Sensing of Biological Fluids and Glucose and Cholesterol Monitoring II, Proceedings of SPIE, 2002, vol. 4624, pp. 1-10.
"Bluetooth Antenna Design", National Semiconductor Application Note, 2005, pp. 1-16.
Bluetooth Core Specification 4.0, Jun. 30, 2010, Master Table of Contents & Compliance Requirements, pp. 1-89.
Bobbioni-Harsch, E. et al., "Lifespan of subcutaneous glucose sensors and their performances during dynamic glycaemia changes in rats," J. Biomed. Eng., 1993, vol. 15, pp. 457-463.
Bonnett, A. H., et al., "Squirrel-Cage Rotor Options for AC Induction Motors", IEEE Transactions on Industry Applications, 2001, vol. 37, No. 4, pp. 1197-1209.

(56) References Cited

OTHER PUBLICATIONS

Brandt, J., et al., "Covalent Attachment of Proteins to Polysaccharide Carriers by Means of Benzoquinone", Biochimica et Biophysica Acta, 1975, vol. 386, pp. 196-202.

Brooks, S. L., et al., "Development of an On-Line Glucose Sensor for Fermentation Monitoring", Biosensors, 1987/88, vol. 3, pp. 45-56.

Brownlee, M., et al., "A Glucose-Controlled Insulin-Delivery System: Semisynthetic Insulin Bound to Lectin", Science, 1979, vol. 206, pp. 1190-1191.

Buhling, K. J., et al., "Optimal timing for postprandial glucose measurement in pregnant women with diabetes and a non-diabetic pregnant population evaluated by the Continuous Glucose Monitoring System (CGMS®)", Journal of Perinatal Medicine, 2005, vol. 33, No. 2, pp. 125-131.

Callaway, Jr., E. H., "Wireless Sensor Networks: Architectures and Protocols", 2004, Chapter 8, Antennas and the Definition of RF Performance, pp. 201-202.

Cass, A.E.G. et al., "Ferrocene-Mediated Enzyme Electrode for Amperometric Determination of Glucose," Anal. Chem., 1984, vol. 56, No. 4, pp. 667-671.

Cass, A.E.G. et al., "Ferricinium Ion as an Electron Acceptor for Oxido-Reductases", Journal of ElectroAnalytical Chemistry, 1985, vol. 190, pp. 117-127.

Castner, J. F., et al., "Mass Transport and Reaction Kinetic Parameters Determined Electrochemically for Immobilized Glucose Oxidase", Biochemistry, 1984, vol. 23, No. 10, pp. 2203-2210.

Cheyne, E.H., et al., "Performance of a Continuous Glucose Monitoring System During Controlled Hypoglycaemia in Healthy Volunteers", Diabetes Technology & Therapeutics, 2002, vol. 4, No. 5, pp. 607-613.

Claremont, D. J., et al., "Biosensors for Continuous In Vivo Glucose Monitoring", Proceedings of the Annual International Conference of the IEEE Engineering in Medicine and Biology Society, 1988, vol. 10, pp. 1-2.

Clark Jr., L. C., et al., "Electrode Systems for Continuous Monitoring in Cardiovascular Surgery", Annals New York Academy of Sciences, 1962, pp. 29-45.

Clark Jr., L. C., et al., "Differential Anodic Enzyme Polarography for the Measurement of Glucose", Oxygen Transport to Tissue: Instrumentation, Methods, and Physiology, 1973, pp. 127-133.

Clark Jr., L. C., et al., "Long-term Stability of Electroenzymatic Glucose Sensors Implanted in Mice", American Society of Artificial Internal Organs Transactions, 1988, vol. XXXIV, pp. 259-265.

Clarke, W. L., et al., "Evaluating Clinical Accuracy of Systems for Self-Monitoring of Blood Glucose", Diabetes Care, 1987, vol. 10, No. 5, pp. 622-628.

Clarke, W., et al., "Statistical Tools to Analyze Continuous Glucose Monitor Data", Diabetes Technology & Therapeutics, 2009, vol. 11, Suppl. 1, pp. S-45-S-54.

Cleo™ 90 Infusion Set, 510(k) Summary of Safety and Effectiveness, Aug. 10, 2004, pp. 1-618.

Cleo® 90 Infusion Set Training Guide, 2011, 1 page.

Compact Plus Blood Glucose Meter retrieved from https://web.archive.org/web/20090316065810/http://www.accu-check.com/us/rewrite/content/en_US/2.1,9:0/article/ACCM_general_article_5136.htm, 2009, pp. 1-3.

Complaint *Abbott Diabetes Care Inc.* v. *Dexcom, Inc.* U.S. District Court Delaware C.A. No. 05-590 filed Aug. 11, 2005.

Complaint, Amended, *Abbott Diabetes Care Inc.* v. *Dexcom, Inc.* U.S. District Court Delaware C.A. No. 05-590 filed Jun. 27, 2006.

Complaint *Abbott Diabetes Care Inc.* v. *Dexcom, Inc.* U.S. District Court Delaware C.A. No. 06-514 filed Aug. 17, 2006.

Cox, M., "An Overview of Continuous Glucose Monitoring Systems", Journal of Pediatric Health Care, 2009, vol. 23, No. 5, pp. 344-347.

Csöregi, E., et al., "Design and Optimization of a Selective Subcutaneously Implantable Glucose Electrode Based on 'Wired' Glucose Oxidase", Analytical Chemistry, 1995, vol. 67, No. 7, pp. 1240-1244.

Csöregi, E., et al., "Design, Characterization, and One-Point in Vivo Calibration of a Subcutaneously Implanted Glucose Electrode", Analytical Chemistry, 1994, vol. 66 No. 19, pp. 3131-3138.

Csöregi, E., et al., "On-Line Glucose Monitoring by Using Microdialysis Sampling and Amperometric Detection Based on 'Wired' Glucose Oxidase in Carbon Paste", Mikrochimica Acta, 1995, vol. 121, pp. 31-40.

Cullen, M.T., et al., "The Changing Presentations of Diabetic Ketoacidosis During Pregnancy", Amer. J. Perinatol, 1996, vol. 13, No. 7, pp. 449-451 (abstract only).

In Vivo Glucose Sensing, Cunningham et al., Eds., 2010, Chemical Analysis, vol. 174, pp. 1-466.

Darley, J., "Is your user experience as good as your technology?", 2019, retrieved from https://www.massdevice.com/is-your-user-experience-as-good-as-your-technology/, pp. 1-16.

Davis, G., "Electromechanical Techniques for the Development of Amperometric Biosensors", Biosensors, 1985, vol. 1, pp. 161-178.

IPR2022-00605 (Ex. 2001) Declaration of Michael Cima, Ph.D dated May 24, 2022, pp. 1-70.

IPR2022-00637 (Ex. 2001) Declaration of Michael Cima, Ph.D dated Jun. 9, 2022, pp. 1-79.

IPR2022-00605 (Ex. 1003) Declaration of Gary D. Fletcher, Ph.D dated Feb. 15, 2022, pp. 1-122.

IPR2022-00605 (Ex. 1003) Corrected Declaration of Gary D. Fletcher, Ph.D dated Feb. 18, 2022, pp. 1-124.

IPR2022-00637 (Ex. 1035) Second Declaration of Gary D. Fletcher, Ph.D dated Feb. 28, 2022, pp. 1-136.

Decuir, J., "Bluetooth 4.0: Low Energy", IEEE SCV Consultants' Network of Silicon Valley, 2012, pp. 1-68.

Degani, Y., et al., "Direct Electrical Communication Between Chemically Modified Enzymes and Metal Electrodes. 1. Electron Transfer from Glucose Oxidase to Metal Electrodes via Electron Relays, Bound Covalently to the Enzyme", The Journal of Physical Chemistry, 1987, vol. 91, No. 6, pp. 1285-1289.

Degani, Y., et al., "Direct Electrical Communication Between Chemically Modified Enzymes and Metal Electrodes. 2. Methods for Bonding Electron-Transfer Relays to Glucose Oxidase and D-Amino-Acid Oxidase", Journal of the American Chemical Society, 1988, vol. 110, No. 8, pp. 2615-2620.

Degani, Y., et al., "Electrical Communication Between Redox Centers of Glucose Oxidase and Electrodes via Electrostatically and Covalently Bound Redox Polymers", Journal of the American Chemical Society, 1989, vol. 111, pp. 2357-2358.

Dehez, B., et al., "Development of a Spherical Induction Motor With Two Degrees of Freedom", IEEE Transactions on Magnetics, 2006, vol. 42, No. 8, pp. 2077-2089.

Delve Talks: Jake Leach, Dexcom, retrieved from https://www.delve.com/podcasts/delve-talks-jake-leach-dexcom, pp. 1-9.

Dementyev, A., et al., "Power Consumption Analysis of Bluetooth Low Energy, ZigBee and ANT Sensor Nodes in a Cyclic Sleep Scenario", IEEE International Wireless Symposium (IWS), 2013, Beijing, China, pp. 1-4.

Denisevich, P., et al., "Unidirectional Current Flow and Charge State Trapping at Redox Polymer Interfaces on Bilayer Electrodes: Principles, Experimental Demonstration, and Theory", Journal of the American Chemical Society, 1981, vol. 103, pp. 4727-4737.

"Dexcom CEO tells investors not to fear new competition from Abbott's Freestyle Libre", 2017, retrieved from https://www.mobihealthnews.com/content/dexcom-ceo-tells-investors-not-fear-new-competition-abbotts-freestyle-libre, pp. 1-3.

Dexcom G5 Mobile System User Guide, 2020, pp. 1-410.

Dexcom G6, Winner Health & Wellness Award, Core77 Design Awards, 2019, retrieved from https://designawards.core77.com/health-wellness/85111/Dexcom-G6, pp. 1-8.

DexCom™ STS™ Continuous Glucose Monitoring System User's Guide, 2006, pp. 1-57.

Dicks, J.M., et al., "Ferrocene Modified Polypyrrole with Immobilised Glucose Oxidase and its Application in Amperometric Glucose Microbiosensors", Annales de Biologie Clinique, 1989, vol. 47, pp. 607-619.

Diem, P., et al., "Clinical Performance of a Continuous Viscometric Affinity Sensor for Glucose", Diabetes Technology & Therapeutics, 2004, vol. 6, pp. 790-799.

(56)　　　　　　References Cited

OTHER PUBLICATIONS

ECMA International Standard ECMA-340, Near Field Communication Interface and Protocol (NFCIP-1), 2nd Edition, 2004, pp. 1-65.

El-Khatib, F. H, et al., "Adaptive Closed-Loop Control Provides Blood-Glucose Regulation Using Subcutaneous Insulin and Glucagon Infusion in Diabetic Swine", Journal of Diabetes Science and Technology, 2007, vol. 1, No. 2, pp. 181-192.

Ellis, C. D., et al., "Selectivity and Directed Charge Transfer through an Electroactive Metallopolymer Film", Journal of the American Chemical Society, 1981, vol. 103, No. 25, pp. 7480-7483.

Engstrom, R. C., "Electrochemical Pretreatment of Glassy Carbon Electrodes", Analytical Chemistry, 1982, vol. 54, No. 13, pp. 2310-2314.

Engstrom, R. C., et al., "Characterization of Electrochemically Pretreated Glassy Carbon Electrodes", Analytical Chemistry, 1984, vol. 56, No. 2, pp. 136-141.

Facchinetti, A., et al., "A New Index to Optimally Design and Compare Continuous Glucose Monitoring Glucose Prediction Algorithms", Diabetes Technology & Therapeutics, 2011, vol. 13, No. 2, pp. 111-119.

Feldman, B., et al., "Electron Transfer Kinetics at Redox Polymer/Solution Interfaces Using Microelectrodes and Twin Electrode Thin Layer Cells", Journal of ElectroAnalytical Chemistry, 1985, vol. 194, pp. 63-81.

Feldman, B., et al., "A Continuous Glucose Sensor Based on Wired Enzyme™ Technology—Results from a 3-Day Trial in Patients with Type 1 Diabetes", Diabetes Technology & Therapeutics, 2003, vol. 5, No. 5, pp. 769-779.

Feldman, B., et al., "Correlation of Glucose Concentrations in Interstitial Fluid and Venous Blood During Periods of Rapid Glucose Change", Abbott Diabetes Care, Inc. Freestyle Navigator Continuous Glucose Monitor Pamphlet, 2004.

File History of U.S. Pat. No. 10,292,632.

File History of U.S. Pat. No. 10,945,649.

File History of U.S. Pat. No. 11,013,440.

U.S. Appl. No. 60/587,787.

U.S. Appl. No. 12/250,760.

Fischer, H., et al., "Intramolecular Electron Transfer Medicated by 4,4'-Bypyridine and Related Bridging Groups", Journal of the American Chemical Society, 1976, vol. 98, No. 18, pp. 5512-5517.

Foulds, N. C., et al., "Enzyme Entrapment in Electrically Conducting Polymers: Immobilisation of Glucose Oxidase in Polypyrrole and its Application in Amperometric Glucose Sensors", Journal of the Chemical Society, Faraday Transactions 1, 1986, vol. 82, pp. 1259-1264.

Foulds, N. C., et al., "Immobilization of Glucose Oxidase in Ferrocene-Modified Pyrrole Polymers", Analytical Chemistry, 1988, vol. 60, No. 22, pp. 2473-2478.

Freedman, D., et al., Statistics: Second Edition, 1991, Chapters, p. 74.

Freestyle Navigator Continuous Glucose Monitor FDA Premarket Approval (PMA), May 2022, pp. 1-6.

Freestyle Navigator Summary of Safety and Effectiveness Data, 2008, pp. 1-27.

Freestyle Navigator User's Guide, 2008, pp. 1-195.

Frenzel, L. E., "Printed-Circuit-Board Antennas", retrieved from https://www.electronicdesign.com/technologies/boards/article/21751417/printedcircuitboard-antennasprint/3266, Electronic Design, 2005, pp. 1-4.

Frew, J. E., et al., "Electron-Transfer Biosensors", Philosophical Transactions of the Royal Society of London, 1987, vol. 316, pp. 95-106.

Fujipoly Silver ZEBRA® Connector Data Sheet FSDS 01-34, Version 5, 2006, pp. 1-7.

Garg, S., et al., "Improvement in Glycemic Excursions with a Transcutaneous, Real-Time Continuous Glucose Sensor", Diabetes Care, 2006, vol. 29, No. 1, pp. 44-50.

Garibotto, J., et al., "An Innovative Application of Shape Memory Alloy Technology Yields a Novel Therapeutic Approach to Diabetes Management", Insulet Corporation, p. A41.

Gilligan, B. J., et al., "Evaluation of a Subcutaneous Glucose Sensor out to 3 Months in a Dog Model", Diabetes Care, 1994, vol. 17, No. 8, pp. 882-887.

Gonzales, W. V., et al., "The Progress of Glucose Monitoring—A Review of Invasive to Minimally and Non-Invasive Techniques, Devices and Sensors", Sensors, 2019, vol. 19, No. 800, pp. 1-45.

Gonzalez, O. L., et al., "Low-Cost Wireless Sensors—Designer Reference Manual", Freescale Semiconductor, 2007, pp. 1-146.

Gorton, L., et al., "Selective Detection in Flow Analysis Based on the Combination of Immobilized Enzymes and Chemically Modified Electrodes", Analytica Chimica Acta, 1991, vol. 250, pp. 203-248.

Gregg, B. A., et al., "Cross-Linked Redox Gels Containing Glucose Oxidase for Amperometric Biosensor Applications," Analytical Chemistry, 1990, vol. 62, No. 3, pp. 258-263.

Gregg, B. A., et al., "Redox Polymer Films Containing Enzymes. 1. A Redox-Conducting Epoxy Cement: Synthesis, Characterization, and Electrocatalytic Oxidation of Hydroquinone", Journal of Physical Chemistry, 1991, vol. 95, No. 15, pp. 5970-5975.

Gregg, T. H., "How Continuous Glucose Monitoring is Transforming Diabetes Treatment", Qualcomm Life Connect, 2013, pp. 1-33.

Guardian® RT Continuous Glucose Monitoring System Ref MMT-7900 User Guide, 2005, pp. 1-128.

Guerra, S., et al., "A Dynamic Risk Measure from Continuous Glucose Monitoring Data", Diabetes Technology & Therapeutics, 2011, vol. 13, No. 8, pp. 843-852.

Güler, N. F., et al., "Theory and Applications of Biotelemetry", Journal of Medical Systems, 2002, vol. 26, No. 2, pp. 159-178.

Gunasingham, et al., "Electrochemically Modulated Optrode for Glucose", Biosensors & Bioelectronics, 1992, vol. 7, pp. 353-359.

Hale, P. D., et al., "A New Class of Amperometric Biosensor Incorporating a Polymeric Electron-Transfer Mediator", Journal of the American Chemical Society, 1989, vol. 111, No. 9, pp. 3482-3484.

Hao, Y., "Wireless body sensor networks for health-monitoring applications", Physiol. Meas., 2008, vol. 29, R27-R56.

Harrison, D. J. et al., "Characterization of Perfluorosulfonic Acid Polymer Coated Enzyme Electrodes and a Miniaturized Integrated Potentiostat for Glucose Analysis in Whole Blood," Anal. Chem., 1988, vol. 60, No. 19, pp. 2002-2007.

Hawkridge, F. M., et al., "Indirect Coulometric Titration of Biological Electron Transport Components", Analytical Chemistry, 1973, vol. 45, No. 7, pp. 1021-1027.

Heftman, G., "Chip Antenna Reduces Cell-Phone Dimensions", Microwaves & RF, 1999, p. 182.

Heise, T., et al., "Hypoglycemia Warning Signal and Glucose Sensors: Requirements and Concepts", Diabetes Technology & Therapeutics, 2003, vol. 5, No. 4, pp. 563-571.

Heller, A., "Electrical Connection of Enzyme Redox Centers to Electrodes," J. Phys. Chem., 1992, vol. 96, No. 9, pp. 3579-3587.

Heller, A., "Electrical Wiring of Redox Enzymes," Acc. Chem. Res., 1990, vol. 23, No. 5, pp. 129-134.

Heller, A., et al., "Amperometric Biosensors Based on Three-Dimensional Hydrogel-Forming Epoxy Networks", Sensors and Actuators B, 1993, vol. 13-14, pp. 180-183.

Heller, A., "Implanted Electrochemical Glucose Sensors for the Management of Diabetes", Annnu. Rev. Biomed. Eng., 1999, vol. 1, pp. 153-175.

Hirsch, I. B., "Introduction: History of Glucose Monitoring", Clinical Compendia, 2018, vol. 2018, No. 1, 1 page.

Hoel, P. G., Elementary Statistics: Fourth Edition, 1976, Chapters, pp. 113-114.

Howe, D., "Comparing the Dexcom G6 to the G5", 2018, retrieved from https://beyondtype1.org/comparing-the-dexcom-g6-to-the-g5Z, pp. 1-10.

Huang, Y., et al., "Antennas from Theory to Practice", 2008, Chapter 8, Antenna Diversity, pp. 322-325.

Ianniello, R. M., et al., "Immobilized Enzyme Chemically Modified Electrode as an Amperometric Sensor", Analytical Chemistry, 1981, vol. 53, No. 13, pp. 2090-2095.

(56)        References Cited

OTHER PUBLICATIONS

Ianniello, R. M., et al., "Differential Pulse Voltammetric Study of Direct Electron Transfer in Glucose Oxidase Chemically Modified Graphite Electrodes", Analytical Chemistry, 1982, vol. 54, No. 7, pp. 1098-1101.

Ikeda, T., et al., "Kinetics of Outer-Sphere Electron Transfers Between Metal Complexes in Solutions and Polymeric Films on Modified Electrodes", Journal of the American Chemical Society, 1981, vol. 103, No. 25, pp. 7422-7425.

Ikeda, T., et al., "Glucose Oxidase-Immobilized Benzoquinone-Carbon Paste Electrode as a Glucose Sensor", Agricultural and Biological Chemistry, 1985, vol. 49, No. 2, pp. 541-543.

Ikeda, T., et al., "Artificial Pancreas—Investigation of the Stability of Glucose Sensors Using a Telemetry System" (English language translation of abstract), Jpn. J. Artif. Organs, 1990, vol. 19, No. 2, pp. 889-892.

"In Vitro Diagnostic Products for Human Use", Federal Register, 1974, vol. 39, No. 126, pp. 24136-24147.

Isermann, R., "Supervision, Fault-Detection and Fault-Diagnosis Methods—An Introduction", Control Engineering Practice, 1997, vol. 5, No. 5, pp. 639-652.

Isermann, R., et al., "Trends in the Application of Model-Based Fault Detection and Diagnosis of Technical Processes", Control Engineering Practice, 1997, vol. 5, No. 5, pp. 709-719.

Jain, A.K., et al., "Wound Rotor Induction Generator With Sensorless Control and Integrated Active Filter for Feeding Nonlinear Loads in a Stand-Alone Grid", IEEE Transactions on Industrial Electronics, 2008, vol. 55, No. 1, pp. 218-228.

James, Jr., et al., "Handbook of Microstrip Antennas", 1969, pp. 1038-1047.

Johnson, J. M., et al., "Potential-Dependent Enzymatic Activity in an Enzyme Thin-Layer Cell", Analytical Chemistry, 1982, vol. 54, No. 8, pp. 1377-1383.

Johnson, K. W., "Reproducible Electrodeposition of Biomolecules for the Fabrication of Miniature Electroenzymatic Biosensors", Sensors and Actuators B, 1991, vol. 5, pp. 85-89.

Johnson, K. W., et al., "In vivo evaluation of an electroenzymatic glucose sensor implanted in subcutaneous tissue," Biosensors and Bioelectronics, 1992, vol. 7, pp. 709-714.

Johnson, P. C., "Peripheral Circulation", John Wiley & Sons, 1978, p. 198.

Jönsson, G., et al., "An Amperometric Glucose Sensor Made by Modification of a Graphite Electrode Surface With Immobilized Glucose Oxidase and Adsorbed Mediator", Biosensors, 1985, vol. 1, pp. 355-368.

Josowicz, M., et al., "Electrochemical Pretreatment of Thin Film Platinum Electrodes", Journal of the Electrochemical Society, 1988, vol. 135, No. 1, pp. 112-115.

Jovanovic, L., "The Role of Continuous Glucose Monitoring in Gestational Diabetes Mellitus", Diabetes Technology & Therapeutics, 2000, vol. 2, Supplement 1, pp. S-67-S-71.

Jungheim, K., et al., "How Rapid Does Glucose Concentration Change in Daily Life of Patients with Type 1 Diabetes?", 2002, pp. 250.

Jungheim, K., et al., "Risky Delay of Hypoglycemia Detection by Glucose Monitoring at the Arm", Diabetes Care, 2001, vol. 24, No. 7, pp. 1303-1304.

Kaplan, S. M., "Wiley Electrical and Electronics Engineering Dictionary", IEEE Press, 2004, pp. 141, 142, 548, 549.

Katakis, I., et al., "L-α-Glycerophosphate and L-Lactate Electrodes Based on the Electrochemical 'Wiring' of Oxidases", Analytical Chemistry, 1992, vol. 6 4, No. 9, pp. 1008-1013.

Katakis, I., et al., "Electrostatic Control of the Electron Transfer Enabling Binding of Recombinant Glucose Oxidase and Redox Polyelectrolytes", Journal of the American Chemical Society, 1994, vol. 116, No. 8, pp. 3617-3618.

Kenausis, G., et al., "'Wiring' of Glucose Oxidase and Lactate Oxidase Within a Hydrogel Made with Poly(vinyl pyridine) complexed with [Os(4,4'-dimethoxy-2,2'-bipyridine)$_2$Cl]$^{+2/2+}$", Journal of the Chemical Society, Faraday Transactions, 1996, vol. 92, No. 20, pp. 4131-4136.

Klonoff, D. C., "A Review of Continuous Glucose Monitoring Technology", Diabetes Technology & Therapeutics, 2005, vol. 7, No. 5, pp. 770-775.

Kondepati, V., et al., "Recent Progress in Analytical Instrumentation for Glycemic Control in Diabetic and Critically Ill Patients", Analytical Bioanalytical Chemistry, 2007, vol. 388, pp. 545-563.

Koudelka, M., et al., "In-Vivo Behaviour of Hypodermically Implanted Microfabricated Glucose Sensors", Biosensors & Bioelectronics, 1991, vol. 6, pp. 31-36.

Kulys, J., et al., "Mediatorless Peroxidase Electrode and Preparation of Bienzyme Sensors", Bioelectrochemistry and Bioenergetics, 1990, vol. 24, pp. 305-311.

Lager, W., et al., "Implantable Electrocatalytic Glucose Sensor", Hormone Metabolic Research, 1994, vol. 26, pp. 526-530.

León, L. P., et al., "Continuous-Flow Analysis for Glucose in Serum, with Use of Hexokinase and Glucose-6-Phosphate Dehydrogenase Co-Immobilized in Tubular Form", Clinical Chemistry, 1980, vol. 26, No. 1, pp. 123-129.

Lindner, E., et al., "Flexible (Kapton-Based) Microsensor Arrays of High Stability for Cardiovascular Applications", Journal of the Chemical Society, Faraday Transactions, 1993, vol. 89, No. 2, pp. 361-367.

Lo, B., et al., "Key Technical Challenges and Current Implementations of Body Sensor Networks", Body Sensor Networks, 2005, pp. 1-5.

Lodwig, V., et al., "Continuous Glucose Monitoring with Glucose Sensors: Calibration and Assessment Criteria", Diabetes Technology & Therapeutics, 2003, vol. 5, No. 4, pp. 573-587.

Lortz, J., et al., "What is Bluetooth? We Explain The Newest Short-Range Connectivity Technology", Smart Computing Learning Series, Wireless Computing, 2002, vol. 8, Issue 5, pp. 72-74.

Loy, M., et al., "ISM-Band and Short Range Device Antennas", Texas Instruments Application Report, 2005, pp. 1-38.

Maidan, R. et al., "Elimination of Electroaxidizable Interferant-Produced Currents in Amperometric Biosensors," Analytical Chemistry, 1992, vol. 64, No. 23, pp. 2889-2896.

Malin, S. F., et al., "Noninvasive Prediction of Glucose by Near-Infrared Diffuse Reflectance Spectoscopy", Clinical Chemistry, 1999, vol. 45, No. 9, pp. 1651-1658.

Mastrototaro, J.J., et al., "An Electroenzymatic Glucose Sensor Fabricated on a Flexible Substrate," Sensors and Biosensors B Chemical, 1991, B5, pp. 139-144.

McGarraugh, G., et al., "Glucose Measurements Using Blood Extracted from the Forearm and the Finger", TheraSense, Inc., 2001, 16 Pages.

McGarraugh, G., et al., "Physiological Influences on Off-Finger Glucose Testing", Diabetes Technology & Therapeutics, 2001, vol. 3, No. 3, pp. 367-376.

McKean, B., et al., "A Telemetry-Instrumentation System for Chronically Implanted Glucose and Oxygen Sensors," IEEE Transactions on Biomedical Engineering, 1988, vol. 35, No. 7, pp. 526-532.

McNeil, C. J., et al., "Thermostable Reduced Nicotinamide Adenine Dinucleotide Oxidase: Application to Amperometric Enzyme Assay", Analytical Chemistry, 1989, vol. 61, No. 1, pp. 25-29.

Medtronic Guardian® REAL-Time Continuous Glucose Monitoring System User Guide, 2006, pp. 1-184.

IPR2022-00605 (Ex. 1027) The Merriam-Webster Dictionary, Merriam Webster, Incorporated (2005), pp. 66, 403, and 415.

Microchip Technology Inc., MRF24J40MA Data Sheet, 2008, pp. 1-30.

IPR2022-00605 (Ex. 2008) MiniMed® Glucose Sensor, Ref MMT-7002, Instructions for Use, pp. 1-4.

MINIMED Technologies, "Tape Tips and Other Infusion Site Information", 1995.

MINIMED Quick-set™ retrieved from https://web.archive.org/web/20010412224824/http://www.minimed.com/patientfam/pf_ipt_pumpinfusion_quickset.shtml, Apr. 12, 2001, pp. 1-2.

(56) References Cited

OTHER PUBLICATIONS

MINIMED Sof-set Micro QR® Sof-set Ultimate QR® retrieved from https://web.archive.org/web/20010412225617/http://www.minimed.com/patientfam/pf_ipt_pumpinfusion_sofset.shtml, Apr. 12, 2001, pp. 1-2.

Miyawaki, O., et al., "Electrochemical and Glucose Oxidase Coenzyme Activity of Flavin Adenine Dinucleotide Covalently Attached to Glassy Carbon at the Adenine Amino Group", Biochimica et Biophysica Acta, 1985, vol. 838, pp. 60-68.

Moatti-Sirat, D., et al., "Evaluating In Vitro and In Vivo the Interference of Ascorbate and Acetaminophen on Glucose Detection by a Needle-Type Glucose Sensor", Biosensors & Bioelectronics, 1992, vol. 7, pp. 345-352.

Moatti-Sirat, D., et al., "Reduction of Acetaminophen Interference in Glucose Sensors by a Composite Nation Membrane: Demonstration in Rats and Man", Diabetologia, 1994, vol. 37, pp. 610-616.

Moatti-Sirat, D., et al., "Towards Continuous Glucose Monitoring: In Vivo Evaluation of a Miniaturized Glucose Sensor Implanted for Several Days in Rat Subcutaneous Tissue," Diabetolocia, 1992, vol. 35, No. 3 (1 page—Abstract only).

IPR2022-00605 (Ex. 2003) "Monitoring Your Blood Sugar", retrieved from https://www.cdc.gov/diabetes/managing/managing-blood-sugar/bloodglucosemonitoring.html, pp. 1-3.

Moore, B., "The Potential Use of Radio Frequency Identification Devices for Active Monitoring of Blood Glucose Levels", Journal of Diabetes Science and Technology, 2009, vol. 3, No. 1, pp. 180-183.

Morak, J., et al., "Design and Evaluation of a Telemonitoring Concept Based on NFC-Enabled Phones and Sensor Devices", IEEE Transactions on Information Technology in Biomedicine, 2012, vol. 16, No. 1, pp. 17-23.

Morbiducci, U., et al., "Improved Usability of the Minimal Model of Insulin Sensitivity Based on an Automated Approach and Genetic algorithms for Parameter Estimation", Clinical Science, vol. 112, 2007, pp. 257-263.

Mougiakakou, S. G., et al., "A Real Time Simulation Model of Glucose-Insulin Metabolism for Type 1 Diabetes Patients", Proceedings of the 2005 IEEE, 2005, pp. 298-301.

Movassaghi, S., et al., "Wireless Technologies for Body Area Networks: Characteristics and Challenges", 2012 International Symposium on Communications and Information Technologies (ISCIT), 2012, Gold Coast, QLD, Australia, pp. 42-47.

"Murata Puts Antenna on a Chip", Passives, 1999, vol. 44, 1 page.

Nagy, G., et al., "A New Type of Enzyme Electrode: The Ascorbic Acid Eliminator Electrode", Life Sciences, 1982, vol. 31, No. 23, pp. 2611-2616.

Nakamura, S., et al., "Effect of Periodate Oxidation on the Structure and Properties of Glucose Oxidase", Biochimica et Biophysica Acta., 1976, vol. 445, pp. 294-308.

Narasimham, K., et al., "p-Benzoquinone Activation of Metal Oxide Electrodes for Attachment of Enzymes", Enzyme and Microbial Technology, 1985, vol. 7, pp. 283-286.

Ohara, T. J., et al., "Glucose Electrodes Based on Cross-Linked [Os(bpy)₂Cl]$^{+/2+}$ Complexed Poly(1-vinylimadazole) Films," Analytical Chemistry, 1993, vol. 65, No. 23, pp. 3512-3516.

Ohara, T. J., et al., "'Wired' Enzyme Electrodes for Amperometric Determination of Glucose or Lactate in the Presence of Interfering Substances", Analytical Chemistry, 1994, vol. 66, No. 15, pp. 2451-2457.

Ohara, T. J., "Osmium Bipyridyl Redox Polymers Used in Enzyme Electrodes", Platinum Metals Review, 1995, vol. 39, No. 2, pp. 54-62.

Olievier, C. N., et al., "In Vivo Measurement of Carbon Dioxide Tension with a Miniature Electrodes", Pflugers Archiv: European Journal of Physiology, 1978, vol. 373, pp. 269-272.

OmniPod Insulet UST400 User Manual, 2011, pp. 1-190.

Opinion of the Court, Supreme Court of the United States, No. 04-1350, *KSR International* co., Petitioner v. *Teleflex Inc. et al.*, Apr. 30, 2007.

Osmonics, Poretics® Polycarbonate Membrane; Product Leaflet; Engineering Purity, 2002, pp. 1-2.

Paddock, R. M., et al., "Electrocatalytic Reduction of Hydrogen Peroxide via Direct Electron Transfer From Pyrolytic Graphite Electrodes to Irreversibly Adsorbed Cyctochrome C Peroxidase", Journal of ElectroAnalytical Chemistry, 1989, vol. 260, pp. 487-494.

Palleschi, G., et al., "A Study of Interferences in Glucose Measurements in Blood by Hydrogen Peroxide Based Glucose Probes", Analytical Biochemistry, 1986, vol. 159, pp. 114-121.

Pankratov, I., et al., "Sol-Gel Derived Renewable-Surface Biosensors", Journal of ElectroAnalytical Chemistry, 1995, vol. 393, pp. 35-41.

Parker, R., et al., "Robust $H_\infty$ Glucose Control in Diabetes Using a Physiological Model", AIChE Journal, 2000, vol. 46, No. 12, 2000, pp. 2537-2549.

Passey, R. B., et al., "Evaluation and Comparison of 10 Glucose Methods and the Reference Method Recommendation in the Proposed Product Class Standard (1974)", Clinical Chemistry, 1977, vol. 23, No. 1, pp. 131-139.

Pathak, C., et al., "Rapid Photopolymerization of Immunoprotective Gels in Contact with Cells and Tissue", Journal of the American Chemical Society, 1992, vol. 114, No. 21, pp. 8311-8312.

Patton, S. R., et al., "Continuous Glucose Monitoring Versus Self-monitoring of Blood Glucose in Children with Type 1 Diabetes—Are there Pros and Cons for Both?", US Endocrinol., 2012, vol. 8, No. 1, pp. 27-29.

Pickup, J., "Developing Glucose Sensors for In Vivo Use", Tibtech, 1993, vol. 11, pp. 285-291.

Pickup, J., et al., "Implantable Glucose Sensors: Choosing the Appropriate Sensing Strategy", Biosensors, 1987/88, vol. 3, pp. 335-346.

Pickup, J. C., et al., "In Vivo Molecular Sensing in Diabetes Mellitus: An Implantable Glucose Sensor With Direct Electron Transfer," Diabetologia, 1989, vol. 32, No. 3, pp. 213-217.

Pickup, J., et al., "Potentially-Implantable, Amperometric Glucose Sensors with Mediated Electron Transfer: Improving the Operating Stability", Biosensors, 1989, vol. 4, pp. 109-119.

Pishko, M. V., et al., "Amperometric Glucose Microelectrodes Prepared Through Immobilization of Glucose Oxidase in Redox Hydrogels," Anal. Chem., 1991, vol. 63, No. 20, pp. 2268-2272.

Poitout, V., et al., "A Glucose Monitoring System for on Line Estimation in Man of Blood Glucose Concentration Using a Miniaturized Glucose Sensor Implanted in the Subcutaneous Tissue and a Wearable Control Unit", Diabetologia, 1993, vol. 36, pp. 658-663.

Poitout, V., et al., "Calibration in Dogs of a Subcutaneous Miniaturized Glucose Sensor Using a Glucose Meter for Blood Glucose Determination", Biosensors & Bioelectronics, 1992, vol. 7, pp. 587-592.

Poitout, V., et al., "In Vitro and in Vivo Evaluation in Dogs of a Miniaturized Glucose Sensor," ASAIO Transactions, 1991, vol. 37, No. 3 (1 page—Abstract only).

Pollak, A., et al., "Enzyme Immobilization by Condensation Copolymerization into Cross-Linked Polyacrylamide Gels", Journal of the American Chemical Society, 1980, vol. 102, No. 20, pp. 6324-6336.

Quinn, C. P., et al., "Kinetics of Glucose Delivery to Subcutaneous Tissue in Rats Measured with 0.3-mm Amperometric Microsensors", The American Physiological Society, 1995, E155-E161.

Ratner, B. D., "Reducing Capsular Thickness and Enhancing Angeiogenesis Around Implant Drug Release Systems", Journal of Controlled Release, 2002, vol. 78, pp. 211-218.

Reach, G., et al., "Can Continuous Glucose Monitoring Be Used for the Treatment of Diabetes?," Analytical Chemistry, 1992, vol. 64, No. 6, pp. 381-386.

Rebrin, K., et al., "Automated Feedback Control of Subcutaneous Glucose Concentration in Diabetic Dogs," Diabetologia, 1989, vol. 32, No. 8, pp. 573-576.

Repas, R., "Sensor Sense: RFID for smart position sensing", retrieved from https://www/machinedesign/com/automation-iiot/article/21818777/sensor-sense-rfid-for-smart-position-sensing, 2010, pp. 1-2.

(56) References Cited

OTHER PUBLICATIONS

Rodriguez, N., et al., "Flexible Communication and Control Protocol for Injectable Neuromuscular Interfaces", IEEE Transactions on Biomedical Circuits and Systems, 2007, vol. 1, No. 1, pp. 19-27.

Roe, J. N., et al., "Bloodless Glucose Measurements", Critical Review in Therapeutic Drug Carrier Systems, vol. 15, Issue 3, 1998, pp. 199-241.

IPR2022-00605 (Ex. 1024) "Rotor," Dictionary of Mechanical Engineering, Fourth Ed., G.H.F. Nayler, Society of Automotive Engineers, Inc., 1996, p. 328.

IPR2022-00605 (Ex. 1025) "Rotor," Random House Kernerman Webster's College Dictionary, K Dictionaries Ltd. (2010), available at https://www.thefreedictionary.com/rotor.

IPR2022-00605 (Ex. 1026) "Rotate," Random House Kernerman Webster's College Dictionary, K Dictionaries Ltd. (2010), available at https://www.thefreedictionary.com/rotate.

Sakakida, M., et al., "Ferrocene-mediated needle-type glucose sensor covered with newly designed biocompatible membrane," Sensors and Actuators B, 1993, vols. 13-14, pp. 319-322.

Sakakida, M., et al., "Development of ferrocene-mediated needle-type glucose sensor as a measure of true subcutaneous tissue glucose concentrations", Artif Organs Today, 1992, vol. 2, No. 2, pp. 145-458.

Salditt, P., "Trends in Medical Device Design and Manufacturing", SMTA News and Journal of Surface Mount Technology, 2004, vol. 17, pp. 19-24.

Salehi, C., et al., "A Telemetry-Instrumentation System for Long-Term Implantable Glucose and Oxygen Sensors", Analytical Letters, 1996, vol. 29, No. 13, pp. 2289-2308.

Samuels, G. J., et al., "An Electrode-Supported Oxidation Catalyst Based on Ruthenium (IV). pH "Encapsulation" in a Polymer Film", Journal of the American Chemical Society, 1981, vol. 103, No. 2, pp. 307-312.

Sandham, W., et al., "Blood Glucose Prediction for Diabetes Therapy Using a Recurrent Artificial Neural Network", $9^{th}$ European Signal Processing Conference, 1998, Rhodes, Greece, pp. 1-4.

Sasso, S. V., et al., "Electropolymerized 1,2-Diaminobenzene as a Means to Prevent Interferences and Fouling and to Stabilize Immobilized Enzyme in Electrochemical Biosensors", Analytical Chemistry, 1990, vol. 62, No. 11, pp. 1111-1117.

IPR2022-00605 (Ex. 1013) Scheduling Order in *Abbott Diabetes Care Inc.*, et al. v. *Dexcom, Inc.*, 1:21-cv-00977 (D. Del.), dated Dec. 2, 2021.

Scheller, F., et al., "Enzyme Electrodes and Their Application", Philosophical Transactions of the Royal Society of London B, 1987, vol. 316, pp. 85-94.

Schmehl, R. H., et al., "The Effect of Redox Site Concentration on the Rate of Mediated Oxidation of Solution Substrates by a Redox Copolymer Film", Journal of ElectroAnalytical Chemistry, 1983, vol. 152, pp. 97-109.

Schmidt, F. J., et al., "Calibration of a Wearable Glucose Sensor", The International Journal of Artificial Organs, 1992, vol. 15, No. 1, pp. 55-61.

Schmidtke, D. W., et al., "Measurement and Modeling of the Transient Difference Between Blood and Subcutaneous Glucose Concentrations in the Rat After Injection of Insulin", Proceedings of the National Academy of Sciences, 1998, vol. 95, pp. 294-299.

Schoepke, E., "Chip Antenna Layout Considerations for 802.11 Applications", Johanson Technology, 2006, retrieved from https://www.johansontechnology.com/chip-antenna-layout-considerations-for-802-11-applications, pp. 1-7.

Sharawi, M. S., "Use of low-cost patch antennas in modern wireless technology", IEEE Potentials, 2006, pp. 35-38 and 47.

Shaw, G. W., et al., "In Vitro Testing of a Simply Constructed, Highly Stable Glucose Sensor Suitable for Implantation in Diabetic Patients", Biosensors & Bioelectronics, 1991, vol. 6, pp. 401-406.

Shichiri, M., et al., "Glycaemic Control in Pancrearetomized Dogs with a Wearable Artificial Endocrine Pancreas," Diabetologia, 1983, vol. 24, No. 3, pp. 179-118.

Shichiri, M., et al., "Membrane Design for Extending the Long-Life of an Implantable Glucose Sensor", Diabetes Nutrition and Metabolism, 1989, vol. 2, pp. 309-313.

Shichiri, M., et al., "Needle-type Glucose Sensor for Wearable Artificial Endocrine Pancreas", Implantable Sensors for Closed-Loop Prosthetic Systems, Chapter 15, 1985, pp. 197-210.

Shichiri, M., et al., "Telemetry Glucose Monitoring Device with Needle-type Glucose Sensor: A Useful Tool for Blood Glucose Monitoring in Diabetic Individuals," Diabetes Care, 1986, vol. 9, No. 3, pp. 298-301.

Shichiri, M., et al., "In Vivo Characteristics of Needle-Type Glucose Sensor—Measurement of Subcutaneous Glucose Concentrations in Human Volunteers," Horm Metab Res Suppl. 1988, vol. 20, pp. 17-20.

Shichiri, M., et al., "Wearable Artificial Endocrine Pancreas With Needle-Type Glucose Sensor," The Lancet, 1982, vol. 2, No. 8308, pp. 1129-1131.

Shults, M., "A Telemetry-Instrumentation System for Monitoring Multiple Subcutaneously Implanted Glucose Sensors," IEEE Transactions on Biomedical Engineering, 1994, vol. 41, No. 10, pp. 937-942.

Sittampalam, G., et al., "Surface-Modified Electrochemical Detector for Liquid Chromatography", Analytical Chemistry, 1983, vol. 55, No. 9, pp. 1608-1610.

Soegijoko, S., et al., "External Artificial Pancreas: A New Control Unit Using Microprocessor", Hormone and Metabolic Research Supplement Series, 1982, vol. 12, pp. 165-169.

Sparacino, G., et al., "Glucose Concentration Can Be Predicted Ahead in Time from Continuous Glucose Monitoring Sensor Time-Series", IEEE Transactions on Biomedical Engineering, 2007, vol. 54, No. 5, pp. 931-937.

Sprules, S. D., et al., "Evaluation of a New Disposable Screen-Printed Sensor Strip for the Measurement of NADH and Its Modification to Produce a Lactate Biosensor Employing Microliter Volumes", Electroanalysis, 1996, vol. 8, No. 6, pp. 539-543.

Sternberg, F., et al., "Calibration Problems of Subcutaneous Glucosensors when Applied "In-Situ" in Man", Hormone and Metabolic Research, 1994, vol. 26, pp. 523-526.

Sternberg, R., et al., "Covalent Enzyme Coupling on Cellulose Acetate Membranes for Glucose Sensor Development", Analytical Chemistry, 1988, vol. 60, No. 24, pp. 2781-2786.

Sternberg, R., et al., "Study and Development of Multilayer Needle-type Enzyme-based Glucose Microsensors", Biosensors, 1988, vol. 4, pp. 27-40.

Suekane, M., et al., "Immobilization of Glucose Isomerase", Zettschrift fur Allgemeine Mikrobiologie, 1982, vol. 22, No. 8, pp. 565-576.

Tajima, S., et al., "Simultaneous Determination of Glucose and 1,5-Anydroglucitol", Chemical Abstracts, 1989, vol. 111, No. 25, p. 394.

Tarasevich, M. R., "Bioelectrocatalysis", Comprehensive Treatise of Electrochemistry, 1985, vol. 10, pp. 231-295.

Tatsuma, T., et al., "Enzyme Monolayer- and Bilayer-Modified Tin Oxide Electrodes for the Determination of Hydrogen Peroxide and Glucose", Analytical Chemistry, 1989, vol. 61, No. 21, pp. 2352-2355.

Taylor, C., et al., ""Wiring" of Glucose Oxidase Within a Hydrogel Made with Polyvinyl Imidazole Complexed with [(Os-4,4'-dimethoxy-2,2'-bipyridine)Cl]$^{+/2+}$", Journal of ElectroAnalytical Chemistry, 1995, vol. 396, pp. 511-515.

Thompson, M., et al., "In Vivo Probes: Problems and Perspectives", Clinical Biochemistry, 1986, vol. 19, pp. 255-261.

Townsend, K., et al., "Getting Started with Bluetooth Low Energy—Chapter 1", 2014, pp. 1-26.

Trojanowicz, M., et al., "Enzyme Entrapped Polypyrrole Modified Electrode for Flow-Injection Determination of Glucose", Biosensors & Bioelectronics, 1990, vol. 5, pp. 149-156.

Tung, S., "Layers of Security for Active RFID Tags", RFID Handbook: Applications, Technology, Security, and Privacy, Edited by Ehson, et al., Chapter 33, 2008, pp. 1-28.

Turner, A.P.F., et al., "Diabetes Mellitus: Biosensors for Research and Management", Biosensors, 1985, vol. 1, pp. 85-115.

(56)         References Cited

OTHER PUBLICATIONS

Turner, R.F.B., et al., "A Biocompatible Enzyme Electrode for Continuous in vivo Glucose Monitoring in Whole Blood", Sensors and Actuators B, 1990, vol. 1, pp. 561-564.

Tuzhi, P., et al., "Constant Potential Pretreatment of Carbon Fiber Electrodes for in Vivo Electrochemistry", Analytical Letters, 1991, vol. 24, No. 6, pp. 935-945.

Umana, M., "Protein-Modified Electrochemically Active Biomaterial Surface", U.S. Army Research Office, Analytical and Chemical Sciences Research Triangle Institute, 1988, pp. 1-9.

United States Court of Appeals for the Federal Circuit, No. 06-1402, *Leapfrog Enterprises, Inc*, v. *Fisher-Price, Inc*, and *Mattel, Inc.*, May 9, 2007.

Updike, S. J., et al., "Principles of Long-term Fully Implanted Sensors with Emphasis on Radiotelemetric Monitoring of Blood Glucose from inside a Subcutaneous Foreign Body Capsule (FBC)", Biosensors in the Body: Continuous In vivo Monitoring, Chapter 4, 1997, pp. 117-137.

Updike, S. J., et al., "A Subcutaneous Glucose Sensor With Improved Longevity, Dynamic Range, and Stability of Calibration", Diabetes Care, 2000, vol. 23, pp. 208-214.

Urban, G., et al., "Miniaturized Thin-Film Biosensors Using Covalently Immobilized Glucose Oxidase", Biosensors & Bioelectronics, 1991, vol. 6, pp. 555-562.

Velho, G., et al., "In Vitro and In Vivo Stability of Electrode Potentials in Needle-Type Glucose Sensors", Diabetes, 1989, vol. 38, No. 2, pp. 164-171.

Velho, G. et al., "Strategies for Calibrating a Subcutaneous Glucose Sensor," Biomed. Biochim. Acta, 1989, 48 (11112), pp. 957-964.

Von Woedtke, T., et al., "In Situ Calibration of Implanted Electrochemical Glucose Sensors", Biomedica Biochimica Acta, 1989, vol. 48, pp. 943-952.

Vreeke, M. S., et al., "Hydrogen Peroxide Electrodes Based on Electrical Connection of Redox Centers of Various Peroxidases to Electrodes through a Three-Dimensional Electron-Relaying Polymer Network", Diagnostic Biosensors Polymers, Chapter 15, 1993, pp. 180-193.

Vreeke, M., et al., "Hydrogen Peroxide and β-Nicotinamide Adenine Dinucleotide Sensing Amperometric Electrodes Based on Electrical Connection of Horseradish Peroxidase Redox Centers to Electrodes through a Three-Dimensional Electron Relaying Polymer Network", Analytical Chemistry, 1992, vol. 64, No. 24, pp. 3084-3090.

Wang, D. L., et al., "Miniaturized Flexible Amperometric Lactate Probe", Analytical Chemistry, 1993, vol. 65, No. 8, pp. 1069-1073.

Wang, J., et al., "Activation of Glassy Carbon Electrodes by Alternating Current Electrochemical Treatment", Analytica Chimica Acta, 1985, vol. 167, pp. 325-334.

Wang, J., et al., "Amperometric Biosensing of Organic Peroxides with Peroxidase-Modified Electrodes", Analytica Chimica Acta, 1991, vol. 254, pp. 81-88.

Wang, J., et al., "Screen-Printable Sol-Gel Enzyme-Containing Carbon Inks", Analytical Chemistry, 1996, vol. 68, No. 15, pp. 2705-2708.

Wang, J., et al., "Sol-Gel-Derived Metal-Dispersed Carbon Composite Amperometric Biosensors", Electroanalysis, 1997, vol. 9, No. 1, pp. 52-55.

Wang, X.H., et al., "Bluetooth: Opening a blue sky for healthcare", Mobile Information Systems, 2006, vol. 2, pp. 151-167.

Waterhouse, R., "Printed Antennas for Wireless Communications," 2007, pp. 116-129 and 284-289.

Williams, D. L., et al., "Electrochemical-Enzymatic Analysis of Blood Glucose and Lactate", Analytical Chemistry, 1970, vol. 42, No. 1, pp. 118-121.

Wilson, G. S., et al., "Progress Toward the Development of an Implantable Sensor for Glucose," Clinical Chemistry, 1992, vol. 38, No. 9, pp. 1613-1617.

Wong, KL, "Planar Antennas for Wireless Communications," 2003, Chapter 1, Introduction and Overview, pp. 4-17, 38-45, and 218-221.

Yabuki, S., et al., "Electro-Conductive Enzyme Membrane", Journal of the Chemical Society, Chemical Communications, 1989, pp. 945-946.

Yang, L., et al., "Determination of Oxidase Enzyme Substrates Using Cross-Flow Thin-Layer Amperometry", Electroanalysis, 1996, vol. 8, No. 8-9, pp. 716-721.

Yao, S. J., et al., "The Interference of Ascorbate and Urea in Low-Potential Electrochemical Glucose Sensing", Proceedings of the Twelfth Annual International Conference of the IEEE Engineering in Medicine and Biology Society, 1990, vol. 12, Part 2, pp. 487-489.

Yao, T., "A Chemically-Modified Enzyme Membrane Electrode as an Amperometric Glucose Sensor", Analytica Chimica Acta, 1983, vol. 148, pp. 27-33.

Ye, L. et al., "High Current Density "Wired" Quinoprotein Glucose Dehydrogenase Electroade," Anal. Chem., 1993, vol. 65, No. 3, pp. 238-241.

Yildiz, A., et al., "Evaluation of an Improved Thin-Layer Electrode", Analytical Chemistry, 1968, vol. 40, No. 7, pp. 1018-1024.

Zamzow, K., et al., "New Wearable Continuous Blood Glucose Monitor (BGM) and Artificial Pancreas (AP)", Diabetes, 1990, vol. 39, pp. 5A-20.

Z-Carbon Connector, retrieved from http://www.zaxisconnector.com/SS_zc.shtml, 2004, 2 pages.

Zhang, Y., et al., "Application of Cell Culture Toxicity Tests to the Development of Implantable Biosensors", Biosensors & Bioelectronics, 1991, vol. 6, pp. 653-661.

Zhang, Y., et al., "Elimination of the Acetaminophen Interference in an Implantable Glucose Sensor", Analytical Chemistry, 1994, vol. 66, No. 7, pp. 1183-1188.

Zhu, J., et al., "Fabrication and Characterization of Glucose Sensors Based on a Microarray $H_2O_2$ electrode", Biosensors & Bioelectronics, 1994, vol. 9, pp. 295-300.

Zisser, H. C., "The OmniPod Insulin Management System: the Latest Innovation in Insulin Pump Therapy", Diabetes Ther, 2010, vol. 1, No. 1, pp. 10-24.

Z-Silver Connector, retrieved from http://www.zaxisconnector.com/SS_zs.shtml, 2004, 2 pages.

U.S. Appl. No. 60/424,099, filed Nov. 5, 2002.

Medtronic MiniMed Sen-Serter® User Guide, 2006, pp. 1-96.

CA 3,120,335 Examiner's Report, dated Mar. 31, 2023.

CA 3,182,961 Examiner's Report, dated Mar. 29, 2023.

CN 201980082748.1 First Office Action, dated Jan. 10, 2023.

EP 20177703.4 Reply to Opposition, dated Feb. 22, 2023.

EP 20177712.5 Reply to Opposition, dated May 23, 2023.

JP 2021-531135 Office Action, dated Feb. 22, 2023.

WO PCT/US2012/062551 ISR and Written Opinion, dated Jan. 2, 2023.

WO PCT/US2023/010054 Invitation to Pay Additional Fee, dated Mar. 24, 2023.

CN 201980082748.1 Second Office Action, dated Jul. 10, 2023.

EP 20177703.4 Reply to Reply to Notice of Opposition, dated Jun. 29, 2023.

EP 20177703.4 Notice of Intervention, dated Jun. 23, 2023.

EP 20177712.5 Reply to Reply to Notice of Opposition, dated Aug. 30, 2023.

EP 20177712.5 Notice of Intervention, dated Jun. 23, 2023.

EP 20177712.5 Reply to Notice of Opposition, dated May 23, 2023.

EP 20195922.8 Reply to Notice of Intervention, dated Aug. 29, 2023.

EP 20195922.8 Reply to Reply to Notice of Opposition, dated Aug. 21, 2023.

EP 20195922.8 Reply to Notice of Opposition, Jun. 20, 2023.

EP 20195922.8 Notice of Intervention, dated Jun. 13, 2023.

MY PI2022007295 Examination Report, dated Jul. 11, 2023.

US Final Written Decision, IPR No. 2022-00605, dated Jul. 10, 2023.

WO PCT/US2012/062551 ISR and Written Opinion, dated Jan. 2, 2013.

WO PCT/US2023/010054 ISR and Written Opinion, dated May 15, 2023.

Anderson, A. J., "Foundations of Computer Technology", 1994, pp. 55-57.

(56)  References Cited

OTHER PUBLICATIONS

Kal, S., "Basic Electronics—Devices, Circuits and IT Fundamentals", 2006, Chapter 13, Microcomputers and Microprocessors, p. 412.

"Abbott Receives CE Mark for Freestyle® Libre, A Revolutionary Glucose Monitoring System for People With Diabetes", 2014, 7 pages.

"Alcove", Webster's New College Dictionary, 2001, p. 26.

Boise, M., "Dexcom CEO Kevin Sayer Explains G6", 2018, retrieved from https://beyondtype1.org/dexcom-ceo-kevin-sayer-explains-g6/, 9 pages.

Preliminary Amendment filed on Apr. 20, 2018 for U.S. Pat. No. 10,827,954, 7 pages.

Excerpts of the File History of U.S. Pat. No. 10,973,443, 22 pages.

CGMs Changing Diabetes Management: Kevin Sayer, DIC Interview Transcript, 2019, retrieved from https://www.diabetesincontrol.com/cgms-changing-diabetes-management-kevin-sayer-dic-interview-transcript/, 10 pages.

"Deciding When to Submit a 510(k) for a Change to an Existing Device, Guidance for Industry and Food and Drug Administration Staff", 2017, pp. 1-77.

"Deciding When to Submit a 510(k) for a Software Change to an Existing Device, Guidance for Industry and Food and Drug Administration Staff", 2017, pp. 1-31.

Dexcom CEO—Prime Position in Our Market—Mad Money—CNBC.mp4, Transcript 2023 by Sonix, 2 pages.

DexCom (DXCM) 2017 Q4 Earnings Call Transcript, 2017, retrieved from https://docoh.com/transcript/1093557/2017Q4/DXCM, 11 pages.

DexCom (DXCM) Q1 2018 Results—Earnings Call Transcript, 2018, retrieved from https://seekingalpha.com/article/4168949-dexcom-dxcm-q1-2018-results-earnings-call-transcript, 4 pages.

Dexcom, Inc. NasdaqGS:DXCM Company Conference Presentation, 2019, 10 pages.

Dexcom, Inc. NasdaqGS:DXCM Company Conference Presentation, 2020, 9 pages.

Dexcom, Inc. NasdaqGS:DXCM Company Conference Presentation, 2021, 16 pages.

Dexcom G6 Continuous Glucose Monitoring System User Guide, 2019, pp. 1-27.

Dexcom G6 Start Here Set up Guide, 2019, pp. 1-8.

Dexcom G6 Using Your G6 Guide, Mar. 2020, pp. 1-7.

Dexcom G7 Inserting Sensor Instructions for Use, 2021, pp. 1-2.

DexcomG7, Start Here, Operational Manual, 2022, pp. 1-9 (English Abstract).

Dexcom G7, User Guide, 2022, p. 1-179 (English Abstract).

Dexcom Seven® Plus Continuous Glucose Monitoring System User's Guide, 2011, pp. 1-144.

DexCom™ STS™M Continuous Glucose Monitoring System FDA Premarket Approval (PMA), 2006, pp. 1-7.

DexCom™ STS™M Continuous Glucose Monitoring System Summary of Safety and Effectiveness Data, 2006, 20 pages.

DexCom STS™M Sensor Instructions for Use, 2006, pp. 1-6.

Dexcom STS-7 Continuous Glucose Monitoring System FDA Premarket Approval (PMA), 2007, pp. 1-7.

Dexcom STS®-7 Continuous Glucose Monitoring System Summary of Safety and Effectiveness Data, 2007, 14 pages.

Dexcom STS®-7 Continuous Glucose Monitoring System User's Guide, 2007, pp. 1-74.

Diglas, J., et al., "Reduced pain perception with Pen Mate™, an automatic needle insertion device for use with an insulin pen", Practical Diabetes International, 1999, vol. 16, No. 2, pp. 39-41.

"Does Dexcom Really Have a Future If It Can't Match Abbott's Scale", 2019, retrieved from https://www.sprucepointcap.com/reports/dxcm_research_thesis_3-21-2019.pdf, p. 46.

Email from John Shaw of Shaw & Keller dated May 16, 2023, 2 pages.

Email chain from Sophie Hood, oldest email dated Jan. 24, 2023, 5 pages.

European Standard, ISO 11607-1, Packaging for terminally sterilized medical devices—Part 1: Requirements for materials, sterile barrier systems and packaging systems, 2006, 32 pages.

European Standard, ISO 13485, Medical devices—Quality management systems—Requirement for regulatory purposes, 2003, 69 pages.

European Standard, ISO 15197, In vitro diagnostic test systems—Requirements for blood glucose monitoring systems for self-testing in managing diabetes mellitus, 2003, 43 pages.

Explore The Monroe Street Market Community, Retrieved from https://www.monroestreetmarket.com/floor-plans/apartment/B-231, 2 pages.

"FDA authorizes first fully interoperable continuous glucose monitoring system, streamlines review pathway for similar devices", FDA News Release, 2018, retrieved from https://www.fda.gov/news-events/press-announcements/fda-authorizes-first-fully-interoperable-continuous-glucose-monitoring-system-streamlines-review, 3 pages.

Food and Drug Administration, HHS, 2009, Code of Federal Regulation § 820.30, Subpart C—Design Controls, pp. 147-148.

Freestyle Libre Pro Flash Glucose Monitoring System Summary of Safety and Effectiveness Data, 2016, 31 pages.

FreeStyle Lite Blood Glucose Monitoring System Owner's Booklet, 2006, 15 pages.

FreeStyle Navigator Continuous Glucose Monitoring System FDA Premarket Approval (PMA), 2008, pp. 1-7.

Hemmerich, K. J., et al., "Sterilization Methods Stand the Test of Time", 2004, retrieved from https://www.mddionline.com/sterilization/sterilization-methods-stand-test-time, pp. 1-8.

Hirsch, I. B., "Realistic Expectations and Practical Use of Continuous Glucose Monitoring for the Endocrinologist", The Journal of Clinical Endocrinology & Metabolism, 2009, VI. 94, No. 7, pp. 2232-2238.

Hoss, U., et al., "Continuous glucose monitoring in the tissue: Do we really need to calibrate in-vivo?", pp. 1-21.

Hoss, U., et al., "Continuous Glucose Monitoring in Subcutaneous Tissue Using Factory-Calibrated Sensors: A Pilot Study", Diabetes Technology & Therapeutics, 2010, vol. 12, No. 8, pp. 591-597.

Hoss, U., et al., "Feasibility of Factory Calibration for Subcutaneous Glucose Sensors in Subjects With Diabetes", Journal of Diabetes Science and Technology, 2014, vol. 8, No. 1, pp. 89-94.

"Housing", "recess", "release", and "retain", Merriam-Webster's Collegiate Dictionary, Tenth Edition, 1999, pp. 563, 975, 987, and 999.

"Housing" and "recess", The New Penguin English Dictionary, 2000, pp. 678 and 1167.

Hughes, M. D., "The Business of Self-Monitoring of Blood Glucose: A Market Profile", Journal of Diabetes Science and Technology, 2009, vol. 3, No. 5, pp. 1219-1223.

IEEE 100 The Authoritative Dictionary of IEEE Standards Terms, Seventh Edition, 2000, 3 pages.

International Standard, ISO 14971, Medical devices—Application of risk management to medical devices, 2007, 90 pages.

Klueh, U., et al., "Inflammation and Glucose Sensors: Use of Dexamethasone to Extend Glucose Sensor Function and Life Span in Vivo", Journal of Diabetes Science and Technology, 2007, vol. 1, No. 4, pp. 496-504.

Klueh, U., et al., "Blood-Induced Interference of Glucose Sensor Function in Vitro: Implications for in Vivo Sensor Function", Journal of Diabetes Science and Technology, 2007, vol. 1, No. 6, pp. 842-849.

Medtronic Guardian@ REAL-Time Continuous Glucose Monitoring System User Guide, 2006, pp. 1-181.

Medtronic MiniMed Guardian RT FDA Premarket Approval (PMA), 2005, pp. 1-6.

Medtronic MiniMed Guardian RT Summary of Safety and Effectiveness Data, 2005, 13 pages.

Medtronic MiniMed Paradigm® Real-Time 522 and 722 Insulin Pumps User Guide, 2008, pp. 1-262.

Occupational Safety and Health Admin., Labor, 2003, 29 CFR § 1910.1030 Bloodborne pathogens, pp. 260-273.

Omnipod image, Exhibit 182 of ADC Reply Brief SJ, Daubert, Sep. 22, 2022, 2 pages.

(56)            References Cited

OTHER PUBLICATIONS

One Touch® Ultra™M Blood Glucose Monitoring System Owner's Booklet, 2000, 23 pages.
OneTouch Ultra2 Blood Glucose Monitoring System Owner's Booklet, 2005, 34 pages.
Order, Federal Communications Commission, 2006, pp. 1-8.
Program, 2nd International Conference on Advanced Technologies & Treatments for Diabetes, Athens, Greece, 2009, 3 pages.
"Recess", Cambridge Dictionary of American English, 2000, pp. 710-711.
"Retract", The Chambers Dictionary, 1998, p. 1410.
"Retract", The New Oxford American Dictionary, 2001, p. 1455.
"Retract", Webster's Third New International Dictionary, 1993, pp. 1939-1940.
"Submission and Review of Sterility Information in Premarket Notification (510(k)) Submissions for Devices Labeled as Sterile, Guidance for Industry and Food and Drug Administration Staff", 2016, pp. 1-11.
Tegnestedt, C., et al., "Levels and sources of sound in the intensive care unit—an observational study of three room types", Acta Anaesthiesiologica Scandinavica, 2013, pp. 1-10.
Watkin, J., "An Introduction to Flash Glucose Monitoring", 14 pages.
CA 2,984,939 Examiner's Report, dated Nov. 15, 2023.
CA 3,182,961 Examiner's Report, dated Dec. 6, 2023.
EP 20177703.4 Reply to Notice of Intervention, dated Nov. 17, 2023.
EP 20177712.5 Reply to Notice of Intervention, Nov. 17, 2023.
EP 20177712.5 Reply to Reply to Notice of Opposition Dexcom, dated Sep. 27, 2023.
EP 20195922.8 Summons to Attend Oral Proceedings, dated Sep. 21, 2023.
EP 23166498.8 Extended Search Report, dated Nov. 17, 2023.
EP 23190032.5 Extended Search Report, dated Nov. 17, 2023.
JP 2021-531135 Office Action, dated Aug. 9, 2023.
US Petition For Inter Partes Review Of U.S. Pat. No. 11,202,591, IPR No. 2023-01409, dated Oct. 11, 2023.
US Petition For Inter Partes Review Of U.S. Pat. No. 11,266,335, IPR No. 2023-01397.
US Petition For Inter Partes Review Of U.S. Pat. No. 11,266,335, IPR No. 2023-01396, dated Oct. 6, 2023.
US Request for Ex Parte Reexamination Under 35.U.S.C. §§ 302-307 and 37 C.F.R. § 1.510 of U.S. Pat. No. 11,013,440, dated Dec. 11, 2023.
US Request for Ex Parte Reexamination Under 35.U.S.C. §§ 302-307 and 37 C.F.R. § 1.510 of U.S. Pat. No. 11,000,216, dated Dec. 11, 2023.
US Request for Ex Parte Reexamination Under 35.U.S.C. §§ 302-307 and 37 C.F.R. § 1.510 of U.S. Pat. No. 10,973,443, dated Nov. 27, 2023.
US Request for Ex Parte Reexamination Under 35.U.S.C. §§ 302-307 and 37 C.F.R. § 1.510 of U.S. Pat. No. 10,959,654, dated Dec. 11, 2023.
US Supplemental Declaration of Gary D. Fletcher, Ph.D, IPR No. 2022-00605, dated Jan. 11, 2023.
US Petitioner's Reply to Patent Owner's Response to Petition, IPR No. 2022-00605, dated Oct. 19, 2022.
US Second Declaration by Dr. Michael Cima in Support of Patent Owner's Response, IPR No. 2022-00605, dated Oct. 19, 2022.
US Patent Owner's Response, IPR No. 2022-00605, dated Oct. 19, 2022.
CA 2,617,192 Examiner's Report, dated Oct. 22, 2012.
CN 200780039416.2 Second Office Action, dated Apr. 25, 2012.
CN 200780039416.2 First Office Action, dated Mar. 30, 2011.
CN 200880005388.7 Second Office Action, dated May 16, 2012.
CN 200880005388.7 First Office Action, dated Jul. 25, 2011.
CN 201980082748.1 Final Office Action, dated Nov. 27, 2023.
EP 06788869.3 Examination Report, dated Sep. 25, 2012.
EP 06788869.3 Extended Search Report, dated Mar. 18, 2010.
EP 06813967.4 Extended Search Report, dated Mar. 4, 2010.

EP 07854298.2 Extended Search Report, dated Mar. 29, 2010.
EP 08730066.1 Extended Search Report, dated Oct. 5, 2012.
EP 10739031.2 Communication from Board of Appeals, dated Feb. 21, 2024.
EP 10739031.2 Summons to Attend Oral Proceedings, dated Oct. 26, 2023.
EP 18741791.0 Examination Report, dated Dec. 15, 2023.
EP 20177703.4 Reply to Reply to Reply to Notice of Opposition ADC, Dec. 18, 2023.
EP 20177712.5 Response to Written Submissions Dexcom, dated Feb. 26, 2024.
EP 20177712.5 Written Submissions ADC, dated Jan. 26, 2024.
EP 20177712.5 Reply to Reply to Reply to Notice of Opposition ADC, dated Dec. 18, 2023.
EP 20195922.8 Written Submissions Dexcom, dated Mar. 15, 2024.
EP 20195922.8 Response to Summons to Attend Oral Proceedings, dated Feb. 15, 2024.
EP 20195922.8 Written Submissions Dexcom, dated Dec. 12, 2023.
EP 20195922.8 Written Submissions ADC, dated Oct. 23, 2023.
EP 21211041.5 Grounds of Opposition Dexcom, Mar. 28, 2024.
EP 21211041.5 Notice of Opposition Dexcom, dated Mar. 28, 2024.
GB Claim No. HP-2021-000025 Approved Judgement, dated Oct. 18, 2023.
JP 2009-534799 Final Office Action, dated Feb. 19, 2013.
JP 2009-534799 Office Action, dated Sep. 27, 2011.
MX MX/a/2009/004322 Office Action, dated Mar. 11, 2013.
MX MX/a/2009/004322 Office Action, dated Sep. 19, 2012.
MY PI2023005466 Examination Report, dated Dec. 28, 2023.
RU 2009135048 Office Action, dated Dec. 20, 2011.
RU 2009119430 Office Action, dated Jun. 5, 2011.
US Third Declaration of Gary Fletcher, Ph.D., IPR No. 2024-00520, dated Jan. 31, 2024.
US Petition For Inter Partes Review Of U.S. Pat. No. 11,266,335, IPR No. 2024-00520, dated Jan. 31, 2024.
US Patent Owner's Preliminary Response, IPR No. 2023-01409, dated Jan. 18, 2024.
US Notice of Filing Date Accorded to Petition and Time for Filing Patent Owner Preliminary Response, IPR No. 2023-01409, dated Oct. 18, 2023.
US Patent Owner's Response to Petitioner's Explanation of Material Differences Between Petitions, IPR Nos. 2023-01396 and 2023-01397, dated Jan. 18, 2024.
US Petitioner's Explanation of Material Differences Between Petitions, IPR No. 2023-01397, dated Oct. 6, 2023.
US Declaration of Gary D. Fletcher, Ph.D, IPR No. 2023-01396 and IPR No. 2023-01397, dated Oct. 6, 2023.
US Patent Owner's Preliminary Response, IPR No. 2023-01396, dated Jan. 18, 2024.
US Notice of Filing Date Accorded to Petition and Time for Filing Patent Owner Preliminary Response, IPR No. 2023-01396, dated Oct. 18, 2023.
US Petitioner's Explanation of Material Differences Between Petitions, IPR No. 2023-01396, dated Oct. 6, 2023.
US Notice of Final Written Decision re Inter Partes Review of the '649 Patent, IPR No. 2022-00605, dated Jul. 13, 2023.
US Reexamination U.S. Appl. No. 90/019,329 Order Granting Request for Reexamination of U.S. Pat. No. 11,013,440, dated Jan. 23, 2024.
US Reexamination U.S. Appl. No. 90/019,307 Order Granting Request for Reexamination of U.S. Pat. No. 10,973,443, dated Dec. 22, 2023.
US Reexamination U.S. Appl. No. 90/019,330 Order Granting Request for Reexamination of U.S. Pat. No. 10,959,654, dated Jan. 23, 2024.
US Declaration of John Mastrototaro, Ph.D in Support of Dexcom's Motion for Summary Judgement, Case No. 21-CV-977-KAJ (D. Delaware), dated May 26, 2023.
WO PCT/US2006/029541 ISR and Written Opinion, dated Apr. 24, 2007.
WO PCT/US2006/033885 ISR and Written Opinion, dated Aug. 3, 2007.
WO PCT/US2007/082121 ISR and Written Opinion, dated May 9, 2008.

(56)  References Cited

OTHER PUBLICATIONS

WO PCT/US2008/054186 ISR and Written Opinion, dated Aug. 8, 2008.

WO PCT/US2008/065154 ISR and Written Opinion, dated Sep. 3, 2008.

WO PCT/US2010/047065 ISR and Written Opinion, dated Dec. 21, 2010.

WO PCT/US2010/047414 ISR and Written Opinion, dated Dec. 27, 2010.

WO PCT/US2010/047415 ISR and Written Opinion, dated Oct. 25, 2010.

"Abbott's Continuous Blood Glucose Monitor Approval Soon", 2006, retrieved from https://www.diabetesincontrol.com/abbotts-continuous-blood-glucose-monitor-approval-soon/, 2 pages.

Bisco® EC2265 Electrically Conductive Solid, Product Data Sheet, 2020, 2 pages.

Boretos, J.W., et al., "Biomedical elastomers", Handbook of Biomaterial Properties, Part II, Chapter 4, 1998, pp. 302-339.

Breton, M. D., et al., "Optimum Subcutaneous Glucose Sampling and Fourier Analysis of Continuous Glucose Monitors", Journal of Diabetes Science and Technology, 2008, vol. 2, No. 3, pp. 495-500.

Conductive—High Consistency Silicone Rubber (HCR), Primasil Silicones Ltd. Technical Data Sheet, retrieved from https://www.primasil.com/media/1255/primasil-carbon-conductive-silicone-compound.pdf on Apr. 3, 2024, 1 page.

Conductive Carbon Filled Silicone (ERC-225), EMI Conductive Rubber, LLC, retrieved from https://www.emiconductiverubberllc.com/carbon-black-filled-silicone.php on Apr. 3, 2024, 5 pages.

Dexcom Leading the Way Brochure, 2010, 12 pages.

Diabetes Close Up—Conferences—#2, Nov. 2003, retrieved from www.closeconcerns.com, 8 pages.

Dowla, F., ed., "The Basics of Radio Frequency Identification (RFID) Technology", Handbook of RF & Wireless Technologies, Chapter 14, 2004, pp. 417-436.

Dufresne, A. T., et al., "How reliable are trial dates relied on by the PTAB in the Fintiv analysis?", 2021, retrieved from https://www.1600ptab.com/2021/10/how-reliable-are-trial-dates-relied-on-by-the-ptab-in-the-fintiv-analysis/, 4 pages.

Electrically Conductive Elastomers, Euro Technologies, retrieved from https://www.euro-technologies.eu/dev/wp-content/uploads/2015/02/Electrically-Conductive-Elastomers.pdf on Apr. 3, 2024, pp. 11-15.

Electrically Conductive Silicone Sheet, Silex Ltd., 2023, 3 pages.

Erhard, G., Designing with Plastics, 2006, pp. 1-520.

Evans, N. E., et al., "Clinical temperature acquisition using proximity telemetry", Journal of Biomed Engineering, 1991, vol. 13, pp. 83-86.

Finkenzeller, K., RFID Handbook: Fundamentals and Applications in Contactless Smart Cards and Identification, Second Edition, 2003, Chapters 1-4 and 11, pp. 1-111 and 309-328.

Form 10-K, Dexcom, Inc., United States Securities and Exchange Commission, 2005, 59 pages.

Form S-1, Dexcom, Inc., United States Securities and Exchange Commission, 2005, 309 pages.

Freestyle Libre Fact Sheet, Abbott Diabetes Care Inc., 2016, 3 pages (English abstract).

Freestyle Libre, Flash Glukose Messystem, Abbott Diabetes Care Inc., 2016, 11 pages (English abstract).

FreeStyle Navigator Continuous Glucose Monitoring System Original Premarket Approval Application, Section VII: Manufacturing Section Steven Label Sensor Sheet Validation Plan, Jun. 2005, vol. 28 of 31, 61 pages.

FreeStyle Navigator Continuous Glucose Monitoring System Premarket Approval Application Amendment, Section III, Device Description, May 2006, vol. 2 of 39, 89 pages.

Fujipoly Silver Zebra® Connector Data Sheet FPDS 01-34, Version 2, 2002, pp. 1-7.

German Health Report, Deutscher Gesundheitsbericht Diabetes 2023, 13 pages (English abstract).

Heide, C., "Silicone Rubber for Medical Device Applications", Medical Plastics and Biomaterials, 1999, pp. 38-44.

Heller, A., "Integrated Medical Feedback Systems for Drug Delivery", AIChE Journal, 2005, vol. 51, No. 4, pp. 1054-1066.

Heller, A., et al., "Electrochemical Glucose Sensors and Their Applications in Diabetes Management", Chem. Rev., 2008, vol. 108, pp. 2482-2505.

Heller, A., et al., "Electrochemistry in Diabetes Management", Accounts of Chemical Research, 2010, vol. 43, No. 7, pp. 963-973.

"An Interview with Kevin Sayer, President and CEO of Dexcom, About The New G6", 2021, 5 pages.

Kass, D., "Fintiv Fails: PTAB Uses 'Remarkably Inaccurate' Trial Dates", 2021, retrieved from https://www.law360.com/articles/1436071/print?section=ip, 1 page.

Kovatchev, B. P., et al., "Evaluating the Accuracy of Continuous Glucose-Monitoring Sensors", Diabetes Care, 2004, vol. 27, No. 8, pp. 1922-1928.

Kreith, F., ed., The CRC Handbook of Mechanical Engineering, 1998, p. 12-33.

Liang, C.K., et al., "An implantable bi-directional wireless transmission system for transcutaneous biological signal recording", Physiological Measurement, 2005, vol. 26, pp. 83-97.

Microchip Technology Inc., microID® 13.56 MHz RFID System Design Guide, 2004, 214 pages.

Microchip Technology Inc., RFID Coil Design Note AN678 Data Sheet, 1998, pp. 1-19.

Microchip Technology Inc., Passive RFID Basics Design Note AN680 Data Sheet, 1998, pp. 1-5.

Moussy, F., et al., "Performance of Subcutaneously Implanted Needle-Type Glucose Sensors Employing a Novel Trilayer Coating", Analytical Chemistry, 1993, vol. 65, No. 15, pp. 2072-2077.

Moussy, F., "32.2: Implantable Glucose Sensor: Progress and Problems", IEEE Sensors, 2002, Orlando, FL, pp. 270-273.

Panteleon, A. E., et al., "The Role of the Independent Variable to Glucose Sensor Calibration", Diabetes Technology & Therapeutics, 2003, vol. 5, No. 3, pp. 401-410.

Parker, S. P., ed., McGraw-Hill Dictionary of Mechanical and Design Engineering, 1984 (excerpted), pp. 1-4.

Princy, K. G., et al., "Studies on Conductive Silicone Rubber and Hardness", Journal of Applied Polymer Science, 1998, vol. 69, pp. 1043-1050.

Radio Frequency Identification RFID, AIM Inc. White Paper, 2001, 17 pages.

Report from Diabetes Technology Meeting, 2003, retrieved from https://archive.childrenwithdiabetes.com/d_0j_129.htm, 2 pages.

Seal Design Guide, 1999, Apple Rubber Products, Inc., retrieved from http://www.applerubber.com:80/sdg/dguide/sec_1/start.cfm, 190 pages.

"Sevenfact", Federal Register, 2021, vol. 86, No. 211, pp. 60827-60829.

Shenoi, B. A., ed., Introduction to Digital Signal Processing and Filter Design, 2006, "Introduction", Chapter 1, pp. 1-30.

Silastic® MDX4-4210, BioMedical Grade Elastomer, Product Information, Dow Corning, 2003-2005, 4 pages.

"Silicone Rubber for Medical Device Applications", Medical Device & Diagnostic Industry, 1999, retrieved from https://www.mddionline.com/news/silicone-rubber-medical-device-applications, 9 pages.

Smith, S. S., ed., The Scientist and Engineer's Guide to Digital Signal Processing, Second Edition, 1997-1999, "Digital Signal Processors", Chapter 28, pp. 503-534.

Sterling® C carbon black, Cabot Product Data Sheet, 2014, retrieved from https://www.cabotcorp.cn/~/media/files/product-datasheets/datasheet-sterling-cpdf.pdf, 2 pages.

Suconvey Custom Medical-Grade Silicone Gasket, 2004, 17 pages.

Suconvey Custom Silicone Gasket in Medical Quality, 2014, 16 pages.

"TheraSense Files Premarket Approval Application for Freestyle Navigator™ Cont", 2003, retrieved from https://www.diabetesincontrol.com/therasense-files-premarket-approval-application-for-freestyle-navigatortm-cont/, 1 page.

"Therasense Navigates Continuous Glucose Monitor PMA, Prepares for Flash", The Gray Sheet, 2003, vol. 29, No. 37, 2 pages.

(56) References Cited

OTHER PUBLICATIONS

Vulcan® XC72 carbon black, Cabot Product Data Sheet, 2022, retrieved from https://www.cabotcorp.com/-/media/files/product-datasheets/datasheet-vulcan-xc72-carbon-black.pdf?la=en&rev=197922109e88415f9aa69717865b31fa, 2 pages.

Ward, W. K., et al., "A Wire-Based Dual-Analyte Sensor for Glucose and Lactate: In Vitro and In Vivo Evaluation", Diabetes Technology & Therapeutics, 2004, vol. 6, No. 3, pp. 389-401.

Z-Carbon LCD Connector, retrieved from http://www.zaxisconnector.com:80/Z-Carbon-LCD-Elastomeric-Connectors.shtml, 2004, 2 pages.

CA 3,120,335 Examiner's Report, dated May 27, 2024.

EP 10739031.2 Decision of Oral Proceedings, Jun. 11, 2024.

EP 10739031.2 Minutes of Oral Proceedings, May 10, 2024.

EP 20177703.4 Summons to Attend Oral Proceedings, dated Apr. 29, 2024.

EP 20177712.5 Summons to Attend Oral Proceedings, dated Jul. 2, 2024.

EP 20195922.8 Notice of Appeal, dated Jul. 4, 2024.

EP 20195922.8 Written Submissions Dexcom, dated May 9, 2024.

EP 20195922.8 Decision Revoking the European Patent, dated May 8, 2024.

EP 20195922.8 Minutes of the Oral Proceedings, dated May 8, 2024.

EP 24152079.0 Partial Search Report, dated Jun. 14, 2024.

US Notice of Filing Date Accorded to Petition and Time for Filing Patent Owner Preliminary Response, IPR No. 2024-00860, dated May 23, 2024.

US Declaration of Dr. Cameron Riviere, Ph.D., IPR No. 2024-00860, dated May 9, 2024.

US Petition For Inter Partes Review Of U.S. Pat. No. 11,510,625, IPR No. 2024-00860, dated May 9, 2024.

US Patent Owner's Authorized Sur-Reply to Petitioner's Reply to Patent Owner's Preliminary Response, IPR No. 2024-00520, dated Jun. 11 ,2024.

US Petiioner's Authorized Reply to Patent Owner's Preliminary Response, IPR No. 2024-00520, dated May 31, 2024.

US Patent Owner's Preliminary Response, IPR No. 2024-00520, dated May 8, 2024.

US Patent Owner's Exhibit List, IPR2024-00520, dated Mar. 25, 2024.

US Telephonic Hearing, IPR2024-00520, Mar. 13, 2024.

US Petitioner's Explanation of Material Differences Between the Petition in IPR2024-00520 and Previously Filed Petitions in IPR2023-01396 and IPR2023-01397, IPR No. 2024-00520, dated Jan. 31, 2024.

US Order, IPR No. 2023-01409, May 30, 2024.

US Notice of Stipulation, IPR No. 2023-01409, May 29, 2024.

US Patent Owner's Objections to Petitioner's Exhibits to the Petition, IPR No. 2023-01409, Apr. 29, 2024.

US Patent Owner's Request for Rehearing by the Director, IPR 2023-01409, dated Apr. 29, 2024.

US Email of Peter McAndrews, IPR 2023-01409, Apr. 29, 2024.

US Decision Granting Institution of Inter Partes Review, IPR No. 2023-01409, dated Apr. 15, 2024.

US Scheduling Order, IPR 2023-01409, dated Apr. 15, 2024.

US Order Conduct of the Proceeding 37 C.F.R. § 42.5, IPR No. 2023-01409, dated Feb. 6, 2024.

US Telephonic Conference Call, IPR No. 2023-01409, dated Feb. 2, 2024.

US Petitioner's Updated Exhibit List, IPR No. 2023-01409, dated Feb. 5, 2024.

US Patent Owner's Updated Mandatory Notices, IPR No. 2023-01409, dated Feb. 2, 2024.

US Email of Andrew M. Mason, IPR 2023-01409, dated Jan. 30, 2024.

US Decision Denying Institution of Inter Partes Review, IPR No. 2023-01397, dated Apr. 16, 2024.

US Patent Owner's Updated Exhibit List, IPR2023-01397, dated Mar. 25, 2024.

US Petitioner's Updated Mandatory Notices Pursuant to 37 C.F.R. § 42.8(a)(3), IPR No. 2023-01397, dated Feb. 19, 2024.

US Patent Owner's Updated Mandatory Notices, IPR No. 2023-01397, dated Feb. 2, 2024.

US Patent Owner's Preliminary Response, IPR No. 2023-01397, dated Jan. 18, 2024.

US Petitioner's Request for Rehearing of Decision Denying Institution, IPR No. 2023-01396, dated May 16, 2024.

US Decision Denying Institution of Inter Partes Review, IPR No. 2023-01396, dated Apr. 16, 2024.

US Patent Owner's Updated Exhibit List, IPR No. 2023-01397, dated Mar. 25, 2024.

US Telephonic Hearing, IPR2023-01396, dated Mar. 13, 2024.

US Petitioner's Updated Mandatory Notices Pursuant to 37 C.F.R. § 42.8(a)(3), IPR No. 2023-01396, dated Feb. 19, 2024.

US Reexamination U.S. Appl. No. 90/019,329 Notification of Concurrent Proceedings, dated May 15, 2024.

US Petition Under 37 CFR § 1.181 and/or § 1.182 to Terminate Reexamination No. U.S. Appl. No. 90/019,329, dated Apr. 26, 2024.

US Reexamination U.S. Appl. No. 90/019,329 Order Granting Request for Reexamination of U.S. Pat. No. 11,013,440, dated Jan. 30, 2024.

US Reexamination U.S. Appl. No. 90/019,329 Declaration of Gary D. Fletcher, Ph.D., dated Dec. 11, 2023.

US Reexamination U.S. Appl. No. 90/019,331 Notification of Concurrent Proceedings, dated May 15, 2024.

US Reexamination U.S. Appl. No. 90/019,331 Order Granting Request for Reexamination of U.S. Pat. No. 11,000,216, dated Jan. 23, 2024.

US Reexamination U.S. Appl. No. 90/019,330 Notice of Intent to Issue Ex Parte Reexamination Certificate of U.S. Pat. No. 11,013,440, dated Jul. 1, 2024.

US Reexamination U.S. Appl. No. 90/019,330 Notification of Concurrent Proceedings, dated May 15, 2024.

US Reexamination U.S. Appl. No. 90/019,330 Declaration of John Mastrototaro, Ph.D., dated Dec. 11, 2023.

US Reference DDX-4 of Defendant Dexcom, Inc.'s Appendix to Motion for Judgment as a Matter of Law or, Alternatively, for a New Trial, Case No. 21-CV-977-KAJ (D. Delaware)—Public Version, dated May 24, 2024.

US Reference DX4731 of Defendant Dexcom, Inc.'s Appendix to Motion for Judgment as a Matter of Law or, Alternatively, for a New Trial, Case No. 21-CV-977-KAJ (D. Delaware)—Public Version, dated May 24, 2024.

US Reference DX4726 of Defendant Dexcom, Inc.'s Appendix to Motion for Judgment as a Matter of Law or, Alternatively, for a New Trial, Case No. 21-CV-977-KAJ (D. Delaware)—Public Version, dated May 24, 2024.

US Reference DX0381 of Defendant Dexcom, Inc.'s Appendix to Motion for Judgment as a Matter of Law or, Alternatively, for a New Trial, Case No. 21-CV-977-KAJ (D. Delaware)—Public Version, dated May 24, 2024.

US Reference DX0189 of Defendant Dexcom, Inc.'s Appendix to Motion for Judgment as a Matter of Law or, Alternatively, for a New Trial, Case No. 21-CV-977-KAJ (D. Delaware)—Public Version, dated May 24, 2024.

US Reference DX0183 of Defendant Dexcom, Inc.'s Appendix to Motion for Judgment as a Matter of Law or, Alternatively, for a New Trial, Case No. 21-CV-977-KAJ (D. Delaware)—Public Version, dated May 24, 2024.

US Reference PDX07 of Defendant Dexcom, Inc.'s Appendix to Motion for Judgment as a Matter of Law or, Alternatively, for a New Trial, Case No. 21-CV-977-KAJ (D. Delaware)—Public Version, dated May 24, 2024.

US Reference PTX-3026 of Defendant Dexcom, Inc.'s Appendix to Motion for Judgment as a Matter of Law or, Alternatively, for a New Trial, Case No. 21-CV-977-KAJ (D. Delaware)—Public Version, dated May 24, 2024.

US Declaration of Karl R. Leinsing, MSME, PE, in Support of Abbott's Motion for Summary Judgement, Case No. 21-CV-977-KAJ (D. Delaware)—Public Version, dated May 19, 2023.

WO PCT/US24/11756 Invitation to Pay Additional Fees, dated May 7, 2024.

(56)          References Cited

OTHER PUBLICATIONS

WO PCT/US24/16127 Invitation to Pay Additional Fees, dated Jun. 4, 2024.

WO PCT/US24/18665 ISR and Written Opinion, dated Jun. 21, 2024.

Baltensperger, B., "Vials, Caps, Septa & Various Products in Comparison", retrieved from http://www.axialscientific.com/files/CombiPal_ArticleCTC_000.pdf on Jul. 10, 2024, 3 pages.

Beardsall, K., et al., "The continuous glucose monitoring sensor in neonatal intensive care", Archives of Disease in Childhood, Fetal and Neonatal Edition, 2005, vol. 90, No. 4, pp. F307-F310.

Black, J., et al., Eds., Handbook of Biomaterial Properties, 1998, pp. 319-322.

Choosing the Right Hamilton Syringe for Your Application, 2003, 4 pages.

Claremont, D. J., et al., "In vivo chemical sensors and biosensors in clinical medicine", Biosensors: Fundamentals and Applications, Chapter 20, 1987, pp. 356-376.

Continuous Glucose Monitoring Systems Product Reference Guide, Diabetes Health, 2006-2007, pp. 50-51.

Das, S. D., et al., "Review—Electrochemistry and Other Emerging Technologies for Continuous Glucose Monitoring Devices", ECS Sensors Plus, 2022, 19 pages.

Decision, Joint Federal Committee, Jun. 16, 2016, 3 pages and translation.

Dexcom G6 Continuous Glucose Monitoring System User Guide, 2022, 346 pages.

Englert, K., et al., "Skin and Adhesive Issues With Continuous Glucose Monitors: A Sticky Situation", Journal of Diabetes Science and Technology, 2014, vol. 8, No. 4, pp. 745-751.

U.S. Appl. No. 61/317,243.

U.S. Appl. No. 61/345,562.

U.S. Appl. No. 61/361,374.

U.S. Appl. No. 61/411,262.

Freckmann, G., et al., "Performance Evaluation of Three Continuous Glucose Monitoring Systems: Comparison of Six Sensors per Subject in Parallel", Journal of Diabetes Science and Technology, 2013, vol. 7, No. 4, pp. 842-853.

Freestyle Libre Brochure, 2016, 10 pages.

Freestyle Libre Fact Sheet, 2016, retrieved from www.FreeStyleLibre.de, 2 pages.

Fujipoly Zebra® Carbon, retrieved from https://www.fujipoly.com:80/products/genProduct.asp?ProductName=Carbon&ProductLine=Zebra, 2003, 3 pages.

Gender of connectors and fasteners, retrieved from https://en.wikipedia.org/wiki/Gender_of_connectors_and_fasteners on Jun. 11, 2024, 6 pages.

Hager, T. L., et al., "Why Double Electrocoat and Powder Coat?", retrieved from https://www.pfonline.com/articles/why-double-electrocoat-and-powder-coat, 1999, 5 pages.

Harris, J. M., et al., "Common Causes of Glucose Oxidase Instability in In Vivo Biosensing: A Brief Review", Journal of Diabetes Science and Technology. 2013, vol. 7, No. 4, pp. 1030-1038.

Hovorka, R., "Continuous glucose monitoring and closed-loop systems", Diabetic Medicine, 2005, vol. 23, pp. 1-12.

Kroschwitz, J. I., Ed., Encyclopedia of Polymer Science and Engineering, vol. 15, 1989, Silicones, pp. 204-308.

Letter from Federal Office of Social Security, Apr. 6, 2021, 9 pages and translation.

Medtronic Enlite Serter User Guide, 2014, 26 pages.

Medtronic MiniMed iPro2 User Guide, 2010, pp. 1-99.

Meltsner, M A, et al., "Observations on rotating needle insertions using a brachytherapy robot", Phys. Med. Biol., 2007, vol. 52, pp. 6027-6037.

Nichols, S. P., et al., "Biocompatible Materials for Continuous Glucose Monitoring Devices", Chem Rev., 2013, vol. 113, No. 4, pp. 2528-2549.

Rice, M. J., et al., "Continuous Measurement of Glucose: Facts and Challenges", Anesthesiology, 2012, vol. 116, No. 1, pp. 199-204.

Rigo, R. S., et al., "Cutaneous Reactions to Continuous Glucose Monitoring and Continuous Subcutaneous Insulin Infusion Devices in Type 1 Diabetes Mellitus", Journal of Diabetes Science and Technology, 2021, vol. 15, No. 4, pp. 786-791.

Rocchitta, G., et al., "Enzyme Biosensors for Biomedical Applications: Strategies for Safeguarding Analytical Performances in Biological Fields", Sensors, 2016. vol. 16, No. 6, 21 pages.

Sclater, N., et al., eds., Mechanisms and Mechanical Devices Sourcebook, Fourth Edition, 2007, Chapter 12—Shaft Couplings and Connections, pp. 290-307.

SlimStack™ SMT Stacking Board-to-Board Connectors, molex®, 2004, 8 pages.

"Transcutaneous", Webster's Third New International Dictionary, 2002, pp. 2426.

Tsumura, R., et al., "Histological Evaluation of Tissue Damage Caused by Rotational Needle Insertion", Proceedings of the Annual International Conference of the IEEE Engineering in Medicine and Biology Society, 2016, pp. 5120-5123.

Wampler, W. A., et al., Rubber Compounding, Chemistry and Applications, 2004, Chater 6—Carbon Black, pp. 239-284.

Xu, J., et al., "Anti-Biofouling Strategies for Long-Term Continuous Use of Implantable Sensors", Chemosensors, 2020, vol. 20 No. 3, 29 pages.

CA 2,984,939 Examiner's Report, dated Aug. 7, 2024.

CN 200880005149.1 Notice of Allowance, dated Jun. 21, 2013.

CN 200880005149.1 Fourth Office Action, dated Dec. 3, 2012.

CN 200880005149.1 Third Office Action, dated Feb. 16, 2012.

CN 200880005149.1 Second Office Action, dated Aug. 17, 2011.

CN 200880005149.1 First Office Action, dated Jul. 29, 2010.

DE Complaint in Litigation of EP 3300658, dated Mar. 20, 2024.

EP 12857506.5 Application as Filed, dated Dec. 30, 2013.

EP 17182379.2 Grounds of Opposition, dated Jul. 12, 2024.

EP 17182379.2 Notice of Opposition, dated Jul. 12, 2024.

EP 17182379.2 Reply to Examination Report, dated Apr. 9, 2021.

EP 17182379.2 Reply to Search Report, dated Oct. 3, 2018.

EP 17182379.2 Application as Filed, Jul. 20, 2017.

EP 19151577.4 Examination Report, dated Oct. 7, 2024.

EP 20177712.5 Summons to Attend Oral Proceedings, dated Oct. 1, 2024.

EP 20177712.5 Response to Summons to Attend Oral Proceedings, dated Aug. 30, 2024.

EP 20195922.8 Grounds of Appeal, dated Sep. 6, 2024.

EP 21152231.3 Reply to Examination Report, dated May 9, 2022.

EP 21152231.3 Application as Filed, dated Jan. 19, 2021.

EP 21211041.5 Summons to Attend Oral Proceedings, dated Sep. 23, 2024.

EP 21211041.5 Reply to Notice of Opposition, dated Jul. 17, 2024.

EP 23166498.8 Examination Report, dated Sep. 2, 2024.

EP 24152079.0 Extended Search Report, dated Sep, 4, 2024.

EP 24183336.7 Extended Search Report, dated Oct. 11, 2024.

EP 24187206.8 Extended Search Report, dated Oct. 9, 2024.

ES Expert Opinion of Fernando Prieto Moran in Litigation of EP 3300658, dated Mar. 22, 2024.

ES Request for Ex Parte Preliminary Injunctions in Litigation of EP 3300658 and EP 3831283, dated Mar. 22, 2024.

GB Claim No. HP-2024-000010 Tomlin Order, dated Jul. 25, 2024.

GB Claim No. HP-2024-000010 Order, dated May 20, 2024.

GB Claim No. HP-2024-000010 Particulars of Infringement, dated Mar. 20, 2024.

GB Claim No. HP-2024-000010 Particulars of Claim, Mar. 20, 2024.

IT Action for an Injunction in Litigation of EP 3300658, dated Mar. 22, 2024.

MX MX/a/2021/007294 Office Action, dated Aug. 20, 2024.

RU 2009134334 Office Action, dated Feb. 7, 2012.

UP First Expert Opinion of Dr Michael Schoemaker in Litigation of EP 3 977 921, dated Jun. 11, 2024.

UP Application pursuant to Rule 9.1 ROP Request to disregard the submitted auxiliary requests in the Litigation of EP 3831283, Jul. 19, 2024.

UP Statement of Appeal Including Statement of Grounds of Appeal in the Proceedings for Provisional Measures Concerning EP 3 831 283, dated Jul. 3, 2024.

(56)        References Cited

OTHER PUBLICATIONS

UP Application for Leave to Change the Claim in the Litigation of EP 3831283, dated Jul. 3, 2024.

UP Order of the Court of First Instance of the Unified Patent Court Local Division The Hague in the Litigation of EP 3831283, dated Jun. 19, 2024.

UP Statement for Revocation in the Litigation of EP 3831283, dated May 15, 2024.

UP Rejoinder Objection to the Application for provisional measures in the Litigation of EP 3831283, dated May 15, 2024.

UP Reply to the Objection to the Application for Provisional Measures in the Litigation of EP 3831283, dated May 8, 2024.

UP Objection to the Application for provisional measures in the Litigation of EP 3831283, dated Apr. 23, 2024.

UP Application for Preliminary Injunction and Other Provisional Measure in the Litigation of EP 3831283 dated Mar. 20, 2024.

UP Appeal against Order of the Local Division The Hague in proceedings regarding Application for Provisional Measures pursuant to Rule 220.1 (c) ROP in the Litigation of EP 2713879, dated Jul. 4, 2024.

UP Order of the Court of First Instance of the Unified Patent Court Local Division The Hague in the Litigation of EP 2713879, dated Jun. 19, 2024.

UP Pleading Notes in the Litigation of EP 2713879, dated May 22, 2024.

UP Rejoinder to Application for Provisional Measures in the Litigation of EP 2713879, dated May 15, 2024.

UP Reply to the Objection to the Application for Provisional Measures in the Litigation of EP 2713879, dated May 8, 2024.

UP Objection to Application for Provisional Measures in the Litigation of EP 2713879, dated Apr. 23, 2024.

UP Application for Preliminary Injunction and Other Provisional Measure in the Litigation of EP 2713879, dated Mar. 20, 2024.

UP Protective Letter in the Litigation of EP 2713879, dated Sep. 29, 2023.

UP Order of the Court of First Instance of the Unified Patent Court Local Division Düsseldorf in the Litigation of EP 2697391, dated Apr. 30, 2024.

US Decision Denying Institution of Inter Partes Review, IPR No. 2024-00520, dated Aug. 8, 2024.

US Declaration of Karl R. Leinsing, MSME, PE, IPR No. 2023-01409, dated Jul. 19, 2024.

US Patent Owner's Response, IPR No. 2023-01409, dated Jul. 19, 2024.

US Deposition of Gary Fletcher, Ph.D., IPR No. 2023-01409, dated Jun. 26, 2024.

US Reexamination U.S. Appl. No. 90/019,307 Petition Under 37 CFR § 1.181 to Terminate, dated Aug. 15, 2024.

US Reexamination U.S. Appl. No. 90/019,307 Decision on Petitions, dated Aug. 7, 2024.

US Reexamination U.S. Appl. No. 90/019,307 Petition Under 37 CFR § 1.59 to Expunge Application Papers, dated Aug. 1, 2024.

US Reexamination U.S. Appl. No. 90/019,307 Petition Under 37 CFR § 1.59 to Expunge Application Papers, dated Jun. 12, 2024.

US Reexamination U.S. Appl. No. 90/019,307 Notification of Concurrent Proceedings, dated May 15, 2024.

US Reexamination U.S. Appl. No. 90/019,307 Petition Under 37 CFR §§ 1.182 and/or § 1.183 to Allow Filing and Consideration of Response to Patent Owner's Extraordinary Petition to Suspend, dated Mar. 19, 2024.

US Reexamination U.S. Appl. No. 90/019,307 Petition Under 37 CFR § 1.181 and/or § 1.183 to Suspend, dated Mar. 1, 2024.

US Reexamination U.S. Appl. No. 90/019,329 Ex Parte Reexamination Certificate, dated Oct. 30, 2024.

US Reexamination U.S. Appl. No. 90/019,329 Notice of Intent to Issue Ex Parte Reexamination Certificate, dated Oct. 8, 2024.

US Reexamination U.S. Appl. No. 90/019,329 Decision on Petition Under 37 C.F.R. § 1.59, dated Sep. 16, 2024.

US Reexamination U.S. Appl. No. 90/019,329 Statutory disclaimer per Manual of Patent Examining Procedure (MPEP) 1490, dated Sep. 3, 2024.

US Reexamination U.S. Appl. No. 90/019,329 Petition Under 37 C.F.R. § 1.182 to Seal Document Versions Filed via IDS and Substitute Redacted Document Versions Therfor, dated Aug. 1, 2024.

US Reexamination U.S. Appl. No. 90/019,329 Petition Under 37 CFR § 1.59 to Expunge Application Papers dated Aug. 1, 2024.

US Reexamination U.S. Appl. No. 90/019,329 Ex Parte Reexamination Interview Summary, dated Jul. 25, 2024.

US Reexamination U.S. Appl. No. 90/019,329 Decision on Petition Under 37 C.F.R. § 1.59, dated Jul. 22, 2024.

US Reexamination U.S. Appl. No. 90/019,329 Decision Sua Sponte Vacating Notice of Intent to Issue Ex Parte Reexamination Certificate, dated Jul. 3, 2024.

US Reexamination U.S. Appl. No. 90/019,329 Petition Under 37 CFR § 1.59 to Expunge Application Papers, dated Jun. 12, 2024.

US Reexamination U.S. Appl. No. 90/019,331 Notice of Intent to Issue Ex Parte Reexamination Certificate, dated Oct. 15, 2024.

US Reexamination U.S. Appl. No. 90/019,331 Decision on Petition Under 37 C.F.R. § 1.59, dated Sep. 16, 2024.

US Reexamination U.S. Appl. No. 90/019,331 Decision Granting Petition, dated Aug. 26, 2024.

US Reexamination U.S. Appl. No. 90/019,331 Petition Under 37 C.F.R. § 1.182 to Seal Document Versions Filed via IDS and Substitute Redacted Document Versions Therfor, dated Aug. 1, 2024.

US Reexamination U.S. Appl. No. 90/019,331 Petition Under 37 CFR § 1.59 to Expunge Application Papers, dated Aug. 1, 2024.

US Reexamination U.S. Appl. No. 90/019,331 Petition to Withdraw From Issue and Reopen the Proceeding, dated Jul. 26, 2024.

US Reexamination U.S. Appl. No. 90/019,331 Decision on Petition Under 37 C.F.R. § 1.59, dated Jul. 16, 2024.

US Reexamination U.S. Appl. No. 90/019,331 Notice of Intent to Issue Ex Parte Reexamination Certificate, dated Jul. 10, 2024.

US Reexamination U.S. Appl. No. 90/019,331 Petition Under 37 CFR § 1.59 to Expunge Application Papers, dated Jun. 12, 2024.

US Ex Parte Reexamination Certificate of U.S. Pat. No. 10,959,654, dated Nov. 5, 2024.

US Reexamination U.S. Appl. No. 90/019,330 Notice of Intent to Issue Ex Parte Reexamination Certificate, dated Oct. 7, 2024.

US Reexamination U.S. Appl. No. 90/019,330 Decision on Petition Under 37 C.F.R. § 1.59, dated Sep. 16, 2024.

US Reexamination U.S. Appl. No. 90/019,330 Decision Granting Petition and Vacating a Reexamination Certificate, dated Aug. 26, 2024.

US Ex Parte Reexamination Certificate of U.S. Pat. No. 10,959,654, dated Aug. 5, 2024.

US Reexamination U.S. Appl. No. 90/019,330 Petition Under 37 C.F.R. § 1.182 to Seal Document Versions Filed via IDS and Substitute Redacted Document Versions Therfor, dated Aug. 1, 2024.

US Reexamination U.S. Appl. No. 90/019,330 Petition Under 37 CFR § 1.59 to Expunge Application Papers, dated Aug. 1, 2024.

US Reexamination U.S. Appl. No. 90/019,330 Petition to Withdraw From Issue and Reopen the Proceeding, dated Jul. 26, 2024.

US Reexamination U.S. Appl. No. 90/019,330 Decision on Petition Under 37 C.F.R. § 1.59, dated Jul. 16, 2024.

US Reexamination U.S. Appl. No. 90/019,330 Petition Under 37 CFR § 1.59 to Expunge Application Papers, dated Jun. 12, 2024.

WO PCT/US2008/054165 ISR and Written Opinion, dated Jun. 5, 2008.

WO PCT/US2008/067791 ISR and Written Opinion, dated Sep. 30, 2008.

WO PCT/US24/11756 ISR and Written Opinion, dated Jun. 28, 2024.

WO PCT/US24/16127 ISR and Written Opinion, dated Sep. 11, 2024.

"27 Winners Announced at the 19th Annual Medical Design Excellence Awards (MDEA) Award Ceremony", UBM Americas, 2017, 4 pages.

(56) References Cited

OTHER PUBLICATIONS

"55 Chosen as Winners in Annual Big Innovation Awards", 2018, retrieved from https://www.bintelligence.com/posts/55-chosen-as-winners-in-annual-big-innovation-awards, 2 pages.
2017 Good Design Award, retrieved from https://www.g-mark.org/gallery/winners/9dda01a3-803d-11ed-af7e-0242ac130002, 9 pages.
"2019 Top 10 Innovations", The Scientist, retrieved from https://www.the-scientist.com/2019-top-10-innovations-66738, 7 pages.
Abbott 2023 Annual Report, retrieved from https://www.abbottinvestor.com/static-files/6cb09c09-2422-40e0-a24b-6545ffcf5267, pp. 1-82.
Abbott Clinical Trials Competitor and Ecosystem Players, 2020, 28 pages.
"Abbott's Freestyle Libre® Is Named Best Medical Technology In Last 50 Years By The Galien Foundation", 2022, PRNewswire, 1 page.
"Abbott's Freestyle® Libre 2 ICGM Cleared in U.S. for Adults and Children With Diabetes, Achieving Highest Level of Accuracy and Performance Standards", retrieved from https://abbott.mediaroom.com/2020-06-15-Abbotts-FreeStyle-R-Libre-2-iCGM-Cleared-in-U-S-for-Adults-and-Children-with-Diabetes-Achieving-Highest-Level-of-Accuracy-and-Performance-tandards#:~:text=FDA%20clears%20Abbott's%20FreeStyle%20Libre,high%20or%20low%20without%20scanning, on Jul. 7, 2024, 3 pages.
"Abbott's Freestyle Libre® 3 Receives U.S. FDA Clearance—Features World's Smallest, Thinnest and Most Accurate 14-Day Glucose Sensor", 2022, PRNewswire, 3 pages.
"Abbott's Freestyle Libre Flash Glucose Monitoring System Wins the IMSTA Most Innovative Product Multi-National Award 2017", retrieved from https://www.ie.abbott/media-center/news/abbotts-freestyle-libre-flash-glucose-monitoring-system-wins-the-imsta-award-2017.html, 2 pages.
"Abbott's Freestyle® Libre 14 Day Flash Glucose Monitoring System Now Approved in U.S.", 2018, PRNewswire, 2 pages.
"Abbott Reports Fourth-Quarter and Full-Year 2203 Results; Issues 2024 Financial Outlook", 2024, retrieved from https://abbott.mediaroom.com/2024-01-24-Abbott-Reports-Fourth-Quarter-and-Full-Year-2023-Results-Issues-2024-Financial-Outlook, 20 pages.
About the Edison Awards retrieved from https://edisonawards.com/about/, 2024, 3 pages.
Accu-chek® Softclix Lancet Device retrieved from file:///C:/Users/afredericks/Downloads/softclix-user-manual.pdf, 2007, 2 pages.
Using your Accu-chek® Multiclix Lancet Device, 2005, retrieved from https://www.northcoastmed.com/wp-content/uploads/2023/03/multiclix_userguide.pdf, 2 pages.
Ahn, D., "Abbott's Euro approved wearable glucose monitor is different than anything on the market", 2014, retrieved from https://www.imedicalapps.com/2014/09/abbotts-wearable-glucose-monitor/, 6 pages.
American National Standard, ANSI/AAMI HE75:2009, Human factors engineering—Design of medical devices, 2010, 465 pages.
Automated Retractable VanishPoint Syringe 510(k) Safety and Effectiveness Summary, 1998, 5 pages.
"BinaxNOW, FreeStyle Libre 2 win BIG innovation honors", 2021, retrieved from https://www.abbott.com/corpnewsroom/strategy-and-strength/binaxnow-freestyle-libre-win-big-innovation-honors.html, 6 pages.
"Bluetooth rival unveiled by Nokia", 2006, retrieved from news.bbc.co.uk/1/hi/technology/5403564.stm, 2 pages.
Blum, A., "Freestyle Libre Glucose Monitoring System", Clinical Pharmacology Update, 2018, vol. 36, No. 2, pp. 203-204.
Breton, M., et al., "Fully Integrated Artificial Pancreas in Type 1 Diabetes: Modular Closed-Loop Glucose Control Maintains Near Normoglycemia", Diabetes, 2012, vol. 61, No. 9, pp. 2230-2237.
Cather, D. E., "CGM Frustrations Survey", 2020, 36 pages.
U.S. Appl. No. 61/149,639, filed Feb. 3, 2009.
CES 2022 Innovation Award Honorees, retrieved from https://www.ces.tech/innovation-awards/honorees/2022/best-of/f/freestyle-libre-3-system.aspx, 1 page.

2019 Chicago Innovation Award Winner Abbott Laboratories, retrieved from https://chicagoinnovation.com/winners/abbott-laboratories/, 4 pages.
Design Concepts Project Status Update, Glucose Sensor Applicator Dexcom (project #2554), 2014, 5 pages.
Dexcom G5 Mobile System User Guide, 2015, pp. 1-260.
Dexcom G5 Quick Start Guide, 2020, pp. 1-31.
Dexcom G6 Start Here Set up Guide, 2022, pp. 18 pages.
Dexcom G6 Continuous Glucose Monitoring (CGM) System Section 510(k) Approval, 2022, 7 pages.
"The Dexcom G7. The most accurate CGM system.[1]" retrieved from https://www.dexcom.com/g7-cgm-system on Jun. 27, 2024, 20 pages.
Dexcom G7 Continuous Glucose Monitoring (CGM) System Section 510(k) Approval, 2022, 10 pages.
Dexcom G7 User Guide, 2024, p. i-186.
"Distal", Oxford English Dictionary, 2023, 1 page.
Edison Awards Announces 2016 Gold, Silver, and Bronze Awards Winners, Edison Awards, 9 pages.
Edison Best New Product Awards™ 2021 Winners retrieved from https://edisonawards.com/2021-winners/, 19 pages.
Edison Best New Product Awards™ 2022 Winners retrieved from https://edisonawards.com/2022-winners/, 52 pages.
Email from Christopher M Dougherty dated Dec. 17, 2019, 68 pages.
European Association for the Study of Diabetes, 59th Annual Meeting, Hamburg, Germany, Oct. 2-6, 2023, 326 pages.
U.S. Appl. No. 61/569,287.
U.S. Appl. No. 62/524,247.
Freestyle Libre FAQ, 2024, retrieved from https://www.freestyle.abbott/uk-en/support/faq/question-answer.html?q=UKFaqquestion-55#, 2 pages.
"FreeStyle Libre Honored by Prix Galien", 2019, 4 pages.
FreeStyle Libre In-Service Guide, 2021, 28 pages.
FreeStyle Libre 2 Get Started Guide, 2023, pp. 1-28.
Freestyle Libre 2 HCP Pulse Report, 2021, 13 pages.
"FreeStyle Libre 2—Zucker messen ohne stechen per Sensor und App", German Innovation Awards Gold Winner, 2020, retrieved from https://www.german-innovation-award.de/preistraeger/preis/gewinner/freestyle-libre-2-zucker-messen-ohne-stechen-per-sensor-und-app/#:~:text=Beschreibung%20Die%20kontinuierliche%20Glukosemessung%20mit, um%20die%20Glukosewerte%20kontinuierlich%20aufzuzeichnen, 1 page.
FreeStyle Libre 3 Get Started Guide, 2023, pp. 1-20.
FreeStyle Libre 3 User's Manual, 2022-2023, pp. iv-241.
The Galien Foundation is proud to announce the laureates of the best-of-the-best from the half century 1970-2020, The 2022 Galien Golden Jubilee Winners, retrieved from https://www.galienfoundation.org/galien-golden-jubilee, 3 pages.
Gough, D. A., et al., "Development of the Implantable Glucose Sensor: What Are the Prospects and Why Is It Taking So Long?", Diabetes, 1995, vol. 44, pp. 1005-1009.
Hermanides, J., et al., "Current Application of Continuous Glucose Monitoring in the Treatment of Diabetes", Diabetes Care, 2011, vol. 34, Suppl. 2, pp. S197-S201.
"Important Announcement—Sibionics is temporarily discontinuing CGM offerings in select European countries.", 2024, retrieved from https://www.sibionicscgm.com/pages/important-announcement-sibionics-is-temporarily-discontinuing-cgm-offerings-in-select-european-countries#:~:text=SIBIONICS%20is%20temporarily%20discontinuing%20CGM, tools%20to%20transform%20our%20health., 6 pages.
Insert Molding, 1996, retrieved from https://www.mddionline.com/equipment/insert-molding, 4 pages.
International Diabetes Device 2022 Blue Book, Seagrove Partners, 142 pages.
International Standard, IEC 62366, Medical devices—Application of usability engineering to medical devices, 2007, 214 pages.
Joseph, J. I., et al., "Glucose Sensing in the Subcutaneous Tissue: Attempting to Correlate the Immune Response with Continuous Glucose Monitoring Accuracy", Diabetes Technology & Therapeutics, 2018, vol. 20, No. 5, pp. 321-324.

(56)          References Cited

OTHER PUBLICATIONS

Kaye, R., et al., "Medical Device Use-Safety: Incorporating Human Factors Engineering into Risk Management", 2000, retrieved from https://www.qualysinnova.com/download/files/MD-Use-Safety. pdf, pp. 1-33.

Lomas, P., "Dexcom G7 Release: The Most Exciting New Features", 2024, retrieved from https://notjustapatch.com/dexcom-g7-features/, 13 pages.

Lovett, L., "What's next for Dexcom? CEO, CTO talk G6 for inpatient use, expanding CGMs for patients without diabetes", 2020, retrieved from https://www.mobihealthnews.com/news/whats-next-dexcom-ceo-cto-talk-g6-inpatient-use-expanding-cgms-patients-without-diabetes, 6 pages.

Medtronic MiniMed One-press Serter User Guide, 2015, 26 pages.

Medtronic MiniMed Paradigm® 512 and 712 Insulin Pumps User Guide, 2005, pp. 1-136.

Microlet® 2 Lancing Device, 2008, retrieved from https://image. tigermedical.com/Manuals/BAY6606-20141216010820833.pdf, 1 page.

Ólafsdóttir, A. F., et al., "A Clinical Trial of the Accuracy and Treatment Experience of the Flash Glucose Monitor FreeStyle Libre in Adults with Type 1 Diabetes", Diabetes Technology & Therapeutics, 2017, vol. 19, No. 3, pp. 164-172.

"Periphery", Cambridge Dictionary of American English, 2000, p. 631.

"Product Review: Abbott FreeStyle Libre Flash Glucose Monitor", DiabetesMine Team, 2021, retrieved from https://www.healthline. com/diabetesmine/abbott-freestyle-libre-review#bottom-line, 6 pages.

"Real-World Data Show Abbott's Freestyle Libre® Systems And GLP-1 Medicines Work Better Together For People With Type 2 Diabetes", 2024, PRNewswire, 2 pages.

Sibionics GS1 Continuous Glucose Monitoring System App User Guide, 2023, 48 pages.

Sibionics GS1 Continuous Glucose Monitoring System User Guide, 2023, 25 pages.

Sibionics GS1 Continuous Glucose Monitoring System Product Insert, 2023, 3 pages.

Sibionics GS1 Quick Start Guide, 2024, 2 pages.

Van Den Boom, L., et al., "Changes in the utilization of blood glucose test strips among patients using intermittent-scanning continuous glucose monitoring in Germany", Diabetes, Obesity and Metabolism, 2020, vol. 22, pp. 922-928.

AU 2019404908 Examiner's Report, dated Feb. 17, 2025.

CA 3,050,721 Examiner's Report, dated Nov. 8, 2024.

DE Reply to Statement of Defence in the Litigation of EP 3300658, dated Dec. 10, 2024.

EP 17182379.2 Examination Report, dated Nov. 11, 2020.

EP 17182379.2 Extended Search Report, dated Mar. 1, 2018.

EP 17182379.2 Application as Filed, dated Jul. 20, 2017.

EP 20177703.4 Response to Withdrawals, dated Jan. 7, 2025.

EP 20177703.4 Withdrawal of Intervention, dated Dec. 27, 2024.

EP 20177703.4 Withdrawal of Opposition, dated Dec. 27, 2024.

EP 20177703.4 Written Submissions Dexcom, dated Nov. 22, 2024.

EP 20195922.8 Withdrawal of Intervention, dated Dec. 27, 2024.

EP 20195922.8 Withdrawal of Opposition, dated Dec. 27, 2024.

EP 21211041.5 Withdrawal of Opposition, dated Dec. 27, 2024.

EP 21211041.5 Minutes of the Oral Proceedings, dated Dec. 23, 2024.

EP 21211041.5 Notice of Appeal, dated Dec. 17, 2024.

EP 21211041.5 Response to Summons to Attend Oral Proceedings Dexcom, dated Nov. 12, 2024.

EP 21211041.5 Response to Summons to Attend Oral Proceedings, dated Nov. 12, 2024.

EP 24152079.0 Examination Report, dated Dec. 2, 2024.

EP 24194029.5 Extended Search Report, dated Nov. 18, 2024.

EP 24201435.5 Extended Search Report, dated Jan. 27, 2025.

JP 2024-31538 Office Action, dated Oct. 16, 2024.

MY PI2022002786 Examination Report, dated Jan. 8, 2025.

UP Statement of Defence in the Litigation of EP 2713879, Nov. 21, 2024.

UP Second Expert Opinion of Dr Michael Schoemaker in Litigation of EP 3977921, dated Nov. 8, 2024.

UP Defence to Revocation in the Litigation of EP 3831283, dated Oct. 2, 2024.

UP Statement of Response Including Statement of Cross-Appeal in the Proceedings for Provisional Measures Concerning EP 2713879, dated Aug. 8, 2024.

US Decision Denying Institution of Inter Partes Review, IPR No. 2024-00860, dated Nov. 20, 2024.

US Patent Owner Preliminary Response Pursuant to 37 C.F.R. § 42.107, IPR No. 2024-00860, dated Aug. 23, 2024.

US Declaration of Julia Castellano, IPR No. 2024-00860, dated Aug. 21, 2024.

US Declaration of Scott E. Davis, IPR No. 2024-00860, dated Jun. 5, 2024.

US Petitioner's Explanation Of Parallel Petitions Challenging U.S. Pat. No. 11,510,325, IPR No. 2024-00860, May 9, 2024.

US Termination Due to Settlement After Institution of Trial, IPR No. 2023-01409, dated Jan. 7, 2025.

US Joint Motion to Treat Settlement Agreement as Business Confidential Information. IPR No. 2023-01409, dated Jan. 3, 2025.

US Joint Motion to Terminate Proceeding Under 35 U.S.C. § 317(a), IPR No. 2023-01409, dated Jan. 3, 2025.

US Order Setting Oral Argument, IPR No. 2023-01409, dated Dec. 11, 2024.

US Patent Owner's Sur-Reply, IPR No. 2023-01409, dated Dec. 10, 2024.

US Deposition of Gary D. Fletcher, Ph.D., IPR No. 2023-01409, dated Dec. 4, 2024.

US Patent Owner's Request For Oral Argument, IPR No. 2023-01409, dated Dec. 3, 2024.

US Petitioner's Request For Oral Argument, IPR No. 2023-01409, dated Dec. 3, 2024.

US Patent Owner's Objections to Petitioner's Exhibits Submitted With Its Reply, IPR No. 2023-01409, Nov. 1, 2024.

US Petitioner's Updated Exhibit List, IPR No. 2023-01409, dated Oct. 25, 2024.

US Second Declaration of Gary Fletcher, Ph.D., IPR No. 2023-01409, dated Oct. 25, 2024.

US Petitioner's Reply to Patent Owner's Response, IPR No. 2023-01409, dated Oct. 25, 2024.

US Deposition of Karl R. Leinsing, MSME, PE, IPR No. 2023-01409, dated Oct. 17, 2024.

US Conference Call Before The Patent Trial And Appeal Board Before Judge Cynthia Hardman, IPR No. 2023-01409, dated Oct. 17, 2024.

US Notice of Joint Stipulation to Modify Schedule, IPR No. 2023-01409, dated Sep. 26, 2024.

US Decision Denying Patent Owner's Request on Rehearing of Decision Denying Institution, IPR No. 2023-01396, Aug. 9, 2024.

US Reexamination U.S. Appl. No. 90/019,307 Decision on Petition, dated Feb. 13, 2025.

US Reexamination U.S. Appl. No. 90/019,331 Ex Parte Reexamination Certificate, dated Nov. 14, 2024.

Abbott Patent Marking Diabetes, 2024, retrieved from https://www. abbott.com/patents/diabetes-patents.html, 6 pages.

Burge, M. R., et al., "Continuous Glucose Monitoring: The Future of Diabetes Management", Diabetes Spectrum, 2008, vol. 21, No. 2, pp. 112-119.

Cable Products for the Medical Industry, Molex®, 2010, 4 pages.

"Choosing Electronic Connectors for Medical Devices", retrieved from https://www.mddionline.com/components/choosing-electronic-connectors-for-medical-devices, 2014, 9 pages.

Clancy, N. T., et al., "A new device for assessing changes in skin viscoelasticity using indentation and optical measurement", Skin Research and Technology, 2010, vol. 16, pp. 210-228.

Cleo® 90 Infusion Set 510(k) Premarket Notification, 2004, 1 page.

Dexcom STS Continuous Monitors FDA Premarket Approval (PMA), 2006, 2 pages.

Dutt-Ballerstadt, R., et al., "A label-free fiber-optic Turbidity Affinity Sensor (TAS) for continuous glucose monitoring", Biosensors and Bioelectronics, 2014, vol. 61, pp. 280-284.

(56) References Cited

OTHER PUBLICATIONS

"Enabling the Devices that Drive Innovation in Healthcare", Molex®, 2013, 12 pages.
Ferguson, B. S., et al., "Real-Time, Aptamer-Based Tracking of Circulating Therapeutic Agents in Living Animals", Science, 2013, vol. 5, No. 213, pp. 1-9.
"The Future is Bright for Veteran-centric Rehabilitation Research Publications", Journal of Rehabilitation Research & Development (JRRD), 2013, retrieved from https://www.rehab.research.va.gov/jrrd/index.html, 2 pages.
Improved Healthcare Monitoring and Patient Safety: Compliant Integrated Solutions for Durable Medical Devices, Molex®, 2015, 2 pages.
Mazze, R. S., et al., "Evaluating the Accuracy, Reliability, and Clinical Applicability of Continuous Glucose Monitoring (CGM): Is CGM Ready for Real Time?", Diabetes Technology & Therapeutics, 2009, vol. 11, No. 1., pp. 11-18.
MediSpec™ MID/LDS Capabilities for High-Density Medical and other Applications, Molex®, 2011, 2 pages.
"Molex—Medical Capabilities—Certifications" available on YouTube since Jul. 1, 2015 retrieved from https://www.youtube.com/watch?v=wMQzhXBd8hw, 6 pages.
"Molex—Product of the Quarter Videos—Micro Products" available on YouTube since Oct. 7, 2013, retrieved from https://www.youtube.com/watch?v=CSV88TUYvy0, 10 pages.
Piper, H. G., et al., "Real-Time Continuous Glucose Monitoring in Pediatric Patients During and After Cardiac Surgery", Pediatrics, 2006, vol. 118, No. 3, pp. 1176-1184.
Rabiee, A., et al., "Numerical and Clinical Accuracy of a Continuous Glucose Monitoring System during Intravenous Insulin Therapy in the Surgical and Burn Intensive Care Units", Journal of Diabetes Science and Technology, 2009, vol. 3, No. 4, pp. 951-959.
Sacks, A. H., et al., "Skin blood flow changes and tissue deformations produced by cylindrical indentors", Journal of Rehabilitation Research and Development, 1985, vol. 22, No. 3, pp. 1-6.
Schneider, M., et al., "Evaluating the use of the Cleo® 90 infusion set for patients on a palliative care unit", International Journal of Palliative Nursing, 2009, vol. 15, No. 8, pp. 372-376.
Stay Connected, Affinity Medical™ Connectors and Cable Assemblies for Patient Critical Applications, Molex®, 2014, 8 pages.
CA 3,228,738 Examiner's Report, dated May 8, 2025.
EP 17182379.2 Reply to Reply to Opposition, dated May 16, 2025.
EP 17182379.2 Reply to Opposition, dated Feb. 27, 2025.
EP 19900891.3 Examination Report, dated May 8, 2025.
EP 21211041.5 Grounds of Appeal, dated Apr. 23, 2025.
EP 23190032.5 Examination Report, dated May 19, 2025.
JP 2023-516522 Office Action, dated Mar. 5, 2025.
JP 2023-514024 Office Action, dated Apr. 16, 2025.
MX MX/a/2021/007294 Second Office Action, dated Feb. 19, 2025.
MY PI2021003022 Examination Report, dated Mar. 5, 2025.
US Patent Owner's Response To Petitioner's Explanation Of Parallel Petitions Challenging U.S. Pat. No. 11,510,325, IPR No. 2024-00860, dated Aug. 23, 2024.
US Petitioner's Explanation Of Parallel Petitions Challenging U.S. Pat. No. 11,510,325, IPR No. 2024-00860, dated May 9, 2024.
US Reexamination U.S. Appl. No. 90/019,307 Office Action, dated Mar. 18, 2025.
US Reexamination U.S. Appl. No. 90/019,329 Decision on Petition Under 37 C.F.R. § 1.181, dated Mar. 18, 2025.
WO PCT/US25/13698 ISR and Written Opinion, dated Jun. 5, 2025.
CN 202180063087.5 First Office Action, dated Aug. 14, 2025.
EP 17182379.2 Response to Summons to Atten Oral Proceedings, dated Aug. 6, 2025.
EP 17182379.2 Summons to Atten Oral Proceedings, dated Jul. 4, 2025.
EP 18741791.0 Examination Report, dated Sep. 12, 2025.
EP 19151577.4 Examination Report, dated Sep. 3, 2025.
EP 20177712.5 Written Submissions Gulde, dated Aug. 21, 2025.
EP 20177712.5 Response to Summons to Attend Oral Proceedings, dated Aug. 21, 2025.

EP 21152231.3 Examination Report, dated Jul. 4, 2022.
EP 21152231.3 Response to Examination Report, dated May 9, 2022.
EP 21152231.3 Examination Report, dated Jan. 3, 2022.
EP 21152231.3 Response to Communication, dated Oct. 4, 2021.
EP 21152231.3 Extended Search Report, dated May 11, 2021.
EP 21192910.4 Notice of Opposition Stolmar, dated Sep. 9, 2025.
EP 21192910.4 Notice of Opposition Strawman, dated Sep. 10, 2025.
EP 24218309.3 Extended Search Report, Jul. 9, 2025.
EP 24194029.5 Examination Report, dated Aug. 26, 2025.
EP 24220160.6 Extended Search Report, dated Jun. 17, 2025.
ES Expert Opinion of Fernando Prieto Moran in Litigation of EP 3831283, dated Mar. 22, 2024.
IT Preliminary Report of Office Technical Consultancy in Litigation of EP 3300658, dated Jul. 14, 2025.
IT Comments of the Resisting Parties in Litigation of EP 3300658, dated Jun. 25, 2025.
IT Observations Of The Claimant Experts To The Preliminary Report Of The Court-Appointed Expert in Litigation of EP 3300658, dated Jun. 20, 2025.
IT Preliminary Report of Court-Appointed Expertise in Litigation of EP 3300658, dated May 27, 2025.
IT Third Technical Brief of the Resisting Parties in Litigation of EP 3300658, dated May 16, 2025.
IT Third Technical Brief of the Claimant Experts For The Technical Expert Appointed By The Court in Litigation of EP 3300658, dated May 16, 2025.
IT Second Technical Brief of the Claimant Experts For The Technical Expert Appointed By The Court in Litigation of EP 3300658, dated Apr. 17, 2025.
IT Second Technical Pleading of the Resisting Parties in Litigation of EP 3300658, dated Apr. 14, 2025.
IT First Technical Brief of the Resisting Parties in Litigation of EP 3300658, dated Mar. 21, 2025.
IT First Technical Brief of the Plaintiff Experts For The Technical Expert Appointed By The Court in Litigation of EP 3300658, dated Mar. 21, 2025.
IT Statement of Defence in Litigation of EP 3300658, dated Jun. 27, 2024.
JP 2023-514023 Final Office Action, dated Aug. 20, 2025.
JP 2023-514024 Office Action, dated Apr. 30, 2025.
JP 2023-532327 Office Action, dated Jul. 23, 2025.
JP 2025-026588 Office Action, dated Aug. 27, 2025.
UP Order in the Litigation of EP 4344633, dated Oct. 17, 2025.
UP Defence to the Counterclaim for Revocation in the Litigation of EP 3831283, Sep. 11, 2025.
UP Reply to the Statement of Defence in the Litigation of EP 3831283, dated Sep. 11, 2025.
UP Application to Amend the Patent Pursuant to Rule 30.1 RoP in the Litigation of EP 3831283, dated Sep. 11, 2025.
UP Statement of Defence in the Litigation of EP 3831283, dated Jul. 9, 2025.
UP Counterclaim for Revocation in the Litigation of EP 3831283, dated Jul. 9, 2025.
UP Procedural Order in the Litigation of EP 3831283, dated May 25, 2025.
UP Defence to the Application to Amend the Patent pursuant to R. 43.3, 55, 32.1 RoP in the Litigation of EP 3831283, dated Mar. 17, 2025.
UP Statement of Claim in the Litigation of EP 3831283, dated Mar. 14, 2025.
UP Application pursuant to Rule 30.1 ROP Request to dismiss the submitted auxiliary requests in the Litigation of EP 3831283, dated Feb. 17, 2025.
UP Order in the Litigation of EP 3831283, dated Feb. 14, 2025.
UP Rejoinder to Reply in the Litigation of EP 3831283, dated Jan. 16, 2025.
UP Application to Amend the Patent Pursuant to Rule 30 in the Litigation of EP 3831283, dated Jan. 16, 2025.
UP Reply to Defence to Revocation in the Litigation of EP 3831283, dated Dec. 2, 2024.

(56)    References Cited

OTHER PUBLICATIONS

UP Statement of Response to Appeal in the Litigation of EP 3831283, dated Aug. 27, 2024.
UP Amended Statement of Defence in the Litigation of EP 2713879, dated Nov. 21, 2024.
UP Statement of Defence in the Litigation of EP 2713879, dated Nov. 21, 2024.
US Reexamination U.S. Appl. No. 90/019,307 Final Office Action, dated Jul. 8, 2025.
WO PCT/US2025/027260 ISR and Written Opinion, dated Sep. 16, 2025.
WO PCT/US25/27260 Invitation to Pay Additional Fees, dated Jul. 24, 2025.
EP 17182379.2 Decision Revoking the European Patent, Nov. 24, 2025.
EP 17182379.2 Minutes of the Oral Proceedings, Nov. 24, 2025.
EP 18741791.0 Examination Report, Sep. 12, 2025.
EP 20177712.5 Decision Revoking the European Patent, Nov. 28, 2025.
EP 20177712.5 Minutes of the Oral Proceedings, Nov. 28, 2025.
EP 2119210.4 Notice of Intervention, Nov. 14, 2025.

EP 221772864.1 Examination Report, Dec. 9, 2025.
EP 23166498.8 Examination Report, Dec. 10, 2025.
EP 23189932.5 Examination Report, Dec. 10, 2025.
EP 24201435.5 Examination Report, Oct. 26, 2025.
MX MX/a/2021/007294 Third Office Action, Sep. 10, 2025.
UP Statement of Grounds of Appeal in Litigation of EP 3831283, Nov. 21, 2025.
UP Reply to Objection for Provisional Measures in the Litigation of EP 3960072, Dec. 5, 2025.
UP Objection to the Application for provisional measures in the Litigation of EP 3960072, Nov. 17, 2025.
UP Statement of Response in the Proceedings for Provisional Measures Concerning EP 4344633, Nov. 21, 2025.
UP Statement of Claim Infringement Action Regarding EP 4344633, Nov. 17, 2025.
UP Statement of Appeal Statement of Grounds of Appeal in Litigation of EP 4344633, Oct. 31, 2025.
UP Reply to Objection for Provisional Measures in Litigation of EP 4344633, Aug. 25, 2025.
UP Formal Response to the Order: Objection to Application for Provisional Measures in Litigation of EP 4344633, Aug. 18, 2025.

* cited by examiner

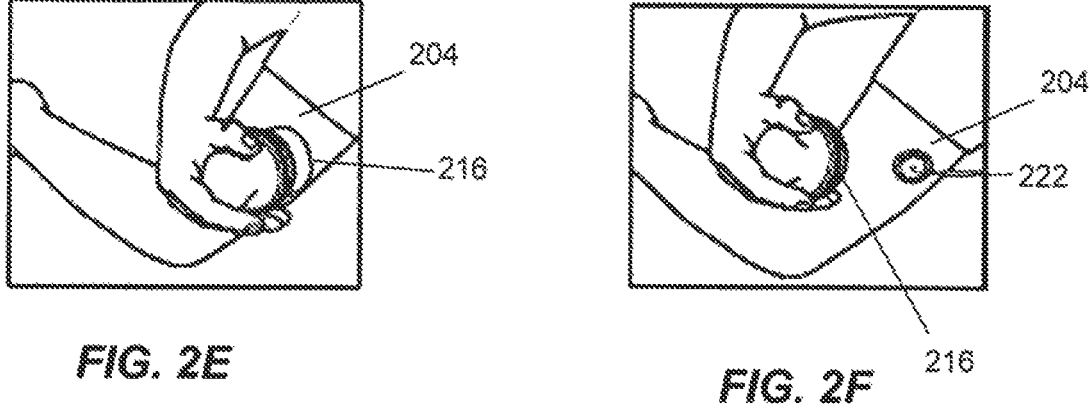
*FIG. 2E*
*FIG. 2F*
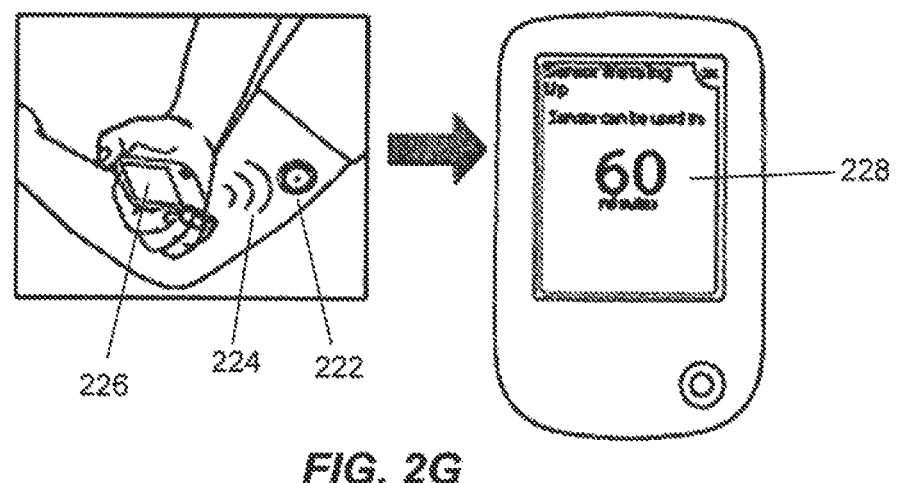
*FIG. 2G*

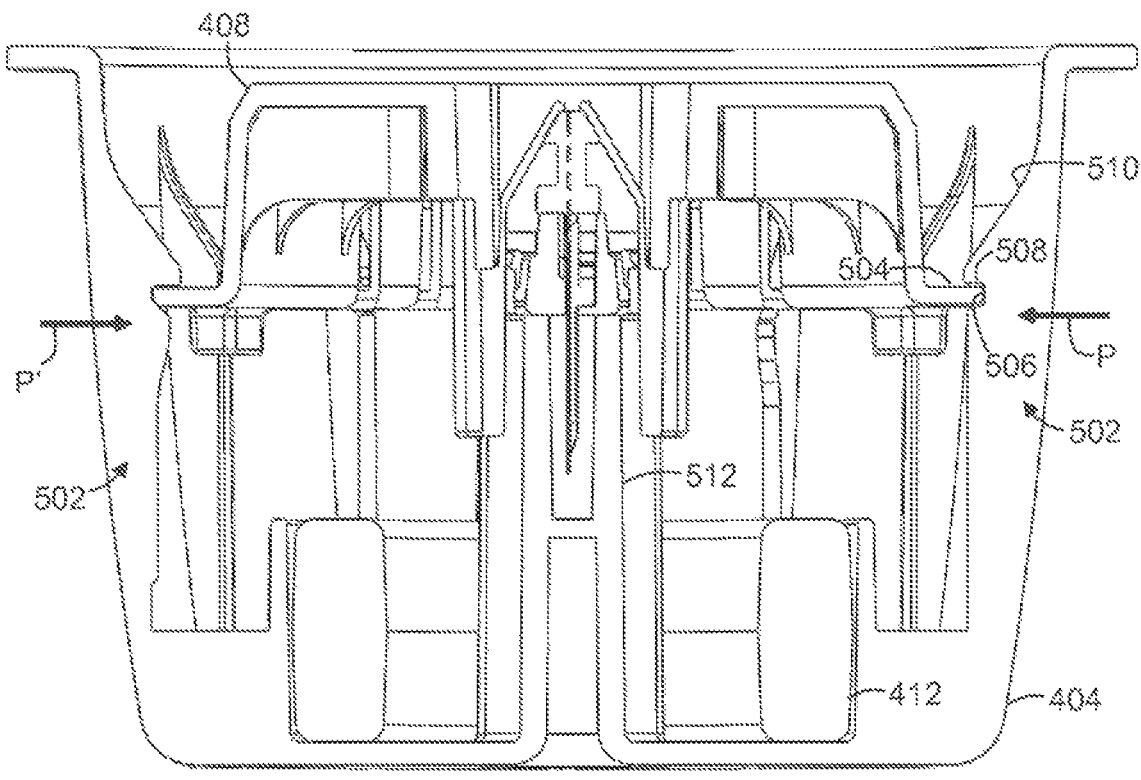
*FIG. 5B*

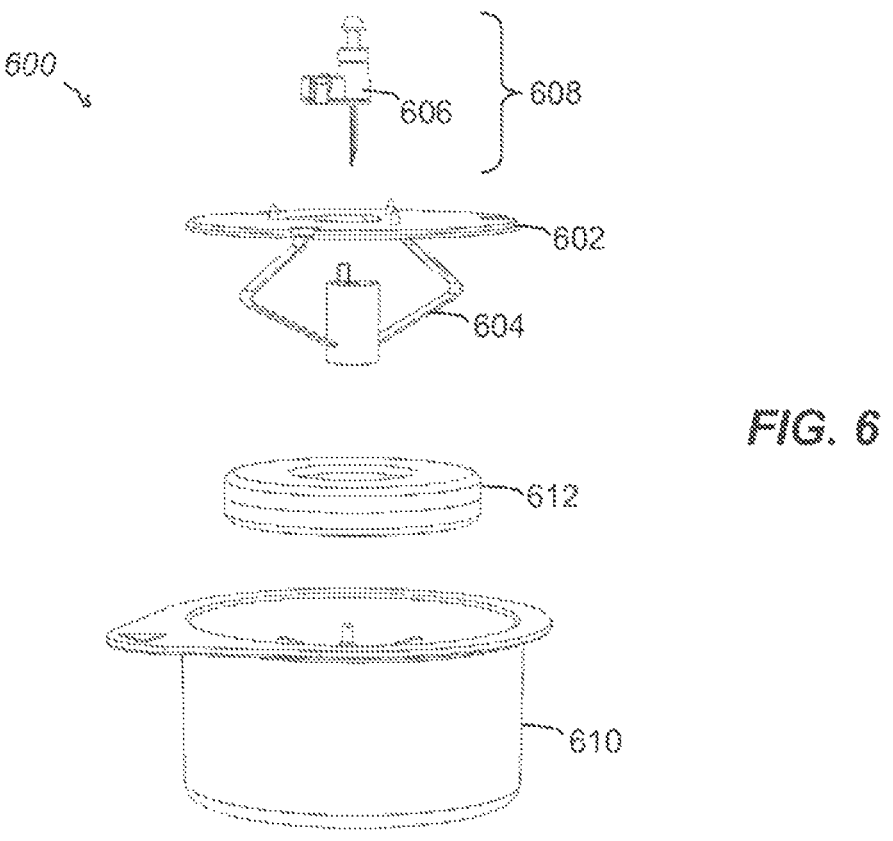
FIG. 6
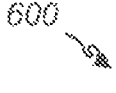
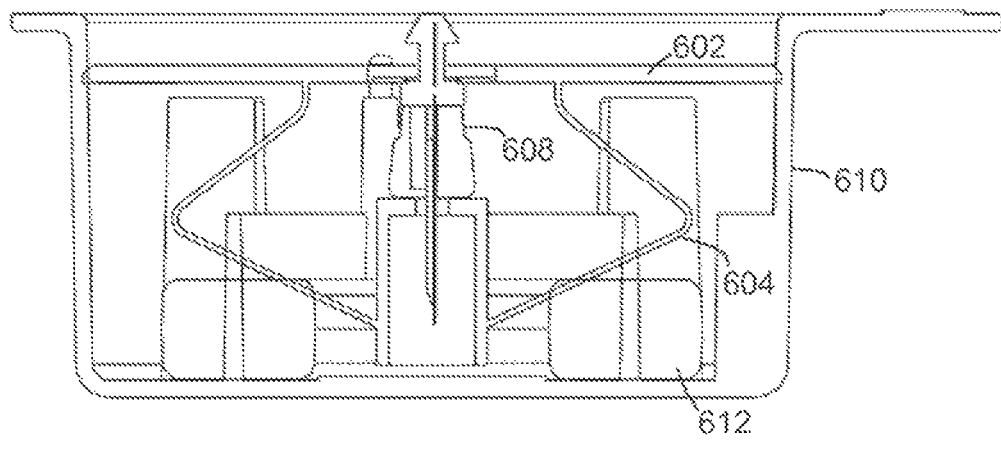
FIG. 7

206

402

408

404

212

314

216

214

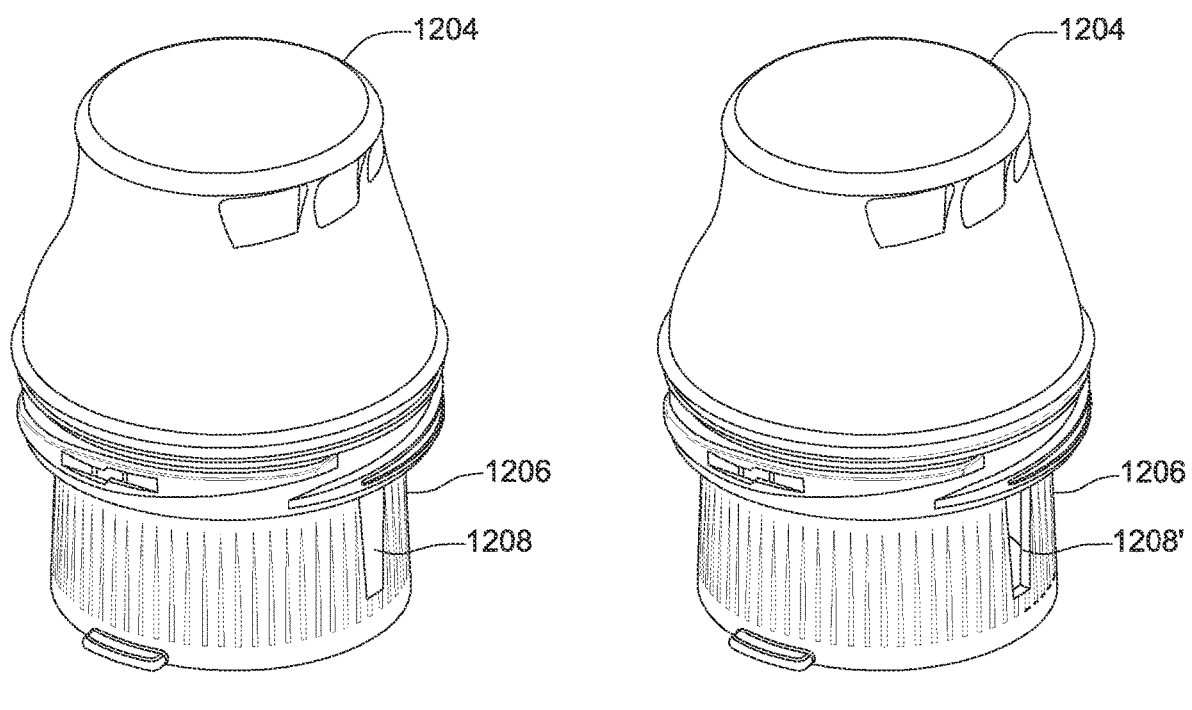
*FIG. 13A*          *FIG. 13B*
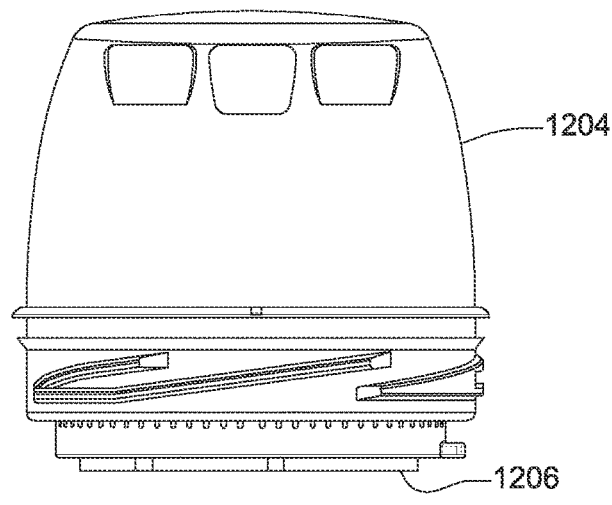
*FIG. 13C*

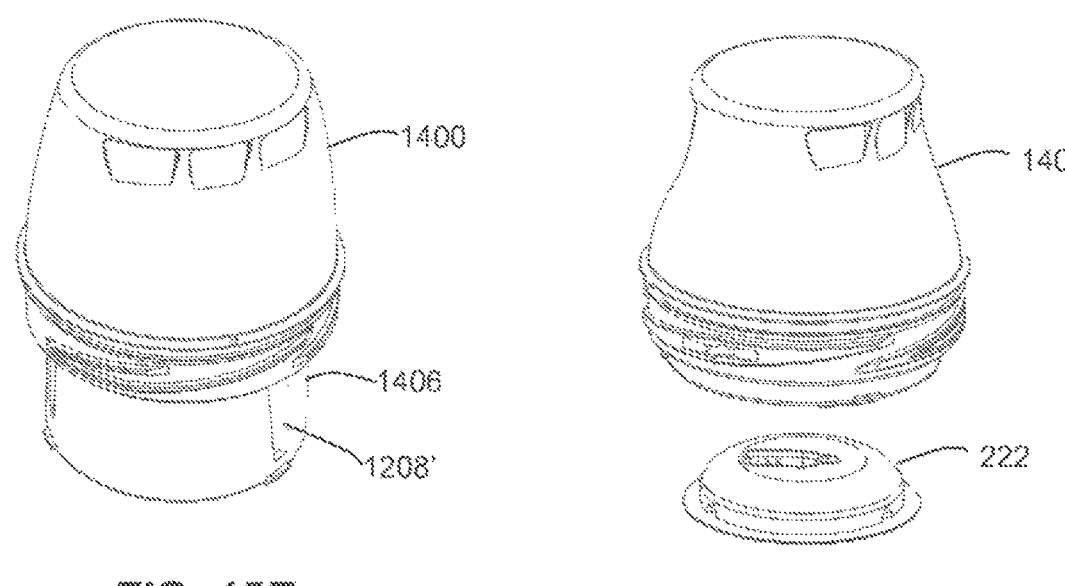
*FIG. 15E*
*FIG. 15F*
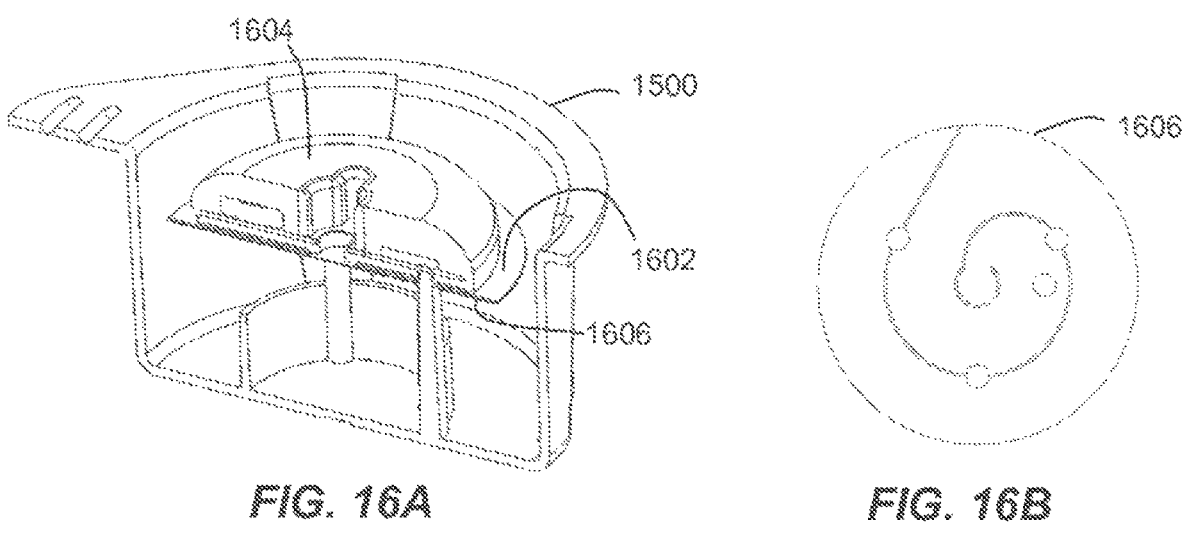
*FIG. 16A*
*FIG. 16B*

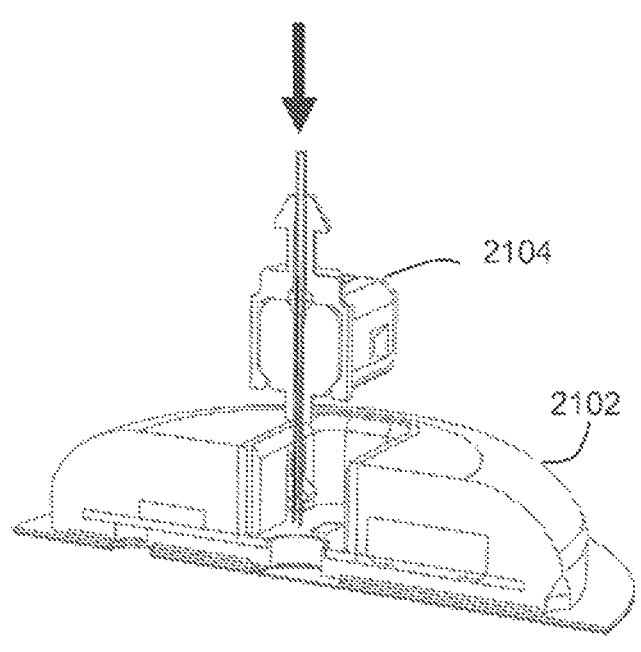
*FIG. 21A*
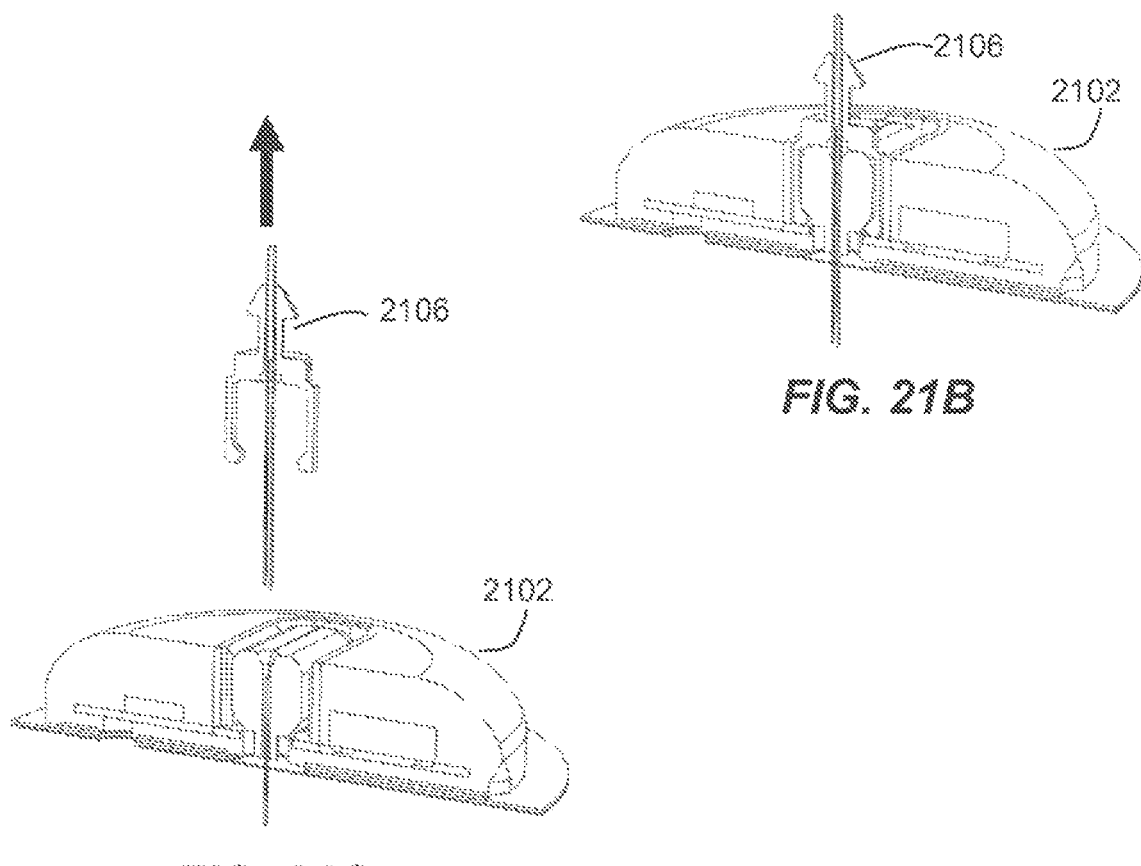
*FIG. 21B*
*FIG. 21C*

2202

2204

2206

2208

2210

2202

2204

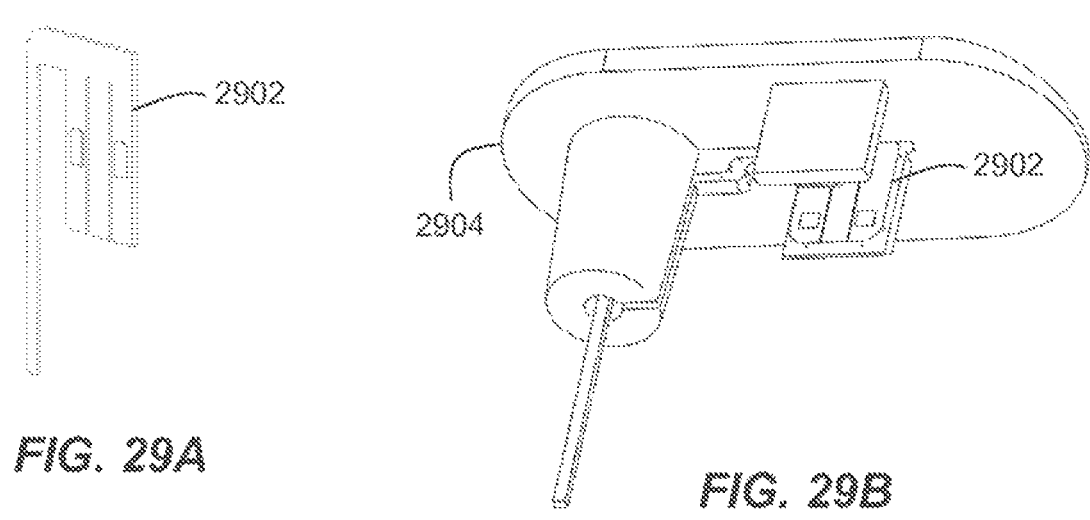
*FIG. 29A*
*FIG. 29B*
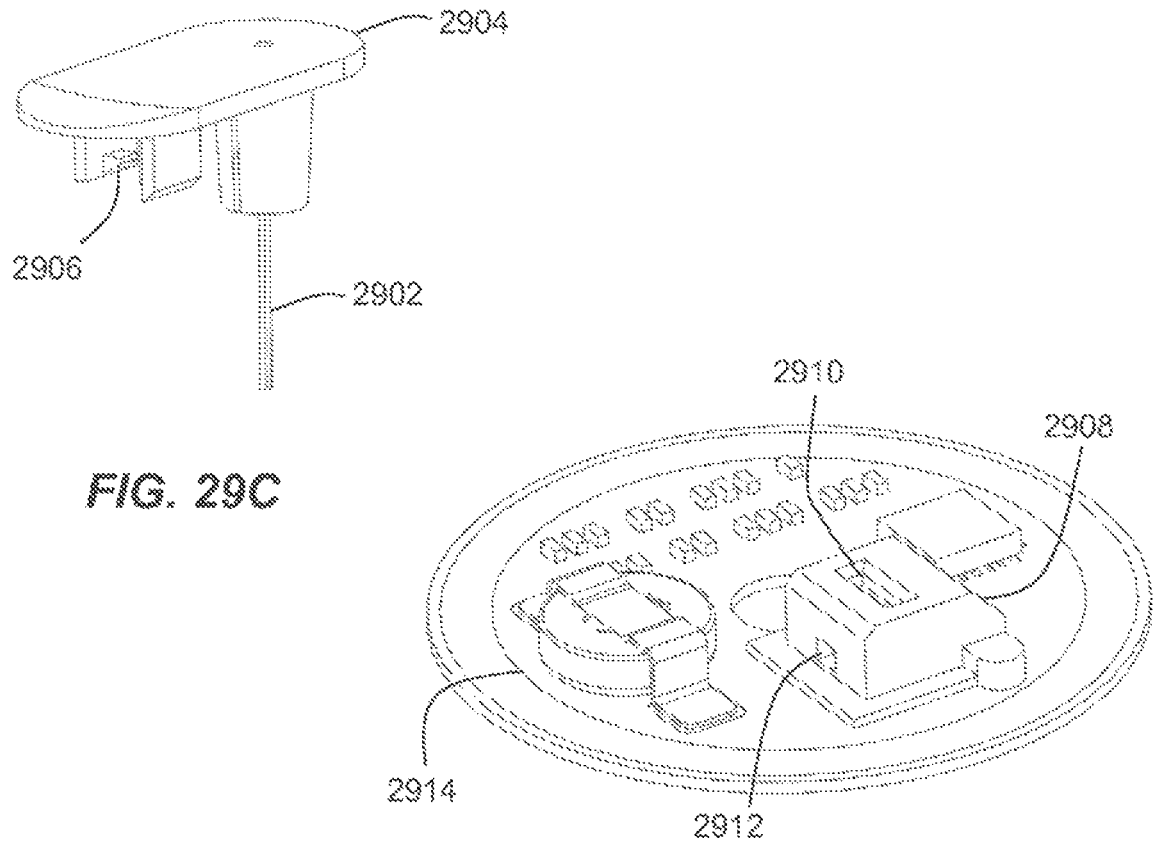
*FIG. 29C*
*FIG. 29D*

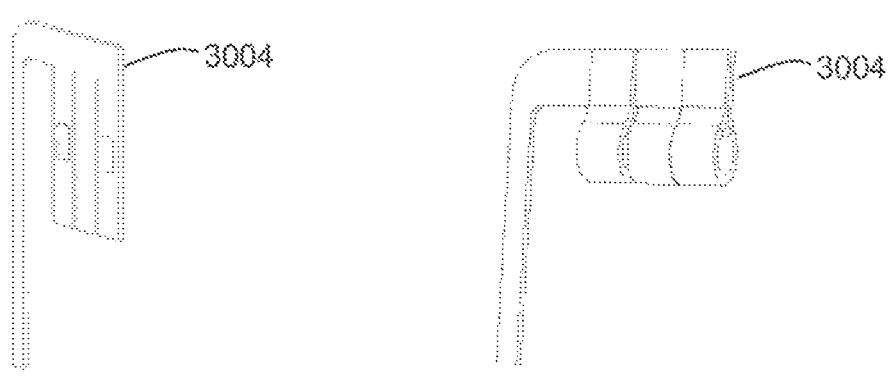
*FIG. 30A*
*FIG. 30B*
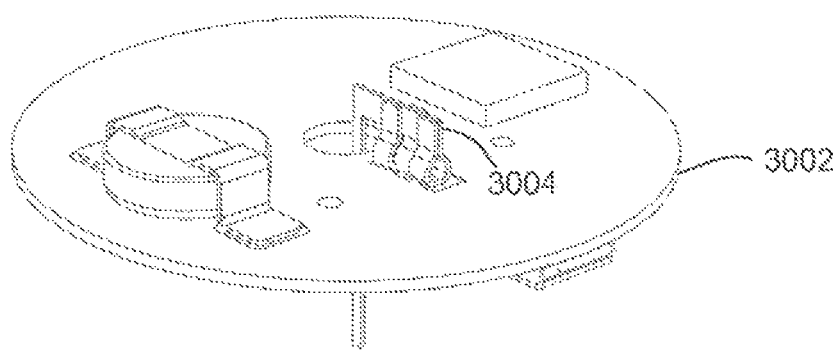
*FIG. 30C*
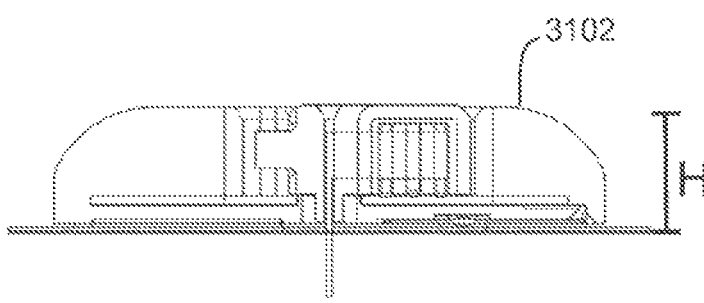
*FIG. 31*

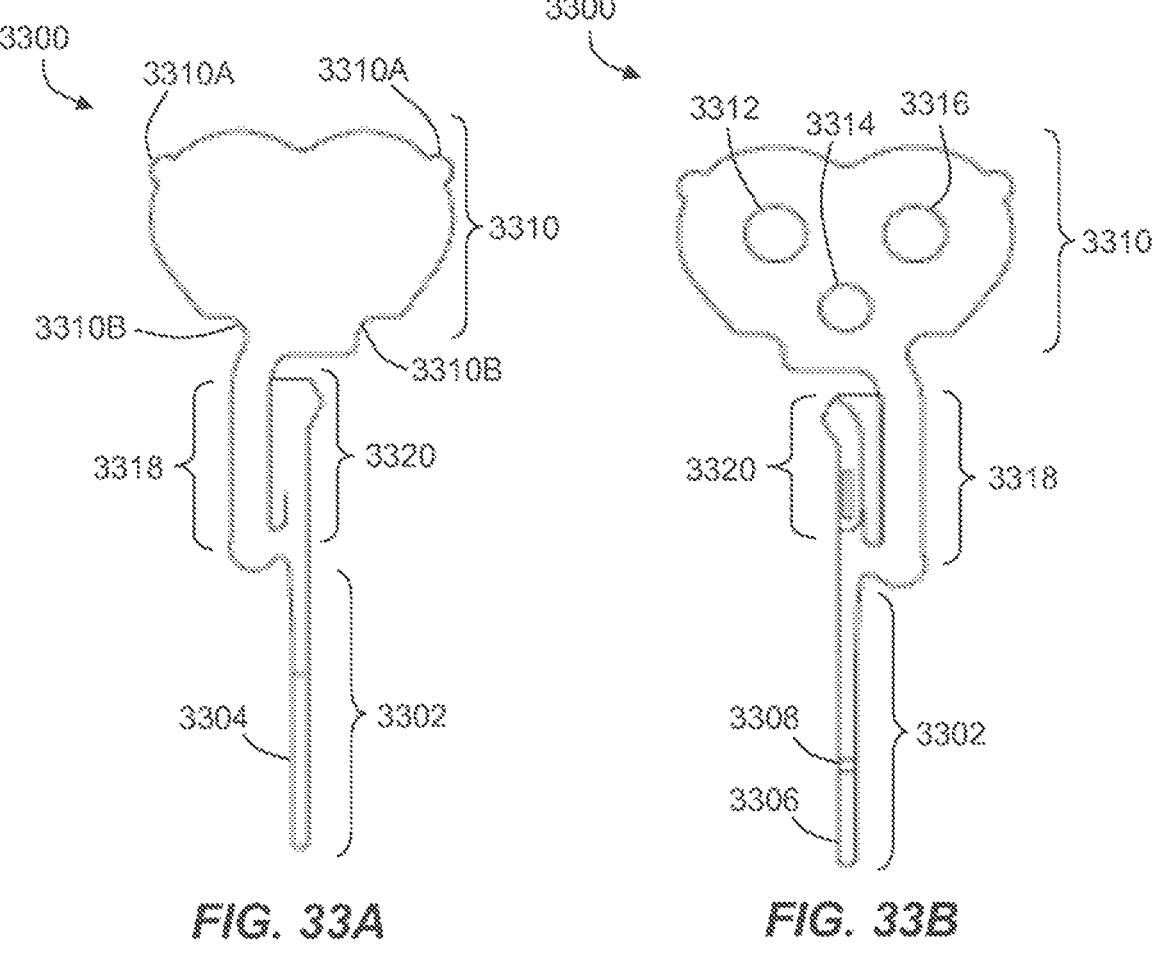
FIG. 33A                    FIG. 33B

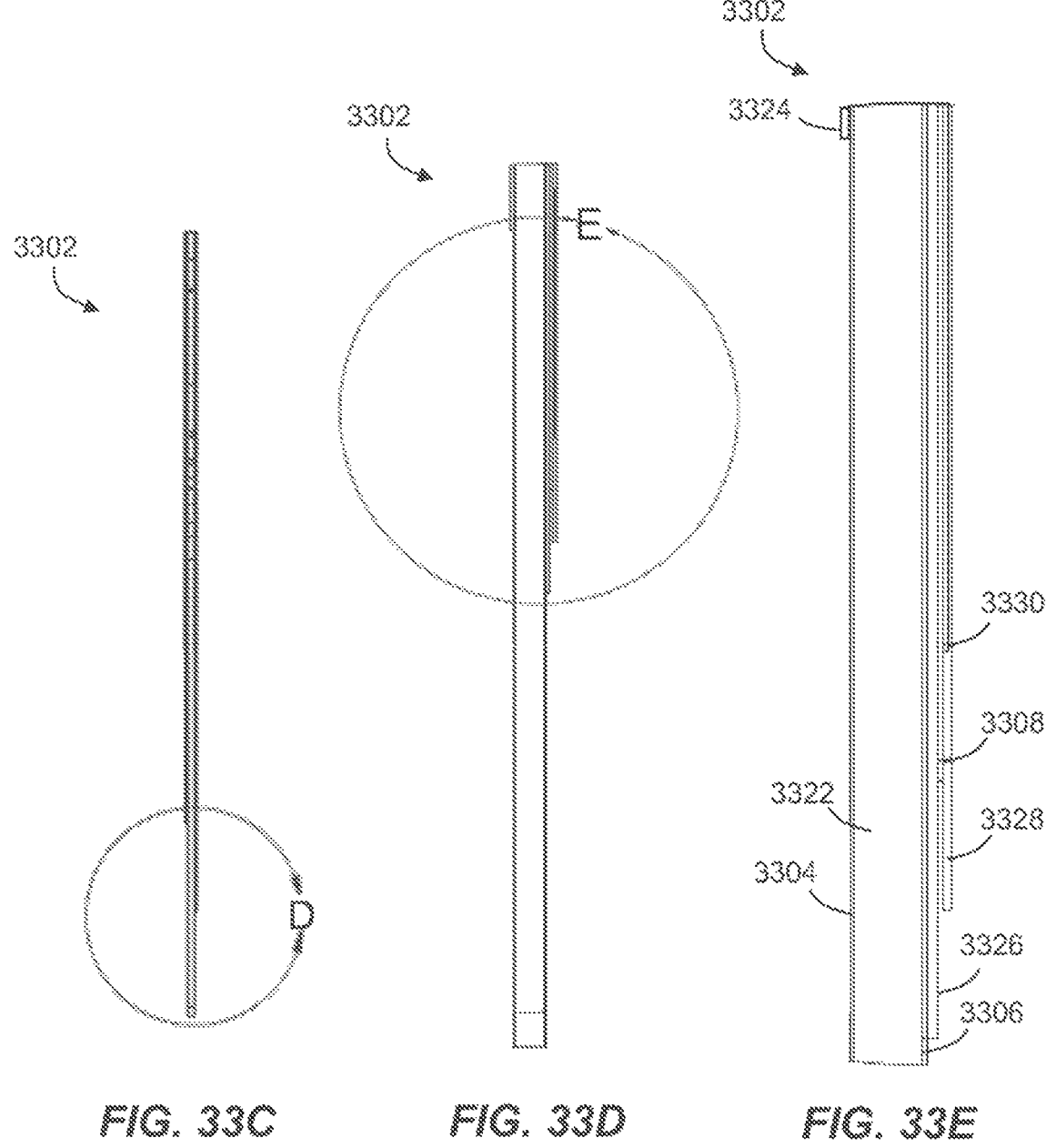
*FIG. 33C*          *FIG. 33D*          *FIG. 33E*

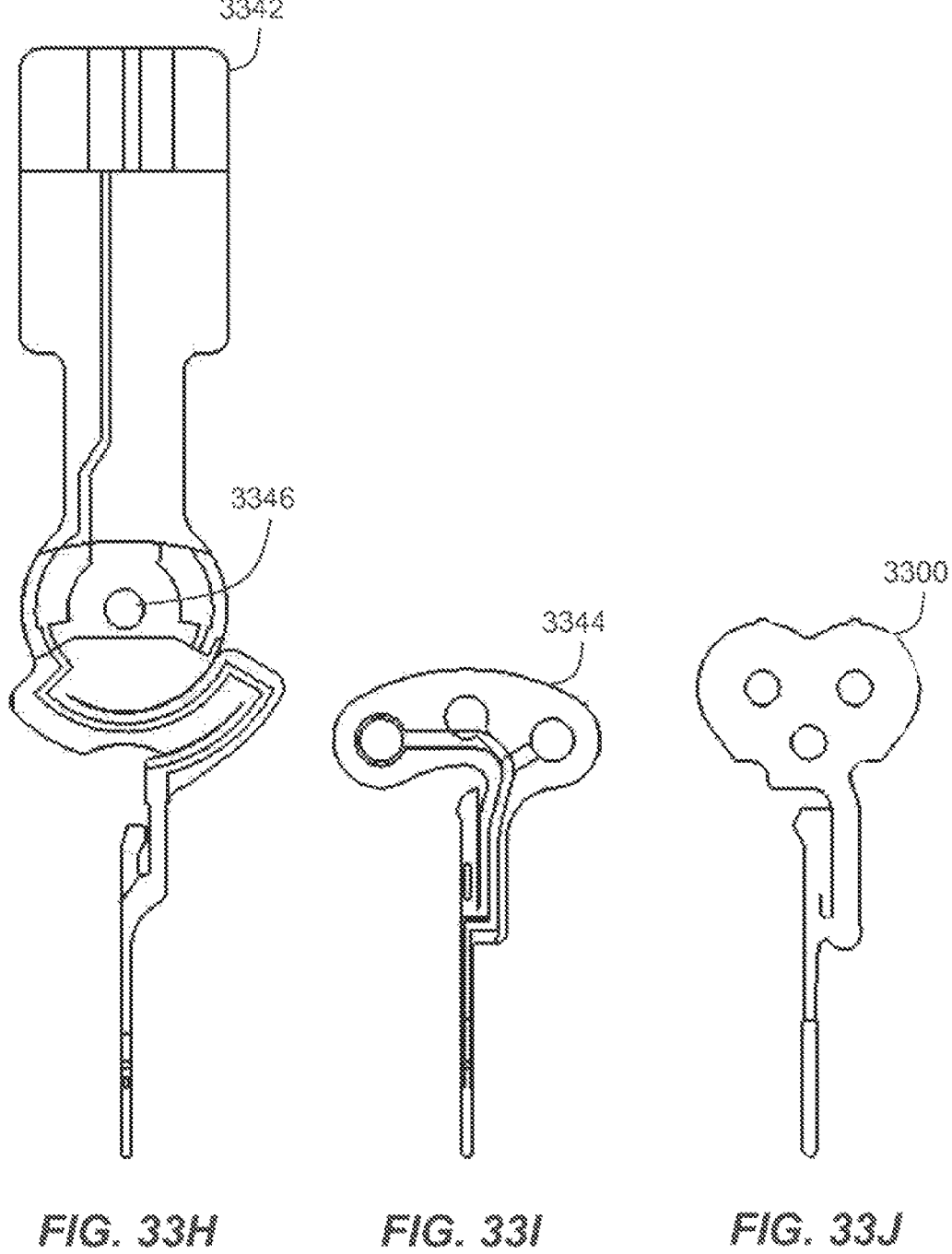
*FIG. 33H*          *FIG. 33I*          *FIG. 33J*

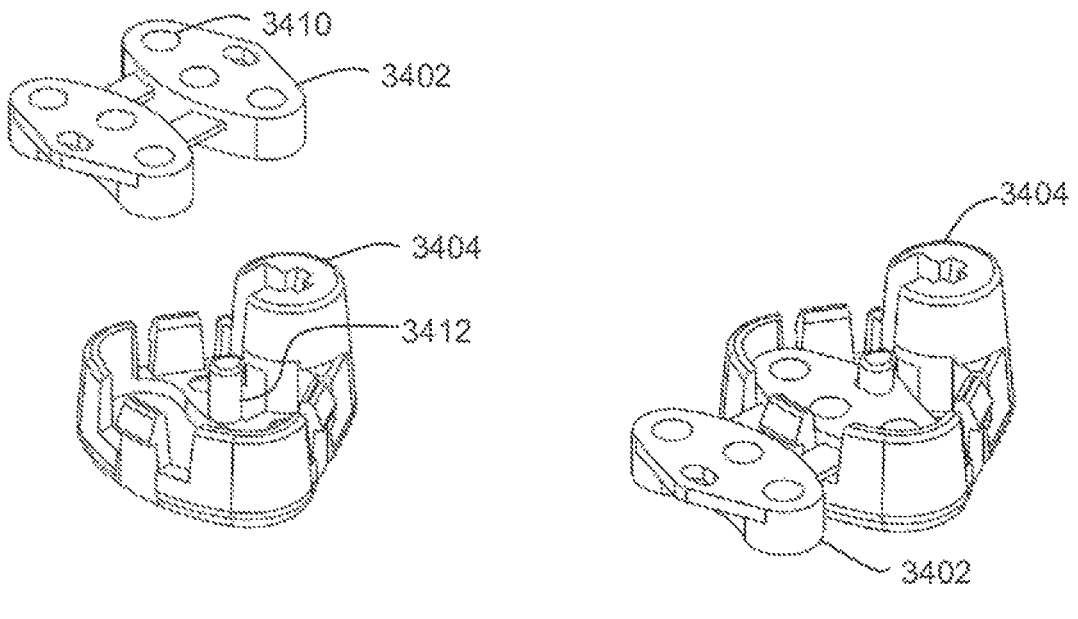
*FIG. 34A*          *FIG. 34B*
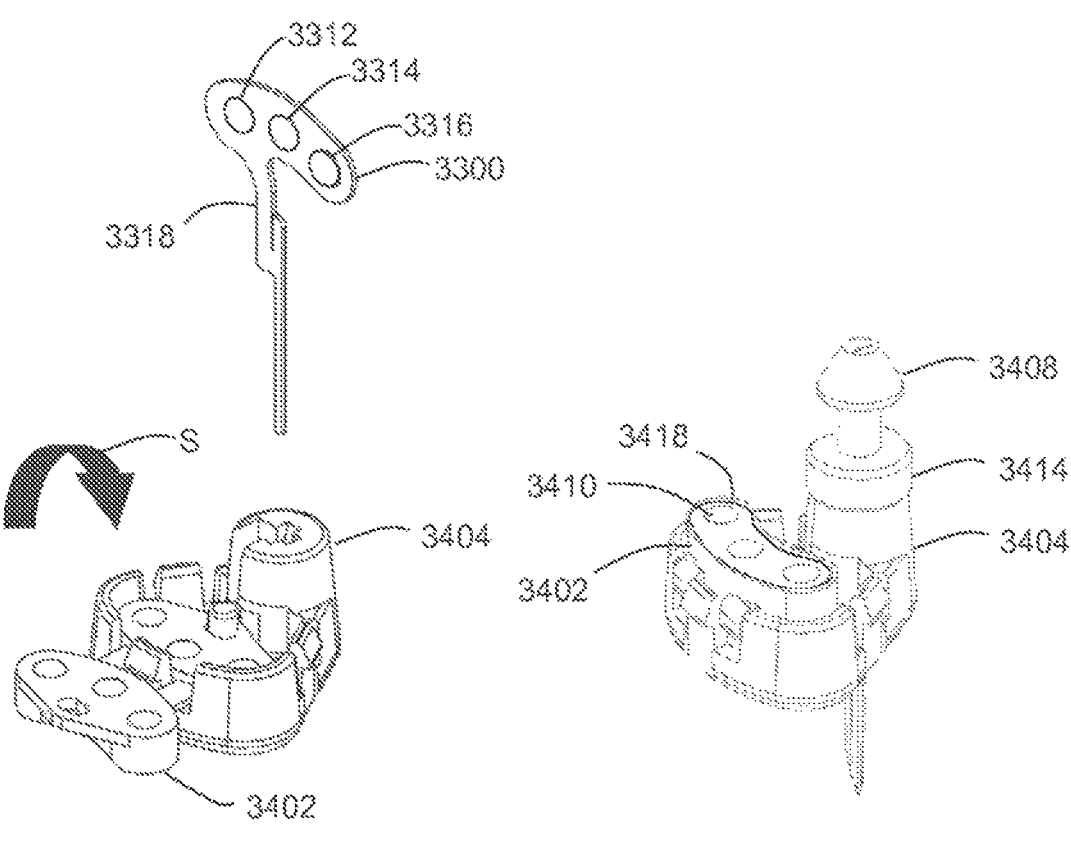
*FIG. 34C*          *FIG. 34D*

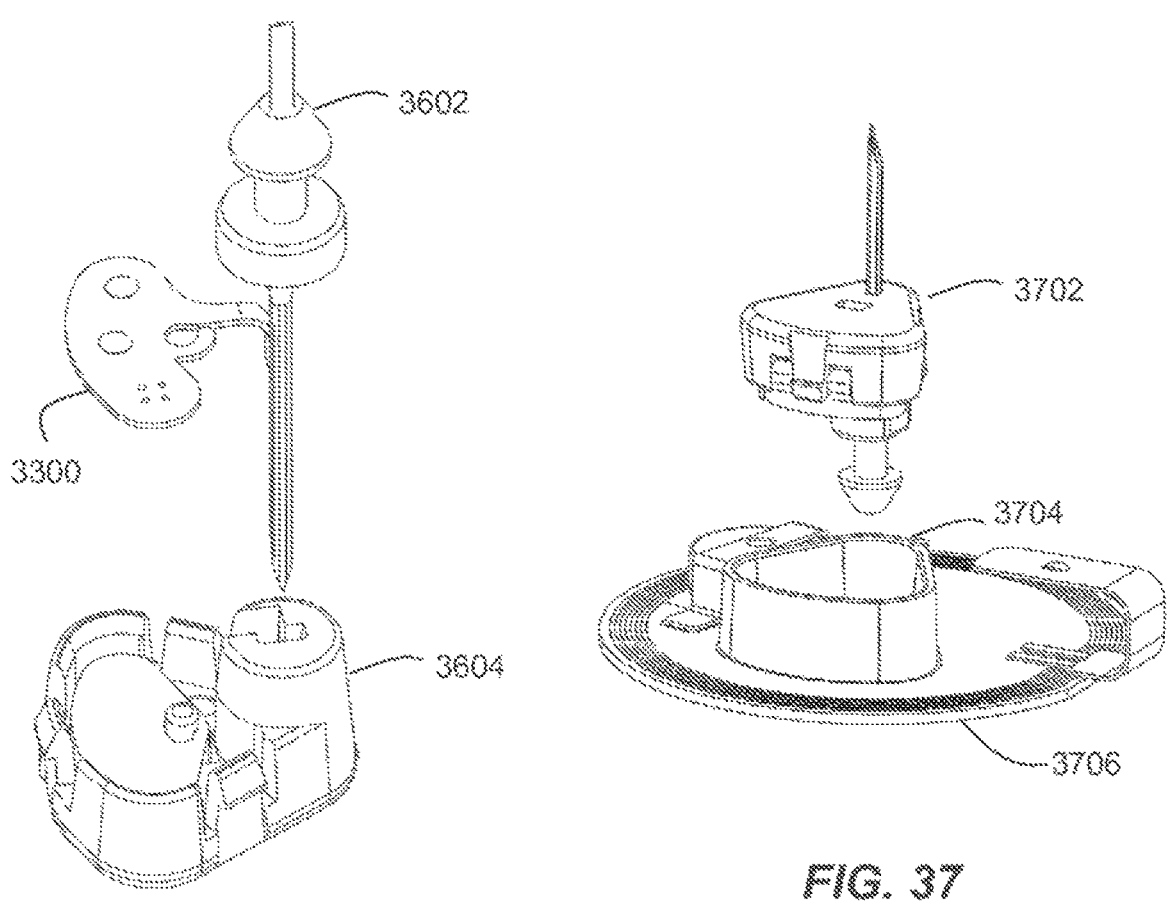
*FIG. 36*
*FIG. 37*
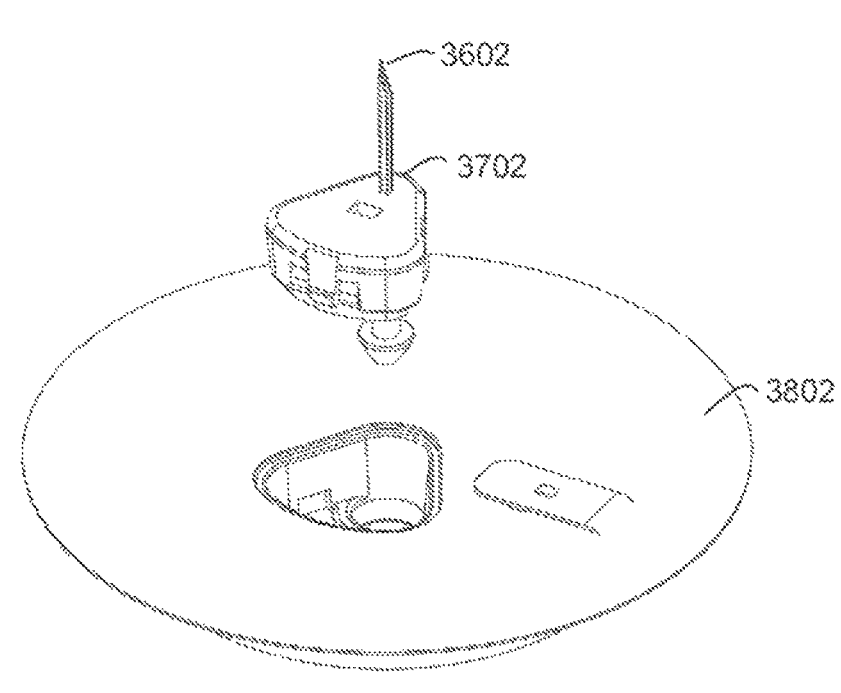
*FIG. 38*

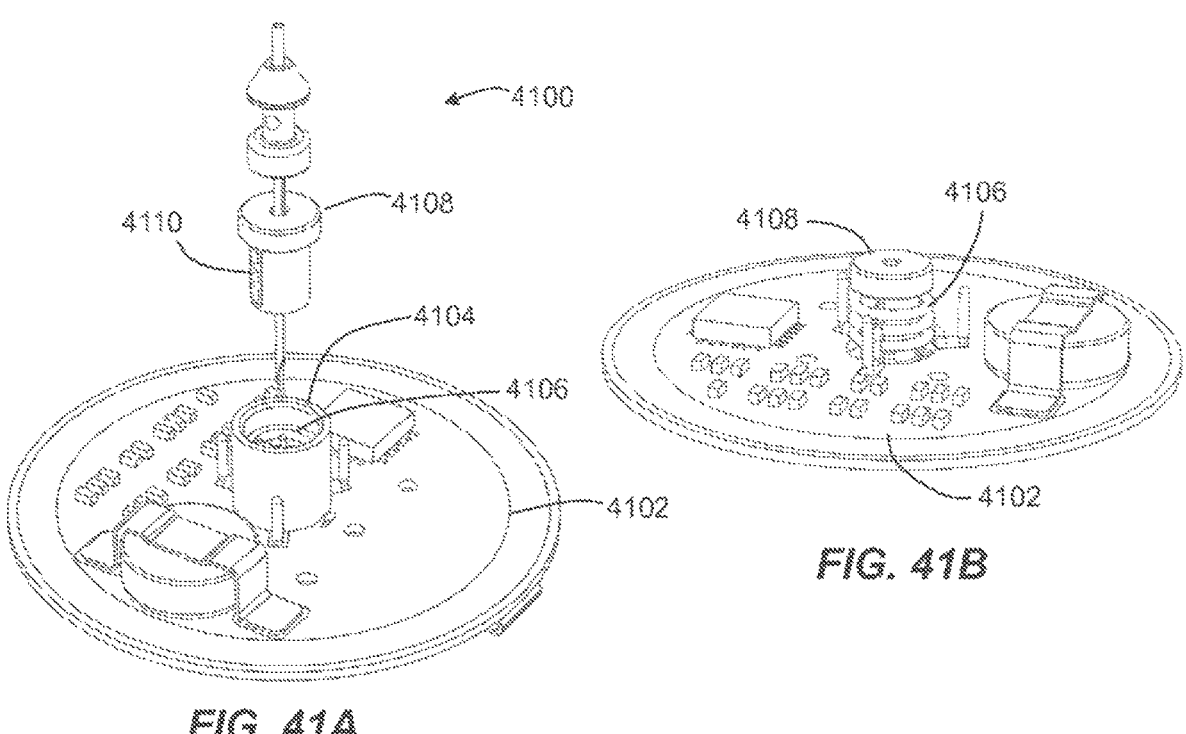
FIG. 41A
FIG. 41B
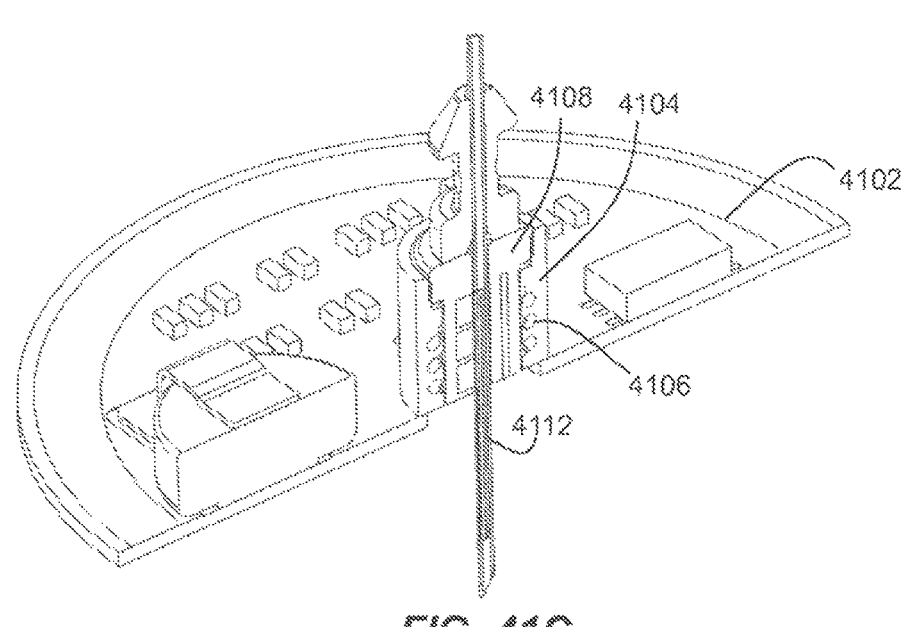
FIG. 41C

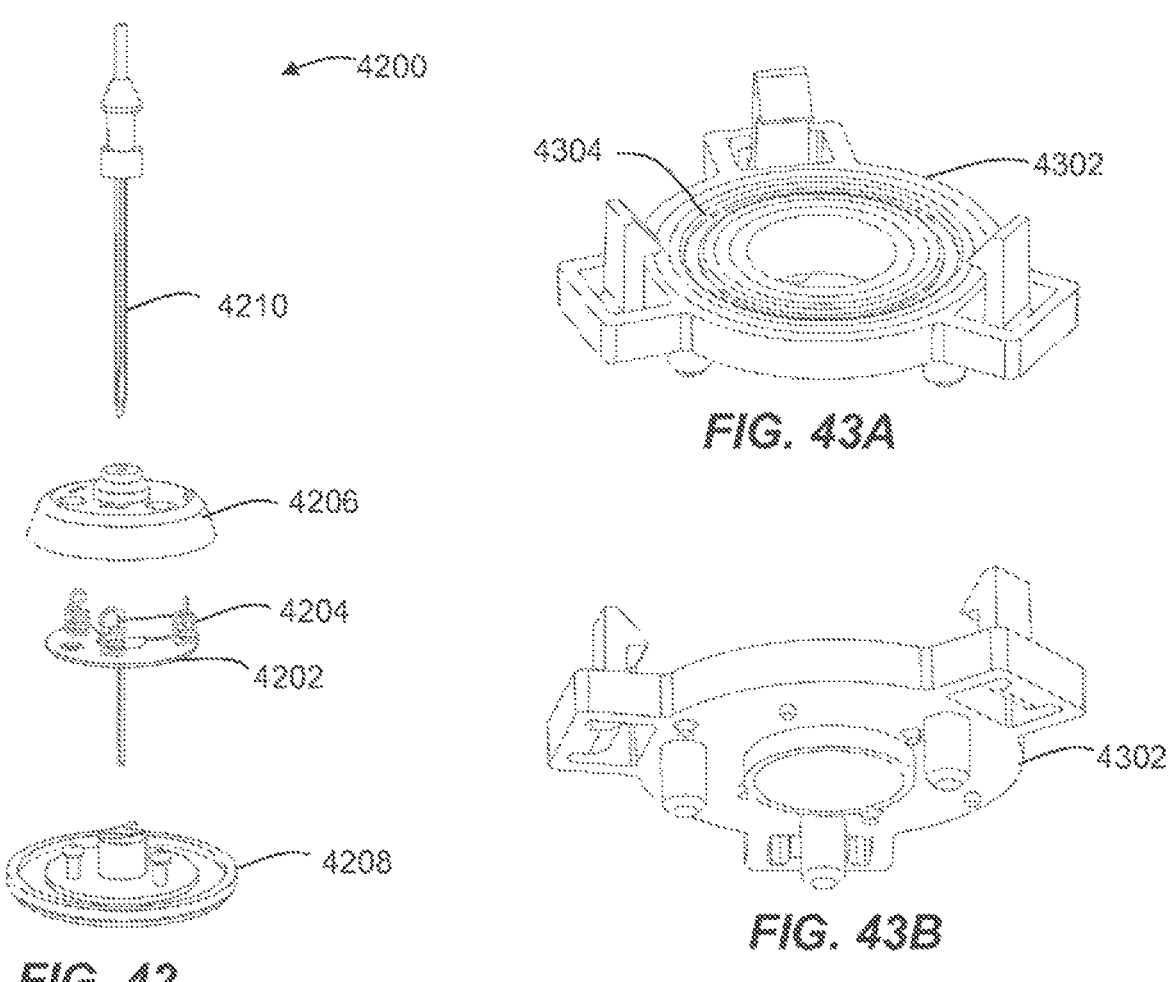
FIG. 43A
FIG. 42
FIG. 43B
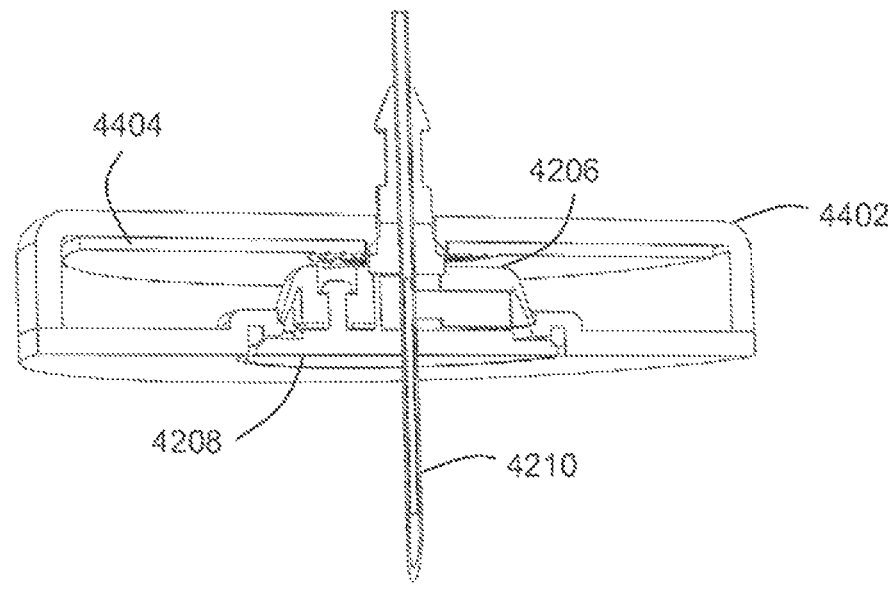
FIG. 44

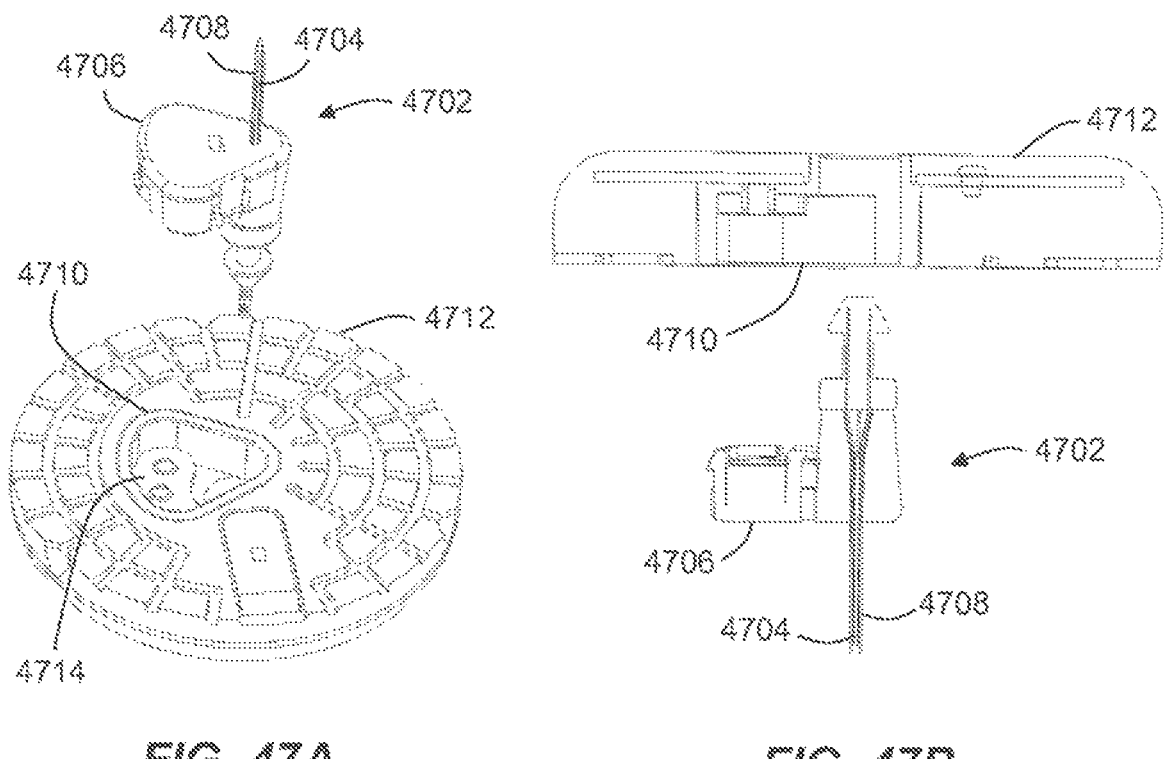
FIG. 47A                 FIG. 47B
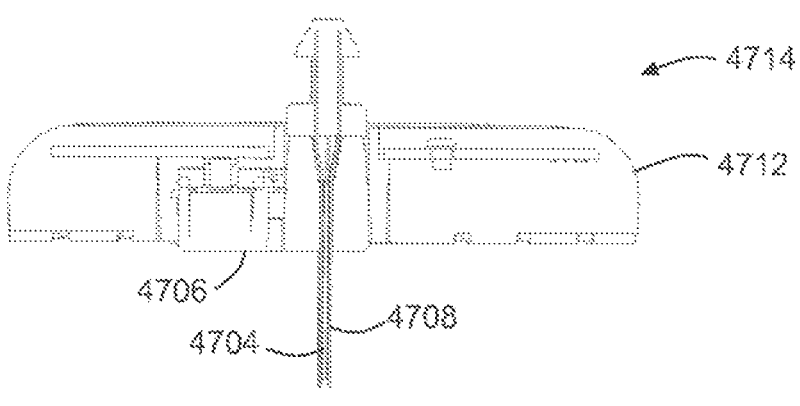
FIG. 47C

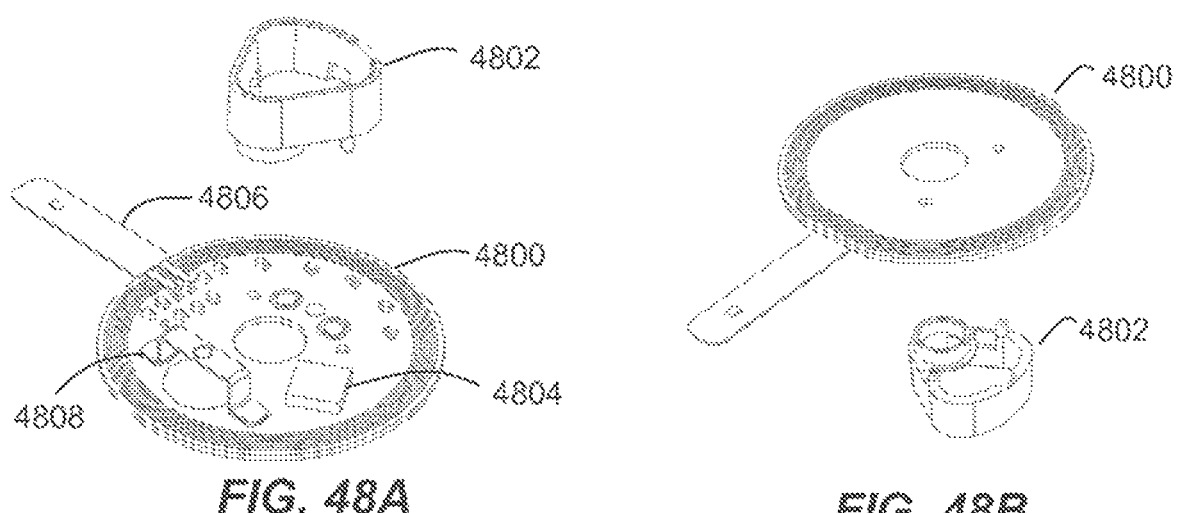
*FIG. 48A*
*FIG. 48B*
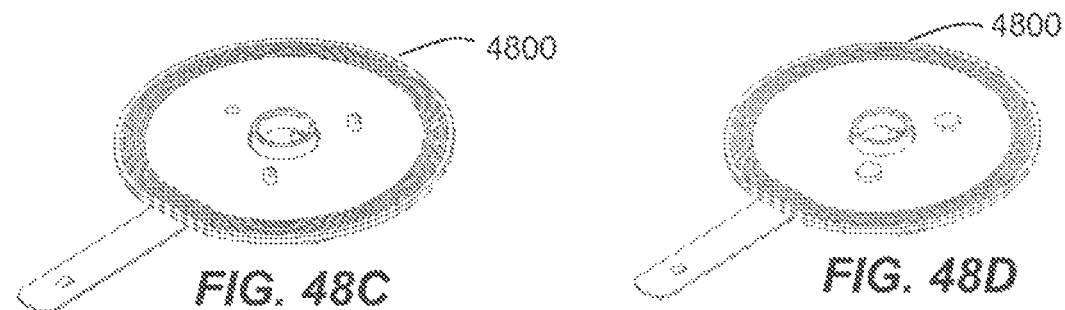
*FIG. 48C*
*FIG. 48D*
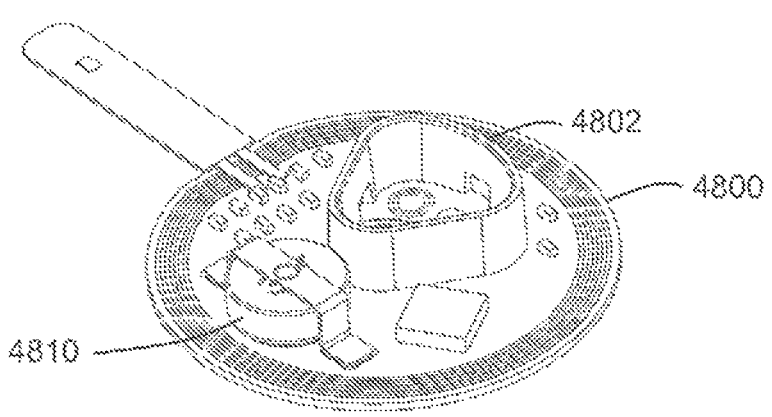
*FIG. 48E*

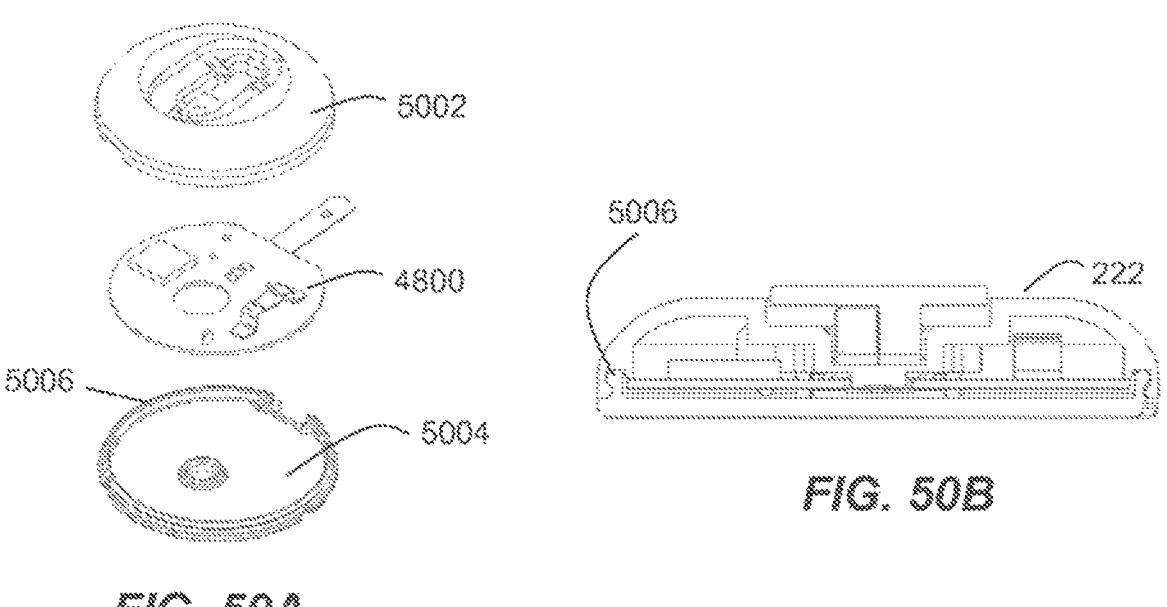
*FIG. 50A*
*FIG. 50B*
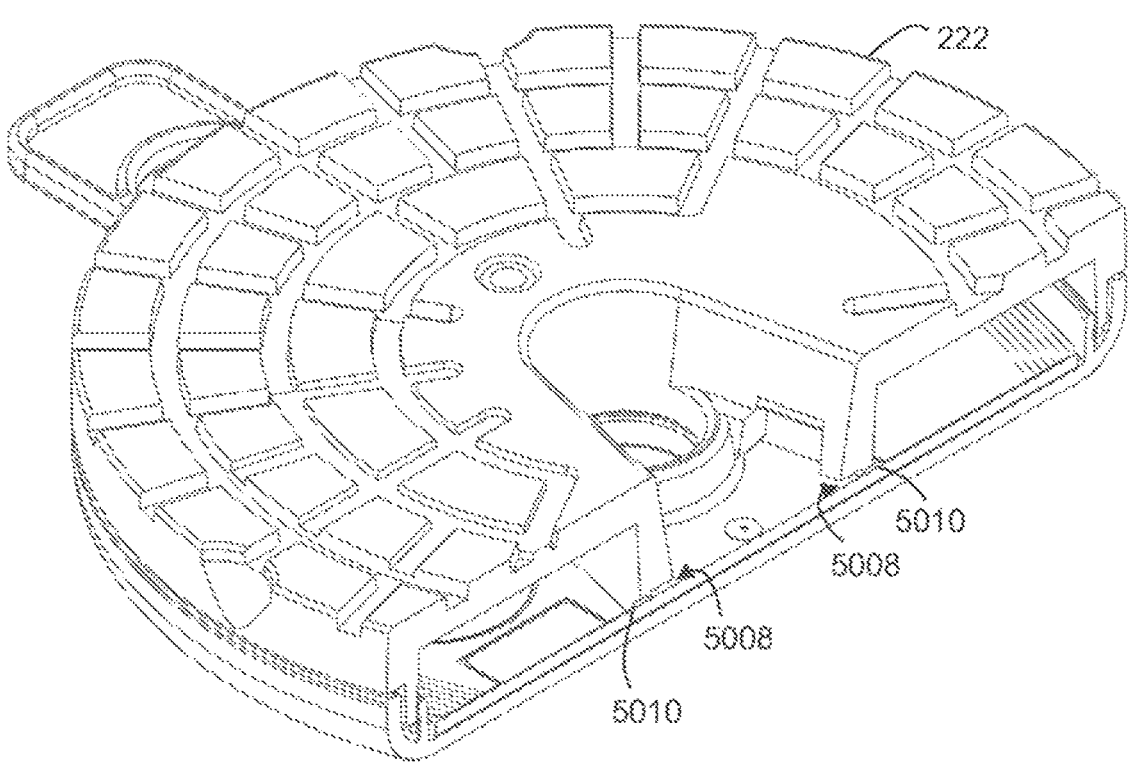
*FIG. 50C*

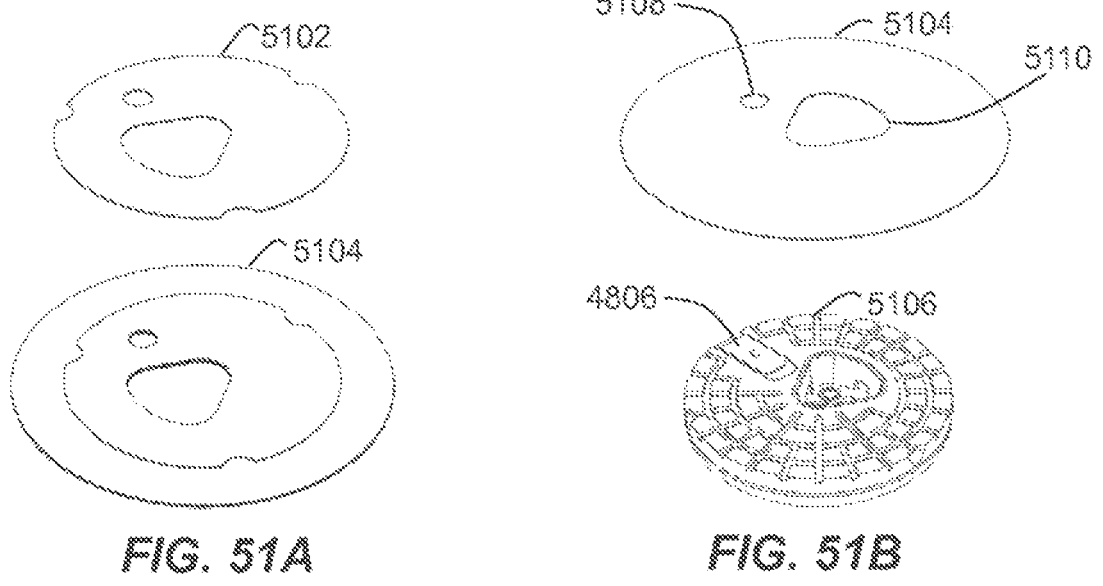
*FIG. 51A*                         *FIG. 51B*
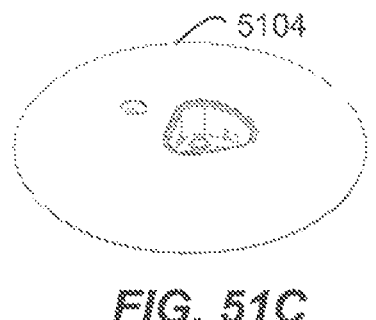
*FIG. 51C*

ANALYTE SENSOR DEVICES, CONNECTIONS, AND METHODS

CROSS-REFERENCE TO RELATED APPLICATIONS

The present application is a continuation of U.S. patent application Ser. No. 17/531,265, filed Nov. 19, 2021, which is a continuation of U.S. patent application Ser. No. 15/908,616, filed Feb. 28, 2018, now U.S. Pat. No. 11,179,068, which is a continuation of U.S. patent application Ser. No. 15/610,334, filed May 31, 2017, now U.S. Pat. No. 9,931,066, which is a continuation of U.S. patent application Ser. No. 15/193,499, filed Jun. 27, 2016, now U.S. Pat. No. 9,693,713, which is a continuation of U.S. patent application Ser. No. 13/710,460, filed Dec. 11, 2012, now U.S. Pat. No. 9,402,570, which claims priority to U.S. Provisional Application No. 61/569,287, filed Dec. 11, 2011, all of which are incorporated herein by reference in their entireties for all purposes.

BACKGROUND

Diabetes Mellitus is an incurable chronic disease in which the body does not produce or properly utilize insulin. Insulin is a hormone produced by the pancreas that regulates blood sugar (glucose). In particular, when blood sugar levels rise, e.g., after a meal, insulin lowers the blood sugar levels by facilitating blood glucose to move from the blood into the body cells. Thus, when the pancreas does not produce sufficient insulin (a condition known as Type 1 Diabetes) or does not properly utilize insulin (a condition known as Type II Diabetes), the blood glucose remains in the blood resulting in hyperglycemia or abnormally high blood sugar levels.

The vast and uncontrolled fluctuations in blood glucose levels in people suffering from diabetes cause long-term, serious complications. Some of these complications include blindness, kidney failure, and nerve damage. Additionally, it is known that diabetes is a factor in accelerating cardiovascular diseases such as atherosclerosis (hardening of the arteries), leading to stroke, coronary heart disease, and other diseases. Accordingly, one important and universal strategy in managing diabetes is to control blood glucose levels.

One element of managing blood glucose levels is the monitoring of blood glucose levels. Conventional in vitro techniques, such as drawing blood samples, applying the blood to a test strip, and determining the blood glucose level using colorimetric, electrochemical, or photometric test meters, may be employed. Another technique for monitoring glucose levels uses an in vivo analyte monitoring system, which measures and stores sensor data representative of glucose levels automatically over time.

Unlike conventional in vitro blood glucose monitoring approaches, in vivo analyte monitoring systems use an insertable or implantable in vivo sensor that is positioned to be in contact with interstitial fluid of a user for a period of time to detect and monitor glucose levels. Prior to use of an in vivo sensor, at least a portion of the sensor is positioned under the skin. An applicator assembly can be employed to insert the sensor into the body of the user. For insertion of the sensor, a sharp engaged with the sensor, pierces the skin of the user and is then removed from the body of the user leaving the sensor in place. The in vivo-positioned sensor can be connected to other system components such as sensor electronics contained in a unit that can be held onto the skin. To realize fully the advantages associated with such systems, what is needed are applicator systems configured to handle insertion, as well as packaging and user interface issues, that are easy-to-use, reliable and minimize both user inconvenience and pain. The present invention provides such solutions and additional or alternative advantages as described below and/or as may be appreciated by those of skill in the art upon review of the subject disclosure.

SUMMARY

The present invention includes packaging, loading systems, applicators, and elements of the on-body devices themselves. According to embodiments of the present invention, an on-body device includes an electronics assembly and a sensor assembly. The sensor assembly includes a sensor and a connector for coupling the sensor to the electronics assembly. In addition, a sharp can be provided that supports the sensor and allows a distal end of the sensor to be placed under a user's skin. In some embodiments, the invention includes the connection of electrochemical analyte sensors to and/or within associated other monitoring components such as system devices that are configured to be held in place on body. The approaches variously involve the use of unique sensor and unique ancillary element arrangements to facilitate assembly of separate on-body devices and sensor assembly units that are kept apart until the user brings them together. Methods associated with such use also form part of the inventive subject matter.

Certain embodiments are described that include an analyte sensor (e.g., a glucose sensor) and an applicator assembly to position a portion of the sensor beneath a skin surface, as well as methods of positioning at least a portion of the sensor and methods of analyte testing or monitoring. Further methods include the manner of preparing the applicator assembly. Namely, such acts associated with user assembly and mating of the component parts of a monitoring system.

As mentioned above, such a monitoring system includes an electronics assembly adapted to adhere to a skin of a subject, a sensor assembly coupled to the electronics assembly to form an on-body device, and an insertion sharp having a longitudinal body including a longitudinal opening to receive at least a portion of the sensor body. The details of the sensor may vary. Exemplary chemistries and constructions are described in any of U.S. Pat. Nos. 5,593,852, 6,284,478, and 6,329,161, each incorporated by reference herein in its entirety. Exemplary form-factors or configurations (e.g., for associated use with an insertion "sharp") are described in any of U.S. Pat. Nos. 6,175,752, 6,565,509, 6,134,461 and 6,990,366 and in U.S. Publication No. 2010/0230285, each incorporated by reference herein in its entirety.

Likewise, the details of the on-body device may vary. For instance, the on-body device may include sensor electronics and other adaptation to communicate with a monitoring device. Various options for communications facilities (e.g., wireless transmitters, transponders, etc.) are described in detail in U.S. Patent Publication Nos. 2010/0198034 and 2011/0213225, the entirety of the applications hereby incorporated by reference, including cited and incorporated references.

In some embodiments, systems and methods are provided for assembling and applying the on-body device including assembling the sensor assembly to the electronics assembly and inserting a portion of the sensor under the skin of a user. Thus, the sensor assembly includes a sensor that has a distal portion for operative contact with a fluid of the user. The on-body device also includes an electronics assembly including a housing defining a distal surface adapted for attachment to the skin of the user and a circuit coupleable to the sensor for detecting electrical signals from the sensor. In some embodiments, the system also includes an applicator assembly that has a sleeve defining a distal surface for placement on the skin of the subject, a handle for a user interface, and various internal support, coupling, guide, grasping, stop and detent features as well as driver elements. In some embodiments, the system may also include a container that stores one or more of the sensor, the sharp, and/or the mount/electronics assembly in a sealed environment within. The container is configured to releasably interface with the applicator assembly for the purpose of loading one or more of the sensor, the sharp, and/or the electronics assembly into the applicator assembly, and readying the applicator assembly for use.

The present disclosure includes the subject systems, devices, kits in which they are included, and methods of use and manufacture. A number of aspects of such manufacture are discussed herein. Further details can be appreciated in reference to the figures and/or associated description.

BRIEF DESCRIPTION OF THE DRAWINGS

A detailed description of various aspects, features, and embodiments of the subject matter described herein is provided with reference to the accompanying drawings, which are briefly described below. The drawings are illustrative and may or may not be drawn to scale, with the possibility of some components and features being exaggerated for clarity. Similar components may be numbered identically or not. The drawings illustrate various aspects and features of the present subject matter and may illustrate one or more embodiment(s) or example(s) of the present subject matter in whole or in part.

FIGS. 2A-2G illustrate such activity with additional detail;

FIGS. 5A and 5B are section views of the container in FIG. 4;

FIG. 6 is an assembly view of an alternative container;

FIG. 7 is a section view of the assembly of FIG. 6;

FIGS. 13A-13C variously illustrate use of the applicator in FIGS. 12A-12D in connection with a locking-sleeve feature;

FIGS. 15A-15F variously illustrate use of the applicator in FIGS. 14A and 14B;

FIGS. 16A and 16B are sectional and detail to views, respectively, of features of the container in FIGS. 15A-15D;

FIGS. 21A-21C are perspective section views illustrating sensor assembly receipt by the sensor mount and sharp withdrawal from the assembled complex;

FIGS. 29A-D are perspective views of another advantageous sensor and sensor connector arrangement;

FIGS. 30A-30B are perspective views illustrating yet another advantageous sensor approach with the sensor as originally produced and modified for use, respectively;

FIG. 30C is a perspective view illustrating the sensor as configured in FIGS. 30A and 30B coupled to a PCB;

FIG. 31 is a side-section view showing a comparative approach, in a final on-body sensor assembly;

FIGS. 33A-33G are plane, side, magnified, and sectional views of an additional sensor configuration;

FIGS. 33H-33J are plane views of various sensor designs;

FIGS. 34A-34D are perspective views illustrating combination electrical connector and sensor isolator in yet another advantageous sensor arrangement;

FIG. 36 is a perspective assembly view illustrating a sensor connection approach related to that in FIGS. 34A-34D for a sensor with contacts on a single side;

FIG. 37 is a perspective partial assembly view illustrating a mount-and-socket interface for the sensor assembly employing the components in FIG. 36;

FIG. 38 is a complete assembly view of that illustrated in FIG. 37;

FIGS. 41A and 41B are partial perspective assembly views of another stacked non-directional sensor connection arrangement;

FIG. 41C is a section view of the complete assembly of the components variously illustrated in FIGS. 41A and 41B;

FIG. 42 is an assembly view of an advantageous radial arrangement sensor connector assembly;

FIGS. 43A and 43B are reversed perspective views of the mount-side sensor connection component for use with an assembly as shown in FIG. 42;

FIG. 44 is a section view of the complete assembly of the components variously illustrated in FIGS. 42, 43A and 43B;

FIG. 47A-47C are assembly and cross-sectional views of an on-body device including an integrated connector for the sensor assembly;

FIGS. 48A-48D are construction views of an on-body subassembly;

FIG. 48E is a perspective view of a complete on-body electronics subassembly;

FIGS. 50A-50C are assembly and sectional views of an alternative snap-together approach with the assembly in FIG. 48E; and FIGS. 51A-51B are assembly views illustrating adhesive backing application in producing a final on-body device ready for use as shown in perspective-view FIG. 51C.

DETAILED DESCRIPTION

Figure 1:
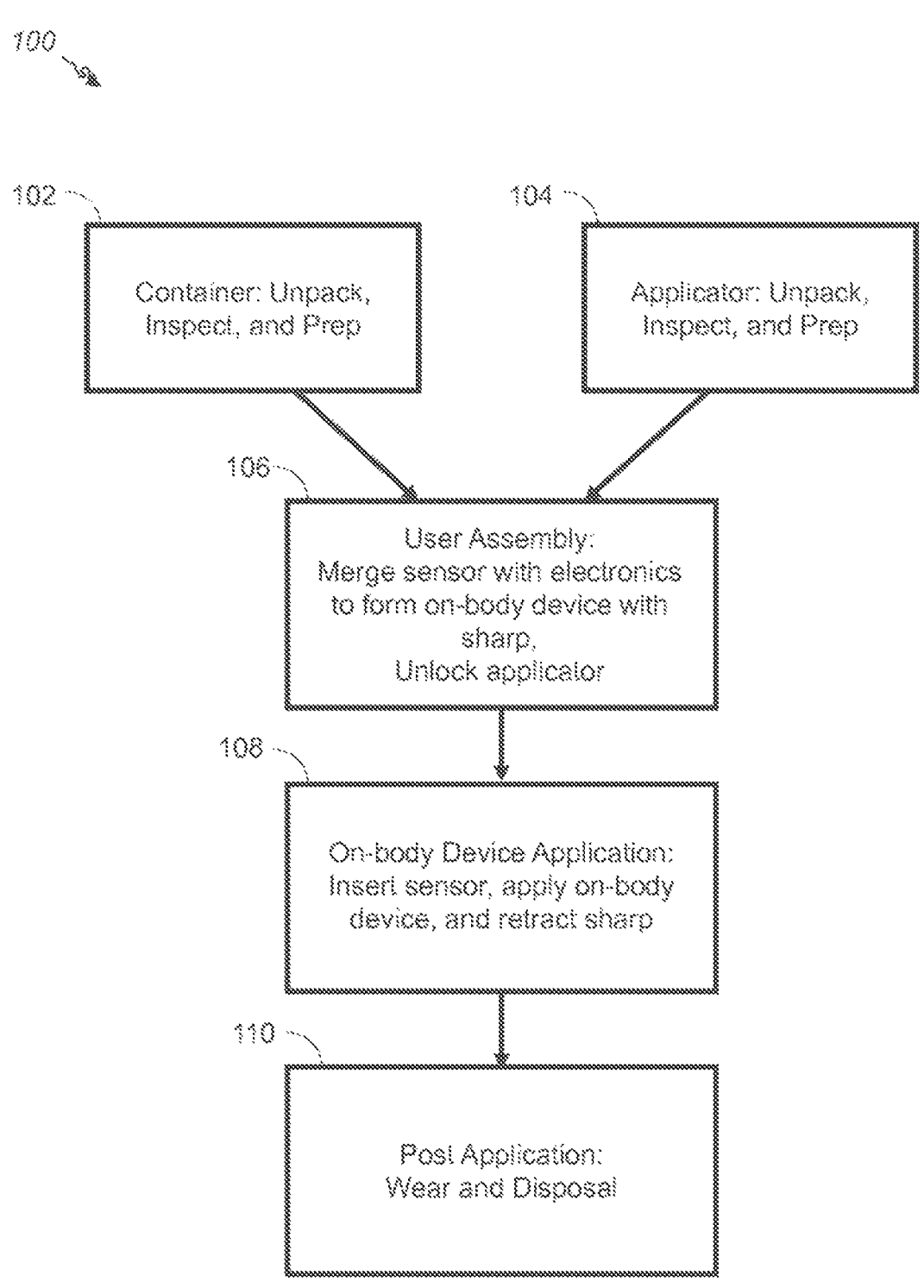
FIG. 1 is a flowchart, indicating user activity in handling the subject devices.

Before the present disclosure is further described, it is to be understood that this disclosure is not limited to the particular embodiments described, as such may, of course, vary. It is also to be understood that the terminology used herein is for the purpose of describing particular embodiments only, and is not intended to be limiting, since the scope of the present disclosure will be limited only by the appended claims.

As will be apparent to those of skill in the art upon reading this disclosure, each of the individual embodiments described and illustrated herein includes discrete components and features which may be readily separated from or combined with the features of any of the other several embodiments without departing from the scope or spirit of the present disclosure.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges, and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, exemplary methods and materials are now described. All publications mentioned herein are incorporated herein by reference to disclose and describe the methods and/or materials in connection with which the publications are cited.

As used herein and in the appended claims, the singular forms "a," "an," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present disclosure is not entitled to antedate such publication by virtue of prior disclosure. Further, the dates of publication provided may be different from the actual publication dates which may need to be independently confirmed.

Various exemplary embodiments of the disclosure are described below. Reference is made to these examples in a non-limiting sense. They are provided to illustrate more broadly applicable aspects of the present disclosure. Various changes may be made to the disclosure described and equivalents may be substituted without departing from the true spirit and scope of the disclosure. In addition, many modifications may be made to adapt a particular situation, material, composition of matter, process, process act(s) or step(s) to the objective(s), spirit or scope of the present disclosure. All such modifications are intended to be within the scope of the claims made herein.

Applicator and Container Overview

Turning to FIG. 1, a flowchart depicting an example method 100 of using various systems of the present invention is provided. In some embodiments, a user starts with unpacking the container (102) and unpacking the applicator (104). Unpacking the container (102) can include removing a cover that provides a sterile seal to the container contents and unpacking the applicator (104) can include removing an end cap that provides a sterile seal to the internal portion of the applicator. Next, in an assembly operation (106), the applicator is inserted into the container to merge or connect the sensor assembly and the electronics assembly together to form an on-body device and an insertion needle or sharp. In some embodiments, the user unlocks the applicator or removes a locking element to ready the applicator for use. The process of the assembly operation (106) and the constituent components are described in detail below.

Next, once the user has chosen an application site, an on-body device application operation (108) is performed. In the application operation (108), the user places the applicator on the skin of the insertion site and then applies a force to install the on-body device. The applicator is driven to insert the distal end of the sensor through the user's skin, adhere the on-body device to the skin surface, and retract the sharp into the applicator for disposal. In some embodiments, the user performs the application operation (108) by applying force to the applicator where the force applied is a single, continuous pushing motion along the longitudinal axis of the applicator that once started, causes the applicator to perform the application operation (108) such that the applicator does not stop operation until completion. The applicator is configured to relay action/audible cues to the user so that all three of the above listed actions happen automatically in response to applying the force to the applicator causing it to trigger. Advantageously, an adhesive of the on-body device does not contact the user until the application operation (108) is performed. So, the even after the applicator has been placed on the skin, the applicator can be moved to a different location up until the application operation (108) is performed without damage to the apparatus or other system components. In a post application stage (110), use of the sensor for monitoring the user's analyte level occurs during wear followed by appropriate disposal.

Figure 2A:
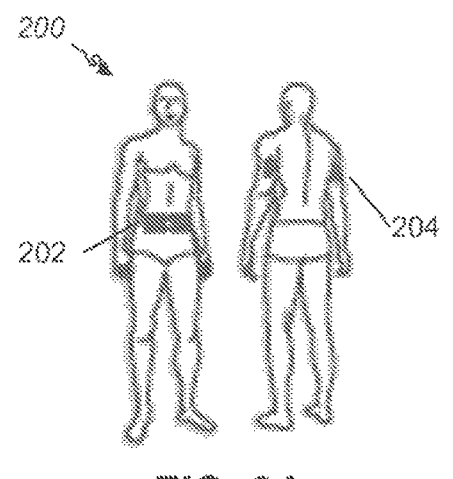

Details of method 100 are illustrated in the sequence of drawings shown in FIGS. 2A to 2G. In FIG. 2A, one of the highlighted application sites 202, 204 on a user 200 is selected. In some embodiments, other application sites may be used. In some embodiments, a site preparation operation may optionally be performed. The application site 202, 204 may be shaved, exfoliated, cleaned, or otherwise treated to better adhere the on-body device. More specifically, the skin at the site of the user's body where the on-body device will be adhered may be prepared to receive the on-body device. For example, the skin may be shaved with a razor, cleaned with isopropyl alcohol (IPA), and exfoliated with an abrasive. A mechanically exfoliating element can be used to remove an outer layer of dead skin and expose newer skin below. These elements include: microfiber exfoliating cloths; pumice or other abrasive mineral; metal-stamped components of a rasp/file type configuration; synthetic scouring material, e.g., Scotch-Brite®; an alternate adhesive tape or patch to be applied and stripped off to remove dead skin; and organic abrasive elements such as salt, crushed almond shells, apricot kernels, etc. Likewise, a chemically exfoliating element may be used to prepare the site, including: mild acids such as alpha hydroxyl acid, beta-hydroxyl acid and salicylic acid; and fruit enzymes. Such chemically abrasive element(s) may be incorporated in a preparation pad, towelette, swab or be supplied otherwise. In some embodiments, the end cap of the applicator may include one or more exfoliating elements. In some embodiments, the end cap may be textured or otherwise formed to provide a surface that can be used to exfoliate the skin of the site where the on-body device will be adhered. Exfoliating away an outer layer of dead skin before application may allow the on-body device to better adhere to the skin for a longer period of time.

Figure 2B:
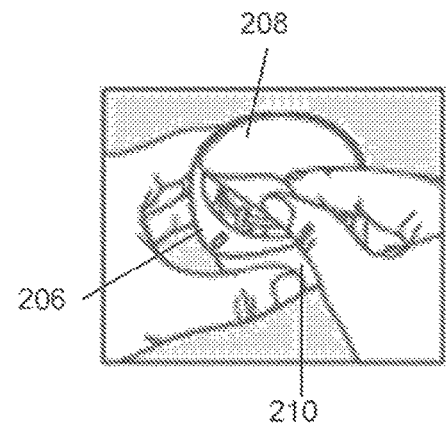
Figure 2C:
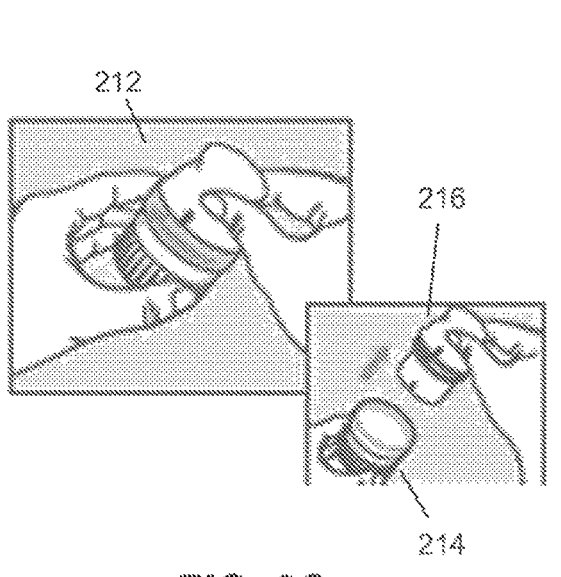

FIG. 2B illustrates loader or container 206 preparation, including removing cover 208 from a casing 210. The container 206 includes the casing 210 which holds the sensor assembly and a sharp (or in some embodiments, the electronics assembly). FIG. 2C illustrates applicator 212 preparation including separating a removable applicator end cap 214 from applicator assembly 216. In some embodiments, container 206 and applicator 212 can initially be packaged connected together to simplify packaging and shipping. For example, the removable applicator end cap 214 may include a boss or other feature that couples or snaps to a corresponding feature on the exterior of the container 206. This connection is only operative to hold the two pieces together for shipping purposes and not for operation of the system. Thus, in some embodiments, before removing the cover 208 from the casing 210 and separating the removable end cap 214 from the applicator assembly 216, in an initial unpacking step, the container 206 and applicator 212 are separated from each other.

Figure 2D:
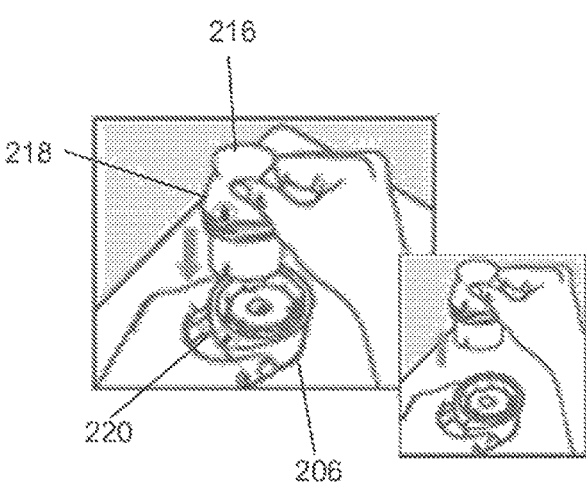

As shown in FIG. 2D, once alignment indicators 218, 220 are aligned, the user assembly operation 106 (FIG. 1) is achieved by pushing the applicator assembly 216 firmly into the container 206 to retrieve a sensor and a sharp from the container and to unlock a guide sleeve of the applicator assembly 216. In FIG. 2E, the assembled and unlocked applicator assembly 216 is placed on the application site 204 (or 202) and pushed down firmly to effect on-body device application 108 (FIG. 1). As shown in FIG. 2F, upon used applicator assembly 216 removal from the application site 204, on-body device 222 is adhered to the user. In some embodiments, as illustrated in FIG. 2G, analyte levels detected by the sensor of the on-body device 222 can be retrieved over a wireless communication link 224 via a communications facility (e.g., a transmitter, a transponder, etc.) within the on-body device 222 by a receiver unit 226 (referred to alternatively as a "reader unit" or "receiver device", or in some contexts, depending on the usage, as a "display unit," "handheld unit," or "meter"). Relevant information (e.g., analyte level trend data, graphs, etc.) is presented on the receiver unit's display 228.

Figure 3:
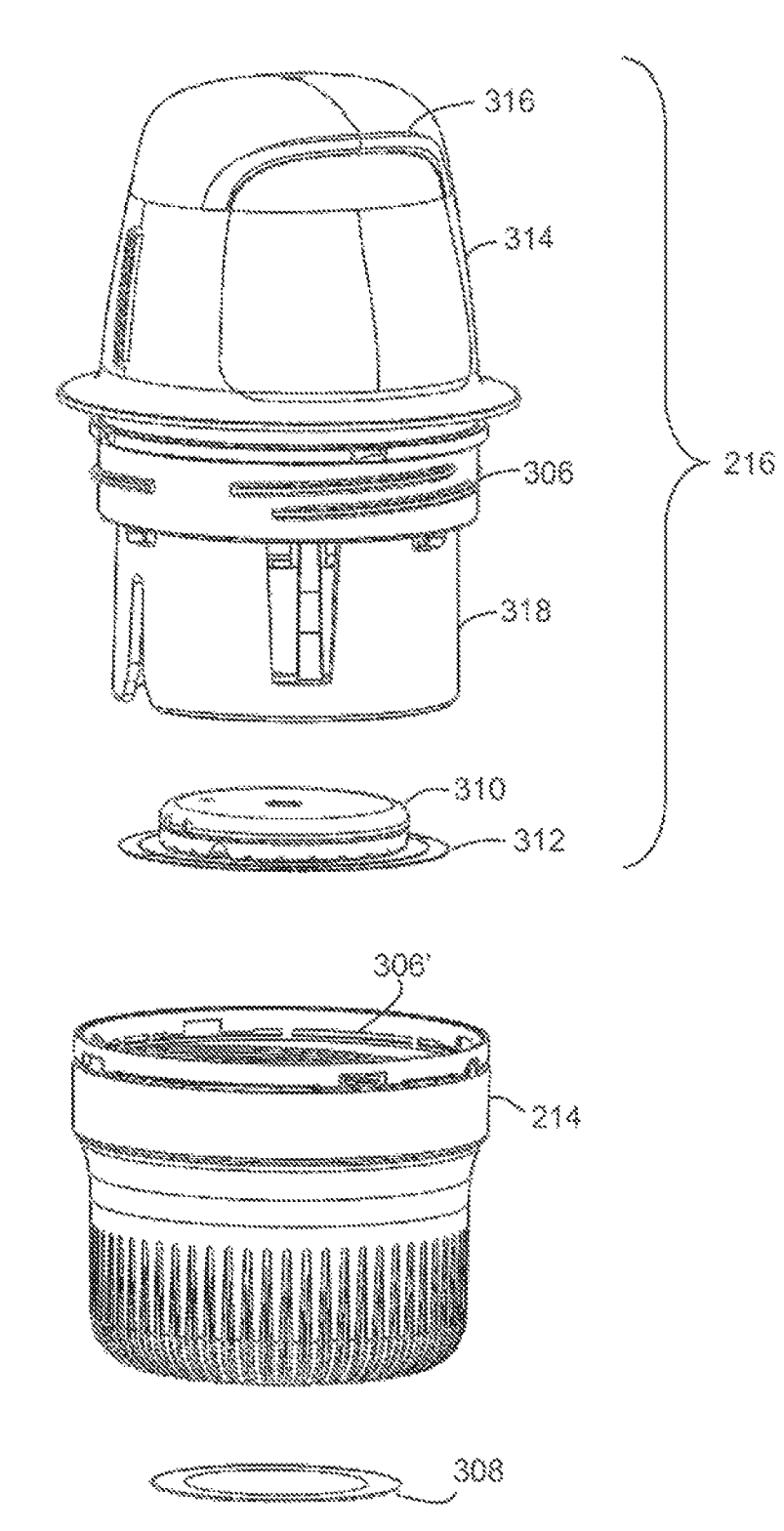
FIG. 3 is an assembly view of an applicator or inserter.
Figure 4:
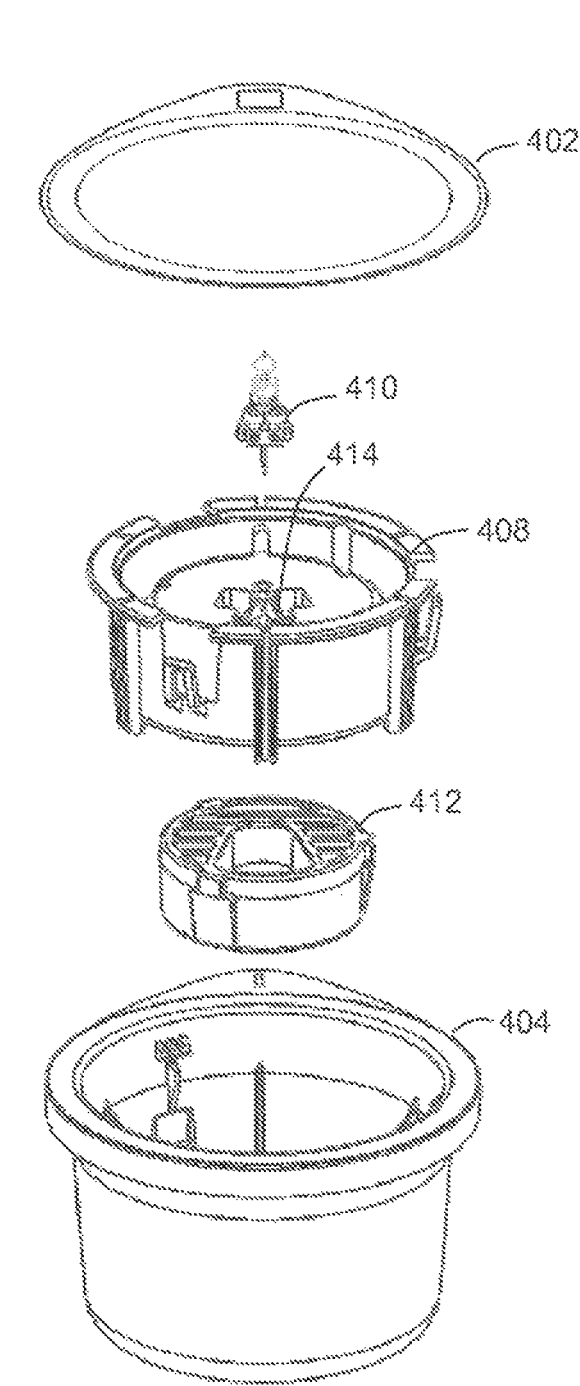
FIG. 4 is an assembly view of a sensor container or loader.

The applicator 212, container 206, and associated components shown in FIGS. 2A to 2G are illustrated in more detail in FIGS. 3 and 4. In addition, numerous other variations are described in detail below. These alternative embodiments may operate differently insofar as their internal workings, but may present no difference concerning user activity.

Turning to FIG. 3, applicator 212 includes a removable cap 214 and applicator assembly 216. The removable cap 214 can be secured to the applicator assembly 216 via complimentary threadings 306, 306'. End Cap 214 fits with the applicator 216 to create a sterile packaging for interior of the applicator 216. Therefore, no additional packaging is required to maintain sterility of the interior of the applicator 216. In some embodiments, the end (not visible) of the removable end cap 214 can include one or more openings, which can be sealed by a sterile barrier material such as DuPont™ Tyvek®, or other suitable material, to form seal 308. Such provision allows for ethylene oxide (ETO) sterilization of the applicator 212 through the seal 308 when closed. In some embodiments, the openings in the removable cap 214 may not be present and the removable cap 214 may be made from a sterile process-permeable material so that the interior of the applicator can be sterilized when the cap is mated to it, but that maintains sterility of the interior of the cap after exposure to the sterility process. In some embodiments, ETO sterilization is compatible with the electronics within the electronics assembly 310 and with the associated adhesive patch 312, both of which can be releasably retained within the applicator assembly 216 until applied to the user. As shown, the applicator assembly 216 includes a housing 314 including integrally formed grip features 316 and a translating sheath or guide sleeve 318.

In reference to FIG. 4, the container 206 includes a cover 402 (e.g., made of a removable material such as foil) and casing 404. Housed within the casing 404 is a desiccant body 412 and a table or platform 408. In some embodiments, the desiccant body 412 can have an annular shape so that the desiccant body 412 can be disposed within the casing 404 and a sensor assembly support (not visible in FIG. 4 but see 512 in FIGS. 5A and 5B) can extend up through the desiccant body 412. This arrangement allows the container 206 to include a desiccant without requiring any additional height to accommodate the desiccant. A sensor assembly 410 is snap-fit or otherwise held by the sensor assembly support 512. The sensor assembly 410 can also be snap-fit or otherwise held by the platform 408 (e.g., using fingers 414). With the cover 402 sealed, the container 206 can be subjected to gamma or radiation (e.g., e-beam) sterilization, an approach compatible with the chemistry of the sensor included in the sensor assembly 410. Like the applicator 212, the container 206 is its own sterile packaging so that no additional packaging, other than the casing 404 and the cover 402, is required to maintain sterility of the interior of the casing.

The container 206 and the applicator 212 may be sterilized by different sterilization approaches. For example, a sensor contained in a container 206 may require one type of sterilization process and the contents of an applicator 212—for example, electronics contained within the interior of the applicator 212—may require another type of sterilization process. The utility of a two-piece separable but combinable system (i.e., the container 206 and the applicator 212) enables the respective sterilization of the two pieces and sterility maintenance before the two are connected together for use. In other words, separately sealing the container 206 and the applicator 212 facilitates the use of otherwise incompatible sterilization methods for these two components. For example, one type of sterilization which could damage the chemistry of the sensor can be used to sterilize the applicator 212 including the electronics assembly 310 including the adhesive patch 312. Likewise, another sterilization process which could damage the electronics in the electronics assembly 310 (and/or the adhesive patch 312 used to adhere the electronics assembly 310 to the user's skin) can be used to sterilize the container 206 including the sensor therein. Still other advantages may exist, given different shelf-life attributes for the active (i.e., electronic, chemical, etc.) elements. In some embodiments, all components can be sterilized using the same sterilization technique, such as, but not limited to ETO and e-beam sterilization, etc.

In some embodiments, the platform 408 in the container 206 functions as an anti-tamper barrier for the sensor assembly 410 and prevents direct handling of the sensor assembly 410 by the user. More specifically, the platform 408 is disposed to protect and assist in the retention of the sensor, a sharp, and an associated connector. In some embodiments, the platform 408 is locked in place within the casing 404 until released by a longitudinally directed force from the applicator assembly 216 during the user assembly operation 106 (FIG. 1). In other words, as the guide sleeve 318 of the applicator assembly 216 is inserted down against the platform 408, the sleeve 318 releases a locking mechanism (e.g., a catch) and allows the platform to translate deeper into the casing 404. Additionally, features of the casing 404 can be employed to unlock a guide sleeve lock feature of the applicator assembly 216. In some embodiments, the platform 408 in the container 206 can only be unlocked if the guide sleeve 318 of the applicator assembly 216 is inserted into the container 206 with alignment marks on the applicator assembly 216 and the container 206 properly aligned. (See FIG. 10C and associated text below).

Figure 5A:
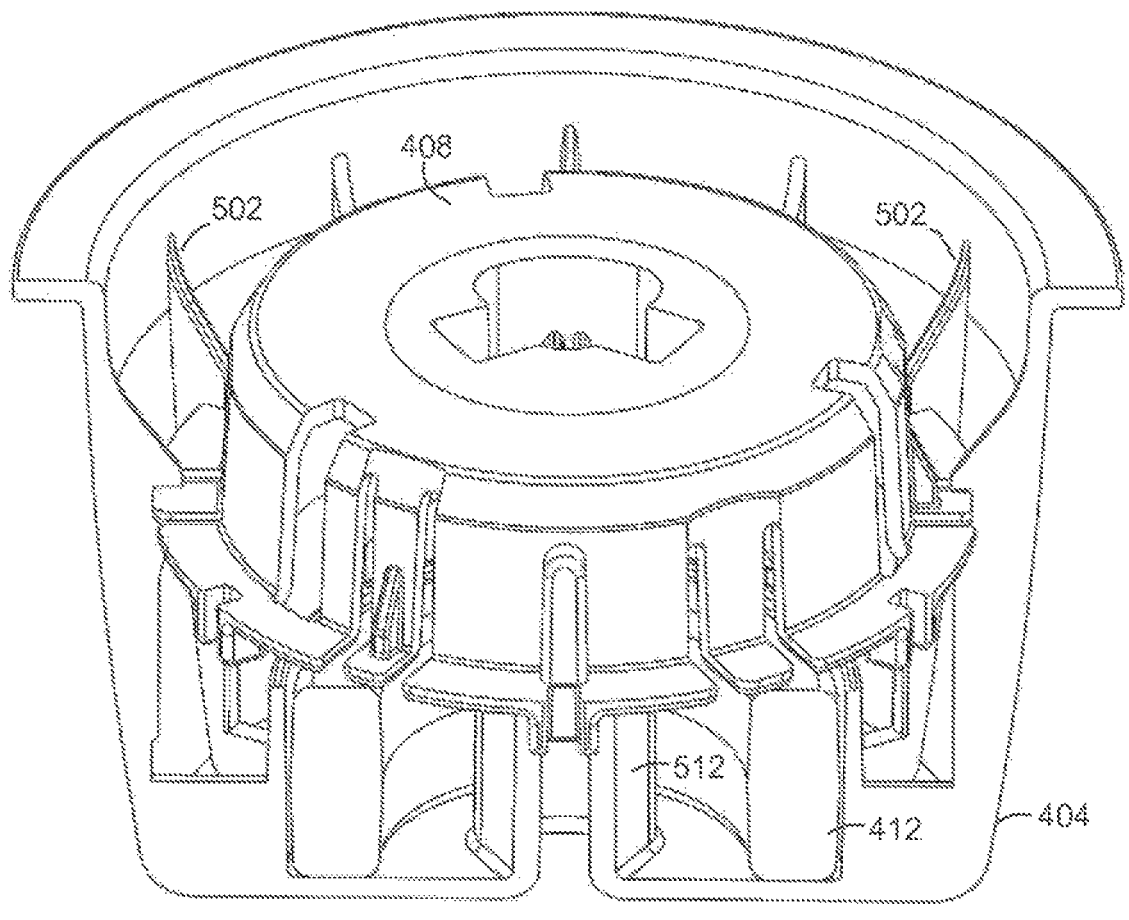

FIG. 5A is an isometric, cross-sectional view of the casing 404 of FIG. 4. FIG. 5B is an assembled, isometric, cross-sectional view of the container 206 of FIG. 4 including the component parts. As can be seen in FIGS. 5A and 5B, platform 408 is surrounded by multiple locking features 502 (at least one is advantageously provided in some embodiments). Each of locking features 502 includes a cantilevered arm 504 with a tongue 506 received in a slot or groove 508. So disposed, the platform 408 is locked in place. When the arm(s) 504 are urged inward, in the direction represented by arrows P and P', from a concentrically disposed sleeve 318 (not shown) of the applicator assembly 216 riding over ramp(s) 510, the locking feature(s) 502 are released and the platform 408 can translate in direction B along a longitudinal axis of the combined applicator assembly 216 interfaced with the container 206. The translation of the platform 408 into the casing 404 provides access to sensor assembly 410 by the applicator assembly 216. Until the platform 408 is unlocked and driven down into the casing 404, the sensor assembly 410 is otherwise isolated from being touched or otherwise handled/accessed by a user. In some embodiments, additional detent ramp features can be provided to hold the platform 408 until depressed with force applied by a user. In addition, various key-and-way or slot-and-groove guidance features can be provided to control such motion and ensure that it is smooth and linear (i.e., to avoid platform canting, binding, etc.)

In some embodiments, the sleeve/ramp interface with associated locks relies only on detent features to maintain the platform's position. So configured, inadvertent handling of the sensor assembly can be avoided. The detent(s) can be tuned to require deliberate action to clear the platform 408.

In some embodiments, alternative mechanisms and arrangements may be employed to provide a platform 408 that collapses upon application of force via the applicator assembly 216 by the user. For example, FIGS. 6 and 7 depict an alternative container 600 embodiment including an alternative platform 602 arrangement. Here, a collapsible armature or linkage 604 supports the platform 602. This linkage 604 is integrally guided and spring-loaded by virtue of the living hinge design of the linkage 604. Alternatively, a coil spring could be employed along with guides for the platform 602. A sleeve 318 (FIG. 3) (FIG. 3) of an applicator 216 or the base of sensor mount unit 606 itself, can be used to translate the platform 602 to provide clearance for sensor assembly 608 access and pick-up by the applicator 216 and incorporation as a complete assembled on-body device 222. The container 600 includes a casing 610 and can also include a desiccant ring 612 to protect the sensor assembly 608 from moisture.

Figure 8:
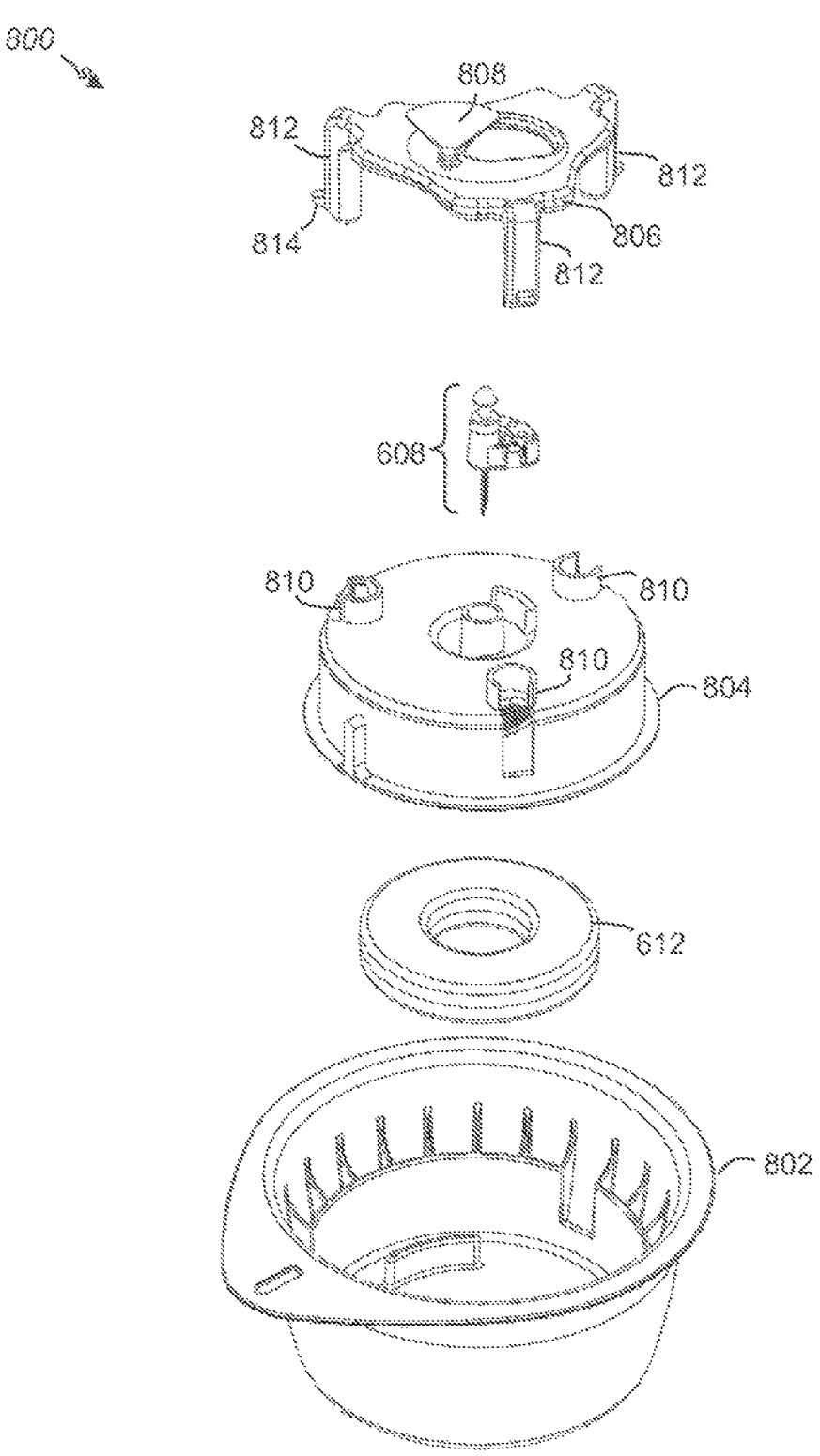
FIG. 8 is an assembly view of yet another sensor container set or loader.
Figure 9A:
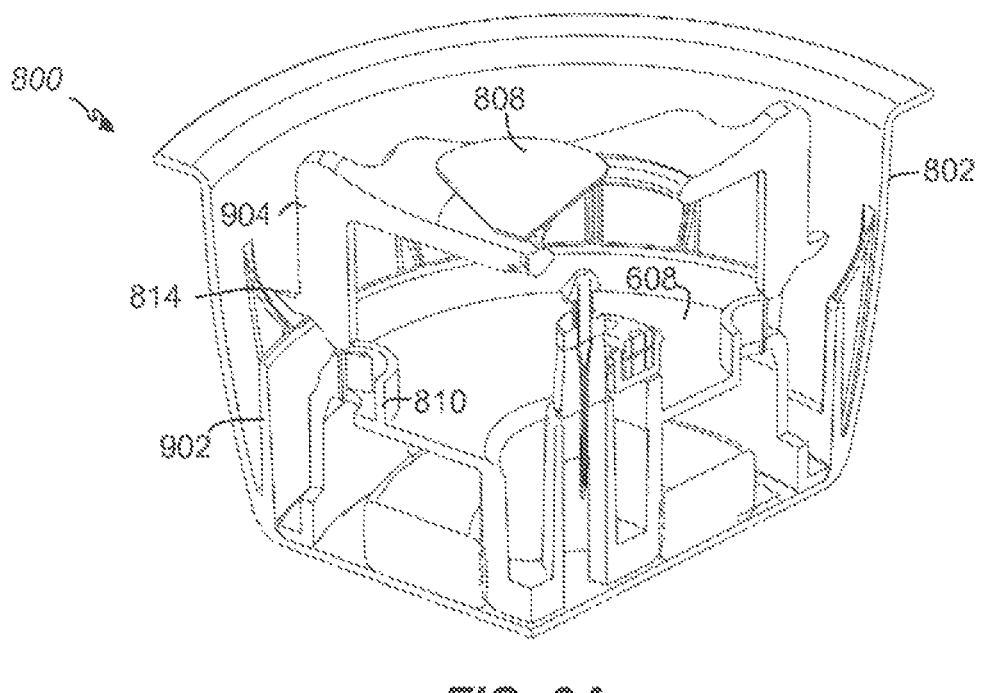
FIGS. 9A and 9B are top and section views, respectively, of the container set assembly of FIG. 8 in stages of operation.
Figure 9B:
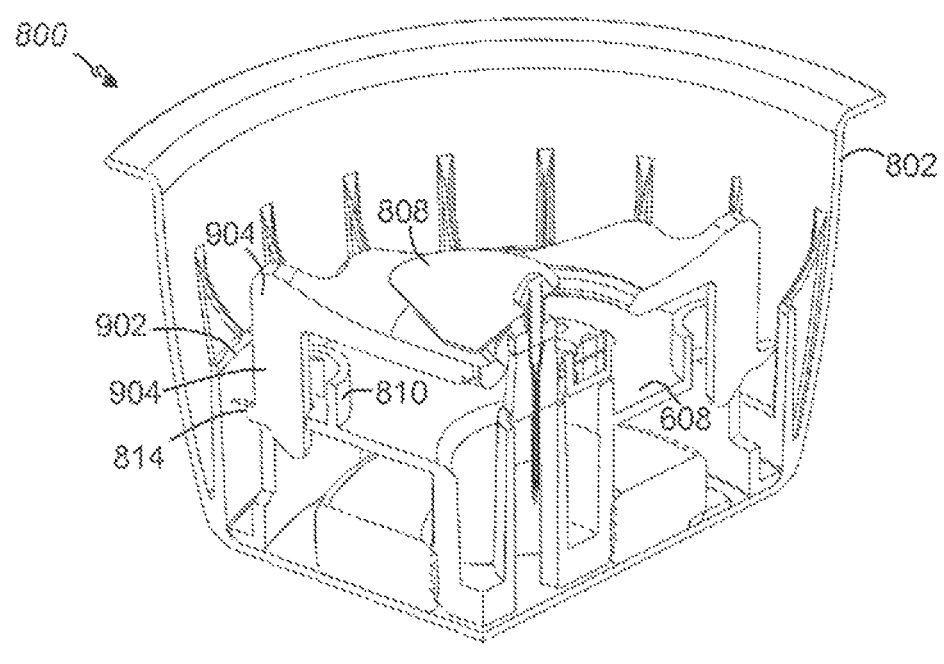

Another embodiment for sensor storage and protection is illustrated in FIG. 8 with container 800. As with the prior embodiments, this embodiment can also include an annular desiccant ring 612. Casing 802 is provided in connection with a support base 804. The support base 804 receives sensor assembly 608 and a frame 806. The frame 806 includes a pivoting door 808. As shown, the support base 804 incorporates three channels 810 for receipt of frame legs 812 to serve as guidance. In its up/closed position shown in FIG. 9A, door 808 protects the sensor assembly 608 from contact by the user. Spiral ramp features interacting between the support base 804 and the frame 806 cause the door 808 to swing open as the frame 806 is moved down as shown in FIG. 9B. Likewise, features of the frame 806 can hold the sensor assembly 608 against the support base 804 until the frame 806 is pushed down by user activity.

Similar to the container embodiment 206 shown in FIGS. 5A and 5B, the frame 806 in container 800 can be locked in place and released by applicator sleeve introduction. A support ring 902 may lock against boss or tang 814 until the boss 814 is urged inward by the action of an applicator sleeve along angled interface surface 904 of each leg 812. In some embodiments, the legs 812 can be biased outward with a preload but in other embodiments, the locking/unlocking function can operate without such biasing. FIG. 9A illustrates the locked configuration, whereas FIG. 9B illustrates unlocked/translated relation of components.

Figure 10A:
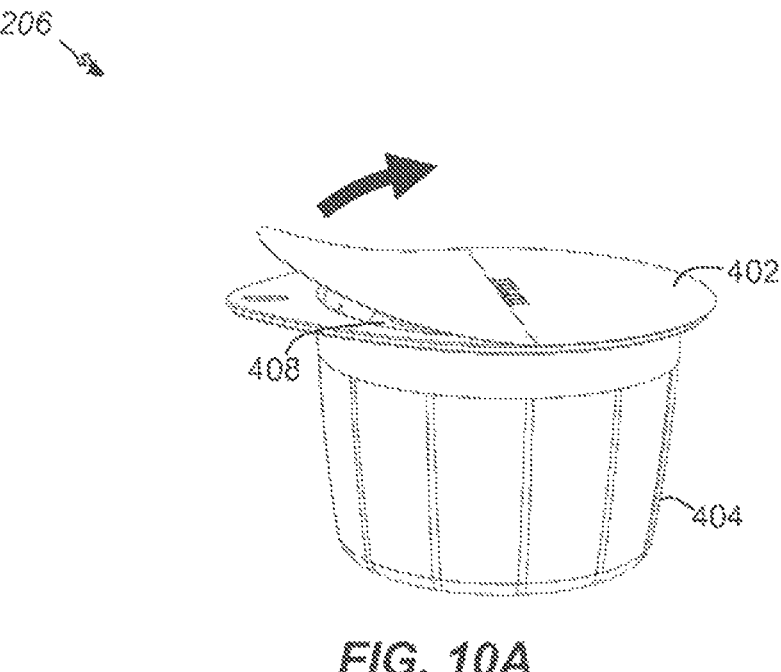
FIGS. 10A-10N variously illustrate the mechanics of preparing the applicator for use.
Figure 10B:
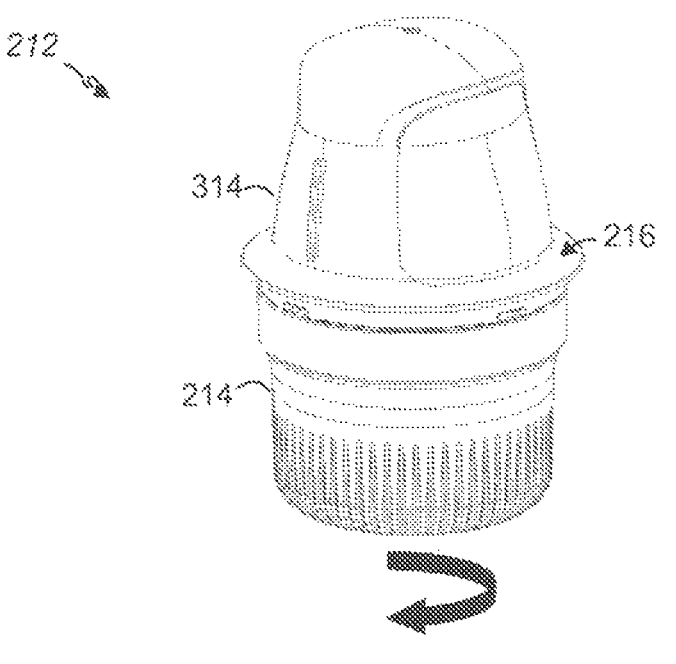
Figure 10C:
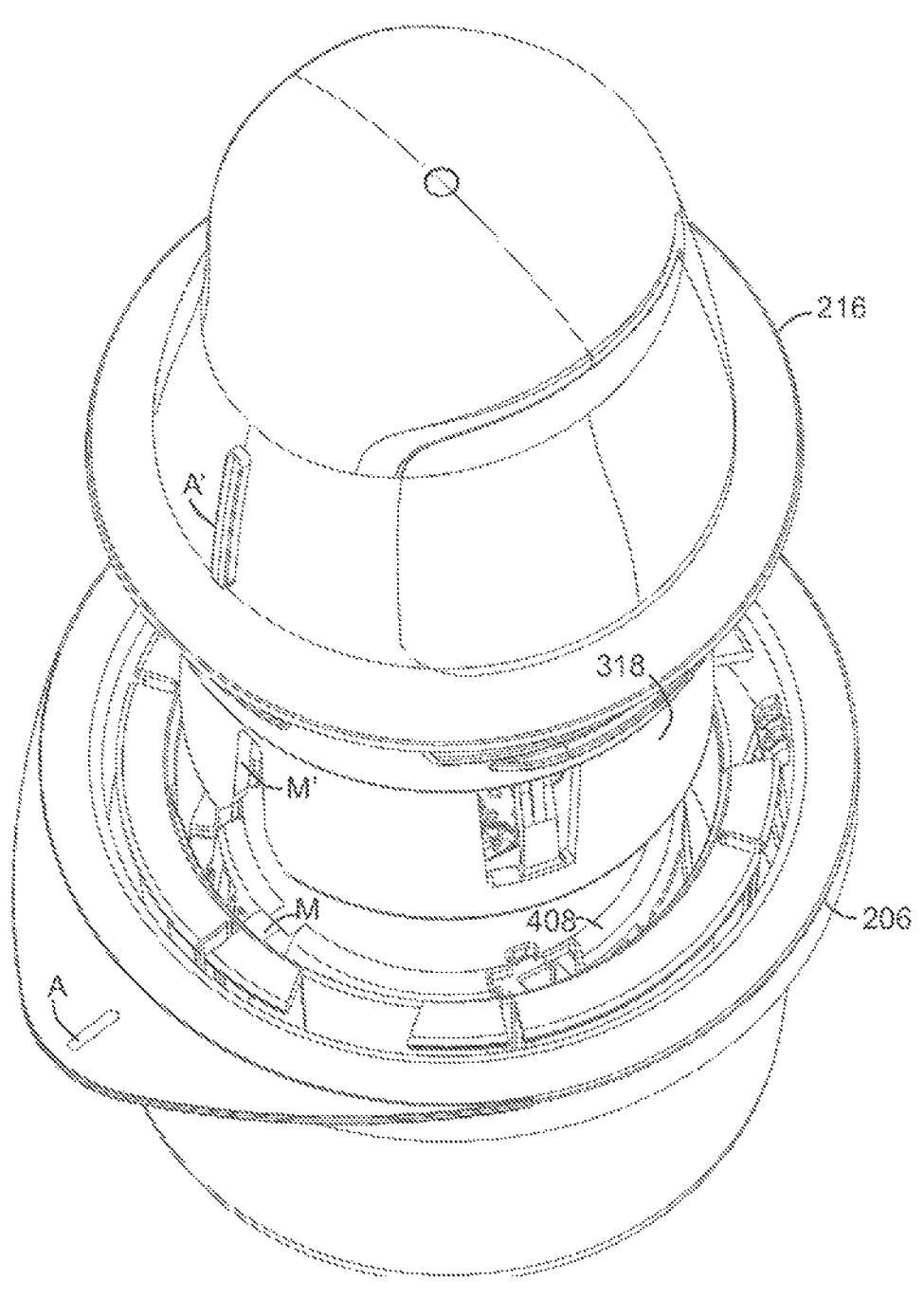
Figure 10D:
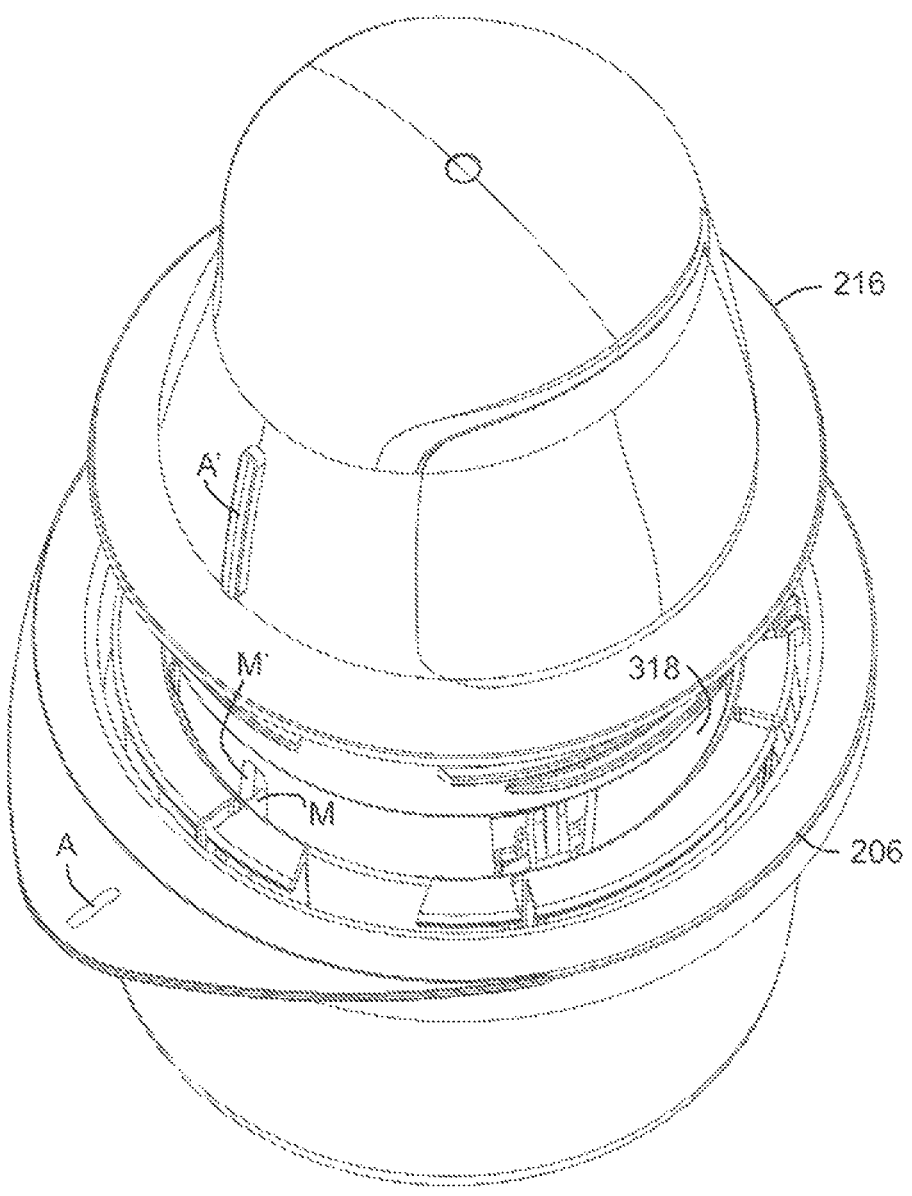
Figure 10E:
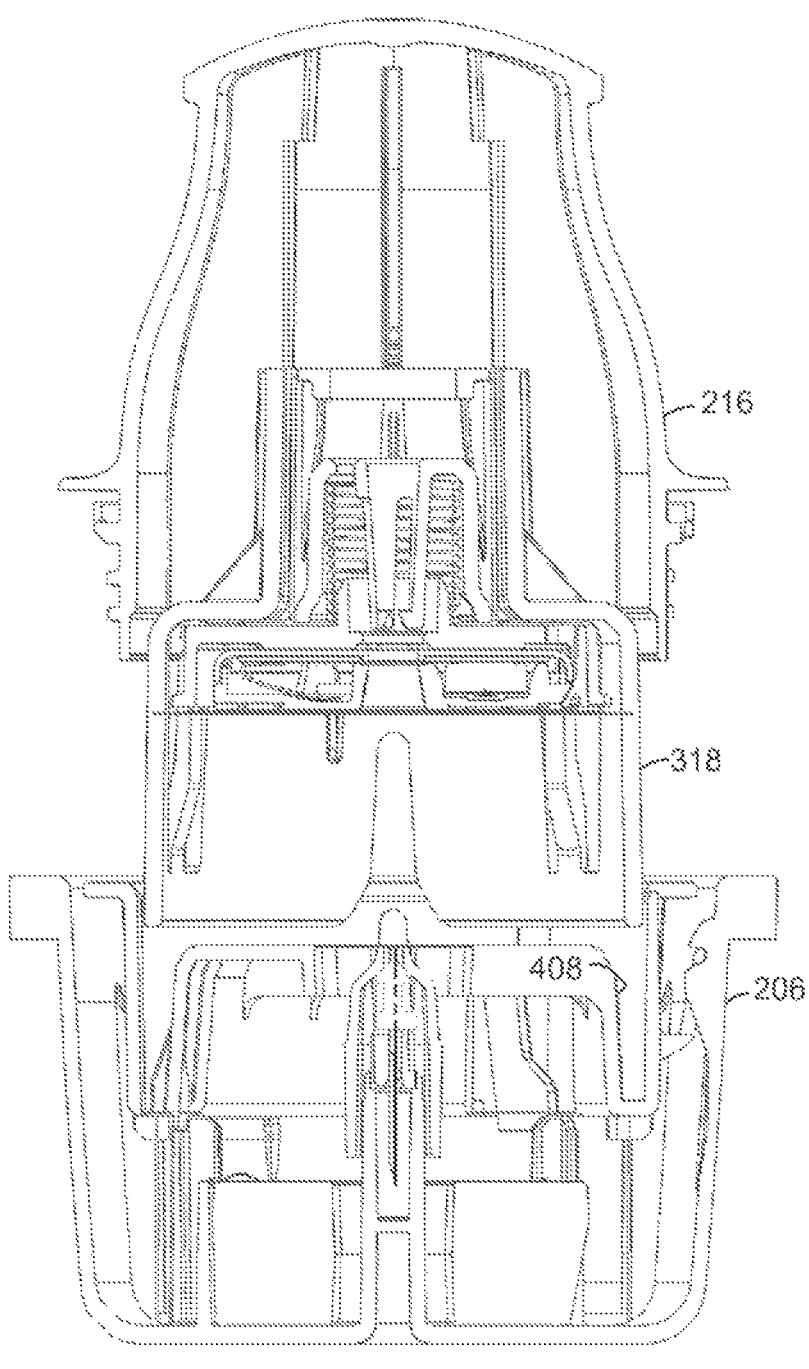
Figure 10F:
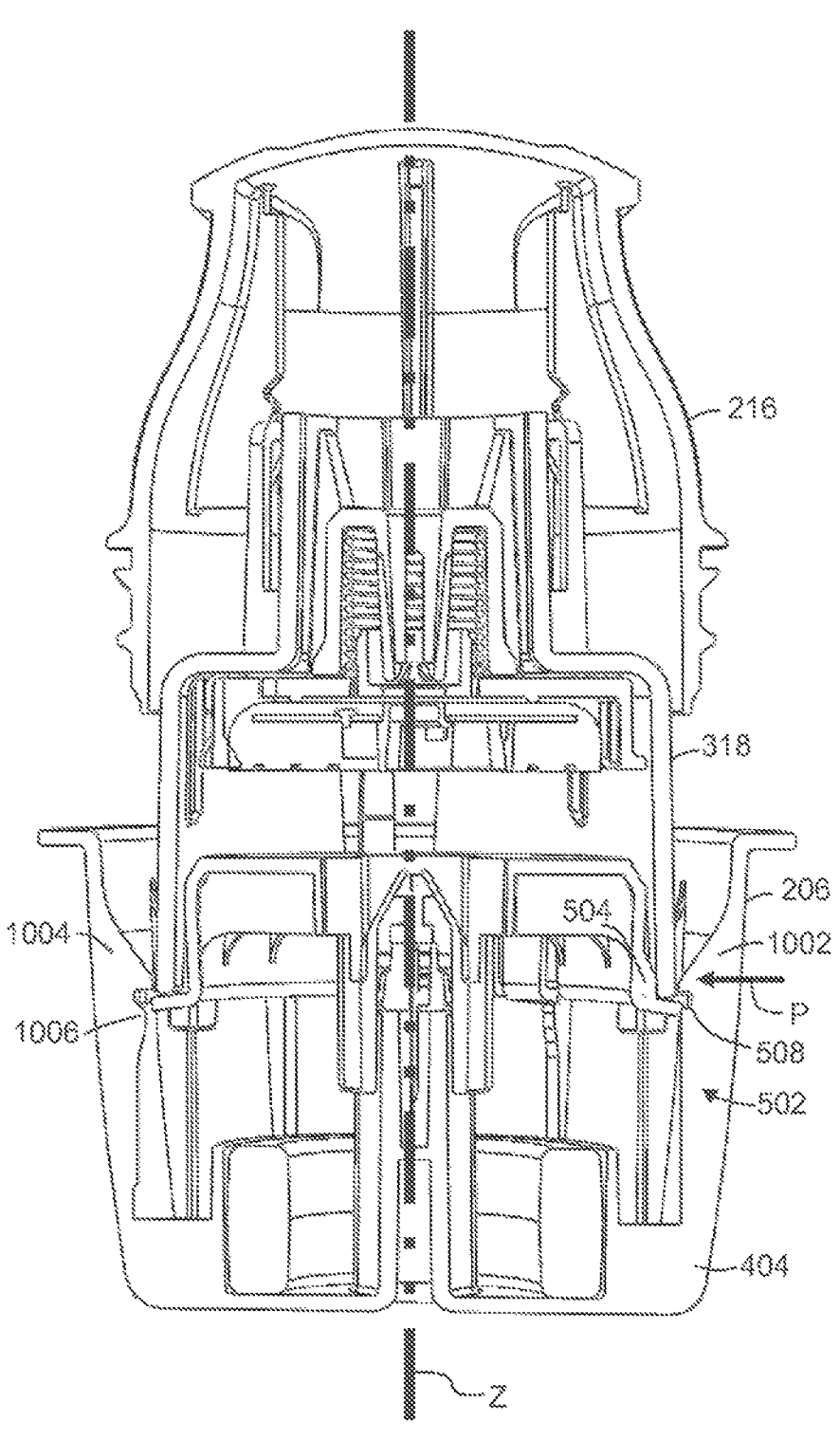
Figure 10G:
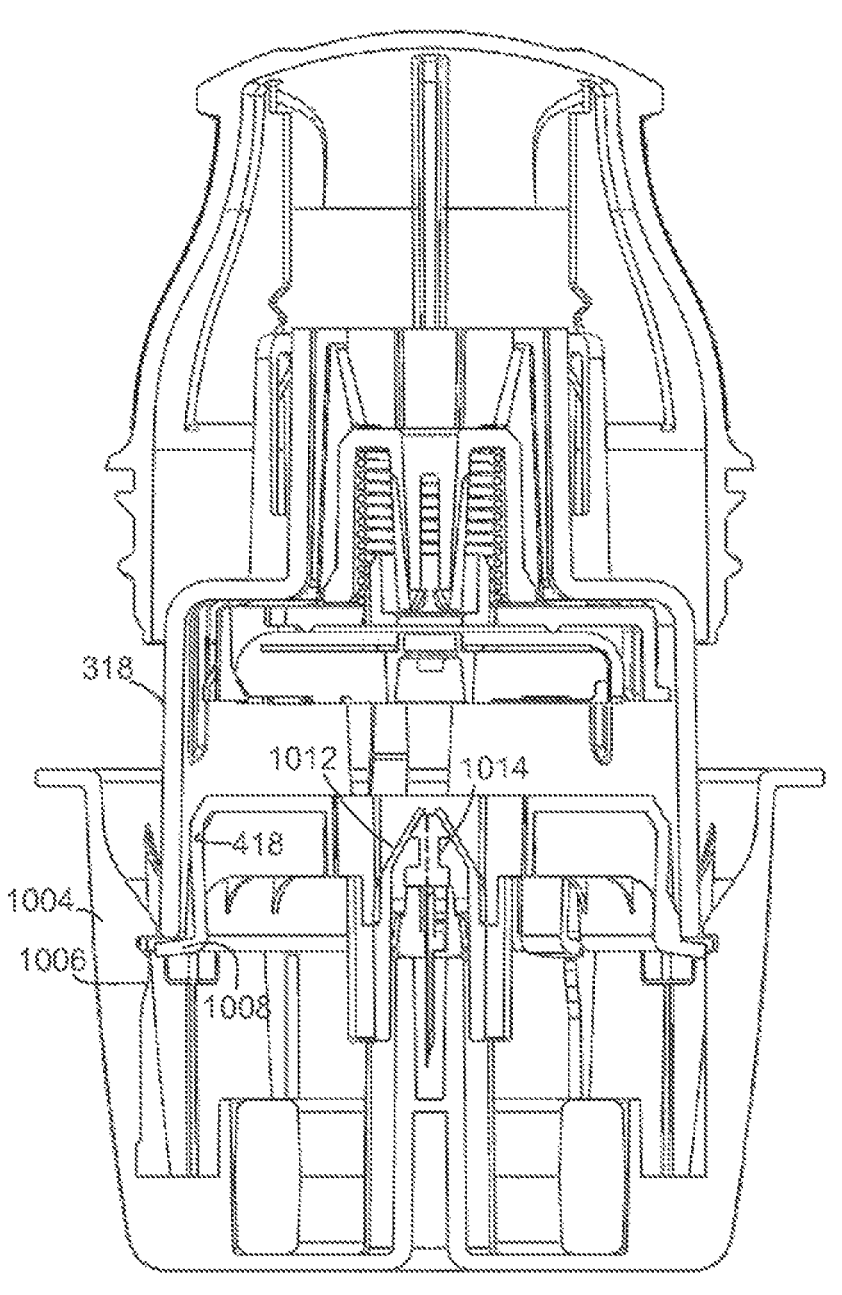
Figure 10H:
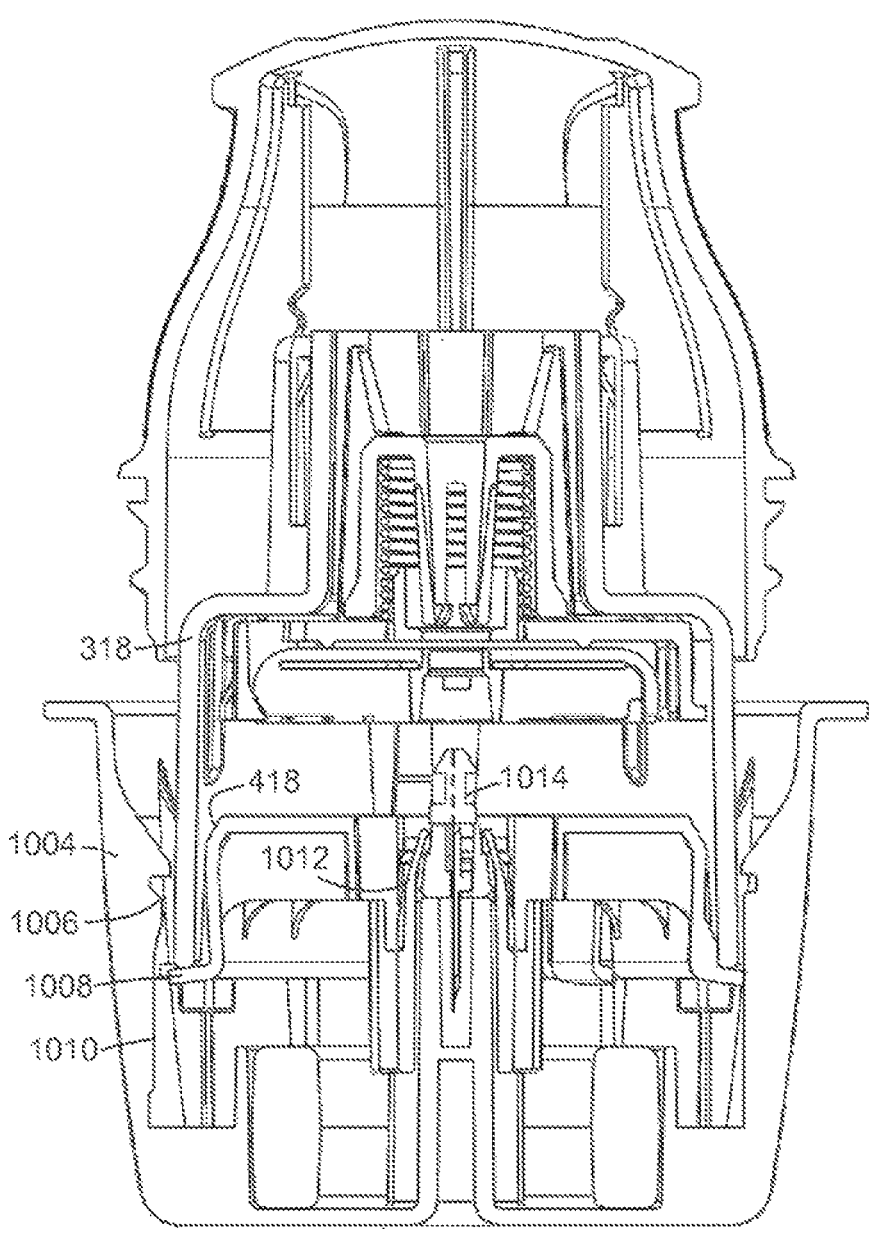
Figure 10I:
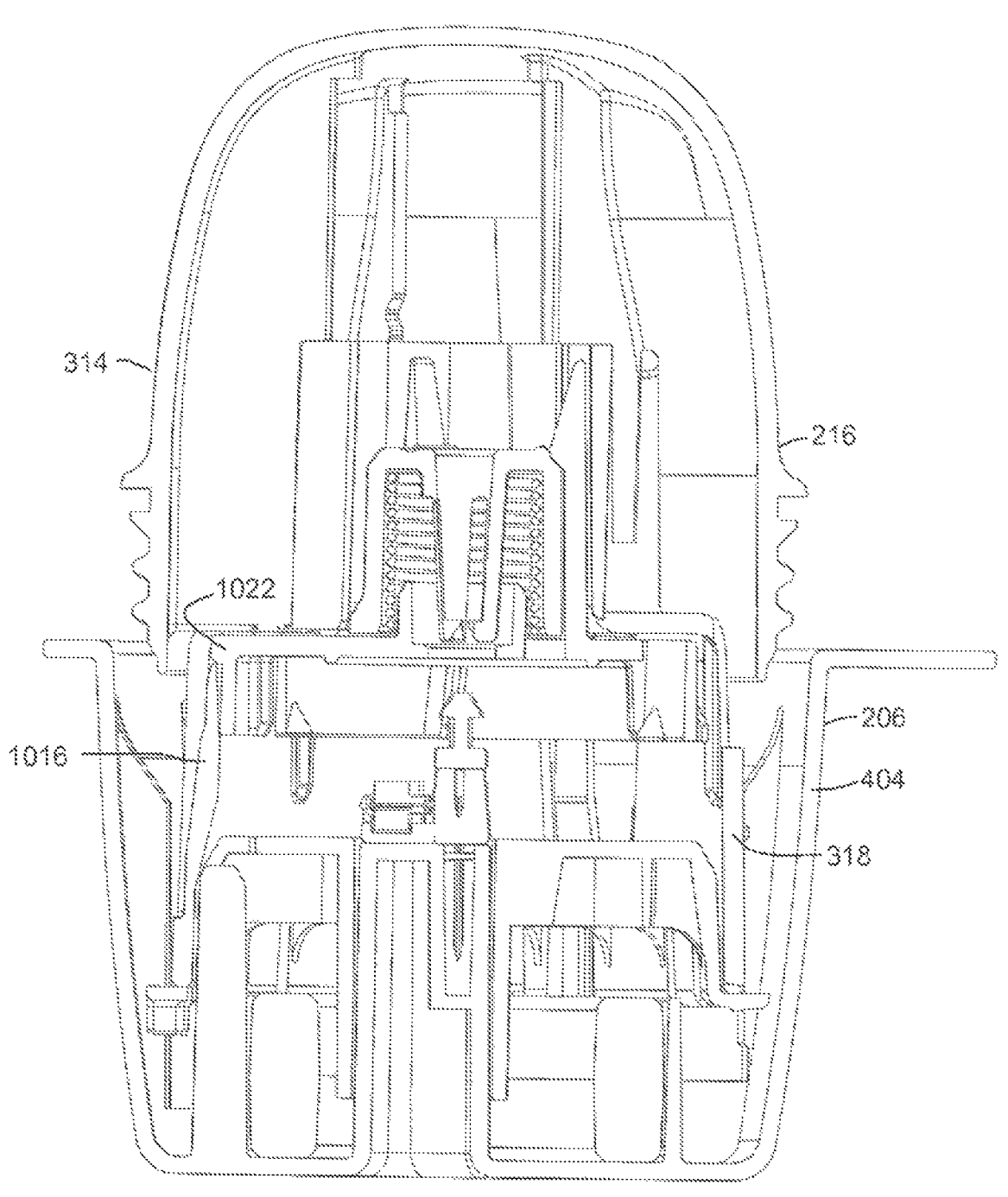
Figure 10J:
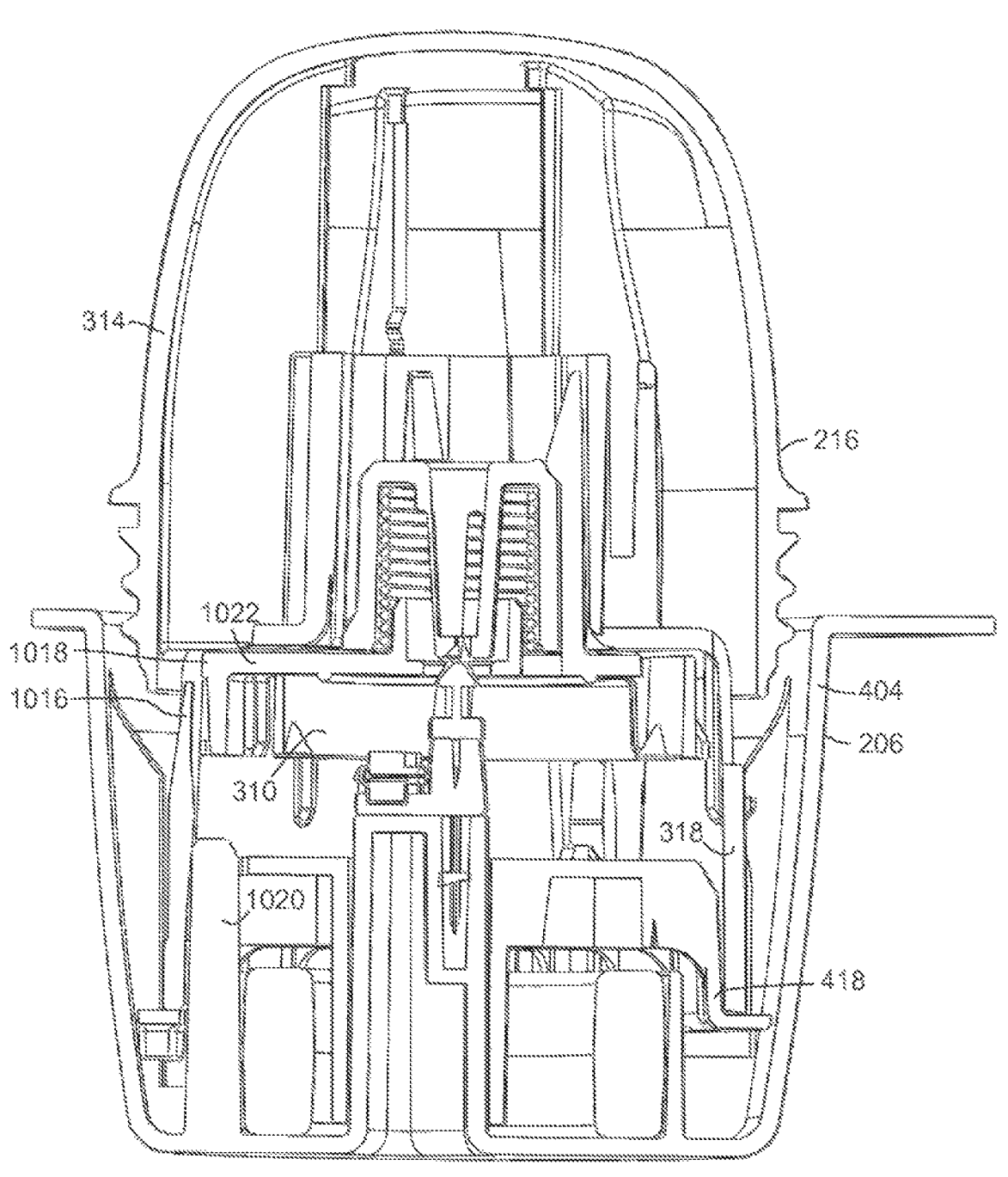
Figure 10K:
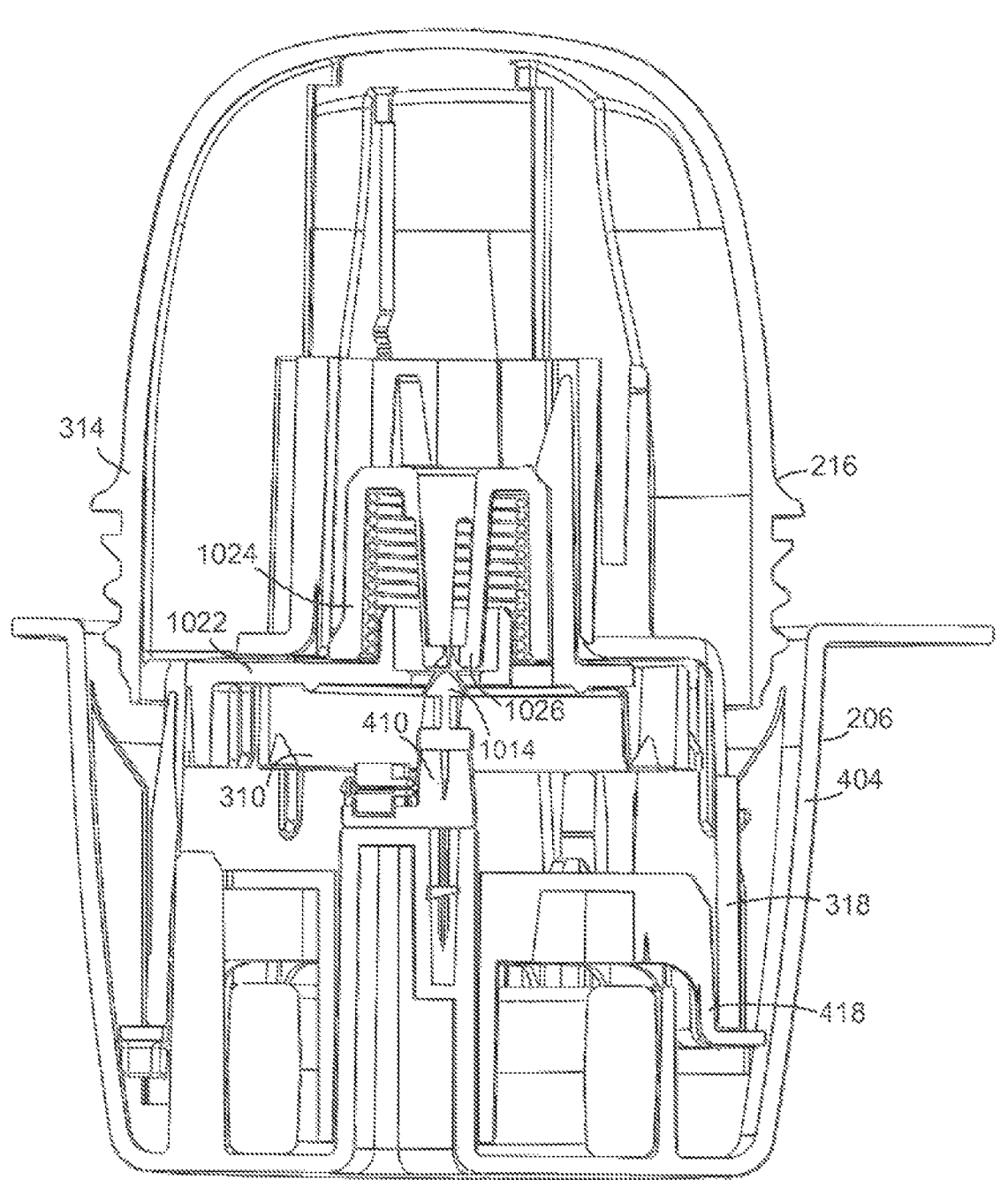
Figure 10L:
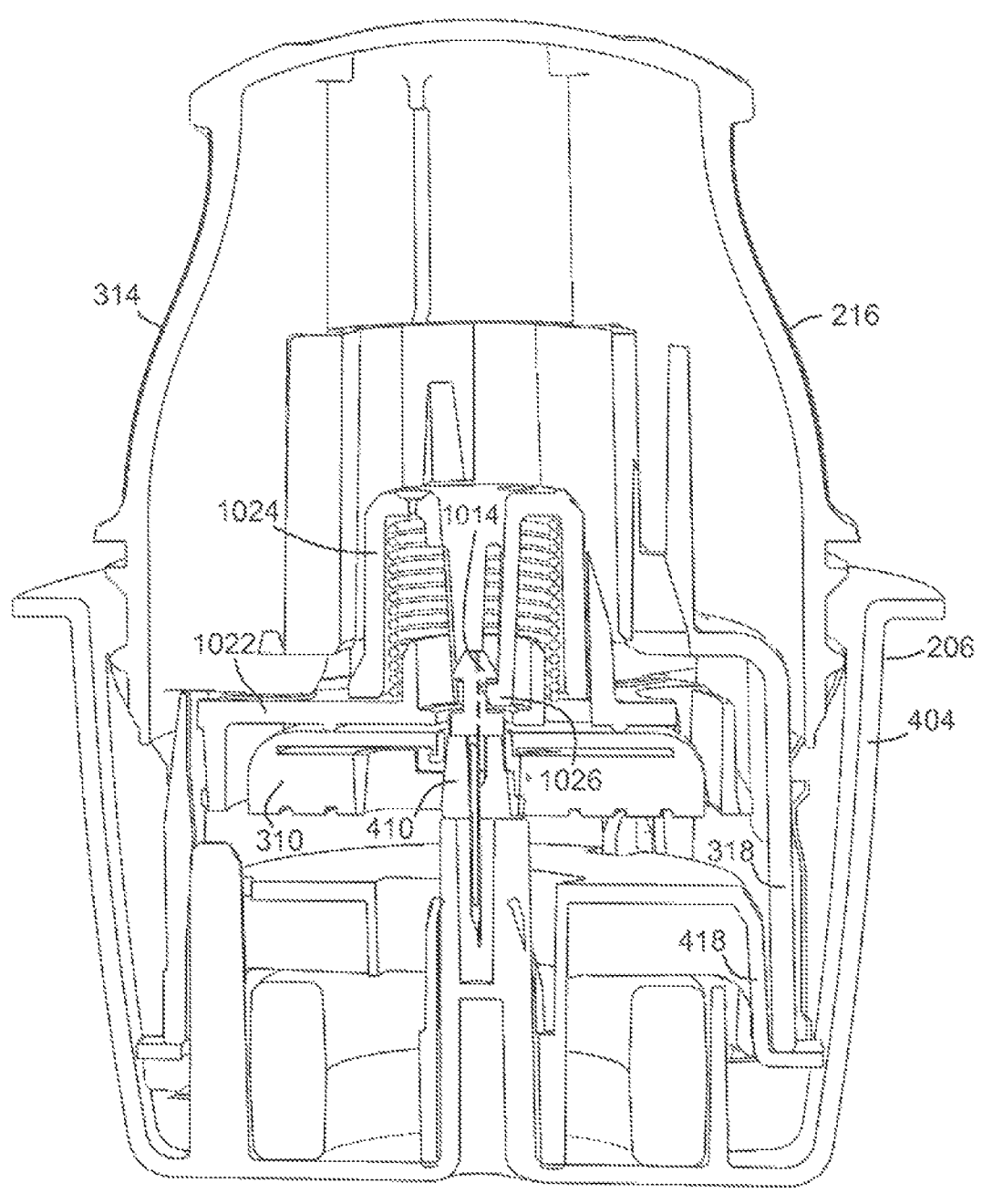
Figure 10M:
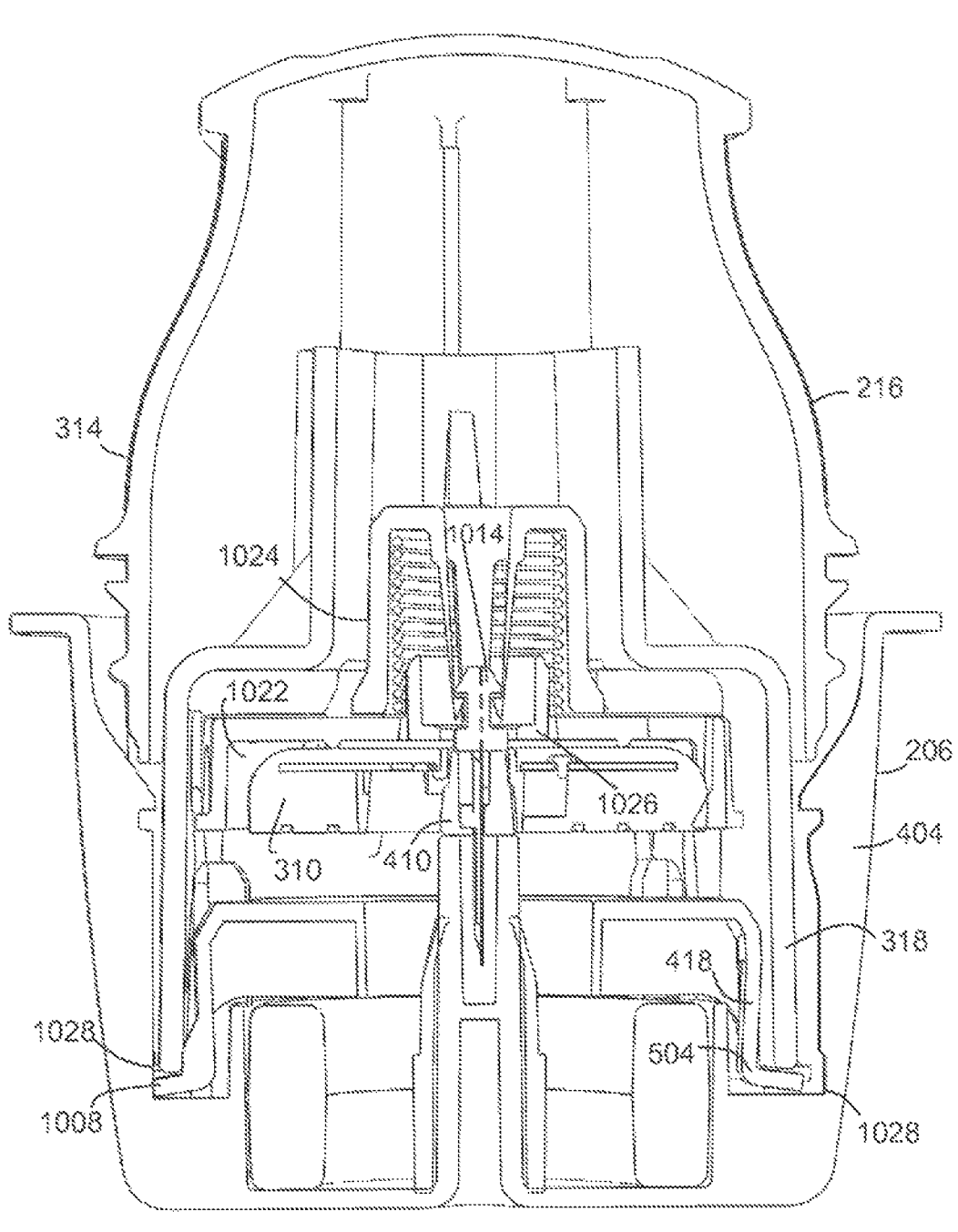
Figure 10N:
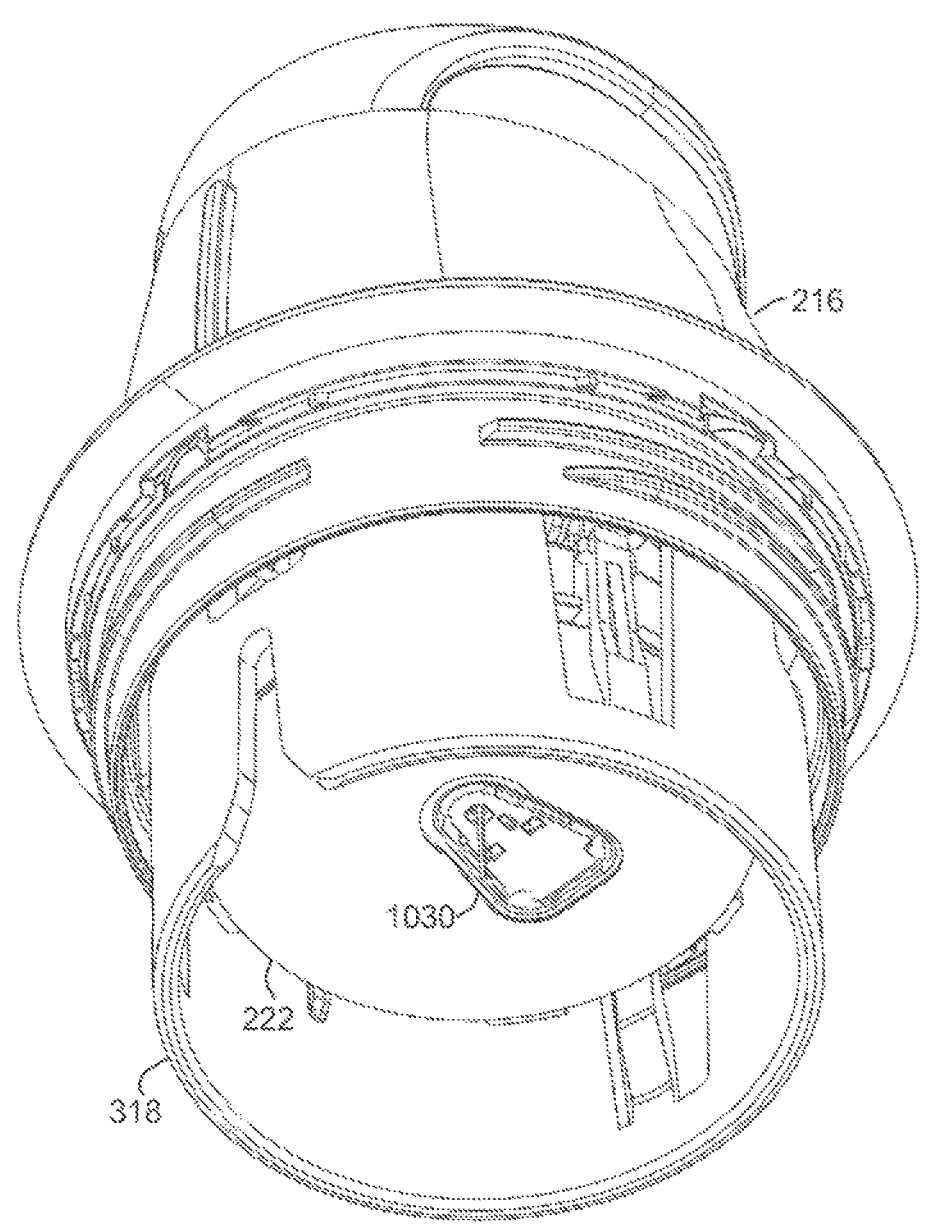

FIGS. 10A to 10N illustrate example details of embodiments of the internal device mechanics of preparing the applicator 212 for use, using the container 206. All together, these drawings represent an example sequence of assembling an on-body device 222 by connecting a sensor assembly 410 stored in the container 206 with an electronics assembly 310 stored in the applicator 212. In addition, the sequence prepares the applicator 212 to apply the assembled on-body device 222 to the user. Modification of such activity for use with the alternative container embodiments (as described above or others) can be appreciated in reference to the same by those with skill in the art.

FIGS. 10A and 10B show container 206 and applicator 212 with their constituent parts, along with arrows indicating the manner of cover 402 and cap 214 removal, respectively. Upon peeling off foil cover 402 from the casing 404, the platform 408 within is locked, thus protecting the sensor assembly 410 (not visible but see FIG. 4) which includes a sensor, a sensor support (also referred to as a plug), a connector, and a sharp. (These components are discussed in detail below.) Likewise, upon removal of cap 214 from the applicator assembly 216, the applicator 212 is locked. As a result of being locked, a guide sleeve 318 (not visible but see FIG. 3) cannot be collapsed into the applicator's housing 314.

In FIG. 10C, applicator assembly 216 is set within container 206. The two components 206, 216 are rotated and advanced until mechanical alignment features M and M' engage, allowing the applicator assembly 216 to register and sit level within the container 206. Visual alignment indicators A and A' assist or guide the user to quickly find the proper alignment position. Note that in some embodiments, the platform 408 cannot be unlocked to translate into the container 206 unless the alignment features M and M' are properly aligned. FIG. 10D depicts the components 206, 216 with the mechanical alignment features M, M' engaged. Sleeve 318 passes over platform 408, with the platform 408 nested concentrically inside the inner diameter of sleeve 318.

Cross-sectional views FIGS. 10E and 10F illustrate the relationship of parts overviewed in FIGS. 10C and 10D. When the sleeve 318 of applicator assembly 216 is seated onto the platform 408 of the container 206 and pushed downward, platform locking features 502 disposed around the platform 408 on locking ribs 1002 are unlocked to allow the platform 408 to translate along a longitudinal axis (labeled "Z") of the interfaced components 206, 216. More specifically, a portion of platform 408 bends and platform locking arms 504 are displaced inward as indicated by arrow P to clear locking grooves 508 in the locking ribs 1002 of casing 404, thus unlocking the platform 408. At this point, the platform 408 is held in place by guide ribs 1004 each providing a detent feature 1006 between the platform 408 and the guide ribs 1004 that can be overcome by further downward pressure applied by the user upon further depression of the applicator assembly 216 in the direction of the longitudinal axis Z.

Turning now to FIGS. 10G and 10H, the dropping of the unlocked platform 418 is illustrated. FIG. 10G depicts further depression of the applicator assembly 216 in the direction of the longitudinal axis Z. The force from the sleeve 318 causes inward, radial deflection of a portion of the platform 408. The effect is that detent arms 1008 are flexed down, inward and away from the detent feature 1006 of guide ribs 1004 as shown. This action releases the platform 418 and the applicator assembly 216 into freefall into the container 206. In some embodiments, the force to flex detent arms 1008, or in other words, the force to overcome the resistance from the detent features 1006, is selected to create a predetermined amount of momentum sufficient to ultimately properly mate the electronics assembly 310 with the sensor assembly 410 and unlock the sleeve 318. In some embodiments, the force to overcome the resistance from the detent features 1006 is from approximately 1 N to approximately 23 N. Other practicable values are possible.

In FIG. 10H, once detent arms 1008 of the platform 418 are past the detent features 1006, a relieve or undercut 1010 in each of the guide ribs 1004 provides increased clearance for the platform 418 to reduce sliding friction as the sleeve 318 and platform 418 slide or telescope further into the container's casing 404 along the longitudinal axis Z (FIG. 10F). Also, one or more flexible grasping arms 1012 previously in contact with the sensor assembly 410, particularly through sharp boss 1014, are moved from a stabilizing configuration in FIG. 10G to a freed state or configuration in FIG. 10H. In other words, as the platform 418 translates further into the container 206, the sharp boss 1014 of the sensor assembly 410 protrudes through a central opening in the platform 418 and pushes the flexible grasping arms 1012 out of the way.

Turning now to FIGS. 10I and 10J, a cross-sectional view depicting a slightly different cut plane than the prior views is provided to illustrate additional features. In FIG. 10I, sleeve lock arms are shown engaged with a sleeve lock ledge 1018. This engagement locks the applicator assembly 216 and prevents the sleeve 318 from being able to be retracted or pushed into the housing 314 of the applicator assembly 216. In FIG. 10J, as the applicator assembly 216 is further advanced into the container 206 along the longitudinal axis Z (FIG. 10F), sleeve unlock features contact and bend the sleeve lock arms 1016 clear of the sleeve lock ledge 1018 thereby unlocking the applicator assembly 216. Note that in the particular example embodiment depicted in FIGS. 10I and 10J, the sleeve lock ledge 1018 is formed in a carrier 1022 of the electronics assembly 310.

When the platform 418 bottoms-out in the container 206 as shown in FIG. 10J, the sleeve 318 of the applicator assembly 216 is fully unlocked/released and ready to move. Note that while the sleeve lock arms 1016 are shown flexing outward to unlock, in some embodiments, the sleeve lock arms 1016 can be oriented to flex radially inward to free the elements. The same may hold true for the various locking/ unlocking features of the present invention. However, the present arrangement offers advantages in terms of a coordinated whole providing an advantageous form factor and minimized container casing size (a factor that affects the user experience) in which the carrier 1022 of the electronics assembly 310 is coaxially arranged. Regarding the carrier 1022, it is advantageously designed with unique carrier arm features as detailed in, for example, U.S. patent application Ser. No. 13/071,461, the disclosure of which is incorporated herein by reference.

In FIGS. 10K and 10L, now that the sleeve 318 of the applicator assembly 216 is fully unlocked, the momentum along the longitudinal axis Z (FIG. 10F) from the force used to overcome the resistance of the detent features 1006 (FIG. 10H) causes three additional concurrent actions. First, even though the sleeve 318 cannot descend any further into the container 206 (since it is in contact with the platform 418 which is bottomed-out), the housing 314 of the applicator assembly 216, the carrier 1022, and the electronics assembly 310 are free to continue to descend into the container 206, now that the sleeve 318 is unlocked as shown in FIG. 10L.

Second, as the electronics assembly 310 descends further along the longitudinal axis Z (FIG. 10F), the sensor assembly 410 is forced into an opening in the electronics assembly 310 which couples the sensor to the electronics and completes assembly of the on-body device 222 (FIG. 2F). In some embodiments, mating snap features on the sensor assembly 410 and the electronics assembly 310 can be used to compel the components to remain locked and compressed together to insure a sealed, reliable connection. As an alternative to mating snap features, in some embodiments, the sensor assembly 410 and the electronics assembly 310 may be coupled by a light press fit or other connection method. However, the positive interaction and lock of snap features is an advantage. So too is the minimal force used to deflect fine locking features that spring back for engagement.

Third, along with the housing 314, the carrier 1022, and the electronics assembly 310, a sharp retraction assembly 1024 also continues to descend into the container 206 along the longitudinal axis Z (FIG. 10F) and is forced to receive the sharp boss 1014 of the sensor assembly 410. The conical head of the sharp boss 1014 is pushed past a radial arrangement of flexible arms 1026 of the sharp retraction assembly 1024. The flexible arms 1026 bend outwardly, as they are forced to ride against the passing conical surface of the head of the sharp boss 1014. The sharp is thus thereby engaged by the sharp retraction assembly 1024 as the flexible arms 1026 snap back into place once the head of the sharp boss 1014 has passed by, securely grasping the head at the narrowed neck portion of the sharp boss 1014. Note that a base of the sharp boss 1014 may be included to limit insertion into the sharp retraction assembly 1024 through interference with a stop limit or shoulder of the flexible arms 1026. FIG. 10K illustrates the arrangement immediately before the above three actions have completed and FIG. 10L illustrates the resulting arrangement immediately after the actions have completed.

In some embodiments, the connection features between the sharp boss 1014 of the sensor assembly 410 and the sharp retraction assembly 1024 can be otherwise configured. For example, the sharp retraction assembly 1024 can include a conical channel formed from a radial arrangement of inwardly biased flexible finger members configured to receive the head of sharp boss 1014 such that once the head has passed through the channel, the flexible fingers conform to the narrowed neck of the sharp boss 1014. With the fingers so conformed, the sharp boss 1014 is captured by the sharp retraction assembly 1024. Retention force is limited only by material strength because the self-energizing lock is not prone to slip between the pieces.

Turning to FIG. 10M, a slightly rotated view, relative to FIG. 10L, is shown. When the sharp boss 1014 is engaged in the sharp retraction assembly 1024, the sensor assembly 410 is coupled to the electronics assembly 310 completing assembly of the on-body-device 222, and the sleeve 318 is unlocked, platform locking arms 504 and detent arms 1008 have engaged undercut grooves 1028 in the container 206, thereby locking the platform 418 in the casing 404. This engagement between the platform 418 and the casing 404 marks the final position of the container 206 from which the loaded applicator assembly 216 is withdrawn for use to apply the on-body device 222 to the user.

Now, once removed from the container 206, the applicator assembly 216 is ready to "fire" as illustrated in FIG. 10N. As such, the applicator assembly 216 is ready to use as in application 108 described in connection with FIG. 2E. Here, the applicator assembly 216 has already been unlocked by interaction with the container 206, and the sensor assembly 410 is coupled to the electronics assembly 310. The sharp 1030 extends from the on-body device 222 which is held in the sleeve 318 of the applicator assembly 216 as shown.

FIGS. 11A to 11F illustrate example details of embodiments of the internal device mechanics of "firing" the applicator assembly 216 to apply the on-body device 222 to a user and including retracting the sharp 1030 safely back into the used applicator assembly 216. All together, these drawings represent an example sequence of driving the sharp 1030 (supporting a sensor coupled to the on-body device 222) into the skin of a user, withdrawing the sharp while leaving the sensor behind in operative contact with interstitial fluid of the user, and adhering the on-body device to the skin of the user with an adhesive. Modification of such activity for use with the alternative applicator assembly embodiments and components can be appreciated in reference to the same by those with skill in the art.

Figure 11A:
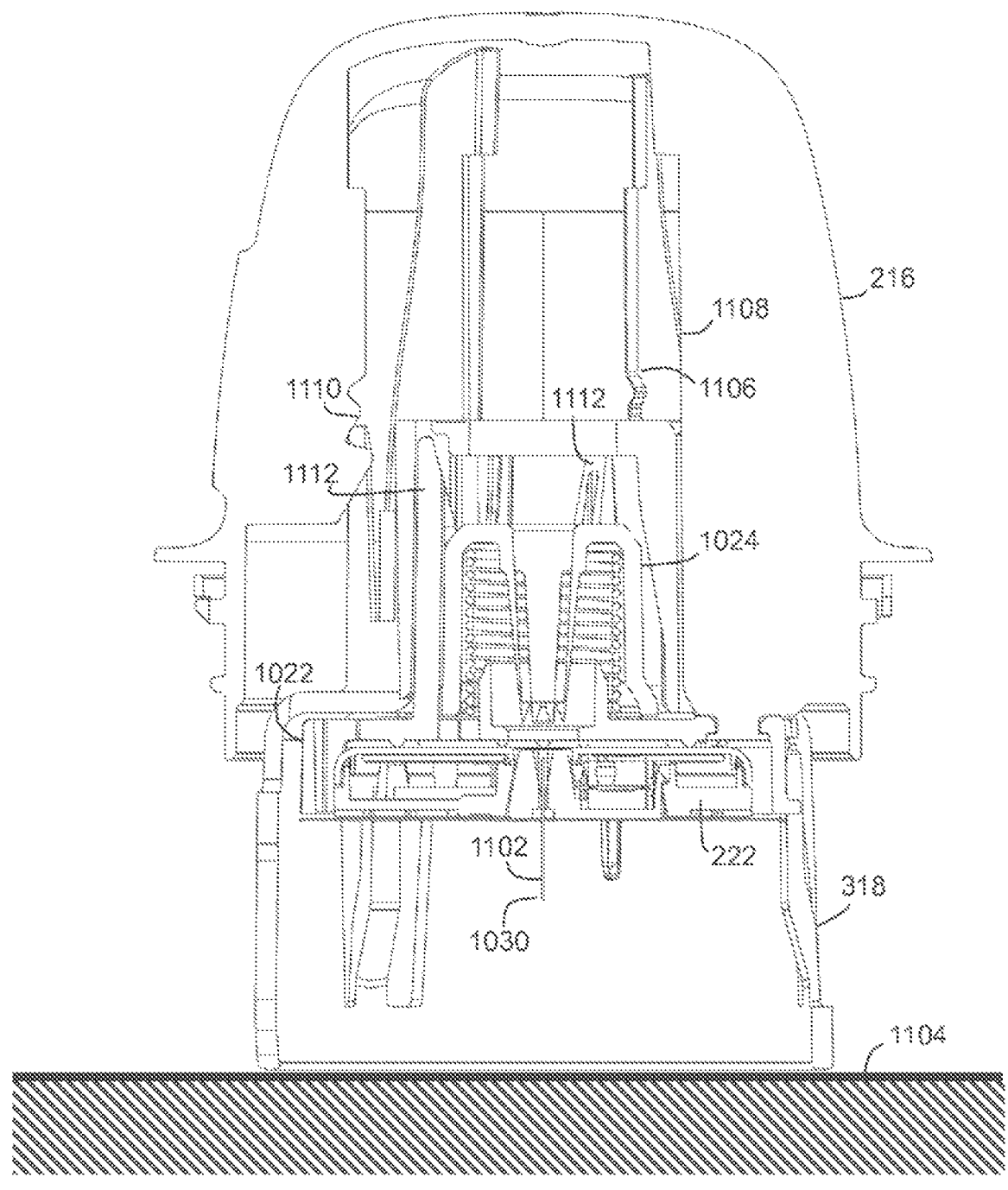
FIGS. 11A-11F illustrate the mechanics of applicator use.

Turning now to FIG. 11A, a sensor 1102 is supported within sharp 1030, just above the skin 1104 of the user. Rails 1106 (optionally three of them) of an upper guide section 1108 may be provided to control applicator assembly 216 motion relative to the sleeve 318. The sleeve 318 is held by detent features 1110 within the applicator assembly 216 such that appropriate downward force along the longitudinal axis of the applicator assembly 216 will cause the resistance provided by the detent features 1110 to be overcome so that the sharp 1030 and on-body device 222 can translate along the longitudinal axis into (and onto) the skin 1104 of the user. In addition, catch arms 1112 of carrier 1022 engage the sharp retraction assembly 1024 to maintain the sharp 1030 in a position relative to the on-body device 222.

Figure 11B:
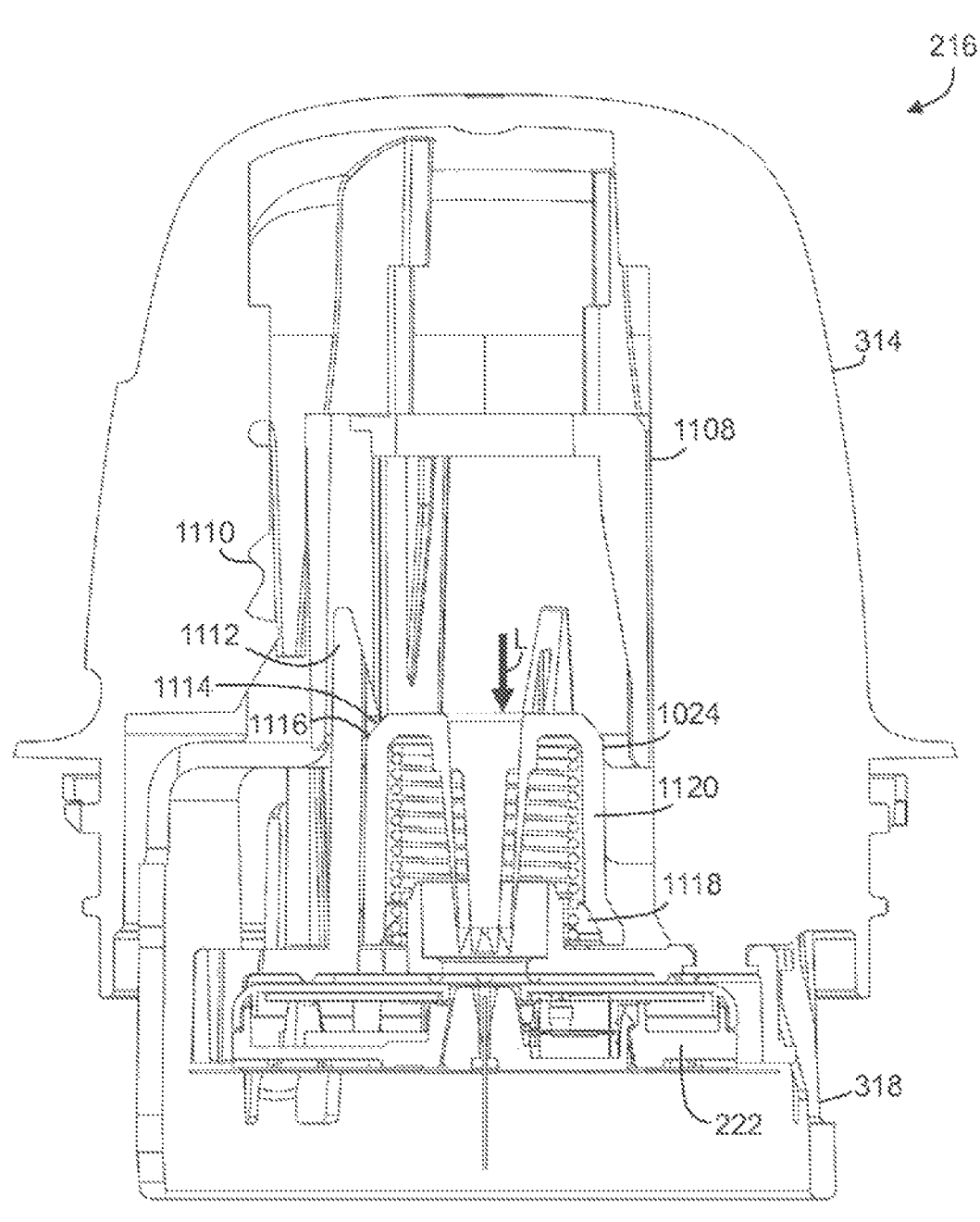

In FIG. 11B, user force is applied to overcome or override detent features 1110 and sleeve 318 collapses into housing 314 driving the on-body device 222 (with associated parts) to translate down as indicated by the arrow L along the longitudinal axis. An inner diameter of the upper guide section 1108 of the sleeve 318 constrains the position of carrier arms 1112 through the full stroke of the sensor/sharp insertion process. The retention of the stop surfaces 1114 of carrier arms 1112 against the complimentary faces 1116 of the sharp retraction assembly 1024 maintains the position of the members with return spring 1118 fully energized.

Figure 11C:
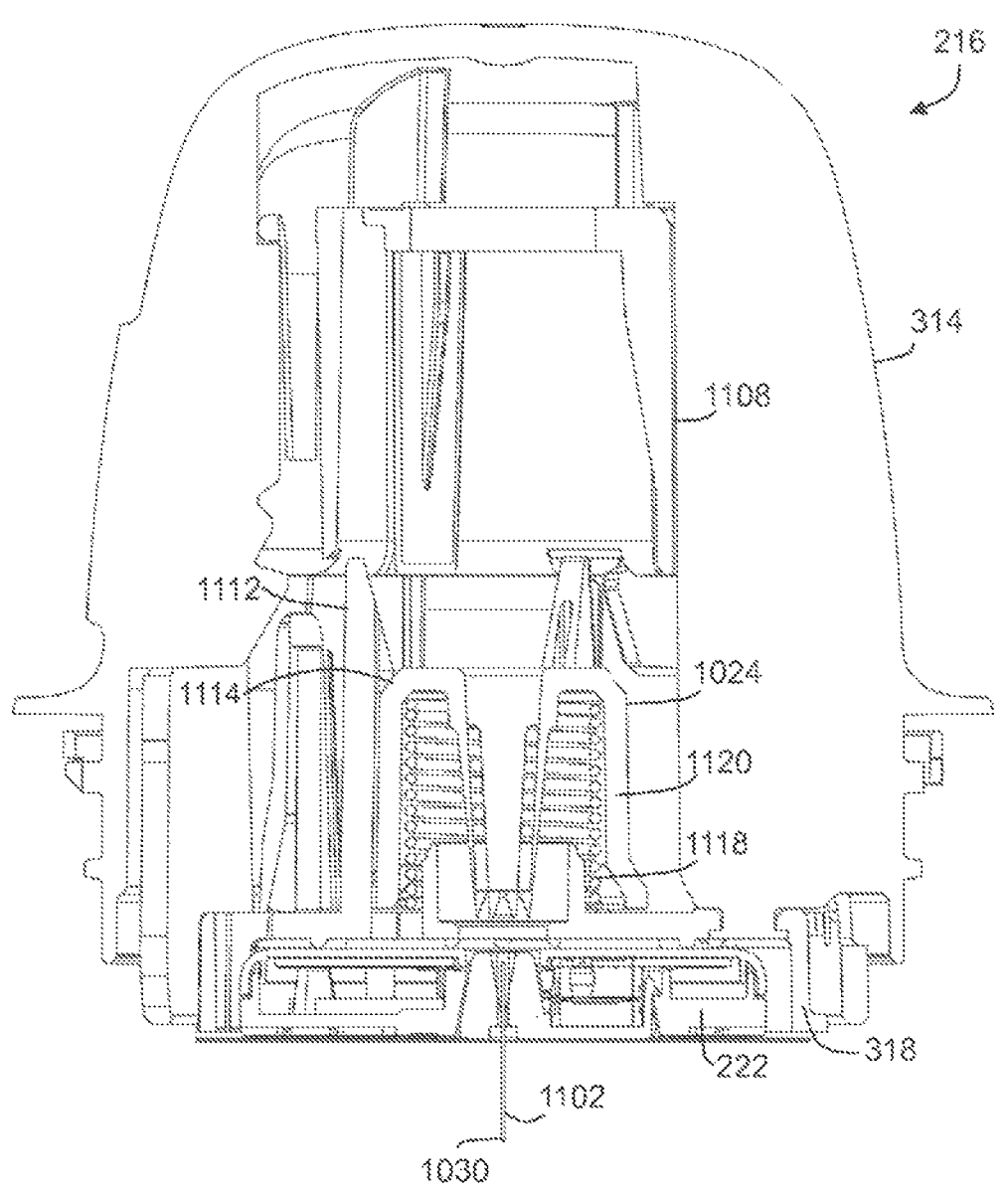
Figure 11D:
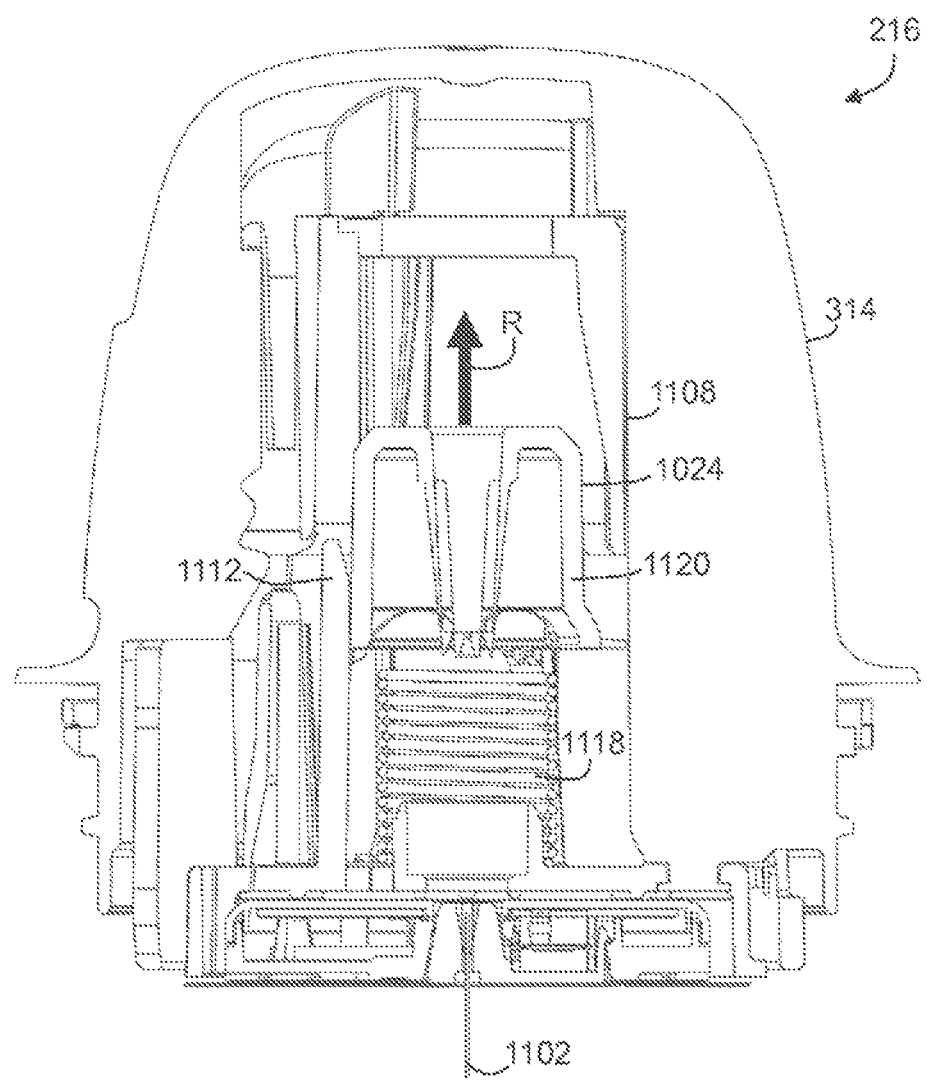

In FIG. 11C, sensor 1102 and sharp 1030 have reached full insertion depth. In so doing, the carrier arms 1112 clear the upper guide section 1108 inner diameter. Then, the compressed force of the coil return spring 1118 drives angled stop surfaces 1114 radially outward, releasing force to drive the sharp carrier 1120 of the sharp retraction assembly 1024 to pull the (slotted or otherwise configured) sharp 1030 out of the user and off of the sensor 1102 as indicated by the arrow R in FIG. 11D.

Figure 11E:
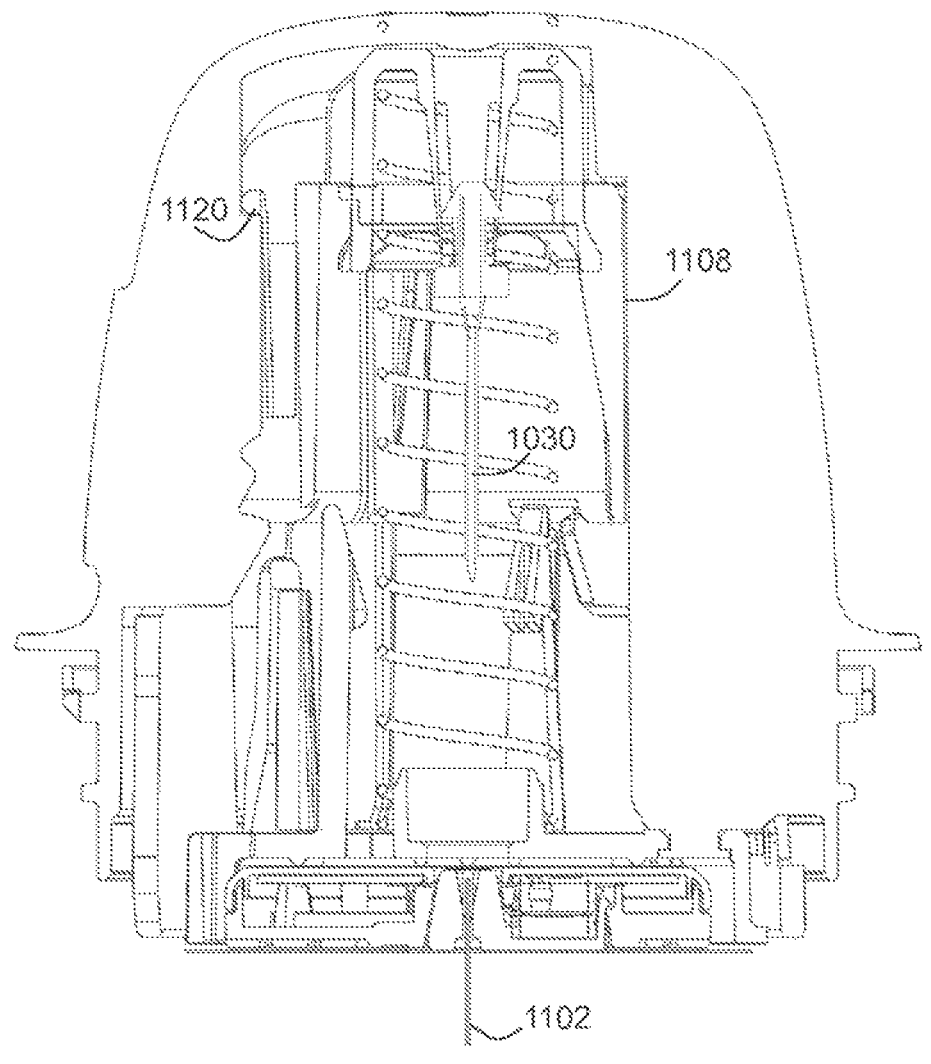
Figure 11F:
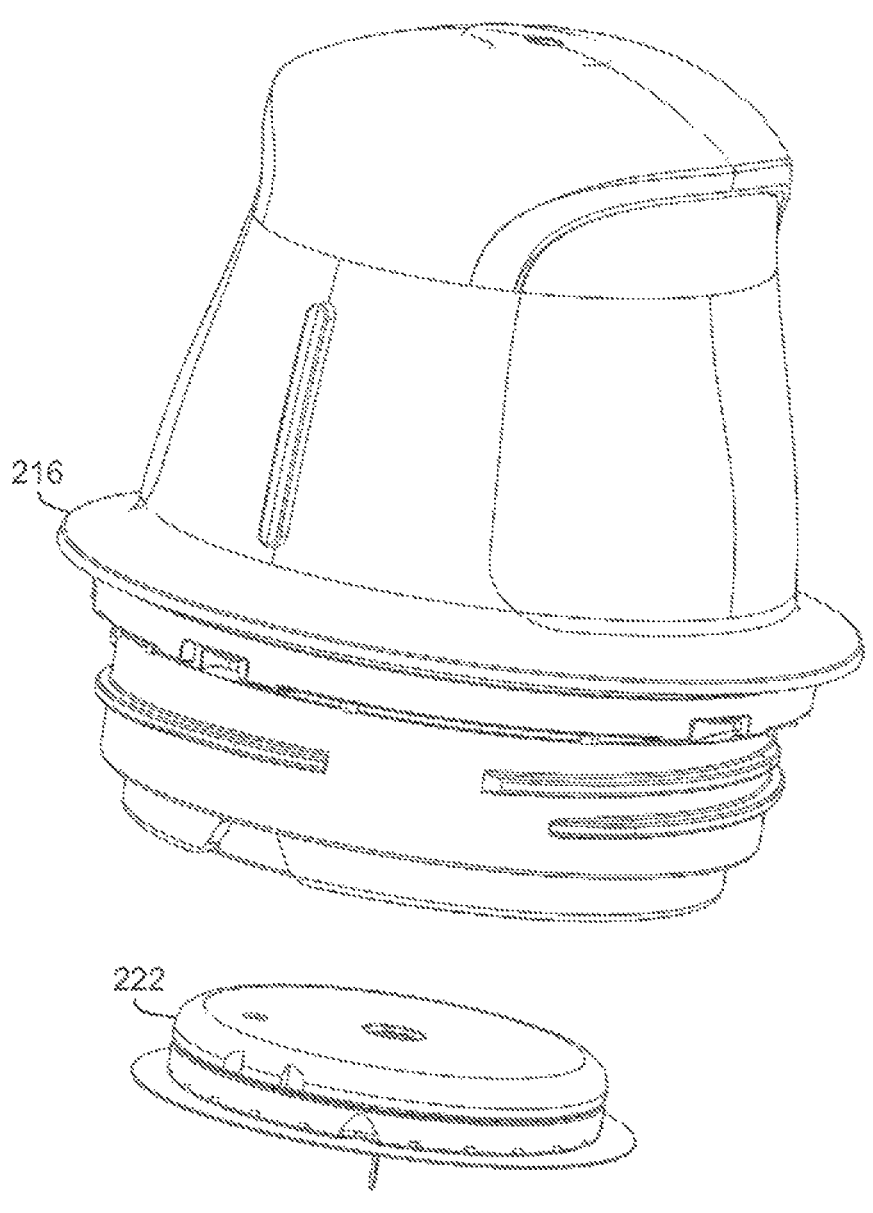

With the sharp 1030 fully retracted as shown in FIG. 11E, the upper guide section 1108 of the sleeve 318 is set with a final locking feature 1120. As shown in FIG. 11F, the spent applicator assembly 216 is removed from the insertion site, leaving behind the on-body device 222, and with the sharp 1030 secured safely inside the applicator assembly 216. The spent applicator assembly 216 is now ready for disposal.

Operation of the applicator 216 when applying the on-body device 222 is designed to provide the user with a sensation that both the insertion and retraction of the sharp 1030 is performed automatically by the internal mechanisms of the applicator 216. In other words, the present invention avoids the user experiencing the sensation that he is manually driving the sharp 1030 into his skin. Thus, once the user applies sufficient force to overcome the resistance from the detent features of the applicator 216, the resulting actions of the applicator 216 are perceived to be an automated response to the applicator being "triggered." The user does not perceive that he is supplying additional force to drive the sharp 1030 to pierce his skin despite that all the driving force is provided by the user and no additional biasing/driving means are used to insert the sharp 1030. As detailed above in FIG. 11C, the retraction of the sharp 1030 is automated by the coil return spring 1118 of the applicator 216.

As for further details of the operation, alternative embodiments may be appreciated in view of related approaches discussed below, others in review of the incorporated subject matter and still more appreciated by those with skill in the art based upon further review of the figures which depict actual hardware produced according to various aspects of the subject disclosure.

Figure 12A:
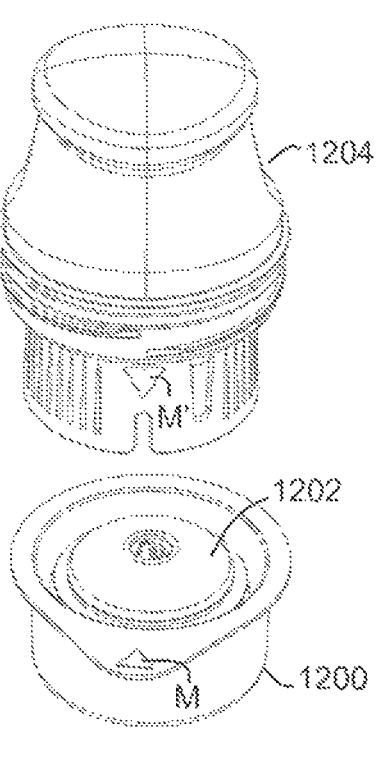
FIGS. 12A-12D are perspectives illustrating another applicator/container set approach in which the container holds the electronics assembly.
Figure 12B:
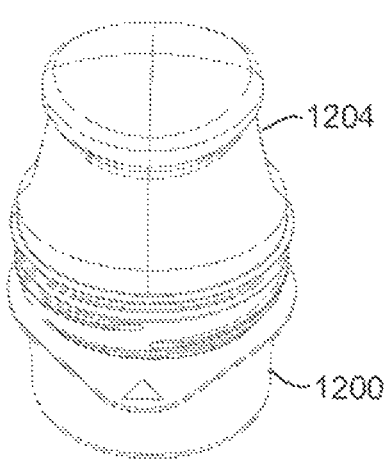
Figure 12C:
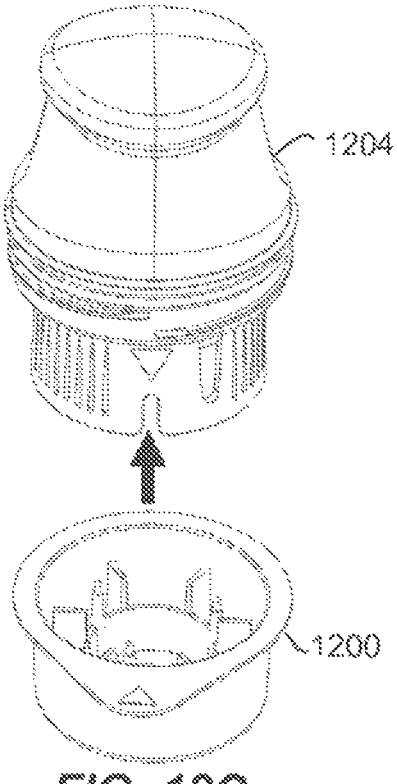
Figure 12D:
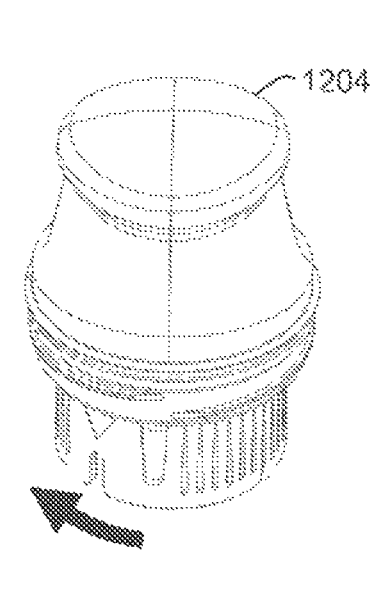

Turning to FIGS. 12A to 12D an alternative applicator/container set approach is now described. As shown in FIG. 12A, the container 1200 holds the electronics assembly 1202. This is in contrast to the above embodiments wherein the relationship between the sensor assembly and the electronics assembly was reversed. Upon aligning markers M and M', the applicator 1204 is inserted in the container 1200. In FIG. 12B, the units are merged. In FIG. 12C, the parts are separated. Finally, in FIG. 12D the applicator 1204 is unlocked (e.g., in some embodiments by twisting the sleeve 1206 within the applicator 1204, in some embodiments by the act of loading the electronics assembly 1202 into the applicator 1204, or in some embodiment by the act of removing a locking strip from the sleeve 1206) and ready for use with the assembled on-body device (not visible) including the sensor assembly loaded therein. These various alternative embodiments are illustrated in FIG. 13A to 15F.

FIGS. 13A to 13C variously illustrate use of the applicator 1204 of FIGS. 12A to 12D in connection with a locking-sleeve feature 1206. FIG. 13A shows the sleeve 1206 locked as indicated by the closed window 1208. After twisting the sleeve 1206 relative to the rest of the applicator 1204 to unlock the sleeve 1206, a visual indication (e.g., open window 1208') is seen when the applicator 1204 is ready for use as presented in FIG. 13B. Upon use, as shown in FIG. 13C, the unit is compressed with the sleeve 1206 collapsed into the applicator 1204.

Figure 14A:
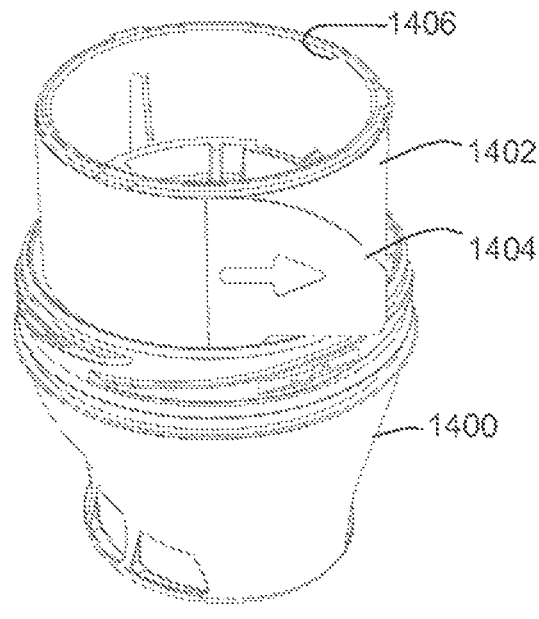
FIGS. 14A and 14B illustrate an applicator with a removable locking strip.
Figure 14B:
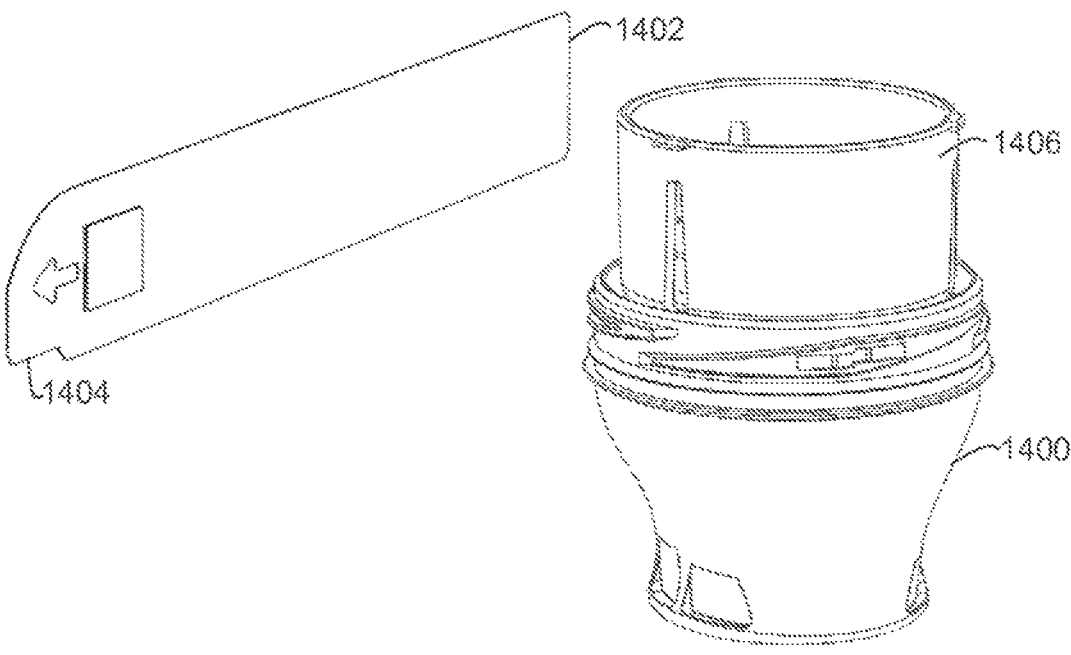

FIGS. 14A and 14B illustrate an alternative applicator 1400 embodiment with a removable locking strip 1402. With the locking strip 1402 in place around the sleeve 1406, the sleeve 1406 cannot be pushed into the applicator 1400. The strip 1402 includes a pull-tab 1404 and adhesive or other fastening member to keep it in place until removed and the applicator 1400 is ready for use.

Figure 15A:
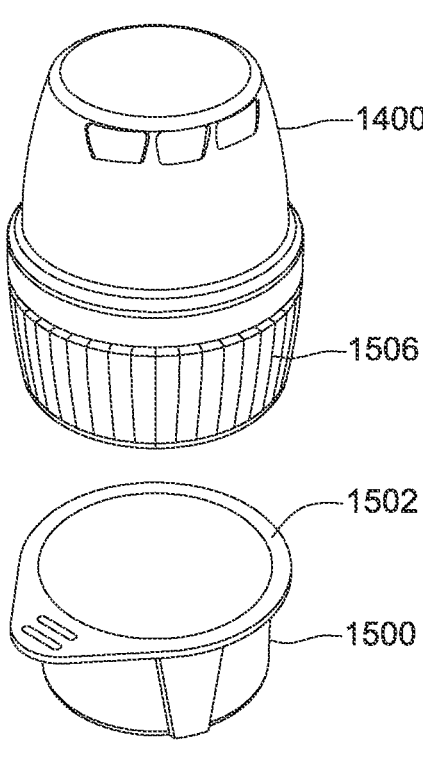
Figure 15B:
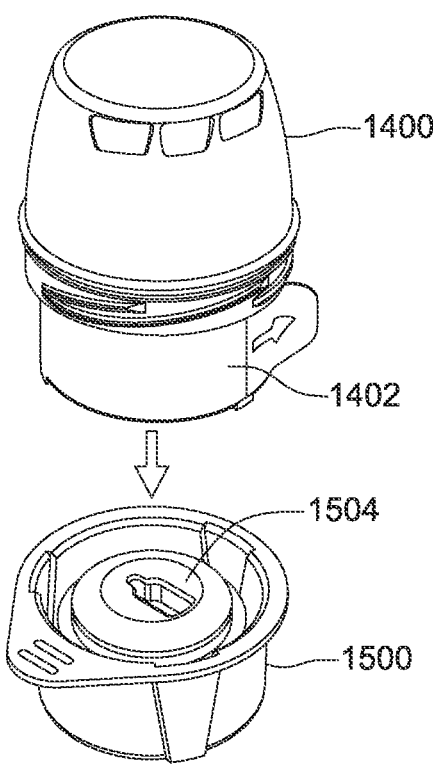
Figure 15C:
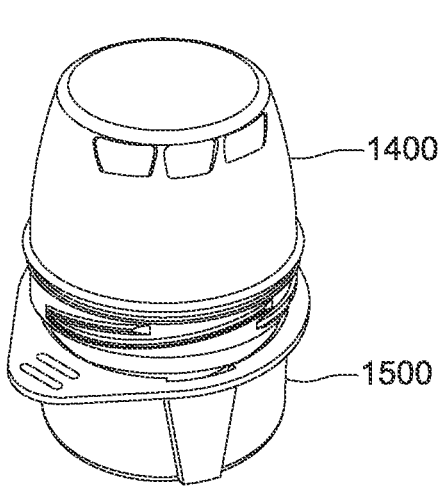
Figure 15D:
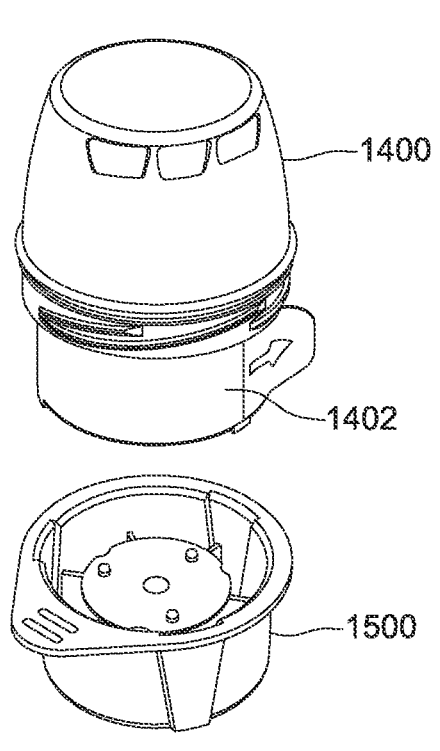
Figure 17A:
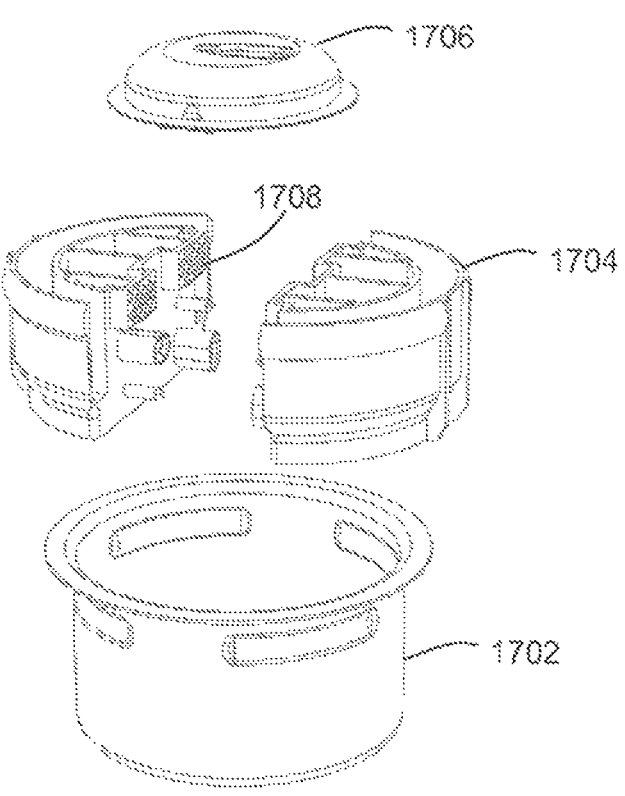
FIGS. 17A and 17B are perspective assembly views illustrating alternative container configurations to that illustrated in FIGS. 16A and 16B.
Figure 17B:
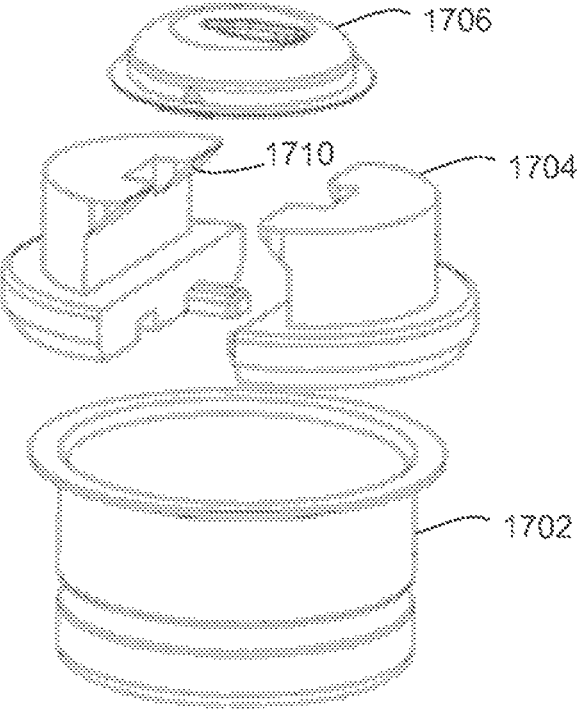

FIGS. 15A to 15F illustrate preparation of the applicator 1400 of FIGS. 14A and 14B for use with a container 1500. Once the cover 1502 has been removed from the container 1500 and the cap 1506 removed from the applicator 1400, the applicator 1400 is inserted into container 1500 to load the electronics assembly 1504 into the applicator 1400 and mate the sensor assembly (not shown) with the electronics assembly 1504 as shown in FIGS. 15B and 15C. Once loaded, the applicator 1400 is removed from the container 1500 as shown in FIG. 15D. FIG. 15E shows the applicator 1400 loaded with the assembled on-body device 222 and ready for sensor/sharp insertion. The locking strip 1402 is removed from the sleeve 1406 and the open ready indicator 1208' signals that the applicator 1400 is ready to be used. FIG. 15F illustrates the system after such action has been taken in transferring the on-body device 222 from the applicator 1400 onto the skin of a user.

FIGS. 16A and 16B are sectional and detail views, respectively, of features of the container 1500 in FIGS. 15A-15F. Specifically, the on-body device 1604 is shown in the container 1500 with an adhesive patch 1602 and its backing 1606. The backing 1606 is spiral-cut and attached to a boss so that when the on-body device 1604 is transferred from the container 1500, the peel-away backing 1606 is left behind. In this fashion, the adhesive patch 1602 remains covered by the backing 1606 so it does not inadvertently adhere to the container 1500.

As an alternative to the spiral peel-around backing approach of FIGS. 16A and 16B, FIGS. 17A and 17B are perspective assembly views illustrating alternative container 1702 configurations for capturing separate peel-off "butterfly" wings or bilateral liner panels from the adhesive-backed patch of the on-body device 1706. In each case, a two-part base 1704 is provided for gripping the peel-away backing liner pieces. Naturally, the base 1704 is adapted to fit in the container casing. In some embodiments, the container 1702 can be configured differently. In the version depicted in FIG. 17A, traction/tread 1708 is provided to assist with grip of the backing. In the version depicted in FIG. 17B, ramps 1710 are provided to assist in removing the backing. In another version, the base can be a one-piece molding incorporating a living hinge in a "clamshell" arrangement. The backing liner piece(s) may be captured along a center line or at an offset location. However configured, the base 1704 may snap into place with complementary band and rib interface features associated with each of the base 1704 and container 1702, snaps, or other features. As with other assemblies described herein, these features may alternatively be press fit, ultrasonically welded or otherwise secured in place.

Figure 18:
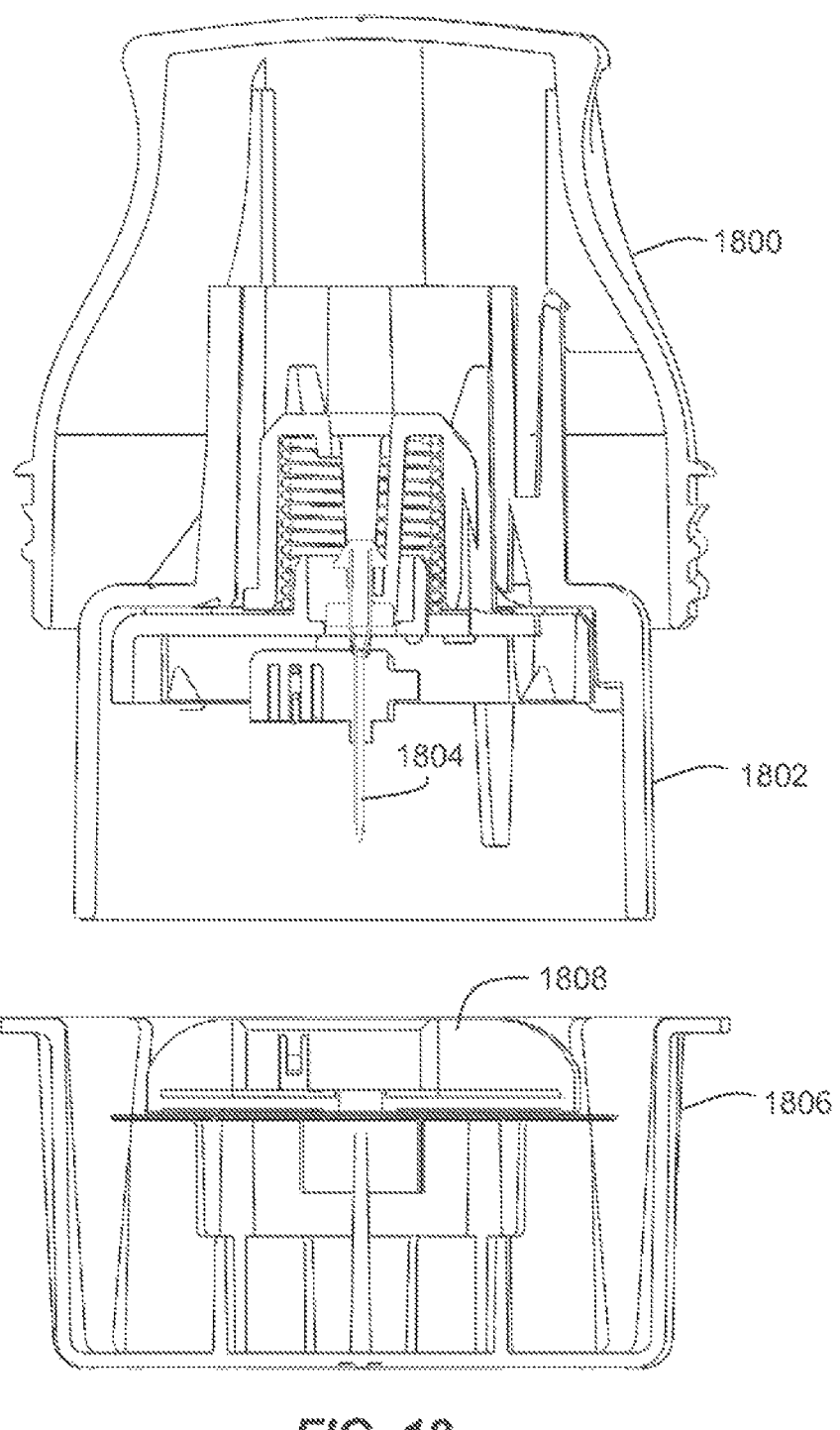
FIG. 18 is a side-section view illustrating the features of the applicator and container sets variously shown in FIGS. 15A-15F.

FIG. 18 is a cross-sectional view illustrating features of the applicator and container sets shown in FIGS. 15A-15F. The embodiment shown in FIG. 18 includes several of the features described in connection with the alternative loading approach above. However, it is simplified in approach. Most notably, the container 1806 includes no active/mobile components. Once the applicator 1800 is pressed down into the container 1806, the on-body device 1808 is assembled (e.g., the sensor assembly is mated with the electronics assembly), released from the container 1806 (e.g., using releasable latches), and held by the applicator 1800 (e.g., using latching arms). This embodiment offers an advantage of not having to expose the adhesive of the on-body device 1808 as in other embodiments. Furthermore, the position of the on-body device 1808 provides a stable surface for the sensor assembly insertion. Other embodiments where the applicator is pre-loaded with the on-body device do provide the advantage of not having to perform the above-described hand-off. Also, the use or inclusion of a protector for the sharp is avoided.

Figures 19A, 19B:
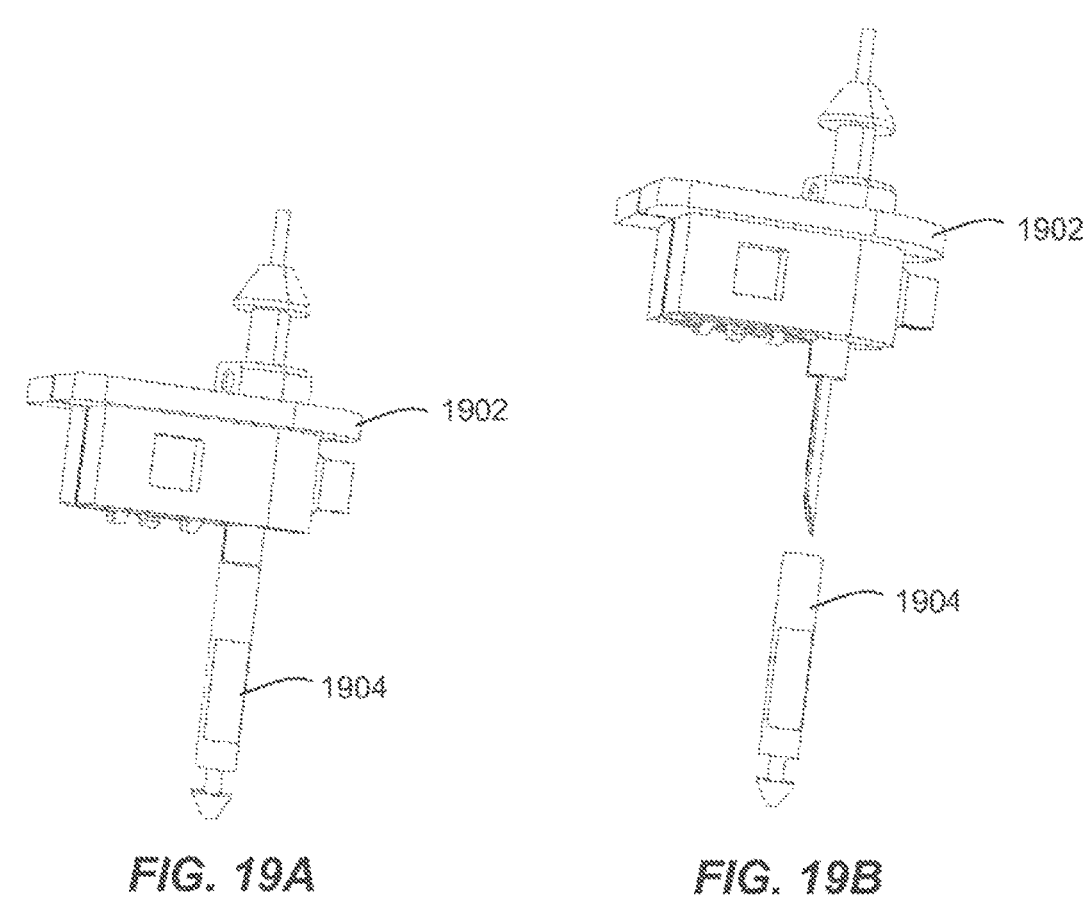
FIGS. 19A and 19B are perspective views of a sensor assembly incorporated in the system shown in FIG. 18.

FIGS. 19A and 19B show a sensor assembly 1902 in association with a needle guard 1904. In use, a distal interface feature (e.g., a barb) of the needle guard 1904 is captured by a complimentary split ring or other feature in the container during the assembly of the on-body device. Then, when the applicator is separated from the container, the needle guard 1904 is retained in the container and the sharp is unsheathed. In some embodiments, the needle guard 1904 may be made from polypropylene with a thermoplastic elastomer (TPE) insert to releasably secure the sharp. Other materials may be selected.

Other materials may be selected for construction of other elements of the present invention. For example, the applicator housing may be made of polycarbonate or any other practicable material. The guide sleeve, container, etc. may be constructed from acetyl (for reason of lubricity of sliding parts). Any number of the parts may be injected molded, thermoformed or otherwise produced.

Figures 20A, 20B:
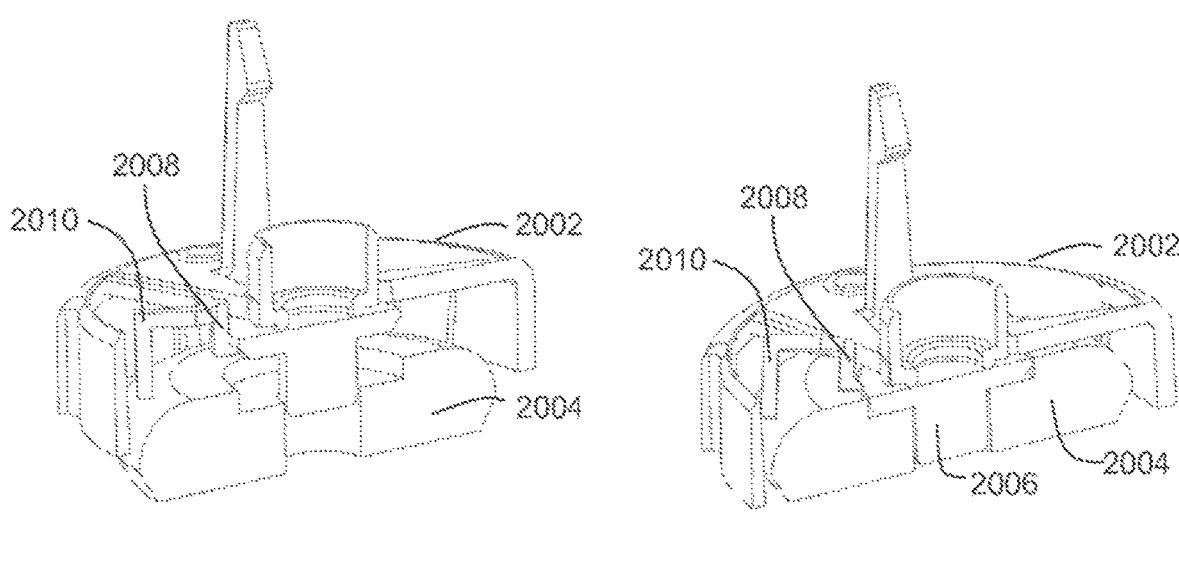
FIGS. 20A and 20B are perspective views of the operation of a sensor assembly retention unit incorporated in the system shown in FIG. 18.

Regarding the sensor assembly hand-off to the electronics assembly, FIGS. 20A and 20B illustrate a manner of holding a sensor assembly boss 2006 to the element 2002 that will pick up the electronics assembly 2004 to form the on-body device. Spring armatures 2008 clip to a lip of the sensor assembly 2006 and hold the sensor assembly 2006 within the applicator during shipping and handling. When the applicator and the container are brought together, lever arms 2010 contact the on-body device 2004, causing the associated spring armatures (or "spring arms") to twist and rotate the connection away from the lip of the sensor assembly, thereby releasing the sensor assembly. A chamfer on the sensor assembly boss can help ensure alignment and proper actuation of the one or more (e.g., three) torqueing spring armatures 2008.

FIGS. 21A-21C illustrate an alternative hand-off approach. In this embodiment, a sensor assembly gripper 2106, with a light snap fit, grabs and orients the sensor assembly 2104 for connection to the electronics assembly 2102. After the sensor assembly 2104 is firmly snapped into the electronics assembly 2102, the sensor assembly gripper 2106 is retracted with an amount of force that overcomes its grip. Such an approach offers simplicity by reducing the number of parts required (given that the snap features may be incorporated in the sharp hub/boss).

Electrical Connections Details

The selection of various hardware options from the above alternative embodiments will depend, at least in part, on the sensor assembly configuration. Sensor assembly configuration, in turn, depends on the mechanism selected for establishing electrical contact between the sensor assembly and the electronics assembly, as well as the method used to seal the contacts. A number of advantageous alternative embodiments are illustrated in FIGS. 22 through 48.

Figure 22:
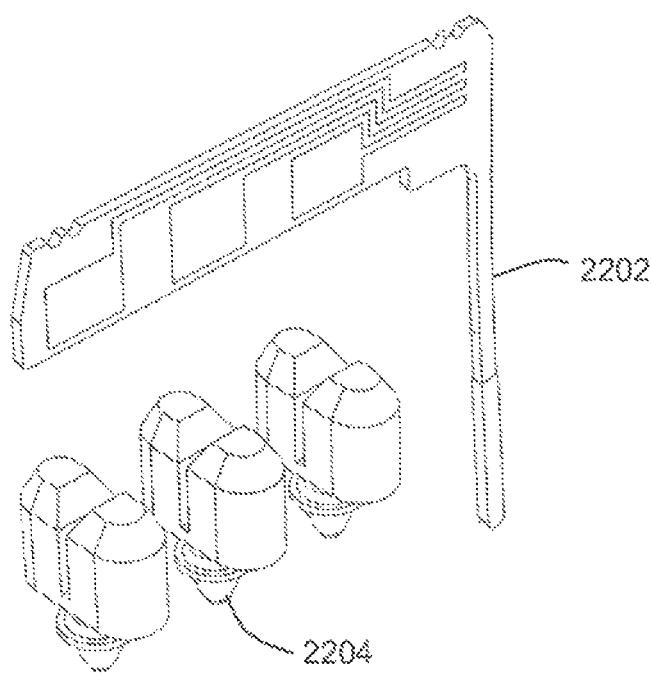
FIG. 22 is a perspective assembly view of advantageous sensor and sensor connector elements.
Figure 23A:
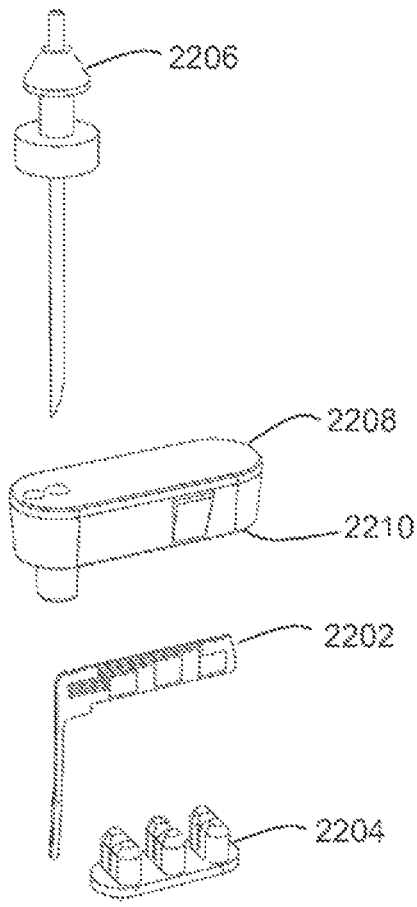
FIGS. 23A and 23B are perspective assembly and final-assembly views, respectively of the sensor components in FIG. 22.
Figure 23B:
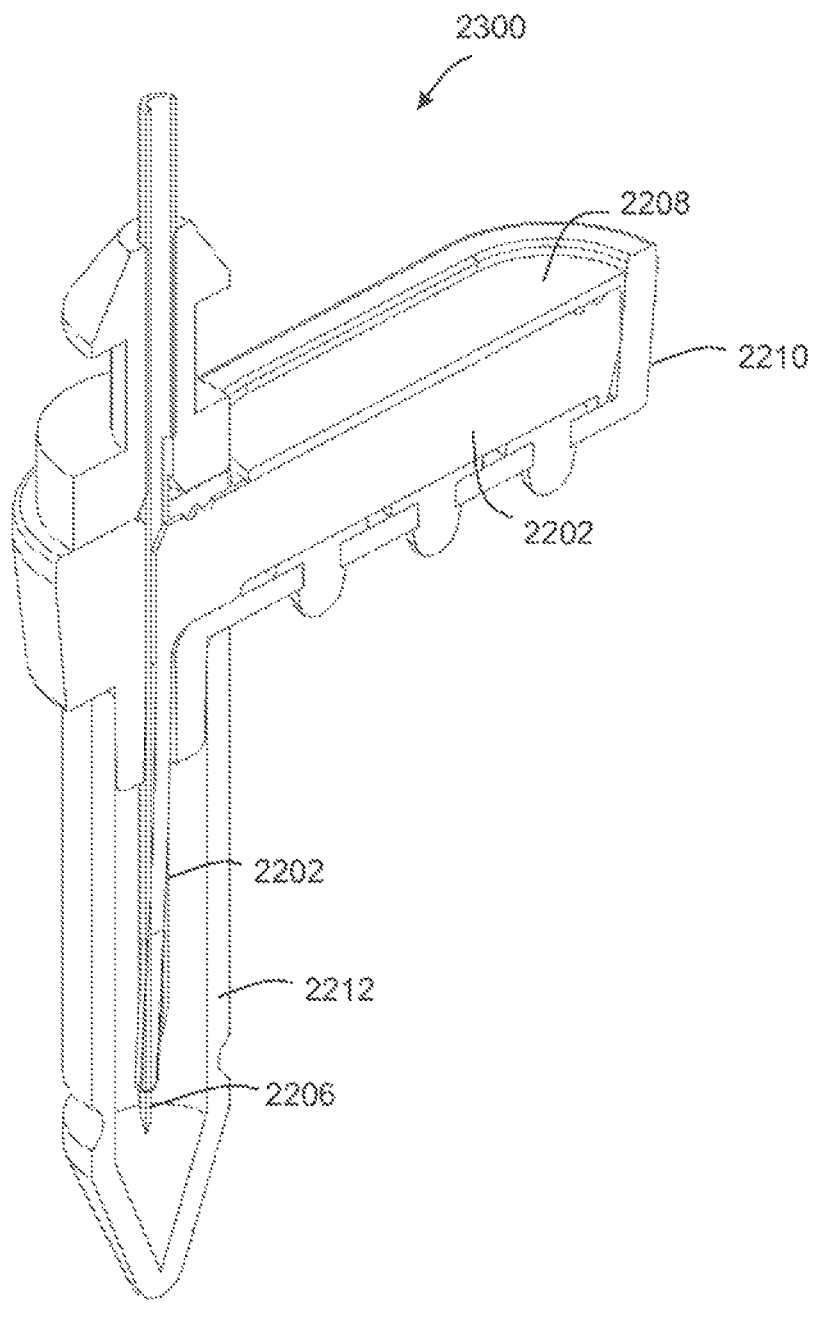

A first example is presented in FIG. 22. Here a sensor 2202 is provided with an elongate "tail" section. The distal portion of the tail is to be inserted through the skin surface guided by a sharp. The proximal portion of the sensor 2202 includes a "flag" type connector region. Three carbon-doped (for conductivity) silicone electrical connectors 2204 are provided to interface with the electrical contacts of the sensor 2202. A split "V" portion of each connector 2204 receives the electrical contacts of the sensor 2202. A flexible nubbin on the opposite side of each connector 2204 is provided for electrical contact with the circuit board incorporated in the electronics assembly. When inserted in a housing 2210, the sensor 2202 and the connector 2204 are advantageously sealed, encased or potted with an adhesive. Epoxy, a UV cure or another type of dielectric (non-conductive) compound may be used. Generally, the compound selected is of such viscosity that it is able to flow around features and fully seal the sensor 2202 within its housing 2210 to avoid leakage. Such an approach avoids contamination and/or current leakage due to fluid intrusion. FIGS. 23A and 23B are perspective assembly and final-assembly cross-sectional views, respectively of the sensor components of FIG. 22. The tail of the sensor 2202 is supported within the sharp 2206 and the sharp 2206 extends through the connector housing 2210. The electrical contacts of the sensor 2202 are seated in the connector 2204 and the assembly is sealed within the housing 2210 including the housing top 2208.

Figures 24A, 24B:
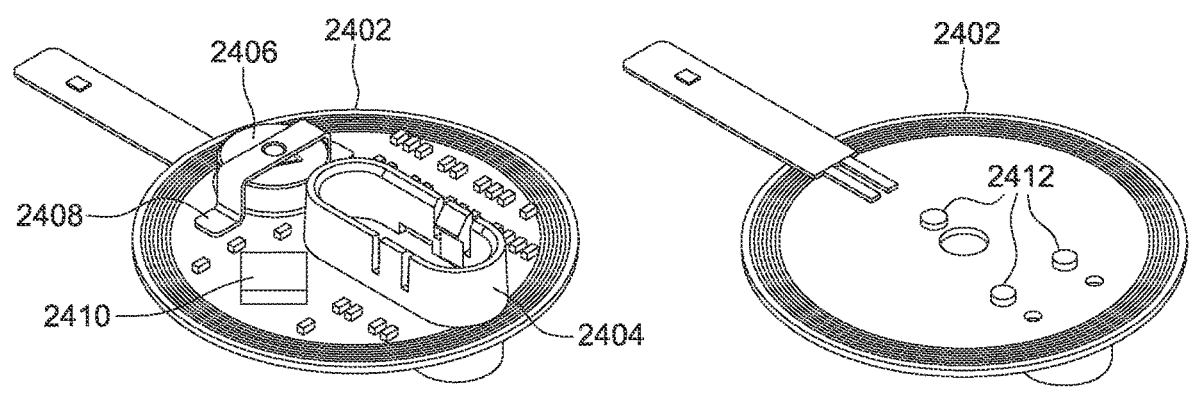
FIGS. 24A and 24B are top and bottom perspective views, respectively of circuit board components to be used with the assembly shown in FIGS. 23A and 23B.

FIGS. 24A and 24B are top and bottom perspective views, respectively of circuit board components to be used with the sensor assembly 2300 of FIGS. 23A and 23B. In each, a custom printed circuit board (PCB) 2402 is shown. The PCB 2402 includes a battery 2406 with mount 2408, an application specific integrated circuit (ASIC) 2410, or other appropriate processing unit, and various other circuitry, including a thermocouple. On its face, the PCB 2402 includes a housing 2404 with snap features for receiving the sensor assembly 2300 of FIGS. 23A and 23B. On the reverse side of the PCB 2402, heat stakes 2412 show the mode of attaching the housing 2404.

Figures 25A, 25B:
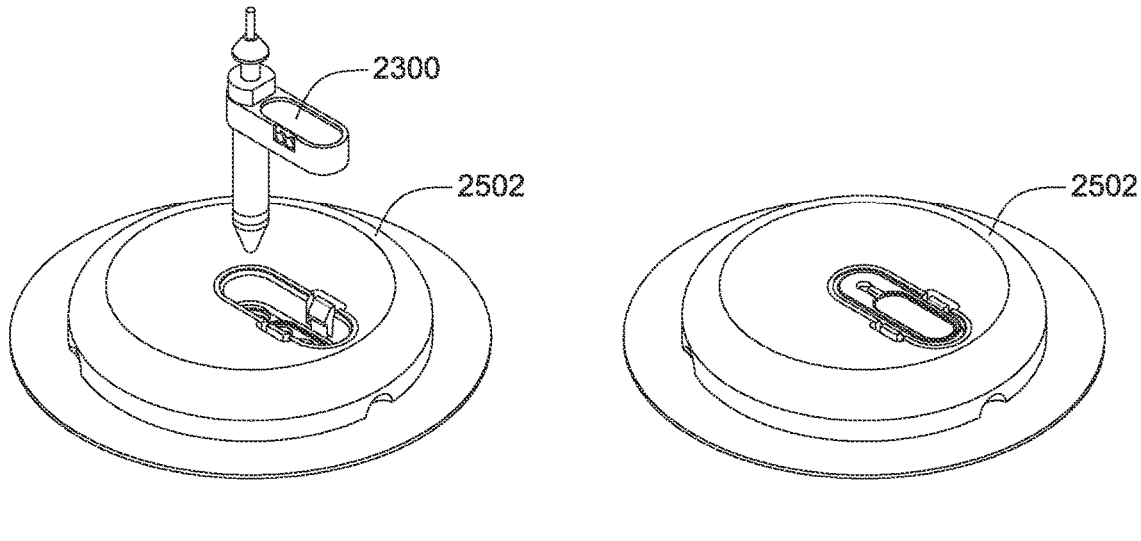
FIGS. 25A and 25B are perspective views illustrating assembly of the subject components in stages.
Figure 26:
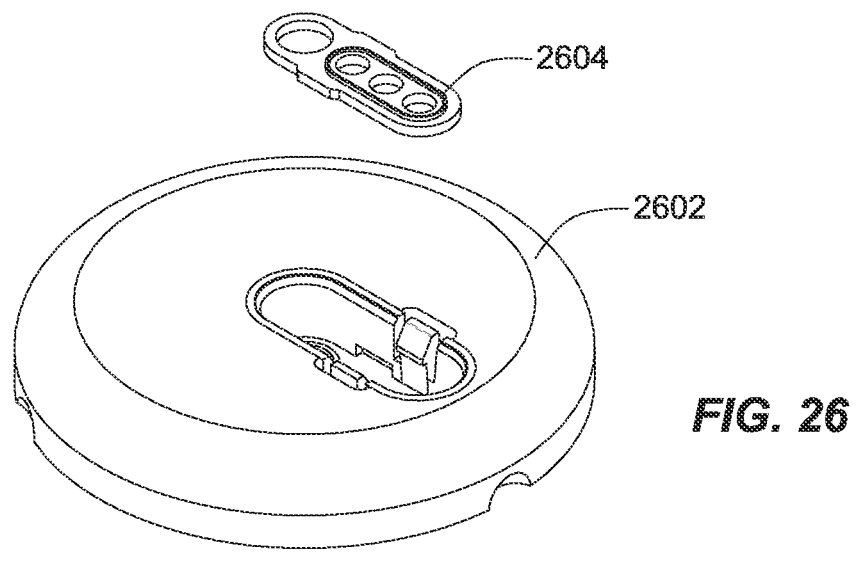
FIG. 26 is an assembly view of the on-body/sensor mount unit in FIGS. 25A and 25B illustrating an advantageous seal element.
Figure 27A:
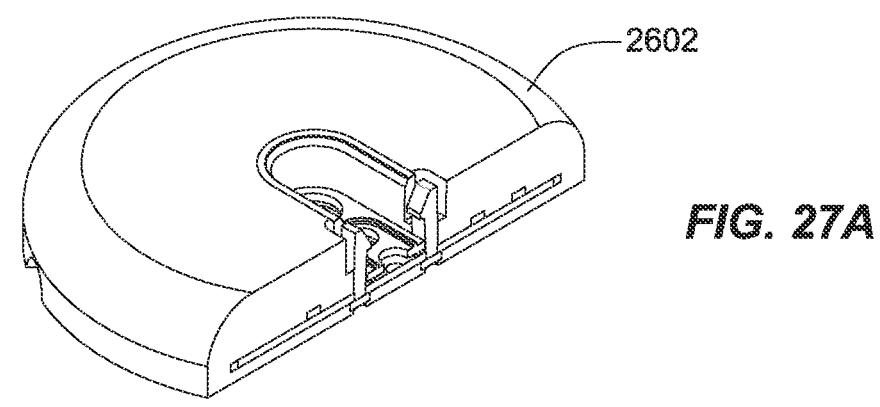
FIGS. 27A and 27B are section views further illustrating the seal element and its relation to the mount in FIG. 26.
Figure 27B:
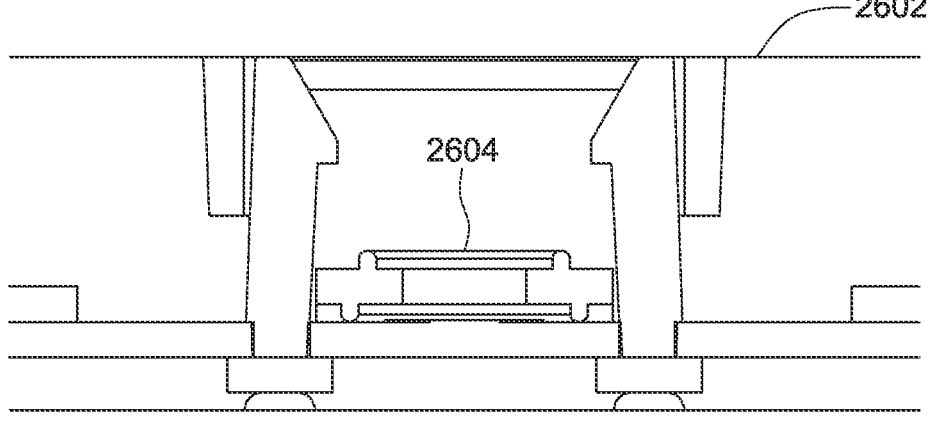

Turning to FIGS. 25A and 25B, in some embodiments, the on-body device 2502 is formed by over molding with a polymer "macromelt" (e.g., a thermoplastic hot-melt based on polyamide) or other compound and then affixing an adhesive patch with a releasable liner thereto. A completed on-body device 2502 is provided once fitted with a complimentary sensor assembly 2300, as illustrated in FIGS. 25A and 25B. Internal to such assembly, it may be desirable to include a seal or gasket 2604 as shown in assembly view FIG. 26. As shown in cross section, in FIG. 27A, and magnified in FIG. 27B, the gasket 2604 advantageously includes discrete ring/rim elements to compress and ensure sealing in critical areas, including around each circuit connection/nubbin.

Figures 28A, 28B, 28C:
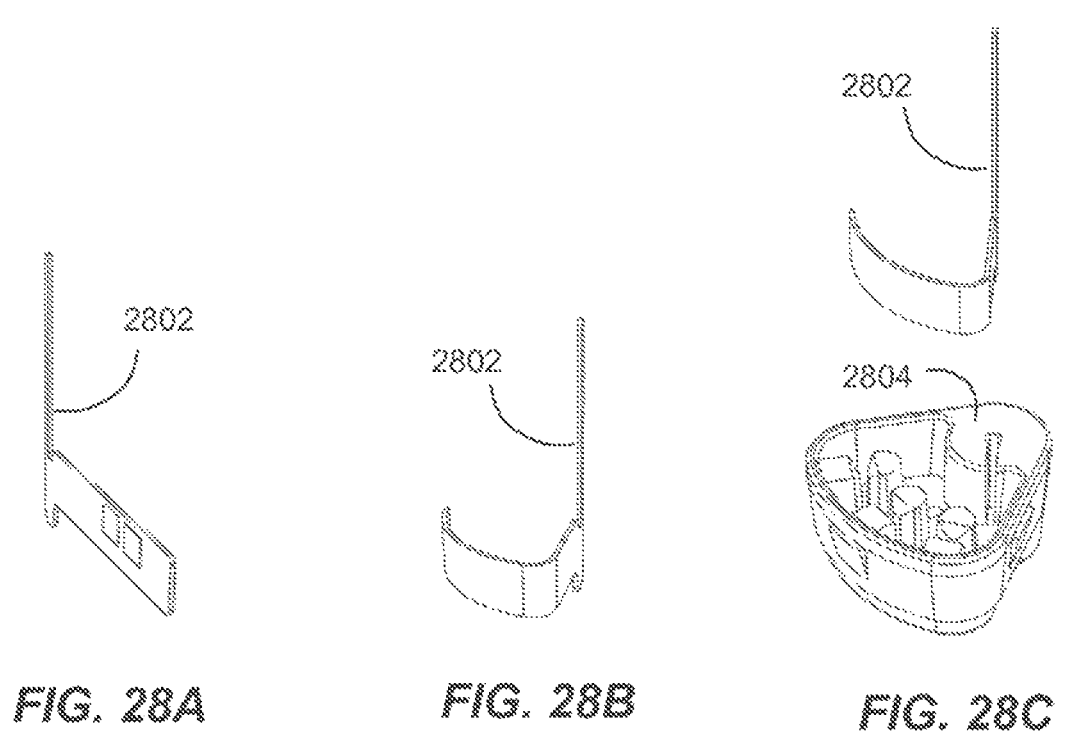
FIGS. 28A-F are perspective views of another advantageous sensor and sensor element arrangement.
Figures 28D, 28E, 28F:
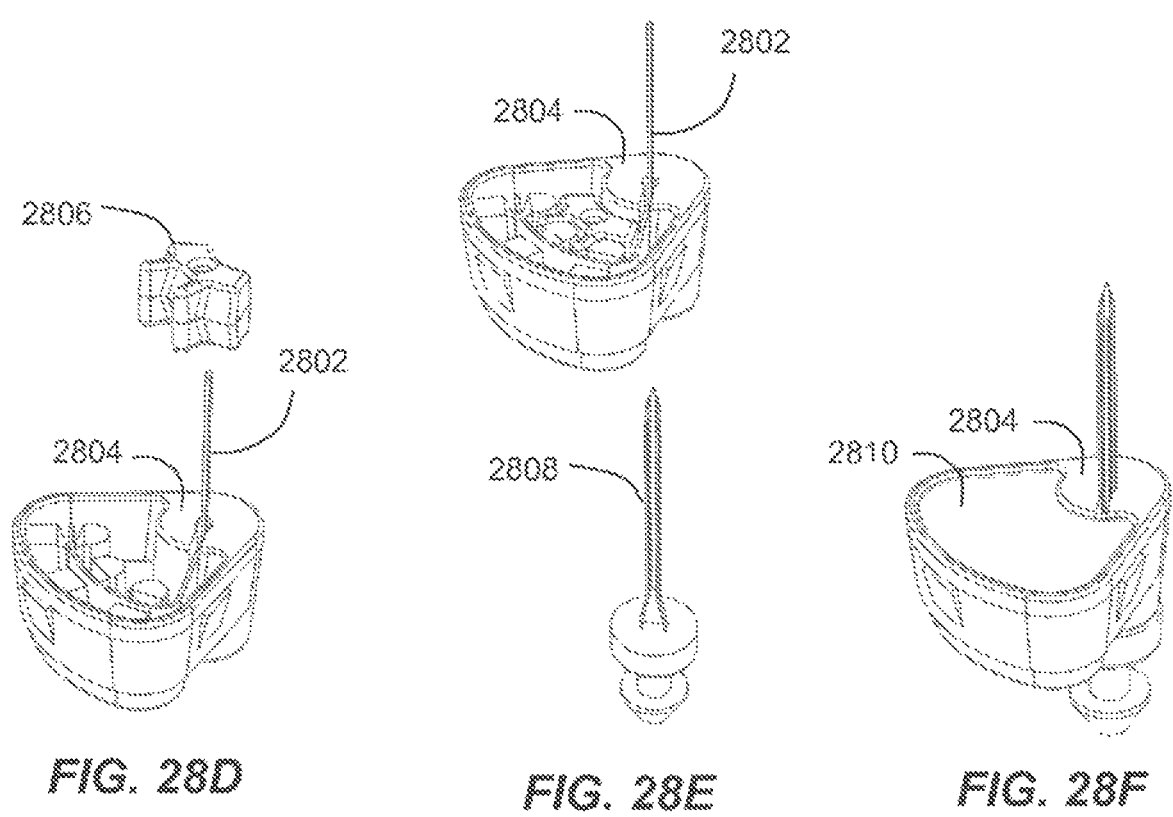

FIGS. 28A-28F illustrate another advantageous sensor 2802 and sensor mount or connector 2804 arrangement. This embodiment resembles the previous approach, but is configured with a bend and a curve imparted to the sensor connection "flag." This permits package and sealing within in a roughly triangular envelope to shorten the length of the connector. Doing so results in a generally more compact sensor assembly body and the ability to downsize all associated components. Yet, it does not significantly complicate manufacture. FIG. 28A depicts the sensor 2802 before it is shaped to fit within the connector 2804. FIG. 28B depicts the bent and curved sensor connection "flag." FIG. 28C depicts the relative orientation of the sensor 2802 as it is inserted into the connector 2804. FIG. 28D depicts a wedge 2806 that is press-fit into the connector 2804 to retain the sensor 2802 and press the connector's electrical contacts against the electrical contacts of the sensor 2802. FIG. 28E depicts the relative orientation of the sharp 2808 as it is inserted into the connector 2804 and FIG. 28F depicts the completed sensor assembly including potting 2810 (e.g., UV potting) used to seal the electrical contacts.

An alternative embodiment is contemplated in connection with the sensor approach illustrated in FIGS. 29A-29D. Using a sensor 2902 with a vertically disposed "flag" connector portion that is supported by coupling 2904, coupling 2904 is configured to snap into connector block 2908 which is attached to PCB 2914. Connector block 2908 includes a connector socket 2910 to receive the contacts portion of the sensor 2902. Connector block 2908 also includes a coupling feature 2912 to receive snap-fit tab 2906 on the coupling 2904 which retains the sensor 2902 in the connector socket 2910.

Another alternative embodiment is contemplated in connection with the sensor approach illustrated in FIGS. 30A-30C. Here, a design is provided that eliminates a connection element and the need for separate spring contacts (be they metal or elastomeric as above). In addition, the approach offers the advantage of effectively converting a sensor with contacts on two sides into a sensor with contacts on a single side after folding. The sensor 3004 shown in FIG. 30A initially has two electrical contacts facing a first direction on the split contact area and one contact facing in a second, opposite direction (obscured by the view). When folded and optionally clamped, glued or otherwise affixed in the orientation shown in FIG. 30B, all of the electrical contacts lie in a single plane, facing the same direction (e.g., downward in the drawing). Set within a housing (not shown) to restrain and/or seal the sensor 3004, the sensor 3004 is coupled to electrical contacts on the PCB 3002 as shown in FIG. 30C.

Such an approach in some embodiments includes a thinner (e.g., lower profile) on-body device relative to the on-body device 3102 variation shown in FIG. 31. The reduced thickness dimension is represented by height H. In FIG. 31, a flag type sensor is shown in a housing with separate electrical connectors. The "stack height" in FIG. 31 includes these connectors as well as the housing. The approach shown in FIG. 30 enables eliminating the connector height above the sensor 3004. Thus, elements are eliminated without losing functionality. Moreover, the elimination of parts reduces cost, and impedance (relative at least to the inclusion of elastomeric connectors as shown in FIG. 22, etc.) between the sensor 3004 and the PCB. Another useful aspect is allowing a sensor with contacts on two sides to connect to the PCB without requiring vias or holes in the sensor, thereby helping with sealing considerations and ease of electrical connection.

Figure 32A:
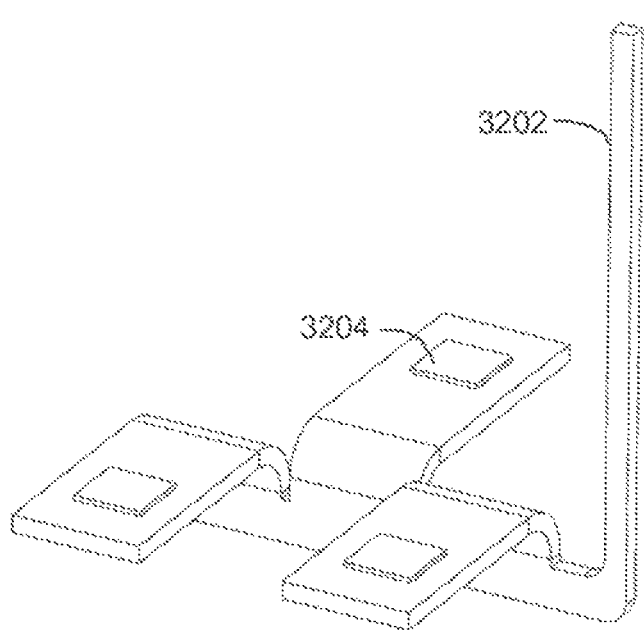
FIGS. 32A and 32B are perspective views of still other advantageous sensor configurations, these figures illustrating split-sensor approaches.
Figure 32B:
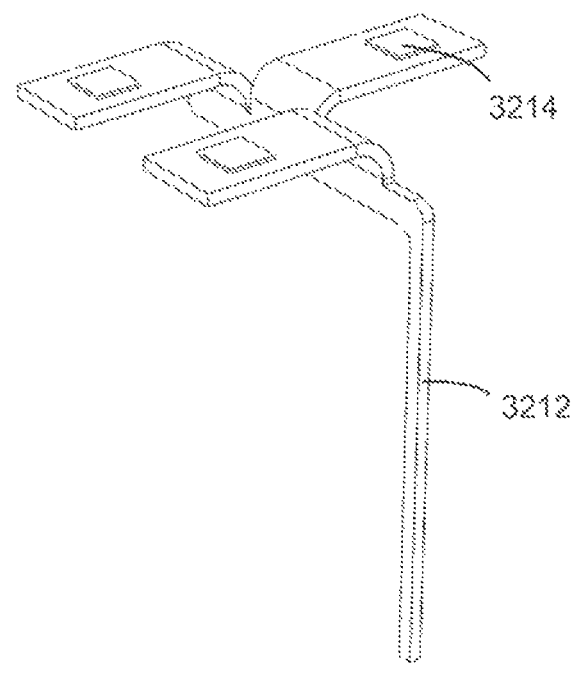

FIGS. 32A and 32B illustrate two additional sensor configurations. In these embodiments, sensors 3202, 3212 with contacts on two sides are split and bent in opposite directions to orient the electrical contacts 3204, 3214 onto a single face or plane. As above, orienting the electrical contacts 3204, 3214 onto a single plane facilitates ease of sealing the electrical connections. Moreover, overall sensor assembly height can be reduced relative to other approaches. Any of conductive adhesives, conductive films and/or mechanical contacts may be used to electrically connect with the sensor contacts so arranged.

Figures 33F, 33G:
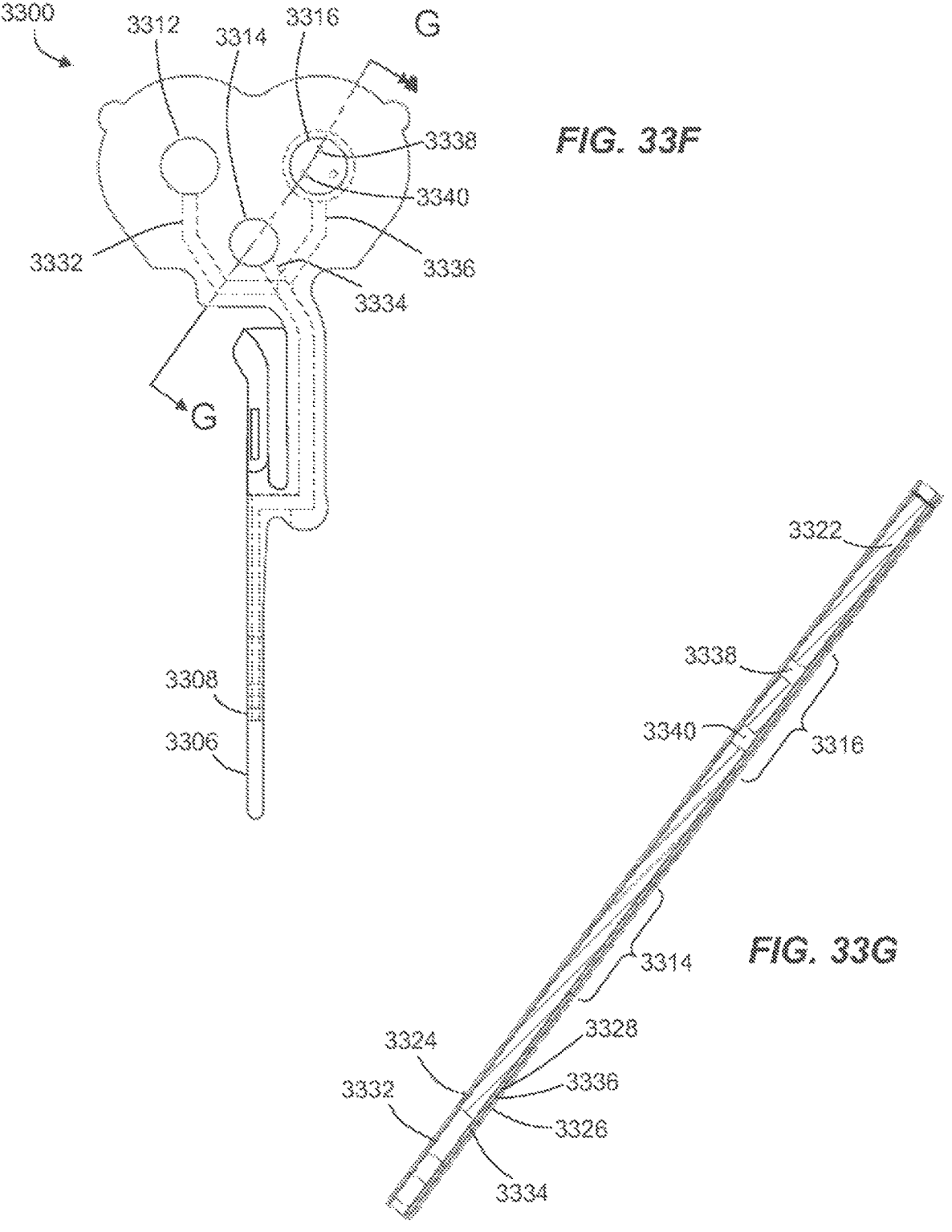

FIGS. 33A-33G depict a low-profile multilayer sensor configuration with the electrical contacts all on one side and some details of its construction. FIGS. 33A and 33B illustrate the two sides of this embodiment of a sensor 3300 and its overall shape. The example sensor 3300 includes a tail portion 3302 that is initially supported by a sharp and then disposed within the user's interstitial fluid or dermal space below the skin upon application of the on-body device. The tail portion 3302 includes electrodes 3304, 3306, 3308 that are used to contact the interstitial fluid and to sense (e.g., transmit and receive) the electrical signals used to measure the analyte concentration within the interstitial fluid. The sensor 3300 also includes an electrical contacts portion 3310 which includes electrical contacts 3312, 3314, 3316 that are disposed all on one side of the sensor 3300 and are in electrical communication with the electrodes 3304, 3306, 3308 via conductive traces (not visible in FIGS. 33A and 33B but see FIG. 33F). Note also that the electrical contacts portion 3310 is shaped to facilitate being securely held and sealed into a connector support that will be described below. For example, the electrical contacts portion 3310 includes securement features that hold the sensor to be secured to the connector support by friction fit, interference fit, etc., herein shown as tabs 3310A and notches 3310B that allow the electrical contacts portion 3310 to be held securely in the connector support which includes mating features.

The sensor 3300 also includes a bendable portion 3318 that allows the electrical contacts portion 3310 to be arranged parallel to the circuit board of the electronics assembly to facilitate a relatively flat or low profile within the electronics assembly. The bendable portion 3318 also allows the tail portion 3302 to extend down from the electronics assembly so that it can be inserted below the skin of the user while the electrical contacts portion 3310 lays parallel to the circuit board. Lastly, the sensor 3300 includes an armature portion 3320 that allows the sensor 3300 to be held securely to the connector support of the sensor assembly. The armature portion 3320 also provides a leverage point to apply a biasing force to compel the tail portion 3302 into a channel of the sharp as described below in FIG. 35D and the associated text.

FIG. 33C depicts a side view of the sensor 3300. The encircled portion labeled D is shown in more detail in FIG. 33D. FIG. 33D provides a magnified side view of the distal most part of the tail portion 3302 of the sensor 3300. The encircled portion labeled E is shown in more detail in FIG. 33E. FIG. 33E provides an even further magnified view of the electrodes 3304, 3306, 3308 of the tail portion 3302. As can be seen in FIG. 33E, the electrodes 3304, 3306, 3308 are formed as layers on a substrate 3322. The substrate 3322 is made of a flexible, non-conductive dielectric material. In some embodiments, a clear, high-gloss, heat stabilized polyester film may be used for the substrate 3322 and conductive carbon ink can be used to create the trace layers used for the electrodes 3304, 3306, 3308. In other embodiments, other materials may be used for the substrate 3322 such as polymeric or plastic materials and ceramic materials and for the trace layers such as carbon or gold.

Dielectric layers 3324, 3326, 3328 are disposed between and upon the electrodes 3304, 3306, 3308 to insulate the electrodes 3304, 3306, 3308 from each other. In some embodiments, an ultraviolet (UV) light curable dielectric material may be used for the dielectric layers 3324, 3326, 3328. In other embodiments, other practicable materials may be used. In the particular example embodiment shown, electrode 3304 is a counter electrode, electrode 3306 is a working electrode, and electrode 3308 is a reference electrode. Note that reference electrode 3308 also includes a secondary conductive layer 3330, e.g., an Ag/AgCl layer. In certain embodiments, the lateral surface of the secondary conducive layer 3330 is covered by a dielectric layer 3328 resulting in only the side edges the secondary conductive layer 3330, which extend along the side edges of the substrate 3322, being uncovered by dielectric layer 3328 and, as such, are exposed to the environment when in operative use. In such embodiments, dielectric layer 3328 covers the entire lateral surface of the secondary conducive layer 3330, i.e., 100% of the lateral surface of the secondary conducive layer 3330 is covered by dielectric layer 3328. As such, dielectric layer 3328 has at least the same lateral width and at least the same length as conductive layer 3330.

Further details of the arrangement, dimensions, chemistry, and manufacturing methods of the sensor 3300 may be found in U.S. patent application Ser. No. 13/526,136, entitled "Connectors For Making Connections Between Analyte Sensors And Other Devices," which was filed Jun. 18, 2012, and which is incorporated by reference herein in its entirety and for all purposes.

FIG. 33F depicts a view of the sensor 3300 of FIGS. 33A and 33B including hidden lines representing different layers of electrically conductive trace lines 3332, 3334, 3336 connecting the electrical contacts 3312, 3314, 3316 to the electrodes 3304, 3306, 3308. The electrical contacts 3314, 3316 for the electrodes on the opposite side of the sensor 3300 are coupled to the respective conductive traces 3334, 3336 using vias 3338, 3340 (only two labeled). FIG. 33G is a cross-sectional view of the sensor 3300 taken along line GG of FIG. 33F. As can be seen, conductive trace 3332 covered by dielectric layer 3324 is on one side of the substrate 3322 while conductive traces 3334, 3336 separated by dielectric layer 3326 and covered by dielectric layer 3328 is on the opposite side on the substrate 3322. The electrical contacts 3314, 3316 are accessible via openings in the dielectric layer 3328.

FIGS. 33H to 33J depict three alternative sensor designs 3342, 3344, 3300 side by side for comparison. Notably sensor 3342 includes an aperture 3346 to receive a rivet or other fastener for physical attachment to the PCB of the electronics assembly. Details of sensor 3342 are provided in previously incorporated U.S. patent application Ser. No. 13/526,136, entitled "Connectors For Making Connections Between Analyte Sensors And Other Devices," which was filed Jun. 18, 2012. Sensors 3344 and 3300 are suitable for use with the alternative connector arrangements described below with respect to FIGS. 34A-35D.

Turning now to FIGS. 34A-35D, an alternative connector arrangement for connecting a circuit board to a sensor 3300 such as depicted in FIGS. 33A, 33B, and 33J is described. As shown in FIG. 34A, a flexible one-piece seal or connector 3402 is molded in silicone or other practicable elastic material. Separate doped silicone conductive elements are set therein which provide electrical contacts 3410 for connection to a circuit board. In some embodiments, the conductive elements can alternatively be over molded or insert-molded into place. The result is a generally malleable/flexible hybrid connection and sealing unit or connector 3402 incorporating a living hinge joining two (as-shown) symmetrical sections. Alternatively, a two-piece design is possible. Yet, with the unitary design, the arrangement can be neatly secured using a single catch boss or post 3412 opposite the hinged section. In some embodiments, two or more posts can be used to secure the connector 3402 folded around and sealing both sides of the contacts portion of the sensor 3300. Thus, even if a dielectric coating on the sensor 3300 fails (e.g., pinhole leaks), the connector 3402 insures that the sensor contacts 3312, 3314, 3316 are protected from moisture or any contaminants. The one-piece design also facilitates assembly as illustrated, in which the flexible connector 3402 is set in a rigid or semi-rigid housing or connector support 3404 with one side located on the post 3412. Then a sensor 3300 is inserted, and bent approximately ninety degrees at the bendable portion 3318 of the sensor 3300. Once bent, the sensor 3300 is then captured with the upper part of the connector 3402 by folding over the connector 3402 as indicated by arrow S in FIG. 34C. The connector 3402 is illustrated as bilaterally symmetrical, however, the connector 3402 can be formed in a direction-specific orientation because in some embodiments, certain of the electrical contacts 3410 may not be necessary. In some embodiments, all the sensor's electrical contacts 3312, 3314, 3316 can be provided on a single side of the sensor 3300 or, in other embodiments, both sides of the sensor 3300.

As shown in FIG. 34D, in some embodiments, the top surface of the connector 3402 includes a raised lip 3418 disposed at the top surface edge of the connector 3402 that encircles the electrical contacts 3410 of the connector 3402. The raised lip 3418 can be integrally formed in the elastomeric material that forms the connector 3402 and is thus compressible when the sensor assembly is inserted into the electronics assembly. Alternatively, the raised lip can be embodied as gasket or O-ring on the top surface of the connector 3402. The raised lip 3418 functions to ensure that a seal is formed around the electrical contacts 3410 of the connector 3402 and the electrical contacts of the PCB before any electrical connectivity between the sensor and the electronics assembly is established. Thus, the raised lip 3418 provides a failsafe against a short by insuring the order of assembly includes creating a seal and then creating electrical connectivity as the sensor assembly is mated with the electronics assembly.

Figures 35A, 35B:
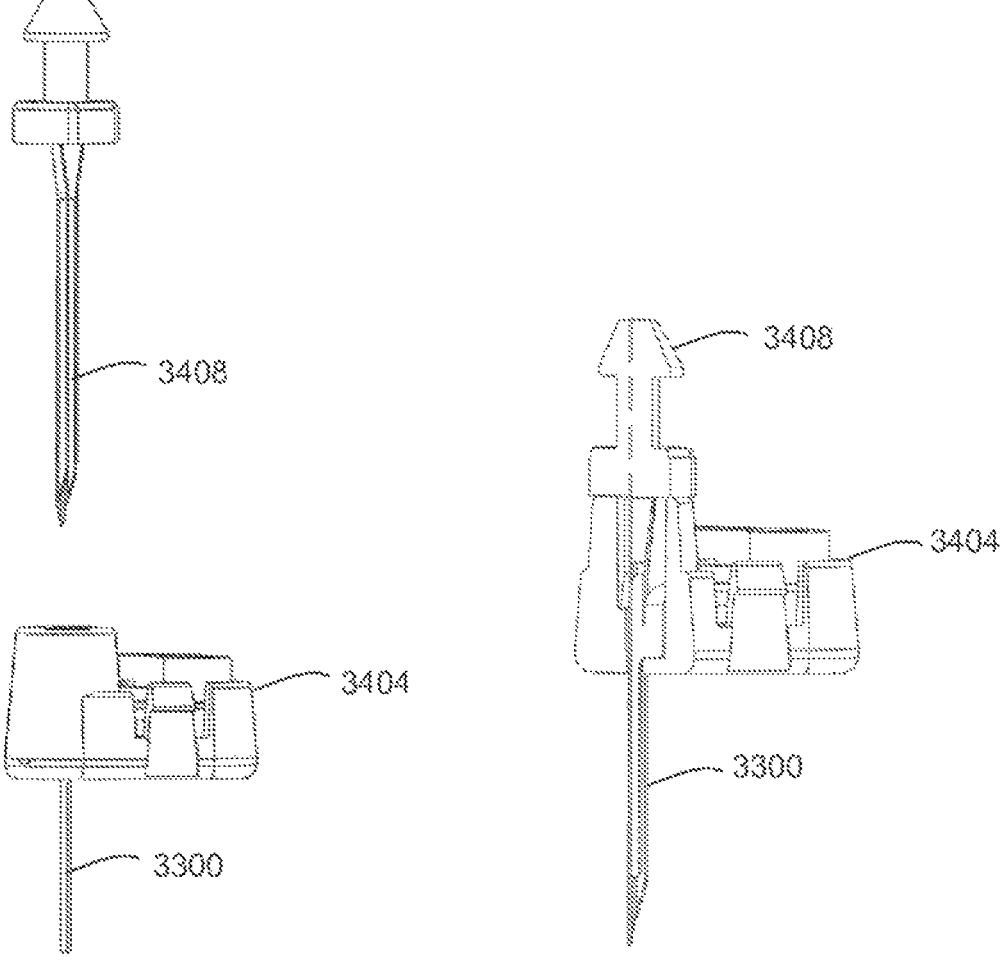
FIGS. 35A and 35B are side assembly and section views, respectively, of the system shown in FIGS. 34A-34D.
Figures 35C, 35D:
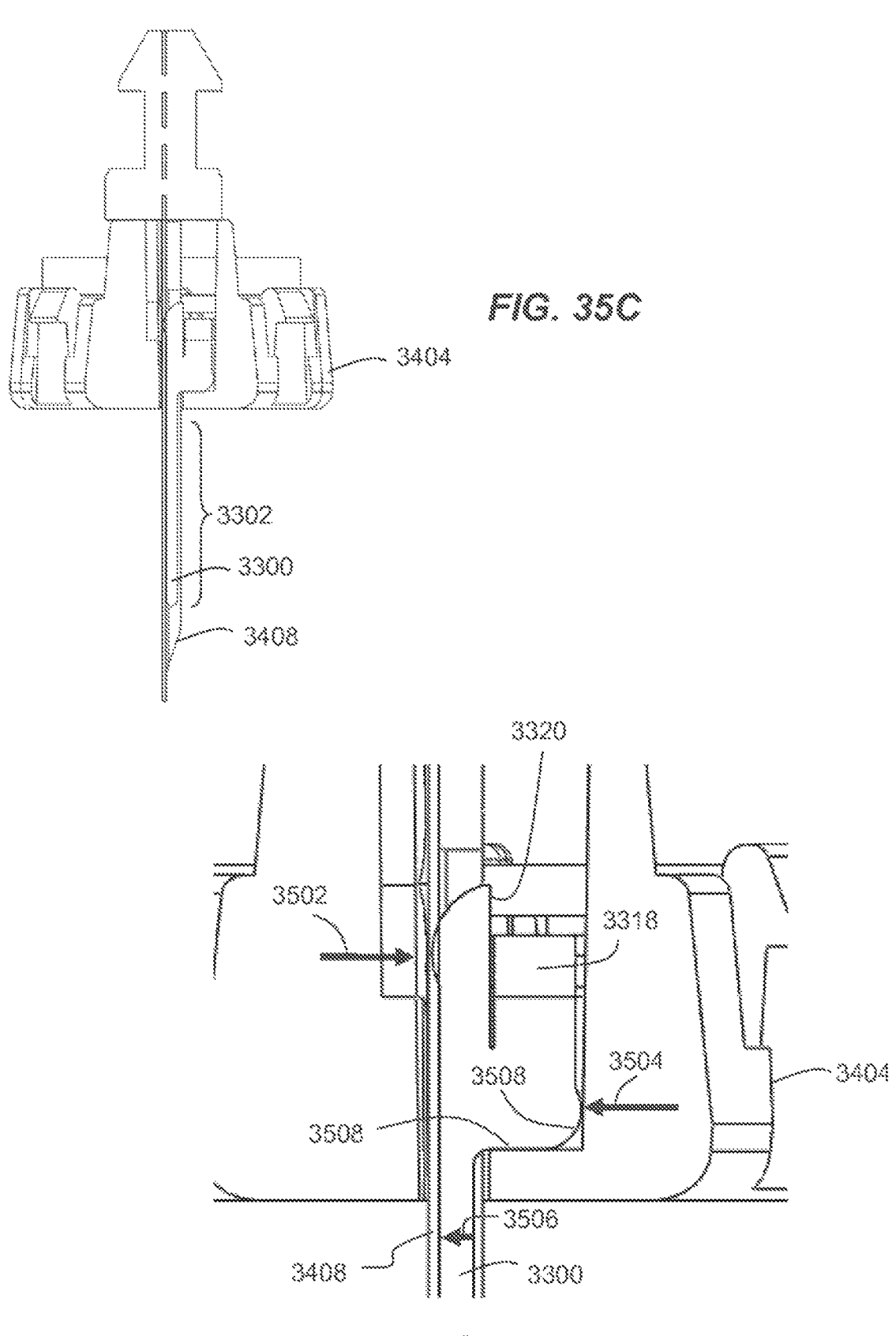
FIG. 35C is an end-section view, with detail view, FIG. 35D, illustrating additional sensor features.

In any case, with the sensor 3300 captured within the seal 3402, a sharp 3408 is then introduced, with its hub 3414 contacting the connector support 3404 as shown in FIG. 34D. FIG. 35A illustrates the orientation of the sharp 3408 prior to the insertion of the sharp 3408 into the connector support 3404. FIGS. 35B and 35C provide a cross-sectional overview of the relationship of the sharp 3408 to the sensor 3300. Notably, once inserted in the connector support 3404, the sharp 3408 surrounds and supports the tail portion 3302 of the sensor 3300. In FIG. 35D, further details of the sensor configuration are visible. Particularly, biasing features are shown that abut surfaces of the connector support 3404 in order to center and bias the sensor 3300 into the channel of the sharp 3408. Specifically, armature portion 3320 abuts the surface at arrow 3502 of the connector support 3404 which causes the biasing feature 3508 to act as a fulcrum at arrow 3504 to push the tail portion 3302 of the sensor 3300 into the sharp 3408 at arrow 3506.

In some embodiments, the curved section 3508 of the sensor 3300 can overlie a corresponding surface of the connector support 3404 to help limit the insertion depth (i.e., provide a depth stop) for the sensor 3300. Sensor 3300 vertical placement, including insertion depth, is also controlled based on the relationship between the seal 3402 halves. As noted with respect to the other sensor assembly housings/supports discussed herein, the sensor assembly of FIG. 35C can also include various clip or snap features for its precise associations with a socket in the electronics assembly within the on-body device.

A related arrangement to that described in connection with FIGS. 34A-34D and 35A-35D is presented in FIGS. 36 to 38. In FIG. 36, a sensor 3300 with all electrical contacts on the same side is shown with a sharp 3602 for insertion in a connector support 3604. The connector support 3604 includes an elastomeric (e.g., silicone) seal backing. Once such a sensor assembly set is in a container (or alternatively in an applicator), the sensor assembly can be coupled to the sensor electronics to form an on-body device 222. As shown in FIG. 37, the sensor assembly 3702 is shaped to fit within a socket 3704 that includes a second elastomeric unit with electrical contacts in the elastomer body of the socket 3704. Note that in FIG. 37, the enclosure of the electronics assembly is not shown so that the socket can be more clearly displayed. The socket 3704 is affixed to a circuit board 3706 via any practicable method. The socket 3704 and/or the connector support 3604 can include various coupling features (e.g., a snap fit lip and hook arrangement) to ensure that the electrical contacts are pressed tightly together and sealed within the socket 3704 and sensor assembly 3702. Once the sensor assembly 3702 is received within the socket 3704, the on-body device (e.g., with the complete over-mold enclosure around the circuit board 3706 and adhesive patch 3802 as shown in FIG. 38) is ready for use.

Figures 39A, 39B, 40:
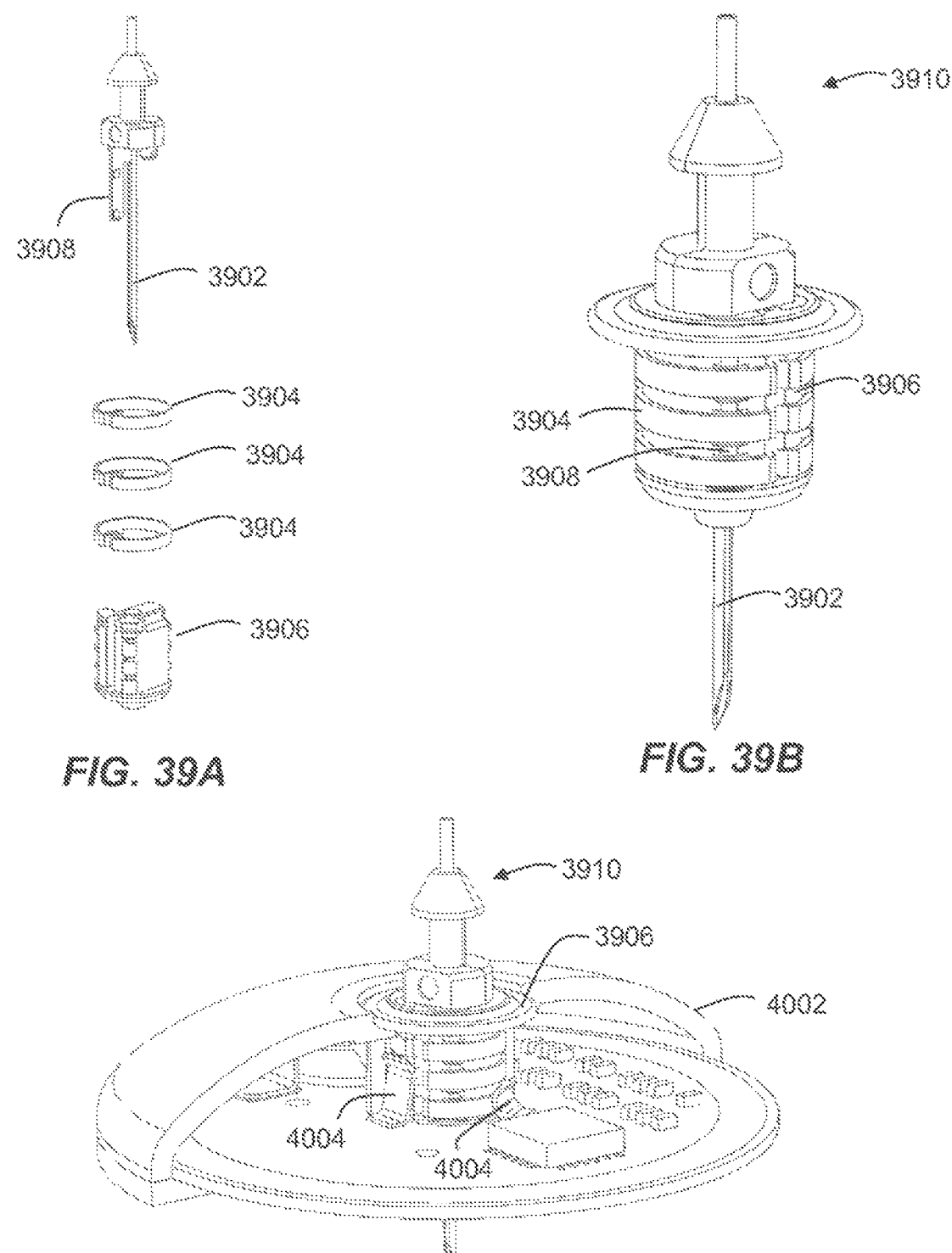
FIGS. 39A and 39B are perspective assembly and as-assembled views of a stacked non-directional sensor connect arrangement.
FIG. 40 is a side partial-sectional view of the sensor in FIG. 39 received within an on-body device.

The electrical contacts/connector approaches described above are "directional." In other words, before the sensor assembly is mated with the electronics assembly, the two are aligned relative to each other both longitudinally and rotationally. In some embodiments, the coupling arrangement is "non-directional" and the sensor assembly can be mated with the electronics assembly without aligning the two rotationally. For example, the sensor assembly construction shown in FIGS. 39A and 39B offers such an approach. Separate conductive (e.g., optionally metal) bands 3904 mounted on a core support 3906 connect to sensor electrical contacts 3908 as shown in FIGS. 39A and 39B. The assembled unit (i.e., the sensor assembly 3910), with sharp 3902 in place, is received in the socket of an electronics assembly 4002 to form an on-body device as illustrated in FIG. 40. In some embodiments, brush-type connectors 4004 on the circuit board in the electronics assembly 4002 reach up to the individual levels of the conductive bands 3904. Such a sensor assembly 3910 can be inserted into the socket of the electronics assembly 4002 in any radial/rotational orientation.

A "reversed" approach is illustrated in the sensor assembly 4100 of FIGS. 41A-41C. Here, the circuit board 4102 includes a socket connector 4104 that has an arrangement of stacked conductive elastomeric O-rings 4106 disposed within the inner diameter of the socket connector 4104. A sensor support 4108 is adapted to hold the electrical contacts 4110 of the sensor 4112 in a corresponding stack facing radially outward. When the sensor support 4108 is inserted into the socket connector 4104, the conductive elastomeric O-rings 4106 align vertically with the electrical contacts of the sensor as shown in FIG. 41B (with the socket connector 4104 not shown so that the conductive elastomeric O-rings 4106 are more clearly visible) and in the cross-sectional view of FIG. 41C. In some embodiments, the electrical contacts 4110 of the sensor 4112 can be formed by rolling up a sensor with contacts all on the same side or using the oppositely directed folding/rolling approach shown in connection with FIG. 40—but oriented vertically. Other approaches may be utilized as well. In any case, the electrical contacts of the sensor subtend less than 360 degrees while the conductive elastomeric O-rings on the circuit board provide a multi-level encircling relationship. As with the approach associated with FIGS. 39A to 40, such a sensor assembly 4100 can be inserted into the socket connector 4104 of the electronics assembly 4102 in any radial/rotational orientation.

The sensor connections associated with the circuit board 4404 in the embodiment shown in FIGS. 42 to 44 are arranged in concentric rings. The sensor 4202 includes electrical contacts 4204 held within housing member 4206 and base 4208. The electrical contacts 4204 include "microspring" wireform connectors. These springs provide compliance as well as a discrete top loop. Each electrical contact 4204 is disposed at a different radial distance from the center corresponding to a different concentric conductive track 4304 on a circuit board coupling 4302. Thus, no matter the rotational orientation of the sensor assembly 4200 relative to the circuit board coupling 4302, the electrical contacts 4204 of the sensor 4202 align with the correct concentric conductive tracks 4304. Very fine wire can be used for the springs, thus producing an easily miniaturized system.

Figures 45A, 45B:
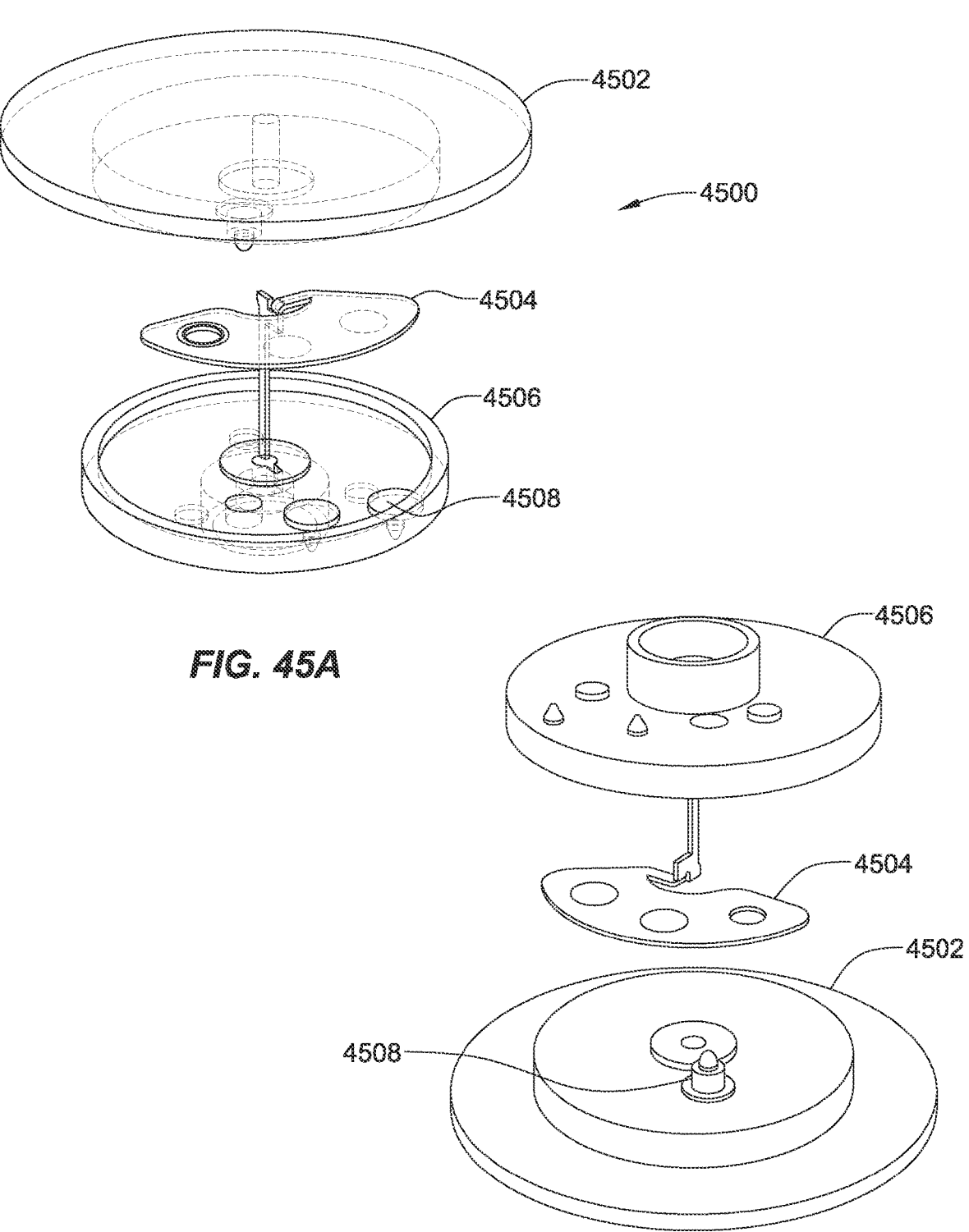
FIGS. 45A and 45B are reversed assembly views of an alternative advantageous sensor connection assembly that can be used like that in FIG. 42.
Figure 46A:
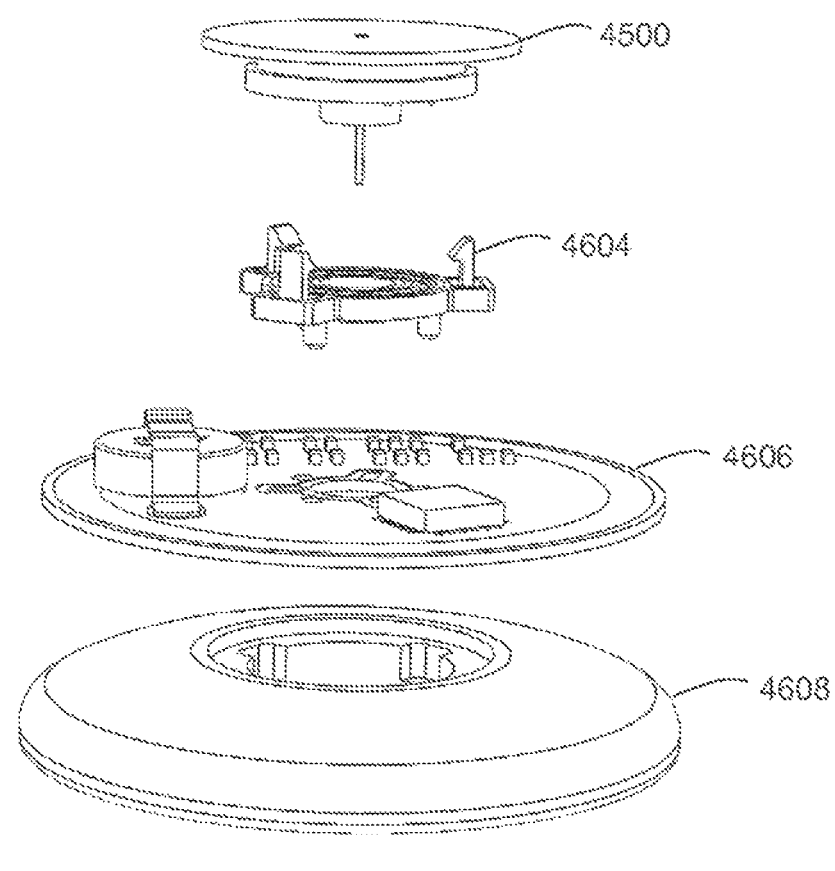
FIGS. 46A and 46B are assembly and sectional views, respectively of a complete on-body device employing the sensor and connection elements illustrated in FIGS. 45A and 45B.
Figure 46B:
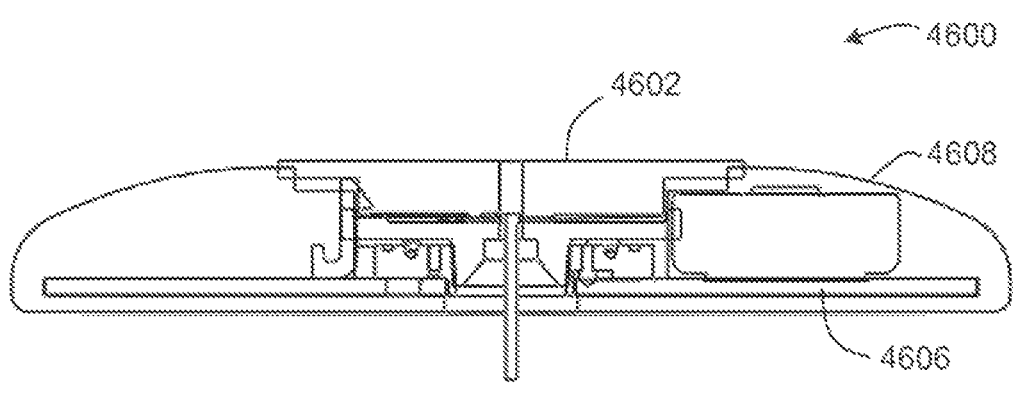

Turning now to FIGS. 45A and 45B, another non-directional sensor assembly connection approach that can be employed with a concentric electronics assembly connection is depicted. As illustrated in the isometric top and bottom views of FIGS. 45A and 45B, a sensor 4504 bent approximately ninety degrees with contacts positioned along different radial paths or arcs, connects with conductive elastomeric contacts 4508 supported by two opposing discs 4502, 4506. Two of the elastomeric contacts 4508 are set on one disc 4506, and a third, configured to pass through a sensor via, is set on the other disc 4502. As shown in FIG. 46A, this sensor assembly 4500 can then be received by a circuit board coupling 4604 which includes concentric tracks for connecting the radially disposed conductive elastomeric contacts 4508 of the sensor assembly 4500 to the circuit board 4606. The enclosure 4608 snap fits or is otherwise adhered to (e.g., using adhesive/welding) a base supporting the circuit board 4606. The as-assembled on-body device 4600 is depicted in FIG. 46B.

Turning now to FIGS. 47A to 47C, an alternative sensor assembly/electronics assembly connection approach is illustrated. As shown, the sensor assembly 4702 includes sensor 4704, connector support 4706, and sharp 4708. Notably, sensor assembly 4702 does not include a separate connector or seal to enclose the sensor's connectors within the connector support 4706 as in the embodiment depicted in FIGS. 34A to 34D (i.e., no seal 3402). Instead, a recess 4710 formed directly in the enclosure of the electronics assembly 4712 includes an elastomeric sealing member 4714 (including conductive material coupled to the circuit board and aligned with the electrical contacts of the sensor 4704). Thus, when the sensor assembly 4702 is snap fit or otherwise adhered to the electronics assembly 4712 by driving the sensor assembly 4702 into the integrally formed recess 4710 in the electronics assembly 4712, the on-body device 4714 depicted in FIG. 47C is formed. This embodiment provides an integrated connector for the sensor assembly 4702 within the electronics assembly 4712.

On-Body Device Construction Details

Certain elements of the on-body device fabrication may apply to any or all of the above electrical connection configurations. FIGS. 48A-48D provide top (FIG. 48A) and bottom (FIG. 48B-48D) construction views of an exemplary on-body device subassembly. A socket 4802 or mount is fit through vias in a printed circuit board 4800 along with other associated components including a processor 4804 (e.g., an ASIC including a communications facility), thermistor/thermocouple 4806, a battery mount 4808, etc. Once the circuit board 4800 has been populated with these components as shown in FIG. 48C, the socket 4802 is adhered to the circuit board 4800 (e.g., using heat stakes). Once a battery 4810 is set in place, the circuit board 4800 as shown in FIG. 48E is prepared for incorporation into an on-body device.

Figure 49A:
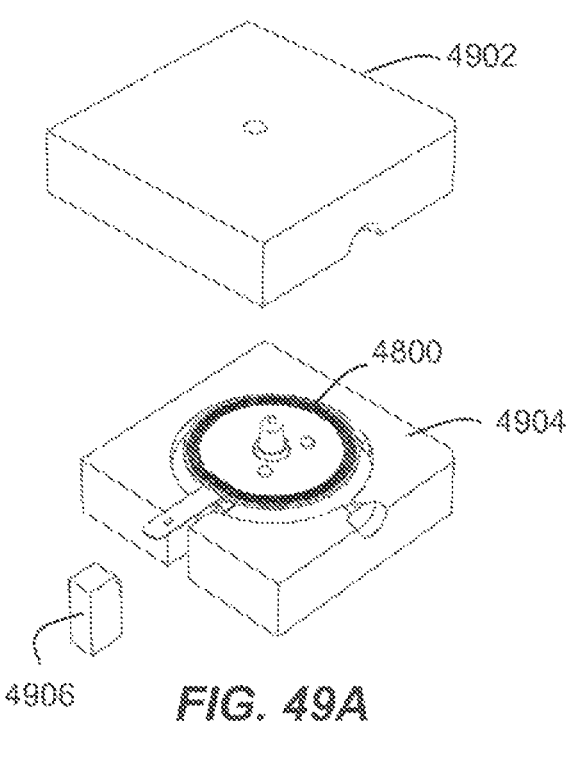
FIGS. 49A-49D illustrate the process of co-molding/ overmolding the assembly in FIG. 48E.
Figure 49B:
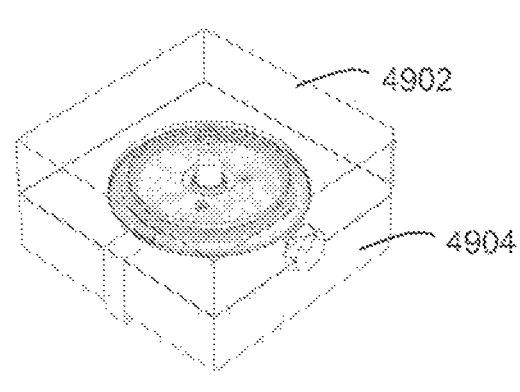
Figure 49C:
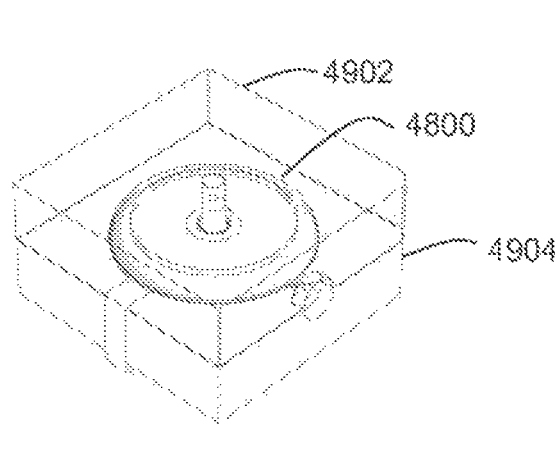
Figure 49D:
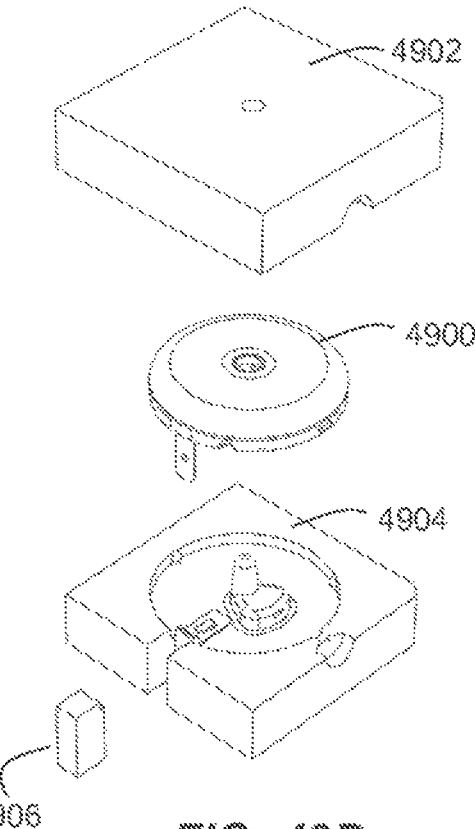

The circuit board 4800 is ready for an over-mold process or other sealing method. As illustrated in FIGS. 49A-49D, the circuit board 4800 is first set in the two-piece mold 4902, 4904. With the mold slide 4906 inserted and mold 4902, 4904 closed as shown in FIG. 49B. As depicted in FIG. 49C, a thermoplastic material is injected into the mold 4902, 4904, encasing the circuit board 4800. The mold 4902, 4904 is opened and the near-final part ejected as shown in FIG. 49D.

Alternatively, the enclosure of the electronics assembly of the on-body device 222 may include elements snap-fit (or welded/adhered) together as illustrated in the assembly view of FIG. 50A, the as-assembled view of FIG. 50B, and in cross-sectional perspective view of FIG. 50C. An enclosure including a top shell 5002 and a mounting base 5004 can be used to sealably enclose and protect the circuit board 4800. When snap-fit, various interference or snap fit elements (e.g., annular rims 5006) may be provided around the entirety of the periphery of the enclosure or as discrete snap-fit connectors (not shown). Notably, such an approach may benefit from additional O-ring sealing elements to avoid fluid intrusion. Alternatively or additionally, adhesive set at the snap junction(s) may be used to ensure good sealing, especially in connection with continuous annular snap-fit features 5006. As seen in FIG. 50C, a trough 5008 or other features can be provided to insure that adhesive 5010 that may be squeezed out during assembly is not forced into areas that could interfere with operation or assembly of the on-body device 222. In some embodiments, when a top shell 5002 and a mounting base 5004 are fit together with a bead of adhesive 5010 in place as shown, the trough 5008 not only provides space to capture the adhesive 5010 squeezed out but also provides additional surface area for a thicker layer of adhesive 5010 to seal the joint.

However constructed, final assembly of the electronics assembly of on-body device 222 involves adhesive patch installation. An exemplary approach is illustrated in FIGS. 51A-51C. First, a double-sided adhesive patch 5104 has the inner liner 5102 removed. This exposed adhesive is set over the on-body device body 5106 (with the temperature sensor 4806 folded to seat within a complimentary pocket) and adhered with a first window 5108 aligned for temperature sensing and second window 5110 for sensor assembly receipt. As such, it is ready for placement in an applicator assembly upon removal of the outer release liner, or alternatively ready for placement in a container with or without the outer liner in place, depending on the presence or absence of any liner-puller features provided therein.

Various other modifications and alterations in the structure and method of operation of the embodiments of the present disclosure will be apparent to those skilled in the art without departing from the scope and spirit of the present disclosure. Although the present disclosure has been described in connection with certain embodiments, it should be understood that the present disclosure as claimed should not be unduly limited to such embodiments. It is intended that the following claims define the scope of the present disclosure and that structures and methods within the scope of these claims and their equivalents be covered thereby.

What is claimed is:

1. An assembly comprising:
an applicator, comprising a sharp;
an on-body device, comprising:
(1) a glucose sensor, comprising:
a proximal portion configured to electrically couple with a printed circuit board; and
a distal portion configured to be positioned under a skin surface and in contact with a bodily fluid of a subject;
(2) a housing, comprising:
a top portion comprising a top exterior surface and a first aperture;
a base portion configured to be adhered to the skin surface of the subject by an adhesive patch; and
an enclosure defined by the top portion and the base portion; and
(3) sensor electronics positioned within the enclosure, the sensor electronics comprising a processor, a battery, and the printed circuit board, wherein the printed circuit board comprises a second aperture,
wherein the base portion of the housing comprises a recess in a bottom exterior surface, the recess comprising a distal-facing opening, and wherein the recess is configured to receive the proximal portion of the glucose sensor via the distal-facing opening,
wherein the housing further comprises a plurality of engagement recesses circumferentially disposed thereon, and wherein the engagement recesses are configured to be detachably engaged with the applicator,
wherein the proximal portion of the glucose sensor is disposed in the recess such that the glucose sensor is electrically coupled with the sensor electronics,
wherein the applicator is configured to advance the on-body device and the sharp from a first position to a second position such that a distal end of the sharp pierces the skin surface of the subject and the base portion of the housing is adhered to the skin surface of the subject, wherein the on-body device and the sharp are entirely disposed within an interior of the applicator when the on-body device and the sharp are in the first position,
wherein the sharp extends through the first aperture of the top portion of the housing and the second aperture of the printed circuit board when the on-body device and the sharp are in the first position, and
wherein the applicator is further configured to automatically retract the distal end of the sharp from within the subject to within the interior of the applicator.

2. The assembly of claim 1, wherein the sensor electronics further comprise a wireless communications facility.

3. The assembly of claim 2, wherein the recess of the base portion is configured to receive the proximal portion of the glucose sensor via the distal-facing opening while the sensor electronics are in the enclosure.

4. The assembly of claim 2, wherein the glucose sensor further comprises a bent section between the proximal portion and the distal portion, wherein the proximal portion and the distal portion are approximately perpendicular to each other when the on-body device and the sharp are in the first position.

5. The assembly of claim 4, wherein a part of the distal portion of the glucose sensor is disposed within the sharp when the on-body device and the sharp are in the first position.

6. The assembly of claim 5, wherein the sharp is a slotted sharp.

7. The assembly of claim 6, wherein automatic retraction of the distal end of the sharp causes the distal end of the sharp to pull away from the part of the distal portion of the glucose sensor.

8. The assembly of claim 5, further comprising the adhesive patch, wherein the adhesive patch is coupled with the base portion when the on-body device and the sharp are in the first position, and wherein the adhesive patch comprises a window aligned with the distal-facing opening.

9. The assembly of claim 5, wherein the housing further comprises a side wall, and wherein the side wall is located between the top exterior surface of the top portion of the housing and the bottom exterior surface of the base portion of the housing.

10. The assembly of claim 9, wherein each engagement recess of the plurality of engagement recesses is disposed on the side wall of the housing, and wherein each engagement recess of the plurality of engagement recesses comprises a concave portion.

11. The assembly of claim 10, wherein the side wall of the housing comprises a first portion and a second portion, wherein the first portion of the side wall is substantially orthogonal to the bottom exterior surface of the base portion of the housing, and wherein the second portion of the side wall is non-orthogonal to the top exterior surface of the top portion of the housing.

12. The assembly of claim 5, wherein the on-body device is configured to communicate data indicative of a glucose level to a receiver unit.

13. The assembly of claim 5, wherein the plurality of engagement recesses is detachably engaged to the applicator when the on-body device and the sharp are in the first position.

14. The assembly of claim 5, wherein the on-body device further comprises a non-conductive compound configured for potting at least a section of the glucose sensor.

15. The assembly of claim 14, wherein the non-conductive compound is further configured to seal the at least a section of the glucose sensor within the on-body device.

16. The assembly of claim 15, wherein the non-conductive compound is an epoxy.

17. The assembly of claim 15, wherein the non-conductive compound is a UV-cured compound.

18. The assembly of claim 5, wherein the proximal portion of the glucose sensor is configured to electrically couple with the printed circuit board via a conductive adhesive.

19. The assembly of claim 5, wherein the housing comprises a single integral unit.

20. The assembly of claim 5, wherein the top portion and the base portion form a single over-molded unit comprising a thermoplastic material, and wherein the single over-molded unit seals the sensor electronics within the enclosure.

21. The assembly of claim 5, wherein the top portion and the base portion are coupled by a snap-fit mechanism such that the sensor electronics are sealed within the enclosure.

22. The assembly of claim 5, wherein the top portion and the base portion are welded together such that the sensor electronics are sealed within the enclosure.

23. The assembly of claim 5, wherein the top portion and the base portion are adhered together such that the sensor electronics are sealed within the enclosure.

24. The assembly of claim 5, wherein the processor of the sensor electronics comprises an application specific integrated circuit (ASIC).

25. The assembly of claim 5, wherein the applicator further comprises a sheath defining a distal surface for placement on the skin surface.

26. The assembly of claim 5, wherein the applicator is further configured to be removed from the skin surface after the distal end of the sharp is automatically retracted from within the subject to within the interior of the applicator, and wherein the on-body device is configured to remain on the skin surface after the applicator is removed.

* * * * *